United States Patent
White et al.

(10) Patent No.: US 10,266,503 B1
(45) Date of Patent: Apr. 23, 2019

(54) SULFOXIDE LIGAND METAL CATALYZED OXIDATION OF OLEFINS

(71) Applicant: The Board of Trustees of the University of Illinois, Urbana, IL (US)

(72) Inventors: M. Christina White, Champaign, IL (US); Stephen E. Ammann, Champaign, IL (US); Wei Liu, Simi Valley, CA (US); Rulin Ma, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/604,377

(22) Filed: May 24, 2017

Related U.S. Application Data

(60) Provisional application No. 62/340,909, filed on May 24, 2016.

(51) Int. Cl.
*C07D 263/10* (2006.01)
*C07C 317/14* (2006.01)

(52) U.S. Cl.
CPC .......... *C07D 263/10* (2013.01); *C07C 317/14* (2013.01); *C07B 2200/07* (2013.01)

(58) Field of Classification Search
None
See application file for complete search history.

(56) References Cited

U.S. PATENT DOCUMENTS 9,090,545 B2    7/2015    Fletcher et al.

FOREIGN PATENT DOCUMENTS

WO    2005012209 A2    2/2005

OTHER PUBLICATIONS

Kondo, Hiroki. Branch-Selective Allylic C—H Carboxylation of Terminal Alkenes by Pd/sox Catalyst. Organic Letters. 16, 2014, 4212-4215.*
Hiroi, Kunio. New chiral sulfoxide ligands in catalytic asymmetric Diels-Alder reactions: double acceleration by the chiralities of the sulfoxides and oxazolines. Tetrahedron Letters. 42 (2001) 7617-7619.*
Allen et al., "Enantioselective Palladium Catalysed Allylic Substitution. Electronic and Steric Effects of the Ligand.," Tetrahedron: Asymmetry, 5(10):1895-1898, Oct. 1994.
Ammann et al., "Enantioselective Allylic C—H Oxidation of Terminal Olefins to Isochromans by Palladium(II)/Chiral Sulfoxide Catalysis," Angew Chem Int Ed Engl., 55(33):9571-9575, Aug. 2016.
Ammann et al., "Enantioselective Allylic C—H Oxidation of Terminal Olefins to Isochromans by Palladium(II)/Chiral Sulfoxide Catalysis," Angew Chem Int Ed Engl., Aug. 2016, 199pgs., Supporting Information.
Ammann et al., "Terminal Olefins to Chromans, Isochromans, and Pyrans via Allylic C—H Oxidation," J Am Chem Soc., 136(31):10834-10837, Aug. 2014.
Chen et al., "Palladium-Catalyzed Cascade Sp2 C—H Functionalization/Intramolecular Asymmetric Allylation: From Aryl Ureas and 1,3-Dienes to Chiral Indolines," Angew Chem Int Ed Engl.,1;56(23):6641-6645, Jun. 2017.
Covell et al., "A Chiral Lewis Acid Strategy for Enantioselective Allylic C—H oxidation," Angew Chem Int Ed Engl., 47(34):6448-6451, Jul. 2008.
Hiroi et al., "New Chiral Sulfoxide Ligands in Catalytic Asymmetric Diels-Alder Reactions: Double Acceleration by the Chiralities of the Sulfoxides and Oxazolines," Tetrahedron Letters, 42(43):7617-7619, Oct. 2001.
Kondo et al., "Branch-Selective Allylic C—H Carboxylation of Terminal Alkenes by Pd/sox Catalyst," Org. Lett., 16(16):4212-4215, Jul. 2014.
Wang et al., "Asymmetric Allylic C—H Oxidation for the Synthesis of Chromans," J Am Chem Soc., 137(40):12732-12735, Sep. 2015.
Yamaguchi et al., "Aromatic C—H Coupling with Hindered Arylboronic Acids by Pd/Fe Dual Catalysts," Chem Sci, 9:3753-3757, Sep. 2013.

* cited by examiner

*Primary Examiner* — Samantha L Shterengarts
(74) *Attorney, Agent, or Firm* — Haukaas Fortius PLLC; Michael H. Haukaas

(57) ABSTRACT

The enantioselective synthesis of isochroman motifs has been accomplished via Pd(II)-catalyzed allylic C—H oxidation from terminal olefin precursors. Critical to the success of this goal was the development and utilization of a novel chiral aryl sulfoxide-oxazoline (ArSOX) ligand. The allylic C—H oxidation reaction proceeds with the broadest scope and highest levels asymmetric induction reported to date (avg. 92% ee, 13 examples ≥90% ee). Additionally, $C(sp^3)$-N fragment coupling reaction between abundant terminal olefins and N-triflyl protected aliphatic and aromatic amines via Pd(II)/sulfoxide (SOX) catalyzed intermolecular allylic C—H amination is disclosed. A range of 52 allylic amines are furnished in good yields (avg. 76%) and excellent regio- and stereoselectivity (avg. >20:1 linear:branched, >20:1 E:Z). For the first time, a variety of singly activated aromatic and aliphatic nitrogen nucleophiles, including ones with stereochemical elements, can be used in fragment coupling stiochiometries for intermolecular C—H amination reactions.

14 Claims, 2 Drawing Sheets

SULFOXIDE LIGAND METAL CATALYZED OXIDATION OF OLEFINS

RELATED APPLICATIONS

This application claims priority under 35 U.S.C. § 119(e) to U.S. Provisional Patent Application No. 62/340,909, filed May 24, 2016, which is incorporated herein by reference.

GOVERNMENT SUPPORT

This invention was made with government support under Grant No. 2RO1 GM076153B awarded by the National Institutes of Health. The government has certain rights in the invention.

BACKGROUND OF THE INVENTION

The enantioselective functionalization of prochiral C—H bonds represents a highly efficient transformation by installing both valuable oxidized functionality and absolute stereochemistry in a single step. Asymmetric allylic C—H oxidations have been pursued over the last five decades; copper catalyzed Kharasch-Sosnovsky reactions have achieved satisfactory enantiomeric excesses, however only with symmetrical, cyclic olefins under synthetically undesirable conditions (excess equivalents of olefin, days at cryogenic temperatures) (Scheme 1A). Palladium has shown a broad scope in enantioselective C—H desymmetrizations and kinetic resolutions, however Pd-catalyzed asymmetric allylic C—H functionalizations have been achieved hereto with only modest levels of asymmetric induction. Additionally, Pd-catalyzed asymmetric C—H to C—O bond-forming reactions are rare.

Due to the ubiquity of C—N bonds in natural products and pharmaceuticals, the cross-coupling of amines with hydrocarbons under fragment coupling conditions (1 equivalent) stands to significantly impacted chemical synthesis. Whereas significant progress has been made in cross-couplings of amines with aryl halides to form $C(sp^2)$-N bonds, the development of analogous $C(sp^3)$-N coupling reactions remains an elusive goal.

Site, chemo- and stereoselective Pd(II)-catalyzed reactions for intermolecular allylic C—H aminations of α-olefins are well-precedented; however, all require use of N-tosyl carbamate nucleophiles. These reactions proceed via near ligandless conditions (e.g. reversibly coordinating sulfoxide ligands) that may lead to catalyst deactivation in the presence of more basic and coordinating nitrogen nucleophiles.

Accordingly, there is a need for transition metal complexes that can catalytically activate an allylic C—H bond under simple reaction conditions to provide $C(sp^3)$-heteroatom functionalized products with efficient regio- and stereoselective catalyst-control.

SUMMARY

Herein is disclosed the development of a chiral diarylated sulfoxide-oxazoline (ArSOX) ligand/Pd(II)-catalyzed asymmetric allylic C—H oxidation system that proceeds with broad scope and high asymmetric induction (avg. 92% ee, 13 examples ≥90% ee), which use mixed sulfoxide-oxazoline ligands (SOX) for asymmetric allylic C—H oxidations to form enantioenriched isochromans via Pd(II)-catalysis. (Scheme 1C, Ammann et al., Angew. Chem. Int. Ed., 2016, 55, 9571-9575). The uniformly high levels of asymmetric induction (>90% ee) observed with these ligands supports the hypothesis that they do not dissociate from the Pd metal during catalysis and thereby may enable the use of more complex, basic amine nucleophiles.

Also, disclosed herein is the discovery of a novel (±)-MeO—SOX ligand (Table 1, L-5) that works with Pd(II) acetate to promote the first allylic C—H amination fragment coupling method. This method enables complex terminal olefins (1.0 equiv.) to be coupled to bench-stable, easy-to-synthesize complex N-trifyl protected primary aliphatic amines (1.0 equiv.) to afford allylic amines in good yields (52 examples, avg. 76%) and excellent regio- and stereoselectivity (>20:1 linear:branched, >15:1 E:Z).

Accordingly, this disclosure provides a compound of Formula I:

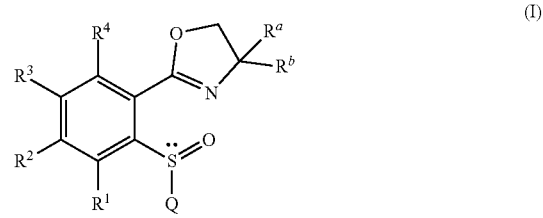

(I)

wherein $R^a$ is H, alkyl, heteroalkyl, cycloalkyl, heterocycle, aryl, or heteroaryl;

$R^b$ is alkyl, heteroalkyl, cycloalkyl, heterocycle, aryl, or heteroaryl;

Q is alkyl, heteroalkyl, cycloalkyl, heterocycle, heteroaryl, phenanthryl, 2-naphthyl, 1-naphthyl provided that $R^1$, $R^2$, $R^3$, or $R^4$ is not H, or Q is the moiety Q1:

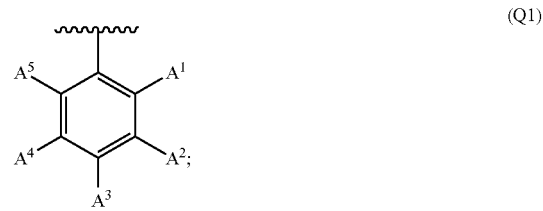

(Q1)

$R^1$, $R^2$, $R^3$, $R^4$, $A^1$, $A^2$, $A^4$, and $A^5$ are each independently H, halo, alkyl, heteroalkyl, trifluoromethyl, trifluoromethoxy, $OR^x$, $N(R^x)_2$, nitro, cycloalkyl, aryl, or heteroaryl;

$A^3$ is H, halo, $(C_2$-$C_8)$alkyl, heteroalkyl, trifluoromethyl, trifluoromethoxy, $OR^x$, $N(R^x)_2$, nitro, cycloalkyl, aryl, heteroaryl, or $A^3$ is methyl when one of $R^1$, $R^2$, $R^3$, $R^4$, $A^1$, $A^2$, $A^4$, and $A^5$ is not H; and each $R^x$ is independently H, $(C_1$-$C_8)$alkyl, or benzyl;

wherein at least one of $R^a$ and $R^b$ is cycloalkyl, heterocycle, aryl, or heteroaryl, or Q is cycloalkyl, heterocycle, heteroaryl, or Q1.

This disclosure also provides a method of inducing an asymmetric oxidative cyclization reaction comprising heating a mixture of an organic substrate, an oxidant, an acid, a palladium(II) compound, and a compound of Formula X:

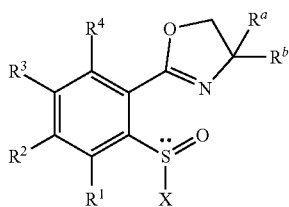

(X)

wherein $R^a$ is H, alkyl, heteroalkyl, cycloalkyl, heterocycle, aryl, or heteroaryl;

$R^b$ is alkyl, heteroalkyl, cycloalkyl, heterocycle, aryl, or heteroaryl;

X is alkyl, heteroalkyl, cycloalkyl, heterocycle, aryl, or heteroaryl;

$R^1$, $R^2$, $R^3$, and $R^4$ are each independently H, halo, alkyl, heteroalkyl, trifluoromethyl, trifluoromethoxy, $OR^x$, $N(R^x)_2$, nitro, cycloalkyl, aryl, or heteroaryl;

each $R^x$ is independently H, $(C_1-C_8)$alkyl, or benzyl; and the $R^a$—C—$R^b$ moiety is in the (S)-configuration and the sulfoxide moiety is in the (R)-configuration, or the $R^a$—C—$R^b$ moiety is in the (R)-configuration and the sulfoxide moiety is in the (S)-configuration;

wherein the organic substrate comprises an allyl group and a hydroxy group, wherein the hydroxyl group is four or five carbon atoms from the terminal olefin moiety of the allyl group;

to provide a cyclic ether with a vinyl substituent alpha to the ether moiety formed by the oxidative cyclization, wherein the stereochemistry of the vinyl substituent is enantiomerically enriched.

Additionally, this disclosure provides a method to couple an activated secondary amine and a terminal olefin comprising contacting an organic substrate having an allyl group, an activated secondary amine, an oxidant, and a palladium(II) compound, and a compound of Formula XI:

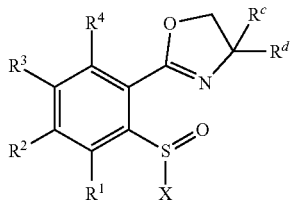

(XI)

wherein $R^b$ and $R^c$ are each independently alkyl, heteroalkyl, cycloalkyl, heterocycle, aryl, or heteroaryl;

X is alkyl, heteroalkyl, cycloalkyl, heterocycle, aryl, or heteroaryl;

$R^1$, $R^2$, $R^3$, and $R^4$ are each independently H, halo, alkyl, heteroalkyl, trifluoromethyl, trifluoromethoxy, $OR^x$, $N(R^x)_2$, nitro, cycloalkyl, aryl, or heteroaryl; and each $R^x$ is independently H, $(C_1-C_8)$alkyl, or benzyl;

to provide a product comprising a tertiary amine wherein the amine is substituted by an allyl group.

Embodiments of the disclosed compounds and methods include a sulfoxide moiety that is in the (S)-configuration, or in the (R)-configuration.

The disclosed ligands are useful for catalytic chemical reactions as represented by the general synthetic procedures shown in Scheme A, parts a) and b). In part a), an alcohol comprising an allylic moiety undergoes C—H oxidation by transition metal catalysis when in contact with a transition metal, a chiral sulfoxide ligand, an oxidizer, and an acid to afford a chiral ether, wherein the newly formed asymmetric center is represented by "*C—O". In part b), an activated amine comprising an activating group (Y), undergoes a transition metal catalyzed coupling reaction with an allylic moiety when in contact with a transition metal (e.g., a palladium catalyst), a sulfoxide ligand, and an oxidizer to afford a compound with a newly formed C—N bond. Subsequently, the activating group can be removed from the nitrogen, for example, by a reduction step.

Scheme A: Generalized synthetic procedures for metal catalyzed reactions using sulfoxide ligands.

a) Enantioselective formation of C—O bond

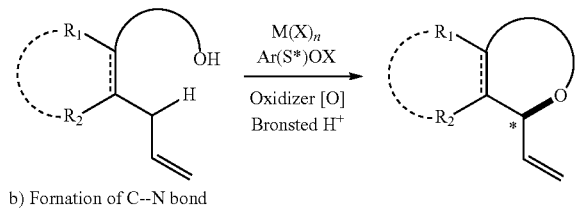

b) Formation of C—N bond

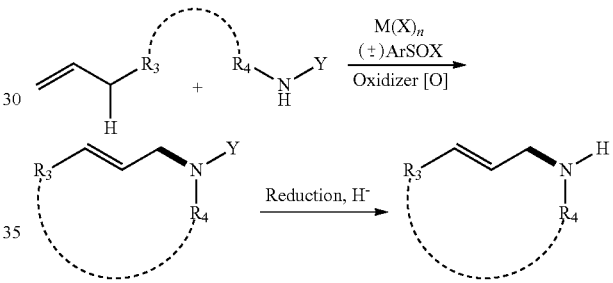

Dotted lines represent an optional bond, or an optional linker between $R^x$-groups, wherein $R^x$ is, for example, $R^1$, $R^2$, $R^3$, or $R^4$ as shown above, and as represented by various structures in the examples below. Accordingly, the amine-terminal olefin coupling reaction can be an intramolecular reaction or an intermolecular reaction (for example, a cross coupling reaction).

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
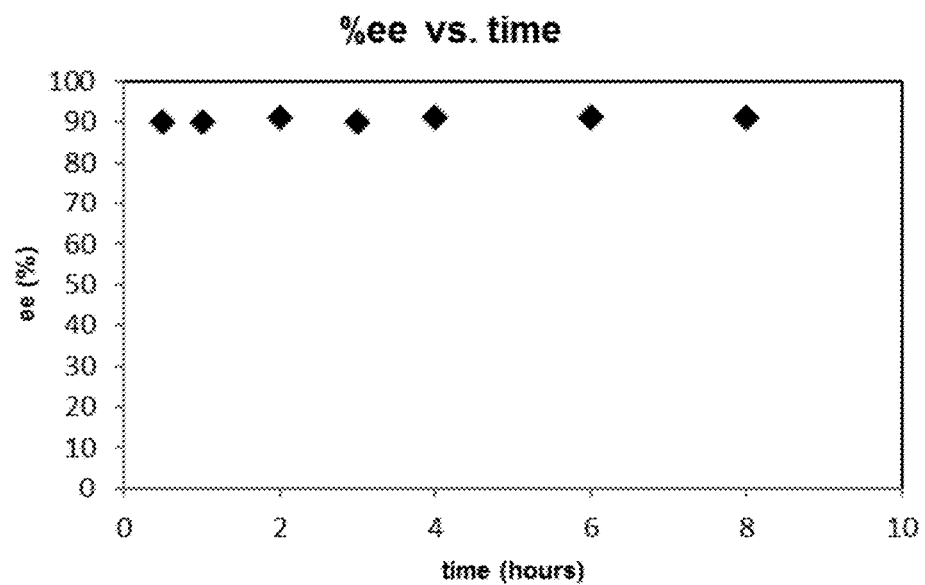
FIG. 1. Plot of enantiomeric excess over time.

Pd(II)/bis-sulfoxide catalysis has proven to be a uniquely general platform for effecting allylic C—H oxidation, amination, fluorination and alkylation of terminal olefins with broad scope, preparative yields, and excellent regio- and E/Z-selectivity. Many of these reactions proceed via a serial ligand catalysis mechanism where the bis-sulfoxide ligand promotes C—H cleavage and benzoquinone (BQ), acting as a π-acidic ligand, promotes functionalization. However, limited success has been achieved in adapting this catalytic platform for asymmetric catalysis. Mechanistic studies have illuminated two significant challenges. The bis-sulfoxide ligand, while effective for C—H cleavage and oxidatively stable, is transiently associated with the Pd metal and does not exert influence during functionalization; benzoquinone acts as a ligand at high concentrations to promote functionalization. Second, rapid π-σ-π isomerization precedes the C—O bond forming step and scrambles any chiral information that may be imparted during C—H cleavage by a chiral bis-sulfoxide ligand. Working within the constraints of these challenges, a chiral Cr Lewis acid co-catalyst was identified that works with BQ to promote enantioinduction during functionalization, albeit with modest enantiomeric excess (Scheme 1B). Alternatively, chiral palladium/phosphoramidite catalysts for allylic C—H functionalizations have previously demonstrated modest enantioselectivity, limited olefin scope (generally doubly activated C—H bonds) and high sensitivity to $O_2$ (Covell et al., Angew. Chem. Int. Ed. 2008, 47, 6448-6451; Trost et al., J. Am. Chem. Soc. 2015, 137, 2776-2784; Wang et al., J. Am. Chem. Soc. 2015, 137, 12732-12735). We hypothesized the ideal catalytic platform would utilize an oxidatively stable, chiral ligand capable of promoting both C—H cleavage and functionalization, thus circumventing the challenges of serial ligand catalysis.

Scheme 1. Enantioselective allylic C-H oxidation.

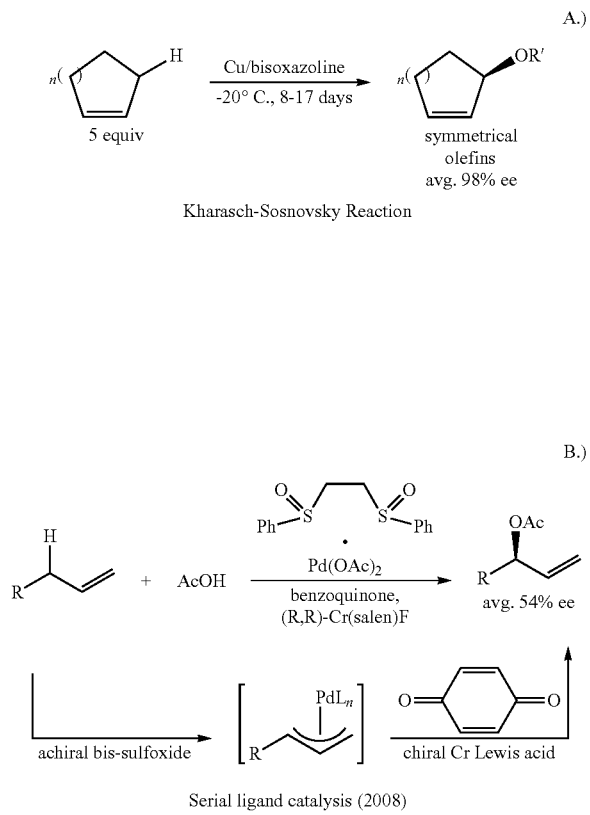

Chiral isochromans are well-represented in natural products and pharmaceuticals, and are classically furnished via diastereoselective cyclizations or chiral resolution of racemates. Enantioselective organocatalytic and metal-catalyzed methods are emerging to furnish this motif, however, generally starting from pre-oxidized precursors. We recently reported the synthesis of racemic cyclic ethers via Pd(II)/bis-sulfoxide-catalyzed, BQ-promoted allylic C—H oxidation (Ammann et al., J. Am. Chem. Soc. 2014, 136, 10834-10837). Given that pre-coordination of the alcohol to Pd was found to be important for functionalization, we hypothesized that such a system might enable high levels of asymmetric induction in the C—O bond forming step, and provide a valuable means to furnish chiral isochromans.

Drawing inspiration from the success of mixed P,N-donor ligands in asymmetric catalysis (Behenna et al., J. Am. Chem. Soc. 2004, 126, 15044-15045), we hypothesized that combining a sulfoxide (promotes C—H cleavage) with the π-acidic/σ-donor properties of an oxazoline (may promote functionalization and effect a static chiral environment at the metal) would enable an efficient asymmetric reaction. Mixed S,N-ligands were known to effect asymmetric induction in Pd(0)-catalyzed allylic substitutions, however with a very limited scope (1,3-diphenylpropenyl acetate). Alkyl-substituted sulfoxide-oxazoline ligands were recently shown to promote Pd-catalyzed branched allylic C—H acetoxylations, however with no asymmetric induction (Kondo et al., Org. Lett. 2014, 16, 4212-4215).

Complex, aliphatic amines are prominent structural elements in biologically active small molecules. In drug development, nearly 35% of reactions involve the formation of $C(sp^3)$-N bonds. While robust and reliable, these reactions often proceed via coupling of amines and pre-functionalized compounds (e.g. N-alkylation, reductive amination and N-acylation-reduction) and necessitate unproductive synthetic steps to install and maintain those functionalities. An alternative approach that requires less synthetic overhead and may tolerate orthogonal functionality is coupling amines directly to hydrocarbons. Recent advances in hydroamination of α-olefins and symmetric internal olefins to furnish aliphatic amines have underscored the advantages of such methods. Direct allylic C—H amination of α-olefins would

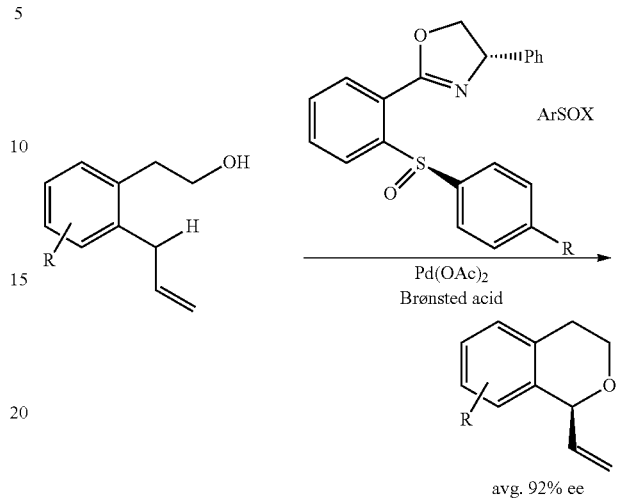

provide an orthogonal approach that furnishes amines where the olefin is maintained for further elaboration and where functionalities prone to reduction are tolerated. Although impressive methods for allylic C—H aminations exist, they uniformly require the use of highly activated nitrogen sources (e.g. N-tosyl carbamates, primary sulfamates, etc. . . . ) or alkyl azides with limited scope that are not amenable to the development of fragment coupling methods between complex terminal olefins and complex aliphatic amines.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

In general, "substituted" refers to an organic group (wherein the organic group is referred to as a substituent by a person skilled in the art) in which one or more bonds to a hydrogen atom contained therein are replaced by one or more bonds to a substituent, for example, a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, —OC(O)N(R')$_2$, —C(S)N(R')$_2$, —(CH$_2$)$_{0-2}$NHC(O)R', —N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

"Halo" as the term is used herein includes fluoro, chloro, bromo, and iodo. A "haloalkyl" group includes mono-halo alkyl groups, and poly-halo alkyl groups wherein all halo atoms can be the same or different. Examples of haloalkyl include trifluoromethyl, 1,1-dichloroethyl, 1,2-dichloroethyl, 1,3-dibromo-3,3-difluoropropyl and the like.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent. The alkyl can also be optionally partially or fully unsaturated. As such, the recitation of an alkyl group can include both alkenyl and alkynyl groups when specifically noted. The alkyl can be a monovalent hydrocarbon radical, as described and exemplified above, or it can be a divalent hydrocarbon radical (i.e., an alkylene).

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times (e.g., 1-5) with any of the groups listed above, for example, amino, hydroxy, cyano, carboxy, nitro, thio, alkoxy, and halogen groups.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 18 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, b-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl, and dimers thereof. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl, 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-, 2-, 3-, 4-, 5-, 6-, or 7-indazolyl), benzimidazolyl (1-, 2-, 3-, 4-, 5-, 6-, 7-, or 8-benzimidazolyl), benzoxazolyl (1-benzoxazolyl, 2-benzoxazolyl), benzothiazolyl (1-, 2-, 3-, 4-, 5-, 6-, or 7-benzothiazolyl), carbazolyl (1-, 2-, 3-, or 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

As would be readily understood by one of skill in the art, an "organic substrate" is an organic compound selected as a starting material for a particular reaction described herein. The organic substrate is typically a solid or liquid, and typically has a molecular weight of at least about 60 Daltons and often less than about 1 KDa. For certain reactions, the organic substrate comprises an allyl group and a hydroxy group, wherein the hydroxyl group is four or five carbon atoms from the terminal olefin moiety of the allyl group. The substrate can have a wide variety of rings and substituents, provided that the hydroxyl group is four or five carbon atoms from the terminal olefin moiety of the allyl group. In other embodiments, the organic substrate can be an organic compound having an allyl group, for example, for coupling to an activated secondary amine.

All chiral, diastereomeric, and racemic forms of a structure are intended, unless the specific stereochemistry or isomeric form is specifically indicated. Compounds described in the present invention include enantiomerically enriched or resolved optical isomers at any or all asymmetric atoms. Both racemic and diastereomeric mixtures, as well as the individual optical isomers can be isolated or synthesized so as to be substantially free of their enantiomeric or diastereomeric partners. Each isomer and diastereomer is within the scope of the invention.

The term "enantiomerically enriched" refers to mixtures that have one enantiomer present to a greater extent than another. In one embodiment, the term "enantiomerically enriched" refers to a mixture having at least about 50% enantiomeric excess ("ee"); in another embodiment, the term refers to a mixture having at least about 75% ee; in another embodiment, the term refers to a mixture having at least about 80%; in another embodiment, the term refers to a mixture having at least about 85%; in another embodiment, the term refers to a mixture having at least about 90%; in another embodiment, the term refers to a mixture having at least about 92%; in another embodiment, the term refers to a mixture having at least about 95%; in another embodiment, the term refers to a mixture having at least about 98%; and in another embodiment, the term "enantiomerically enriched" refers to a mixture having at least about 99% ee. The term "enantiomerically enriched" includes enantiomerically pure mixtures, which are mixtures that are substantially free of the species of the opposite optical activity or one enantiomer is present in very low quantities, for example, about 0.01%, about 0.001% or about 0.0001%.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form.

Embodiments of the Invention

Various embodiments of this disclosure include a compound of Formula I:

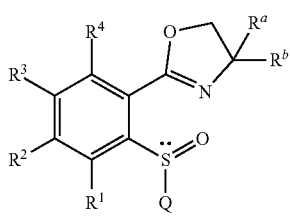

(I)

wherein $R^a$ is H, alkyl, heteroalkyl, cycloalkyl, heterocycle, aryl, or heteroaryl; $R^b$ is alkyl, heteroalkyl, cycloalkyl, heterocycle, aryl, or heteroaryl; Q is alkyl, heteroalkyl, cycloalkyl, heterocycle, heteroaryl, phenanthryl, 2-naphthyl, 1-naphthyl provided that $R^1$, $R^2$, $R^3$, or $R^4$ is not H, or Q is the moiety Q1:

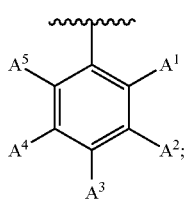

(Q1)

$R^1$, $R^2$, $R^3$, $R^4$, $A^1$, $A^2$, $A^4$, and $A^5$ are each independently H, halo, alkyl, heteroalkyl, trifluoromethyl, trifluoromethoxy, $OR^x$, $N(R^x)_2$, nitro, cycloalkyl, aryl, or heteroaryl; $A^3$ is H, halo, $(C_2-C_8)$alkyl, a heteroalkyl, a trifluoromethyl, trifluoromethoxy, $OR^x$, $N(R^x)_2$, nitro, cycloalkyl, aryl, heteroaryl, or $A^3$ is methyl when one of $R^1$, $R^2$, $R^3$, $R^4$, $A^1$, $A^2$, $A^4$, and $A^5$ is not H; and each $R^x$ is independently H, $(C_1-C_8)$alkyl, or benzyl; wherein at least one of $R^a$ and $R^b$ is cycloalkyl, heterocycle, aryl, or heteroaryl, or Q is cycloalkyl, heterocycle, heteroaryl, or Q1.

Each definition of a group, such as alkyl, heteroalkyl, cycloalkyl, aryl, heteroaryl, benzyl, heterocycle, and $(C_1-C_8)$alkyl, can be optionally substituted with one or more (e.g., 1-5) substituents, such as a substituent J, which substituents are described and defined herein. In some embodiments, the groups are unsubstituted. In other embodiments, the groups are optionally substituted. In some embodiments, the substituent J is methoxy, hydroxy, methoxymethyl acetal (MOM), benzyloxymethyl acetal (BOM), tetrahydropyranyl acetal (THP), —V(MOM), —V(BOM), or —V(THP), wherein V is O, N, or S.

In some embodiments, the sulfoxide moiety is in the (S)-configuration, or in some other embodiments the sulfoxide moiety is in the (R)-configuration. In various embodiments, the $R^a$—C—$R^b$ moiety is in the (S)-configuration, or is in the (R)-configuration.

In additional embodiments of Formula I, $R^a$ is H, $(C_1-C_8)$alkyl, heteroalkyl, $(C_3-C_8)$cycloalkyl, or phenyl, wherein phenyl is optionally substituted with 1-5 substituents J; $R^b$ is $(C_1-C_8)$alkyl, heteroalkyl, $(C_3-C_8)$cycloalkyl, or phenyl, wherein phenyl is optionally substituted with 1-5 substituents J; Q is $(C_1-C_8)$alkyl, heteroalkyl, $(C_3-C_8)$cycloalkyl, or Q1; $R^1$, $R^2$, $R^3$, $R^4$, $A^1$, $A^2$, $A^4$ and $A^5$ are each independently H, halo, $(C_1-C_8)$alkyl, trifluoromethyl, trifluoromethoxy, $OR^x$, $N(R^x)_2$, nitro, $(C_3-C_8)$cycloalkyl, or phenyl, wherein phenyl is optionally substituted with 1-5 substituents J; $A^3$ is H, halo, $(C_2-C_8)$alkyl, trifluoromethyl, trifluoromethoxy, $OR^x$, $N(R^x)_2$, nitro, $(C_3-C_8)$cycloalkyl, or phenyl, wherein phenyl is optionally substituted with 1-5 substituents J; and each J is independently H, halo, $(C_1-C_8)$alkyl, trifluoromethyl, trifluoromethoxy, $OR^x$, $N(R^x)_2$, nitro, or $(C_3-C_8)$cycloalkyl.

In other embodiments of Formula I, $R^a$ is H, methyl, ethyl, n-propyl, 2-propyl, cyclopropyl, n-butyl, tert-butyl, iso-butyl, cyclopentyl, cyclohexyl, phenyl, p-tolyl, 4-methoxyphenyl, 4-trifluoromethylphenyl, or 4-trifluoromethoxyphenyl; and $R^b$ is methyl, ethyl, n-propyl, 2-propyl, cyclopropyl, n-butyl, tert-butyl, iso-butyl, cyclopentyl, cyclohexyl, phenyl, p-tolyl, 4-methoxyphenyl, 4-trifluoromethylphenyl, 4-trifluoromethoxyphenyl, 4-tert-butylphenyl, 4-tert-butoxylphenyl, 3,4,5-trimethoxyphenyl, or 3,5-di-tert-butyl-4-methoxyphenyl.

In yet other embodiments of Formula I, Q is isopropyl, cyclohexyl, 4-methylcyclohexyl, phenyl, 4-bromophenyl, 4-methoxyphenyl, 4-trifluoromethylphenyl, 4-trifluoromethoxyphenyl, 4-tert-butylphenyl, 4-tert-butoxylphenyl, 3,5-dimethylphenyl, 3,5-di-tert-butyl-4-methoxyphenyl, or 9-phenanthryl.

Additionally, Formula I can include embodiments where $R^1$, $R^2$, $R^3$, $R^4$, $A^1$, $A^2$, $A^4$ and $A^5$ are each independently fluoro, chloro, bromo, methyl, ethyl, 2-propyl, tert-butyl, cyclopropyl, cyclopentyl, cyclohexyl, trifluoromethoxy, nitro, trifluoromethyl, pentafluoroethyl, $OR^x$, or $N(R^x)_2$; $A^3$ is fluoro, chloro, bromo, ethyl, 2-propyl, tert-butyl, cyclopropyl, cyclopentyl, cyclohexyl, trifluoromethoxy, nitro, trifluoromethyl, pentafluoroethyl, $OR^x$, or $N(R^x)_2$; and each $R^x$ is independently H, methyl, ethyl, n-propyl, iso-propyl, cyclopropyl, n-butyl, sec-butyl, tert-butyl, or benzyl.

In other embodiments, the compound of Formula I is a compound of Formula II:

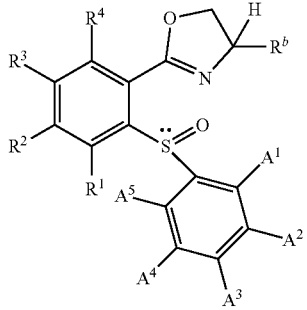

(II)

wherein $R^b$ is $(C_1\text{-}C_8)$alkyl, $(C_3\text{-}C_8)$cycloalkyl, or phenyl, wherein phenyl is optionally substituted with 1-5 substituents J; $R^1$, $R^2$, $R^3$, $R^4$, $A^1$, $A^2$, $A^4$ and $A^5$ are each independently H, halo, $(C_1\text{-}C_8)$alkyl, trifluoromethyl, trifluoromethoxy, $OR^x$, $N(R^x)_2$, nitro, $(C_3\text{-}C_8)$cycloalkyl, or phenyl, wherein phenyl is optionally substituted with 1-5 substituents J; $A^3$ is H, halo, $(C_2\text{-}C_8)$alkyl, trifluoromethyl, trifluoromethoxy, $OR^x$, $N(R^x)_2$, nitro, $(C_3\text{-}C_8)$cycloalkyl, or phenyl, wherein phenyl is optionally substituted with 1-5 substituents J; each J is independently H, halo, $(C_1\text{-}C_8)$alkyl, trifluoromethyl, trifluoromethoxy, $OR^x$, $N(R^x)_2$, nitro, or $(C_3\text{-}C_8)$cycloalkyl; and the H—C—$R^b$ moiety is in the (S)-configuration and the sulfoxide moiety is in the (R)-configuration, or the H—C—$R^b$ moiety is in the (R)-configuration and the sulfoxide moiety is in the (S)-configuration.

Furthermore, in additional embodiments, the compound of Formula II is a compound of Formula III:

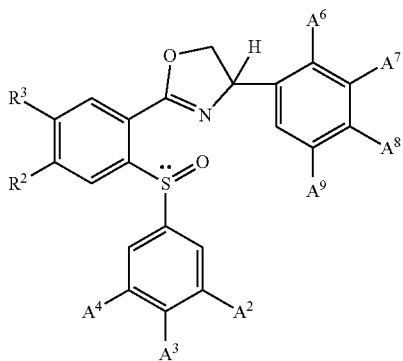

(III)

wherein $R^2$, $R^3$, $A^2$, $A^4$, $A^6$, $A^7$, $A^8$, and $A^9$ are each independently H, halo, $(C_1\text{-}C_8)$alkyl, trifluoromethyl, trifluoromethoxy, $OR^x$, $N(R^x)_2$, nitro, $(C_3\text{-}C_8)$cycloalkyl, or phenyl, wherein phenyl is optionally substituted with 1-5 substituents J; $A^3$ is H, halo, $(C_2\text{-}C_8)$alkyl, trifluoromethyl, trifluoromethoxy, $OR^x$, $N(R^x)_2$, nitro, $(C_3\text{-}C_8)$cycloalkyl, or phenyl, wherein phenyl is optionally substituted with 1-5 substituents J; each J is independently H, halo, $(C_1\text{-}C_8)$alkyl, trifluoromethyl, $OR^x$, trifluoromethoxy, $N(R^x)_2$, nitro, or $(C_3\text{-}C_8)$cycloalkyl; and the dihydrooxazole moiety is in the (S)-configuration at position-4 and the sulfoxide moiety is in the (R)-configuration, or the dihydrooxazole moiety is in the (R)-configuration at position-4 and the sulfoxide moiety is in the (S)-configuration.

In yet other embodiments, the compound of Formula I is a compound of Formula IV:

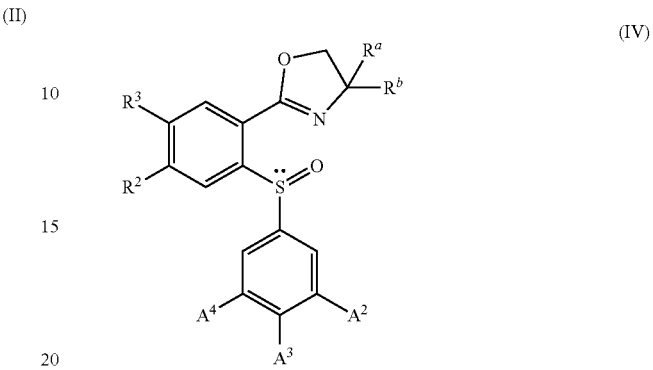

(IV)

wherein $R^a$ and $R^b$ are each independently methyl, ethyl, n-propyl, 2-propyl, cyclopropyl, tert-butyl, iso-butyl, cyclopentyl, cyclohexyl, phenyl, 4-tolyl, 4-methoxyphenyl, 4-trifluoromethylphenyl, or 4-trifluoromethoxyphenyl; $R^2$, $R^3$, $A^2$, $A^3$, and $A^4$ are each independently, fluoro, chloro, bromo, methyl, ethyl, 2-propyl, tert-butyl, cyclopropyl, cyclopentyl, cyclohexyl, trifluoromethoxy, nitro, trifluoromethyl, pentafluoroethyl, $OR^x$, or $N(R^x)_2$; and each $R^x$ is independently H, methyl, ethyl, n-propyl, iso-propyl, cyclopropyl, n-butyl, sec-butyl, tert-butyl, or benzyl.

Additional embodiments of Formula I include compounds of Formula IIA:

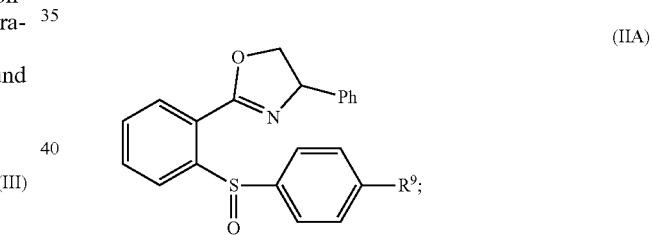

(IIA)

wherein $R^9$ is methoxy, t-butyl, or trifluoromethoxy; or a compound of Formula IVA:

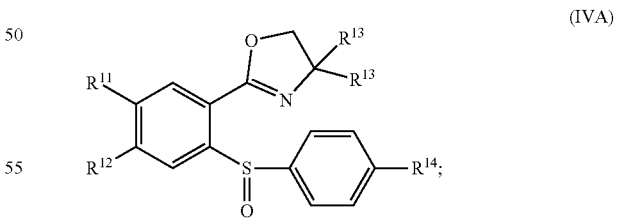

(IVA)

wherein $R^{11}$ and $R^{12}$ are each independently H or methoxy; $R^{13}$ is methyl or phenyl; and $R^{14}$ is methyl, methoxy, or phenyl.

This disclosure also provides a method of inducing an oxidative cyclization reaction. The method can be an asymmetric oxidative cyclization reaction. The method includes combining and/or heating a mixture of an organic substrate, an oxidant, an acid, a palladium(II) compound, and a compound of Formula X:

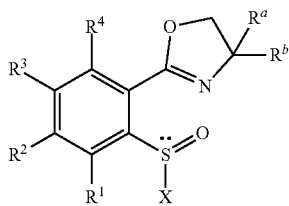

(X)

wherein $R^a$ is H, alkyl, heteroalkyl, cycloalkyl, heterocycle, aryl, or heteroaryl; $R^b$ is alkyl, heteroalkyl, cycloalkyl, heterocycle, aryl, or heteroaryl; X is alkyl, heteroalkyl, cycloalkyl, heterocycle, aryl, or heteroaryl; $R^1$, $R^2$, $R^3$, and $R^4$ are each independently H, halo, alkyl, heteroalkyl, trifluoromethyl, trifluoromethoxy, $OR^x$, $N(R^x)_2$, nitro, cycloalkyl, aryl, or heteroaryl; each $R^x$ is independently H, $(C_1-C_8)$alkyl, or benzyl; and the $R^a$—C—$R^b$ moiety is in the (S)-configuration and the sulfoxide moiety is in the (R)-configuration, or the $R^a$—C—$R^b$ moiety is in the (R)-configuration and the sulfoxide moiety is in the (S)-configuration; wherein the organic substrate comprises an allyl group and a hydroxy group, wherein the hydroxyl group is four or five carbon atoms from the terminal olefin moiety of the allyl group; to provide a cyclic ether with a vinyl substituent alpha to the ether moiety formed by the oxidative cyclization, wherein the stereochemistry of the vinyl substituent is enantiomerically enriched such that the chiral center that is formed predominates in one stereochemical configuration, for example, the formed chiral center predominates in the (S)-configuration, or the formed chiral center predominates in the (R)-configuration. Enantiomeric enrichment can result in a product having an enantiomeric excess (e.e.) of about 55% to about 99%, about 60% to about 99%, about 70% to about 99%, about 80% to about 99%, about 85% to about 99%, about 90% to about 99%, about 95% to about 99%, or about 75% to about 100%, or at least about any one of the preceeding values.

In embodiments of this disclosure, the $R^a$—C—$R^b$ moiety of Formula X is in the (S)-configuration and the sulfoxide moiety is in the (R)-configuration, or the $R^a$—C—$R^b$ moiety of Formula X is in the (R)-configuration and the sulfoxide moiety is in the (S)-configuration. In various other embodiments, the oxidant is a benzoquinone compound and the acid is a Bronsted acid. In additional embodiments, the oxidant is any oxidant that in combination with a disclosed general method using a disclosed sulfoxide catalyst results in the formation of enantiomerically enriched allyl ethers, or results in the formation of allyl amines using a general procedure disclosed for C—N bond formation. In yet other embodiments the quinone can be a any variety of quinones, such as a para-quinone, an ortho-quinone, a tetrahydroxyquinone, or any commercially available quinoine. In other additional embodiments, the Bronsted acid can be, for example, any commercially available acid that is a proton donor, and when used in combination with a disclosed general method using a disclosed sulfoxide catalyst results in the formation of enantiomerically enriched allyl ethers.

Other embodiments include a reaction mixture that is exposed air and moisture. Additional embodiments include a reaction mixture that comprises air, moisture or a combination thereof; or a reaction mixture wherein no precautions are used to exclude air or moisture. The reaction mixture may comprise 0.1% air or more by volume. The reaction mixture may comprise 0.1% moisture or more by volume. The percent by volume of air or moisture in the reaction mixture can each range from 0.1% to 5%, 0.1% to 4%, 0.1% to 3%, 0.1% to 2%, 0.1% to 1%, 0.1% to 0.5%, 0.2% to 2%, 0.2% to 1%, 0.5% to 3%, 0.5% to 2%, 0.5% to 1%, 1% to 5%, 1% to 4%, 1% to 3%, or 1% to 2%.

In various other embodiments, the substrate comprises a 1,2-substituted phenyl, wherein one substituent is an allyl group and a second substituent is a 2-hydroxyethyl group, and wherein the allyl moiety and the hydroxyl moiety cyclize to form a product comprising an isochroman ring system.

Embodiments of this disclosure include compounds of Formula X, as shown:

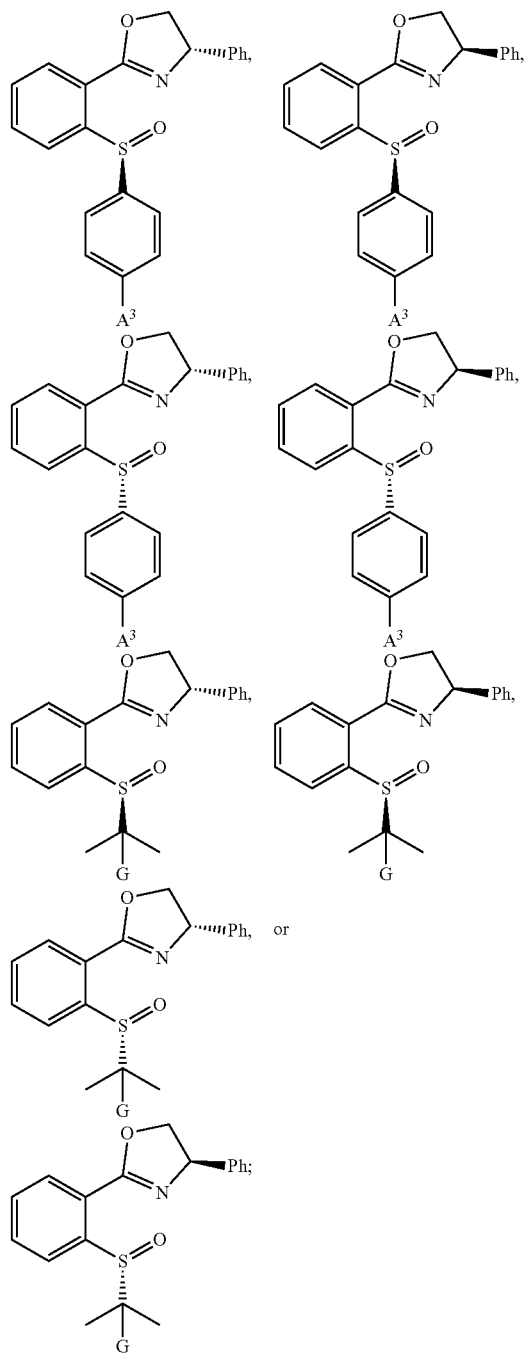

wherein $A^3$ is H, halo, $(C_1-C_8)$alkyl, trifluoromethyl, trifluoromethoxy, $OR^x$, $N(R^x)_2$, nitro, $(C_3-C_8)$cycloalkyl, or phenyl, wherein phenyl is optionally substituted with 1-5 substituents J; each J is independently H, halo, $(C_1-C_8)$alkyl, trifluoromethyl, trifluoromethoxy, $OR^x$, $N(R^x)_2$, nitro, or $(C_3-C_8)$cycloalkyl; each $R^x$ is independently H, $(C_1-C_8)$ alkyl, or benzyl; and G is H or methyl.

In other various embodiments, a method to couple an activated secondary amine and a terminal olefin comprises contacting an organic substrate, an activated secondary amine, an oxidant, and a palladium(II) compound, and a compound of Formula XI:

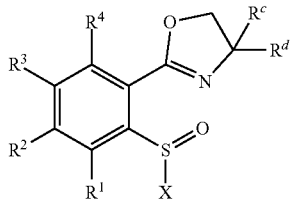
(XI)

wherein $R^b$ and $R^c$ are each independently alkyl, heteroalkyl, cycloalkyl, heterocycle, aryl, or heteroaryl; X is alkyl, heteroalkyl, cycloalkyl, heterocycle, aryl, or heteroaryl; $R^1$, $R^2$, $R^3$, and $R^4$ are each independently H, halo, alkyl, heteroalkyl, trifluoromethyl, trifluoromethoxy, $OR^x$, $N(R^x)_2$, nitro, cycloalkyl, aryl, or heteroaryl; and each $R^x$ is independently H, $(C_1-C_8)$alkyl, or benzyl; to provide a product comprising a tertiary amine wherein the amine is substituted by an allyl group. The said tertiary amine also is substituted by the activating group (Y), as shown in Scheme A, wherein the tertiary amine can be reduced by a reducing agent to remove the activating group to provide a secondary amine. An activated secondary amine is a disubstituted nitrogen atom wherein one of the substituents is an electron withdrawing group. The activating group on the nitrogen atom of the amine can comprise a sulfone group, for example, $-S(O)_2-R^g$, wherein $R^g$ is alkyl, aryl, methyl, tolyl, 4-nitrophenyl, $-OCH_2CCl_3$, $-OCH_2CF_3$, and the like.

In various additional embodiments, the compound of Formula XI is a compound of Formula V:

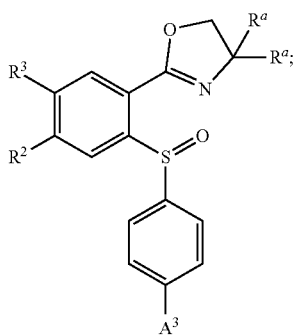
(V)

wherein each $R^a$ is independently $(C_1-C_8)$alkyl, $(C_3-C_8)$cycloalkyl, or phenyl, wherein phenyl is optionally substituted with 1-5 substituents J; and $A^3$, $R^2$ and $R^3$ are each independently H, halo, $(C_1-C_8)$alkyl, trifluoromethyl, trifluoromethoxy, $OR^x$, $N(R^x)_2$, nitro, $(C_3-C_8)$cycloalkyl, or phenyl, wherein phenyl is optionally substituted with 1-5 substituents J; and each J is independently H, halo, $(C_1-C_8)$ alkyl, trifluoromethyl, trifluoromethoxy, $OR^x$, $N(R^x)_2$, nitro, $(C_3-C_8)$cycloalkyl.

In other embodiments, the compound of Formula V is:

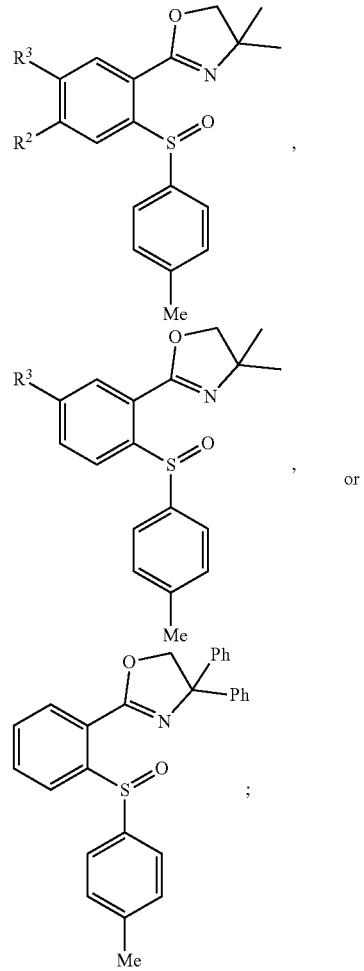

wherein $R^2$ and $R^3$ are each independently H, methyl, methoxy, trifluoromethyl, or trifluoromethoxy.

In various embodiments, the ligand (e.g., a compound of any Formula disclosed herein) can be any one or more of the following compounds: (S)-4-phenyl-2-(2-((R)-p-tolylsulfinyl)phenyl)-4,5-dihydrooxazole; (R)-4-phenyl-2-(2-((R)-p-tolylsulfinyl)phenyl)-4,5-dihydrooxazole; (S)-4-phenyl-2-(2-((S)-p-tolylsulfinyl)phenyl)-4,5-dihydrooxazole; (R)-4-phenyl-2-(2-((S)-p-tolylsulfinyl)phenyl)-4,5-dihydrooxazole; (S)-4-phenyl-2-(2-((R)-(4-(trifluoromethyl)phenyl)sulfinyl)phenyl)-4,5-dihydrooxazole; (R)-4-phenyl-2-(2-((R)-(4-(trifluoromethyl)phenyl)sulfinyl)phenyl)-4,5-dihydrooxazole; (S)-4-phenyl-2-(2-((S)-(4-(trifluoromethyl)phenyl)sulfinyl)phenyl)-4,5-dihydrooxazole; (R)-4-phenyl-2-(2-((S)-(4-(trifluoromethyl)phenyl)sulfinyl)phenyl)-4,5-dihydrooxazole; (S)-4-phenyl-2-(2-((S)-phenylsulfinyl)phenyl)-4,5-dihydrooxazole; (R)-4-phenyl-2-(2-((S)-phenylsulfinyl)phenyl)-4,5-dihydrooxazole; (S)-4-phenyl-2-(2-((R)-phenylsulfinyl)phenyl)-4,5-dihydrooxazole; (R)-4-phenyl-2-(2-((R)-phenylsulfinyl)phenyl)-4,5-dihydrooxazole; (S)-2-(2-((S)-(4-(tert-butyl)phenyl)

sulfinyl)phenyl)-4-phenyl-4,5-dihydrooxazole; (R)-2-(2-((S)-(4-(tert-butyl)phenyl)sulfinyl)phenyl)-4-phenyl-4,5-dihydrooxazole; (S)-2-(2-((R)-(4-(tert-butyl)phenyl)sulfinyl)phenyl)-4-phenyl-4,5-dihydrooxazole; (R)-2-(2-((R)-(4-(tert-butyl)phenyl)sulfinyl)phenyl)-4-phenyl-4,5-dihydrooxazole; (S)-2-(2-((S)-(4-methoxyphenyl)sulfinyl)phenyl)-4-phenyl-4,5-dihydrooxazole; (R)-2-(2-((S)-(4-methoxyphenyl)sulfinyl)phenyl)-4-phenyl-4,5-dihydrooxazole; (S)-2-(2-((R)-(4-methoxyphenyl)sulfinyl)phenyl)-4-phenyl-4,5-dihydrooxazole; (R)-2-(2-((R)-(4-methoxyphenyl)sulfinyl)phenyl)-4-phenyl-4,5-dihydrooxazole; 2-(5-methoxy-2-((4-methoxyphenyl)sulfinyl)phenyl)-4,4-dimethyl-4,5-dihydrooxazole; 2-(2-([1,1'-biphenyl]-4-ylsulfinyl)phenyl)-4,4-diphenyl-4,5-dihydrooxazole; 4,4-dimethyl-2-(2-(p-tolylsulfinyl)phenyl)-4,5-dihydrooxazole; 4,4-dimethyl-2-(2-(p-tolylsulfinyl)-4-(trifluoromethyl)phenyl)-4,5-dihydrooxazole; 2-(4-methoxy-2-(p-tolylsulfinyl)phenyl)-4,4-dimethyl-4,5-dihydrooxazole; 2-(5-methoxy-2-(p-tolylsulfinyl)phenyl)-4,4-dimethyl-4,5-dihydrooxazole; 2-(2-((4-methoxyphenyl)sulfinyl)phenyl)-4,4-dimethyl-4,5-dihydrooxazole; 2-(4,5-dimethoxy-2-(p-tolylsulfinyl)phenyl)-4,4-dimethyl-4,5-dihydrooxazole; (S)-4-(tert-butyl)-2-(2-((S)-p-tolylsulfinyl)phenyl)-4,5-dihydrooxazole; (R)-4-(tert-butyl)-2-(2-((S)-p-tolylsulfinyl)phenyl)-4,5-dihydrooxazole; (S)-4-(tert-butyl)-2-(2-((R)-p-tolylsulfinyl)phenyl)-4,5-dihydrooxazole; (R)-4-(tert-butyl)-2-(2-((R)-p-tolylsulfinyl)phenyl)-4,5-dihydrooxazole; (S)-4-isopropyl-2-(2-((S)-p-tolylsulfinyl)phenyl)-4,5-dihydrooxazole; (R)-4-isopropyl-2-(2-((S)-p-tolylsulfinyl)phenyl)-4,5-dihydrooxazole; (S)-4-isopropyl-2-(2-((R)-p-tolylsulfinyl)phenyl)-4,5-dihydrooxazole; (R)-4-isopropyl-2-(2-((R)-p-tolylsulfinyl)phenyl)-4,5-dihydrooxazole; (S)-2-(2-((S)-isopropylsulfinyl)phenyl)-4-phenyl-4,5-dihydrooxazole; (R)-2-(2-((S)-isopropylsulfinyl)phenyl)-4-phenyl-4,5-dihydrooxazole; (S)-2-(2-((R)-isopropylsulfinyl)phenyl)-4-phenyl-4,5-dihydrooxazole; (R)-2-(2-((R)-isopropylsulfinyl)phenyl)-4-phenyl-4,5-dihydrooxazole; (S)-2-(2-((S)-p-tolylsulfinyl)phenyl)-4-(3,4,5-trimethoxyphenyl)-4,5-dihydrooxazole; 2,6-dimethoxy-4-((S)-2-(2-((S)-p-tolylsulfinyl)phenyl)-4,5-dihydrooxazol-4-yl)phenol; (S)-2-(2-((S)-p-tolylsulfinyl)-4-(trifluoromethyl)phenyl)-4-(3,4,5-trimethoxyphenyl)-4,5-dihydrooxazole; (S)-4-(3,4,5-trimethoxyphenyl)-2-(2-((S)-(2',4',6'-trimethyl-[1,1'-biphenyl]-4-yl)sulfinyl)phenyl)-4,5-dihydrooxazole; 2,6-dimethoxy-4-((S)-2-(2-((S)-p-tolylsulfinyl)-4-(trifluoromethyl)phenyl)-4,5-dihydrooxazol-4-yl)phenol; (S)-2-(2-((S)-(4-(anthracen-9-yl)phenyl)sulfinyl)phenyl)-4-(3,4,5-trimethoxyphenyl)-4,5-dihydrooxazole; (S)-4-(4-(benzyloxy)-3,5-dimethoxyphenyl)-2-(2-((S)-p-tolylsulfinyl)-4-(trifluoromethyl)phenyl)-4,5-dihydrooxazole; (S)-4-(4-(benzyloxy)-3,5-dimethoxyphenyl)-2-(2-((S)-p-tolylsulfinyl)phenyl)-4,5-dihydrooxazole; (4S)-4-(3,5-dimethoxy-4-((tetrahydro-2H-pyran-2-yl)oxy)phenyl)-2-(2-((S)-p-tolylsulfinyl)phenyl)-4,5-dihydrooxazole; (S)-4-(3,5-dimethoxy-4-(methoxymethoxy)phenyl)-2-(2-((S)-p-tolylsulfinyl)phenyl)-4,5-dihydrooxazole; (S)-4-(4-(tert-butoxy)-3,5-dimethoxyphenyl)-2-(2-((S)-p-tolylsulfinyl)phenyl)-4,5-dihydrooxazole; (S)-4-(4-(tert-butoxy)-3,5-dimethoxyphenyl)-2-(2-((S)-p-tolylsulfinyl)-4-(trifluoromethyl)phenyl)-4,5-dihydrooxazole; (S)-4-(4-((benzyloxy)methoxy)-3,5-dimethoxyphenyl)-2-(2-((S)-p-tolylsulfinyl)-4-(trifluoromethyl)phenyl)-4,5-dihydrooxazole; (S)-4-(3,5-dimethoxy-4-(methoxymethoxy)phenyl)-2-(2-((S)-p-tolylsulfinyl)-4-(trifluoromethyl)phenyl)-4,5-dihydrooxazole; (4S)-4-(3,5-dimethoxy-4-((tetrahydro-2H-pyran-2-yl)oxy)phenyl)-2-(2-((S)-p-tolylsulfinyl)-4-(trifluoromethyl)phenyl)-4,5-dihydrooxazole; (S)-4-(4-((benzyloxy)methoxy)-3,5-dimethoxyphenyl)-2-(2-((S)-p-tolylsulfinyl)phenyl)-4,5-dihydrooxazole; 2,6-dimethoxy-4-((S)-2-(2-((S)-p-tolylsulfinyl)-4-(trifluoromethyl)phenyl)-4,5-dihydrooxazol-4-yl)aniline; 2,6-dimethoxy-4-((S)-2-(2-((S)-p-tolylsulfinyl)phenyl)-4,5-dihydrooxazol-4-yl)aniline; or 4-((S)-2-(2-((S)-p-tolylsulfinyl)phenyl)-4,5-dihydrooxazol-4-yl)aniline.

Part A. Enantioselective Allylic C—H Oxidation of Terminal Olefins to Isochromans Via Pd(II)/Chiral Sulfoxide Catalysis.

We identified ArSOX ligand L1 (Table 1, entry 1) as effective for asymmetric Pd(II)-catalyzed formation of isochroman 2a, though in low yield. Based on our recent studies showing that Brønsted acids enhance the reactivity of Pd(II)-sulfoxide catalyzed allylic C—H oxidations (Osberger et al., *J. Am. Chem. Soc.* 2014, 136, 11176-11181), we surveyed Brønsted acid additives (Table 1, entries 2-5) for the reaction. Whereas the Bronsted acid did not significantly impact asymmetric induction, a significant enhancement in yield was observed. Utilizing the diastereomer L2 resulted in dramatically lowered yield and enantioinduction (entry 6), suggesting that the relative stereochemistry of the sulfoxide and the oxazoline is important. Examining the previously reported alkyl-substituted sulfoxide-oxazoline ligands resulted in significantly diminished yields and enantioselectivity (entries 7, 8). We next turned to modifications at the sulfoxide: utilizing an isopropyl group was beneficial for enantioselectivity, but significantly diminished reactivity (entry 9). Further examination of aryl sulfoxides revealed that a para-methoxy-substituent was not beneficial (entry 10), however both para tert-butyl- and para trifluoromethyl-benzene moieties resulted in enantioselectivities above 90% ee (entries 11, 12).

We selected tBu-ArSOX for further study due to its combination of high enantioinduction and reactivity, and its relative ease of synthesis. However, $CF_3$—ArSOX is optimal in cases where enantiomeric excesses fall below 90% ee, and product yields may be improved by extending reaction times (vide infra). Utilizing chiral bis-sulfoxide L9 (entry 13) or chiral oxazoline L10 (entry 14) ligands resulted in minimal enantioinduction. Notably, examination of phosphoramidite L11 under both our standard conditions and conditions previously reported (Wang et al., *J. Am. Chem. Soc.* 2015, 137, 12732-12735) resulted in trace formation of 2a (entry 15). Replacing the sterically-bulky 2,6-dimethylbenzoquinone with benzoquinone as the stoichiometric oxidant diminished enantioselectivity (entry 16), possibly due to an undesirable competition between benzoquinone and tBu-ArSOX as a ligand for Pd(II).

TABLE 1

Reaction Development.

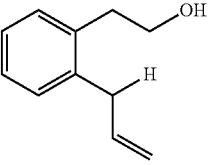

TABLE 1
Reaction Development (cont' d).

| Entry | Ligand | Additive | % Yield[a] | % ee |
|---|---|---|---|---|
| 1 | L1 ("ArSOX") | none | 8 | 83 |
| 2 | L1 | benzoic acid | 13 | 84 |
| 3 | L1 | (nBuO)$_2$PO$_2$H | 54 | 87 |
| 4 | L1 | (PhO)$_2$PO$_2$H | 47 | 82 |
| 5 | L1 | Ph$_2$PO$_2$H | 63 | 87 |
| 6 | L2 | Ph$_2$PO$_2$H | 32 | 19 |
| 7 | L3 ("iPrSOX") | Ph$_2$PO$_2$H | 31 | 76 |
| 8 | L4 ("tBuSOX") | Ph$_2$PO$_2$H | 8 | 25 |
| 9 | L5 | Ph$_2$PO$_2$H | 24 | 88 |
| 10 | L6 | Ph$_2$PO$_2$H | 60 | 86 |
| 11 | tBu-ArSOX (L7) | Ph$_2$PO$_2$H | 70 | 92 |
| 12 | CF$_3$-ArSOX (L8) | Ph$_2$PO$_2$H | 49 | 93 |
| 13[b] | L9 | Ph$_2$PO$_2$H | 31 | −6 |
| 14[b] | L10 | Ph$_2$PO$_2$H | 13 | 12 |
| 15[c] | L11 | Ph$_2$PO$_2$H | <5 | N.D. |
| 16[d] | L7 | Ph$_2$PO$_2$H | 59 | 77 |

[a]Reactions run under air, average of two isolated runs.
[b]rxn run for 72 hours at [0.5M].
[c]rxn also run under argon with conditions reported in ref. 5, also resulting in trace product yield.
[d]p-benzoquinone used in place of 2,6-DMBQ.
2,6-DMBQ = 2,6-dimethylbenzoquinone.
N.D. = not determined.

We next examined the scope of the reaction for furnishing the vinylisochroman motif (Scheme 2). Gratifyingly, broad aromatic substitution is tolerated, with both electron-rich substrates (entries 2b, 2c, 2d) and electron-deficient substrates (entries 2e, 2f, 2g, 2h, 2i) furnishing the desired products in good yields and high enantioselectivities. Broad tolerance for electronic substitution on aryls has not been previously shown for other asymmetric allylic C—H methods, which show either decreased enantioselectivity for electron-rich aryl moieties, or inconsistent trends for aryl tolerance. Bromide and chloride substitution is well tolerated, and these groups serve as handles for further manipulation (products 2e, 2h). Products 2d and 2i were improved to >90% ee by utilizing CF$_3$—ArSOX in place of tBu-ArSOX.

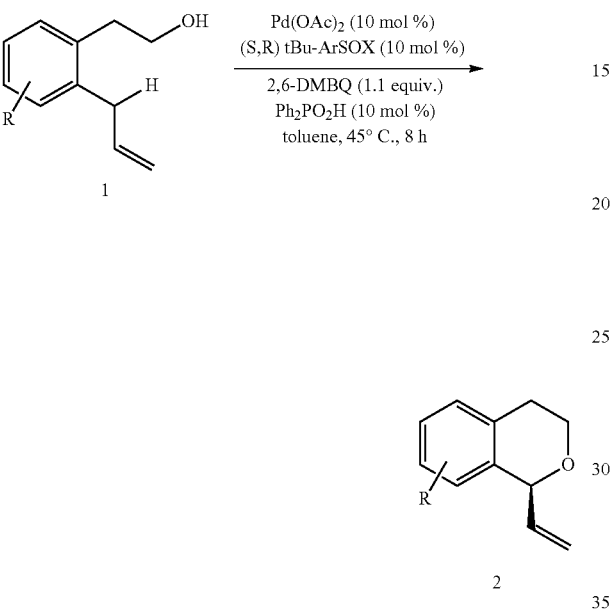

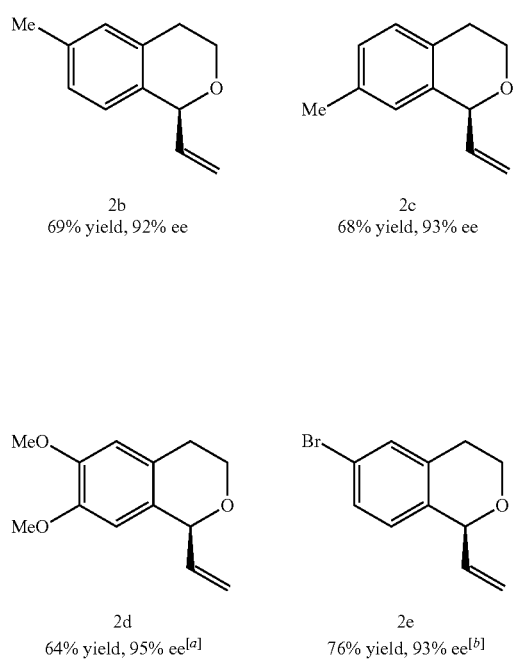

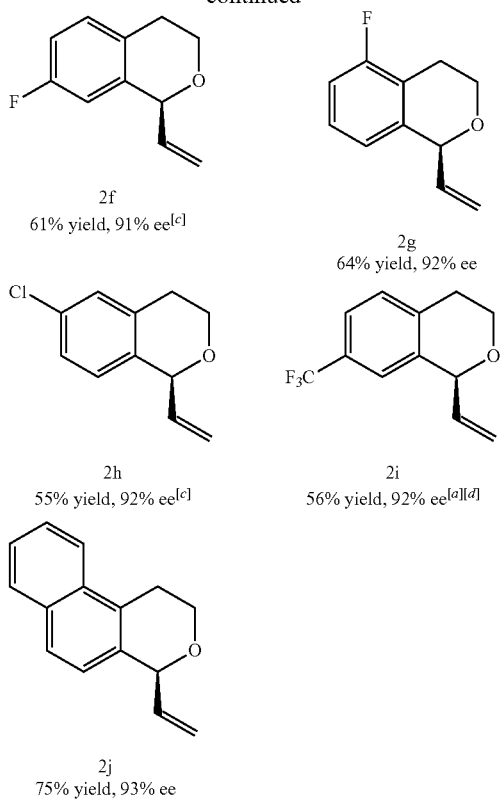

Reaction conditions: alcohol 1 (0.2 mmol), Pd(OAc)$_2$ (0.1 equiv), tBu-ArSOX (0.1 equiv), Ph$_2$PO$_2$H (0.1 equiv), 2,6-DMBQ (1.1 equiv), toluene (0.15M), 45° C. Yields reported are isolated, average of three runs. [a] CF$_3$—ArSOX used in place of tBu-ArSOX. [b] Reaction run for 9 h. [c] Reaction run for 10 h. [d] Reaction run for 48 h.

Stereochemically-defined substitutions in isochromans at both the 3- and 4-positions are well represented in biologically-active compounds. In the case of 1,3-disubstituted 4, a motif found in such compounds as the antibiotic elutherin and D1 agonist A77636, syntheses are generally achieved via Pictet-Spengler reaction under diastereoselective substrate control; catalyst-controlled diastereoselectivity has not been demonstrated. Notably, allylic C—H oxidation in the presence of achiral Pd(II)/bis-sulfoxide L12 furnishes 4 with a modest 1.5:1 d.r. favoring the cis-diastereomer 4a (Table 2, Section A). When the reaction is run with Pd(II)/(S,R) tBu-ArSOX, the d.r. is increased to >20:1 favoring 4a. Significantly, when the reaction is run with the "mismatched" Pd(II)/(R,S) tBu-ArSOX, the d.r. is overturned to 1:2.8, favoring the trans-diastereomer 4b. The ability to influence diastereoselectivity with this Pd(II)/tBu-ArSOX—catalyzed asymmetric C—H oxidation method is similarly observed in the formation of structurally-distinct 1,4-disubstituted 6. Allylic C—H oxidation in the presence of achiral Pd(II)/bis-sulfoxide L12 furnishes the cis-diastereomer in 3.6:1 d.r. The use of matched Pd(II)/(S,R) tBu-ArSOX once again increased the d.r. to >20:1 favoring 6a, and mismatched Pd(II)/(R,S) tBu-ArSOX d.r. turned over the d.r. to 1:1.4 favoring 6b (Table 2, Section B).

TABLE 2

Catalyst influence on diasteroselective C—H cyclization.

A.

| Entry | Ligand | % Yield | d.r.(4a:4b) |
|---|---|---|---|
| 1 | meso-1,2-bis(phenylsulfinyl)ethane (L12) | 16 | 1.5:1 |
| 2 | (S,R) tBu-ArSOX | 62 | >20:1 |
| 3 | (R,S) tBu-ArSOX | 49 | 1:2.8 |

B.

| Entry | Ligand | % Yield | d.r.(6a:6b) |
|---|---|---|---|
| 1 | meso-1,2-bis(phenylsulfinyl)ethane (L12) | 60 | 3.6:1 |
| 2 | (S,R) tBu-ArSOX | 67 | >20:1 |
| 3 | (R,S) tBu-ArSOX | 68 | 1:1.4 |

PNU-109291 (8) is a pharmaceutical compound that functions as a selective 5HT$_{1D}$ agonist. Previous asymmetric syntheses of this target suffered from the need for chiral resolution of racemates. We evaluated our enantioselective method in the context of a more efficient synthesis (Scheme 3, Section A). Starting from aryl amide 1k (see Section on Examples for preparation), vinylisochroman 2k is formed via C—H oxidation in good yield and enantioselectivity, demonstrating this reaction's tolerance of N-Boc protected amides that may chelate palladium.

Subsequent hydroboration/oxidation of 2k furnished alcohol 7 in good yield. Nucleophilic displacement of alcohol 7 with aryl piperazine furnished piperazine 8. Overall, starting from commercial materials, the asymmetric C—H oxidation route resulted in a higher overall yield. Additionally, we sought to exploit the latent reactivity of the products' allylically substituted terminal olefin, demonstrating orthogonality to past efforts that have focused on late-stage modifications to the aryl moiety. Isochroman 2a may be diversified into α,β-unsaturated amide 9 via ruthenium-catalyzed cross-metathesis, into aliphatic amine 10 via copper-catalyzed hydroamination, and also into terminal alcohol 11 via hydroboration oxidation (Scheme 3, Section B). Importantly, these manipulations proceeded without racemization of the stereocenter. 11 is a precursor to (S)-Sonepiprazole (12), whose synthesis via asymmetric C—H oxidation proceeds with a higher overall yield than the reported synthesis via kinetic resolution.

Scheme 3. Vinylisochromans as versatile chiral intermediates.

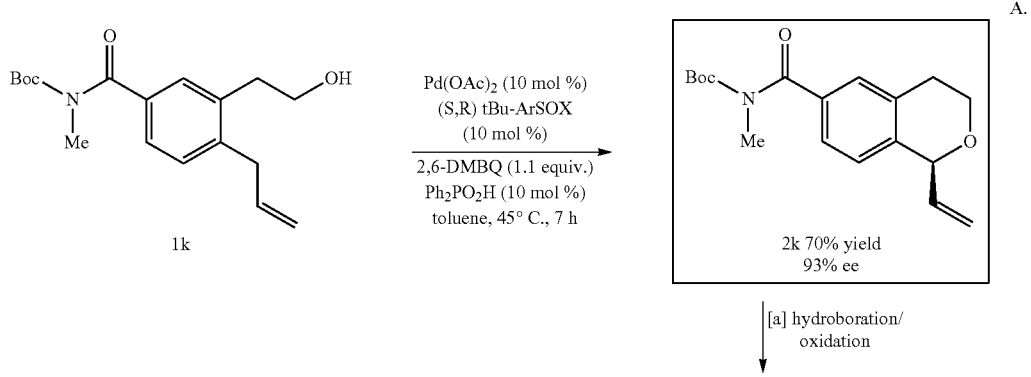

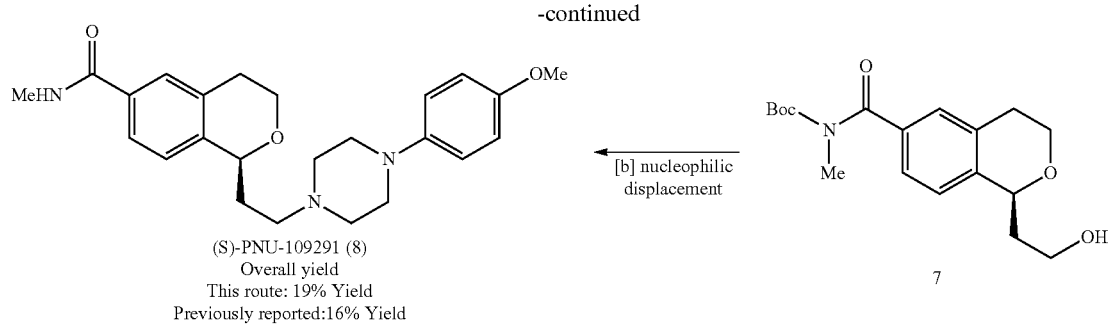
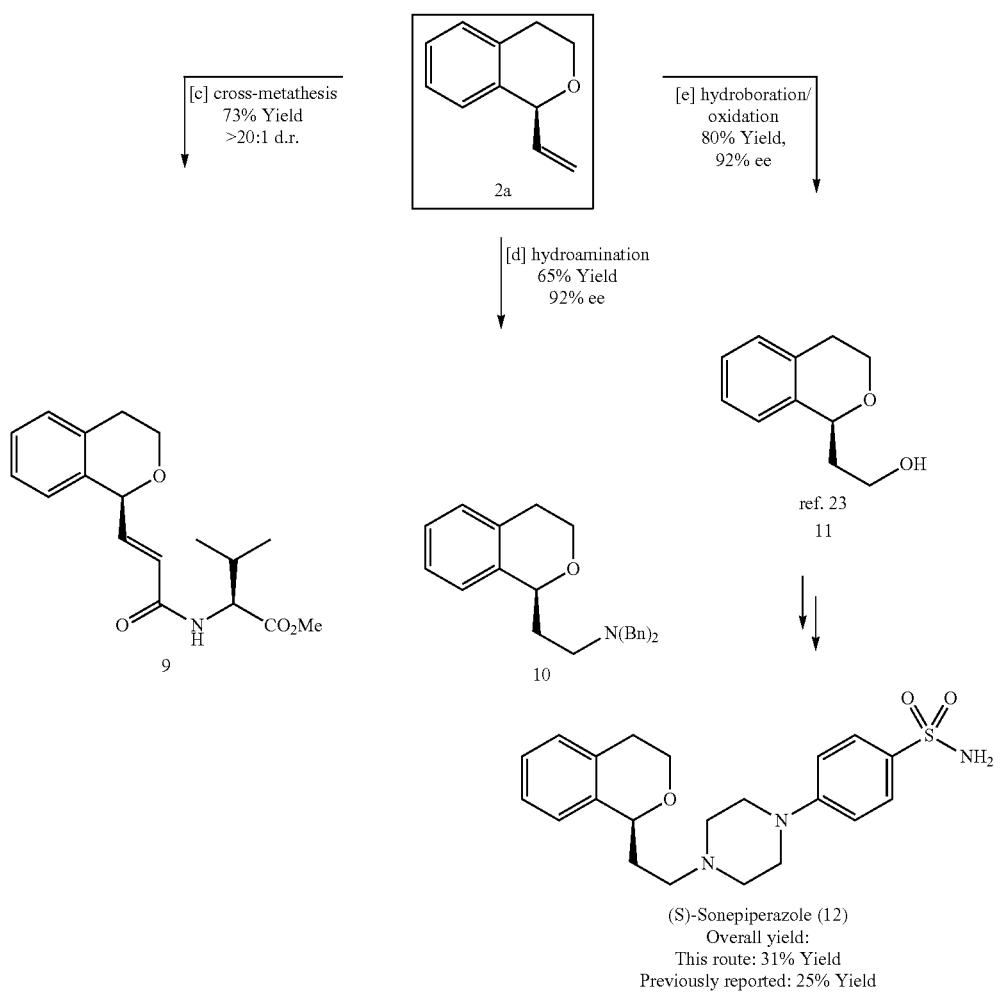

Reaction conditions: [a] 9-BBN (1.5 equiv), THF, 0° C., then NaBO3 (5 equiv), 80% yield. [b] MsCl (1.05 equiv), DMAP (5 mol %), DIPEA (2.5 equiv), THF, then aryl piperazine (1.5 equiv), 50% yield, 92% ee. [c] Hoveyda-Grubbs II (7 mol %), olefin (2 equiv), CH2Cl2. [d] Cu(OAc)2 (4 mol %), DTBM-SEGPHOS (4.4 mol %), amine (1.2 equiv), DEMS (2 equiv), THF. [e] 9-BBN (1.5 equiv), THF, then NaBO3 (5 equiv).

As a preliminary mechanistic investigation, we sought to distinguish between an oxypalladation or C—H cleavage/ π-allylPd pathway. To evaluate an olefin isomerization/ oxypalladation mechanism, we subjected internal olefin 13 to the reaction conditions, and observed no formation of 2a (Scheme 4, Section A), indicating an oxypalladation pathway is not operative. We probed the capacity of this catalyst system to effect allylic C—H cleavage with unactivated C—H bonds, which has been demonstrated previously under Pd/bis-sulfoxide catalysis. With chiral catalyst Pd/(R,S)-tBuArSOX, alcohol 14 furnishes pyran 15 in good yield and enhanced diastereoselectivity relative to achiral Pd(II)/bis-sulfoxide L12 (19:1 d.r. versus 8:1 d.r., Scheme 4, Section B). We next sought to elucidate which step of the reaction is responsible for asymmetric induction. Evaluation of the reaction with substrate 1a-$_d$ furnished 2a-$_d$ with complete scrambling of the deuterium at the terminal alkene (Scheme 4, Section C). This signifies π-σ-π isomerization of the π-allylPd intermediate and indicates that C—H cleavage cannot be the enantiodetermining step. Additionally, we evaluated another scenario where the isochromans might undergo a subsequent resolution to enhance the product's enantioenrichment. However, exposure of racemic 2a to the reaction conditions does not result in enantioenriched 2a, and no change in isochroman enantioenrichment was observed over time (see section on Examples). Thus, from these experiments we infer that the catalyst imparts asymmetric induction during functionalization.

Scheme 4. Mechanistic Investigation.

Part B. C—H to C—N Cross-Coupling of Amines with Olefins

Reaction Development.

We initiated our investigation by examining the reactivity of a prototypical aliphatic amine nucleophile that bears one strongly electron withdrawing group, N-triflyl phenethylamine, with allyl cyclohexane under previously reported allylic C—H amination conditions (Table 3, entry 1-2; Reed et al., *J. Am. Chem. Soc.,* 2009, 131, 11701). Using the considerably more basic aliphatic amine nucleophile, we observed trace reactivity with the Pd(II)/bis-sulfoxide catalytic system. However, under the reported Pd(II)/SOX-catalyzed asymmetric allylic C—H oxidation conditions, using a simple racemic (±)—SOX ligand (L-1) we were delighted to observe that the reaction proceeds in 30% yield with outstanding regio- and stereoselectivity (entry 3, >20:1 linear: branched, >20:1 E:Z). Evaluation of readily available quinone oxidants indicated that steric bulk was beneficial: benzoquinone (BQ) diminished the reactivity (entry 4), whereas 2,5-dimethylbenzoquinone (2,5-DMBQ) boosted reactivity furnishing product in 52% isolated yield (entry 5). The highly modular nature of the SOX ligand framework enables rapid evaluation of electronic and steric modifications. We found exchanging the dimethyl groups on the oxazoline for diphenyls lowered the yield to 21% (entry 6). Whereas electronic modifications on the aryl backbone para to the oxoazoline did not significantly positively impact the yield (entry 7, 8), electron donating methoxy substituents para to the sulfoxide on both the ligand backbone and the aryl sulfoxide moiety resulted in substantial improvements in yield (entry 9, 10). No synergy was observed by combining these electron donating modifications (entry 11, 12). A catalyst comprised of (±)-MeO—SOX ligand (L-5)/Pd(OAc)₂ was therefore selected for further study. As described above, addition of a Brønsted acid additive, previously shown to enhance intramolecular allylic C—H oxidation reactivity with an SOX/Pd(OAc)₂ catalyst, did not have a beneficial effect on the yield (entry 13 versus 9). Lowering the (±)-MeO—SOX ligand (L-5)/Pd(OAc)₂ catalyst loading to 5% maintained a preparatively useful yield (entry 14). Omission of (±)-MeO—SOX ligand (L-5) gave no detectable product. (entry 15).

TABLE 3

Reaction development.

| entry | Pd(II) | Ligand | quinone | % yield |
|---|---|---|---|---|
| 1* | Pd(OAc)₂ | bis-sulfoxide | BQ | <5 |
| 2† | Pd(OAc)₂ | bis-sulfoxide | BQ | <5 |

TABLE 3-continued

Reaction development.

Cy-CH(H)-CH=CH2 (1.0 equiv) + TfHN-CH2CH2-Ph (1.0 equiv) → [Pd(OAc)2 (10 mol %), Ligand (10 mol %), quinone (1.1 equiv.), Toluene (1.0M), 45° C., 72 h] → Cy-CH=CH-CH2-N(Tf)-CH2CH2-Ph (1), >20:1 E/Z, >20:1 L/R

| # | Pd | Ligand | Quinone | Yield |
|---|---|---|---|---|
| 3 | Pd(OAc)$_2$ | L-1 | 2,6 DMBQ | 30 |
| 4 | Pd(OAc)$_2$ | L-1 | BQ | 24 |
| 5 | Pd(OAc)$_2$ | L-1 | 2,5 DMBQ | 52 |
| 6 | Pd(OAc)$_2$ | L-2 | 2,5 DMBQ | 21 |
| 7 | Pd(OAc)$_2$ | L-3 | 2,5 DMBQ | 32 |
| 8 | Pd(OAc)$_2$ | L-4 | 2,5 DMBQ | 55 |
| 9 | Pd(OAc)$_2$ | L-5 | 2,5 DMBQ | 75 |
| 10 | Pd(OAc)$_2$ | L-6 | 2,5 DMBQ | 62 |
| 11 | Pd(OAc)$_2$ | L-7 | 2,5 DMBQ | 55 |
| 12 | Pd(OAc)$_2$ | L-8 | 2,5 DMBQ | 74 |
| 13[‡] | Pd(OAc)$_2$ | L-5 | 2,5 DMBQ | 73 |
| 14 | Pd(OAc)$_2$ (5%) | L-5 (5%) | 2,5 DMBQ | 53 |
| 15[§] | Pd(OAc)$_2$ | none | 2,5 DMBQ | ND |

Bis-sulfoxide: Ph-S(=O)-CH2CH2-S(=O)-Ph

Sox ligands: [oxazoline with R$_3$, R$_3$ substituents on aromatic ring with R$_1$, R$_2$ and sulfinyl group S(=O)-C$_6$H$_4$-R$_4$]

L-1: R$_1$ = H, R$_2$ = H, R$_3$ = Me, R$_4$ = Me;
L-2: R$_1$ = H, R$_2$ = H, R$_3$ = Ph, R$_4$ = Ph;
L-3: R$_1$ = H, R$_2$ = CF$_3$, R$_3$ = Me, R$_4$ = Me;
L-4: R$_1$ = H, R$_2$ = OMe, R$_3$ = Me, R$_4$ = Me;
L-5: R$_1$ = OMe, R$_2$ = H, R$_3$ = Me, R$_4$ = Me;
L-6: R$_1$ = H, R$_2$ = H, R$_3$ = Me, R$_4$ = OMe;
L-7: R$_1$ = OMe, R$_2$ = OMe, R$_3$ = Me, R$_4$ = Me;
L-8: R$_1$ = OMe, R$_2$ = H, R$_3$ = Me, R$_4$ = OMe.

Isolated yields are average of two runs.
*Conditions: 0.2 mmol (1.0 equiv.) olefin, 0.2 mmol amine nucleophile, 10 mol% white catalyst (Pd(OAc)$_2$/bis-sulfoxide), 2.0 equiv. BQ, 6% Cr(salen)Cl, 0.66M TBME, 45° C., 72 h
[†]Conditions: 0.2 mmol (1.0 equiv.) olefin, 0.2 mmol amine nucleophile, 10 mol% white catalyst (Pd(OAc)$_2$/bis-sulfoxide), 2.0 equiv. BQ, 6% DIPEA, 0.66M TBME, 45° C., 72 h
[‡]10% Ph$_2$P(O)OH was added.
[§]96% recover amine nucleophile.

Reaction Scope and Generality.

Having established optimal reaction conditions, we first explored the substrate scope with respect to the amine component (Table 4a). Biologically relevant aniline and benzyl amines could be introduced with good yields and excellent regio- and stereoselectivities (Table 4a, 2-4). More basic aliphatic amines including methylamine and butylamine are also well tolerated in the reaction (5, 6). The ability of this reaction to tolerate functionality on the amine nucleophile is notable. Amines that may be challenging to directly alkylate via traditional methods all afforded linear aminated product in preparatively useful yields: ethylene diamine (7), aminoethanol (8), bromoethanamine (9) and trifluoroethanamine (10). Significantly, amino acid derived nucleophiles with α-stereocenters underwent efficient intermolecular allylic C—H amination with no epimerization (11-13).

We next explored the scope with respect to the olefin component (Table 4b). Olefins with remote electrophilic carbonyl functionality such esters, amides, and ketones and even a terminal epoxide that may be problematic under reductive conditions were well tolerated under the oxidative conditions of this intermolecular allylic C—H amination reaction (Table 4b, 14-17). Di- and trisubstituted internal olefins can be accommodated with the allylic C—H amination that is completely chemoselective for terminal olefins (18, 19). A diben[b,f]zazepine derived substrate (20) as well as sugar derivative (21) were tolerated in allylic C—H amination with good yields and selectivities. Methyl- and silylether-containing stereocenters found in the homoallylic position of the olefin substrates did not undergo any epimerization upon allylic C—H amination (22-26). The ability to pre-install stereogenic centers in both the olefin and amine components and couple them via a C—N bond forming reaction that retains the stereochemistry of each component enables rapid generation of optically enriched allylic amine products as all possible diastereomers. For example, stereodefined homoallylically substituted α-olefins can be coupled to either (L)- or (D)-phenyl alanine derivatives to generate different diastereomers (23-26).

N-benzylcinnamylamines comprise the core structure of many bioactive molecules. We explored the capacity for the allylic C—H amination cross-coupling reaction to efficiently generate this medicinally relevant core (Table 4c). Electronically varied para-, ortho-, and meta-substitution on allylbenzene, including oxidatively sensitive aldehydes and alcohols, were well tolerated (Table 4c, 27-35). A range of benzyl amines could also be used, most notably ones with highly basic catechol and N, N-dimethyl aniline aromatic substitution (36-38). α-Methyl allylbenzene, a challenging olefin for allylic C—H aminations, was readily aminated to furnish a trisubstituted (E)-allylic amine with good yield and high stereoselectivity (39, E:Z=15:1). Medicinally relevant allylated 2-aryl oxadiazole, benzothiophene, and coumarin readily coupled with benzylamine-, naphthylmethylamine- and chiral α-methylated benzylamine-derived nucleophiles, collectively underscoring the high functional group tolerance of this allylic C—H amination reaction (40-42). It is important to note that in many cases the catalyst loading could be reduced to 5 mol % with no diminishment in yields (27-29, 31-33).

TABLE 4

Examples of Substrate Scope.

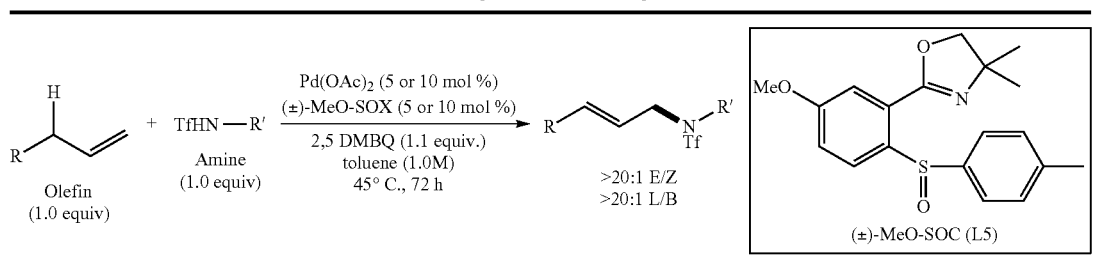

a. Amine scope

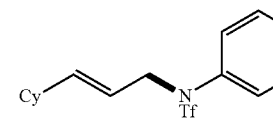

2, 70%

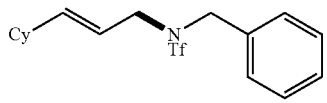

3, 82%

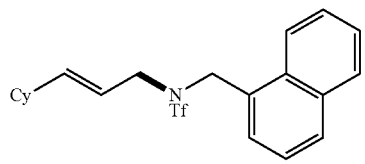

4, 70%

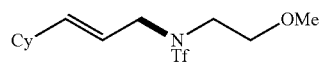

8, 63%

9, 60%

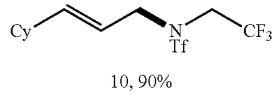

10, 90%

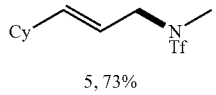

5, 73%

TABLE 4-continued
Examples of Substrate Scope.
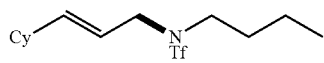
6, 51%
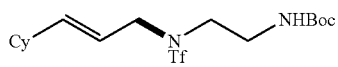
7, 63%
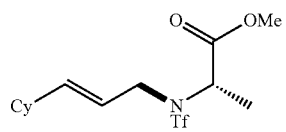
(−)-11, 80%
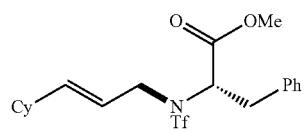
(−)-12, 70%*
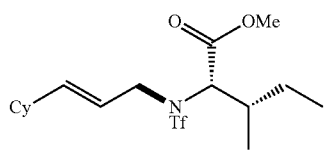
(−)-13, 75%
b. Fragment coupling between diverse olefins and amines
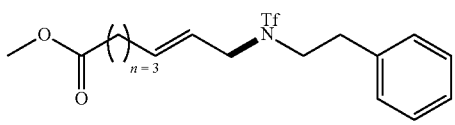
14, 60%
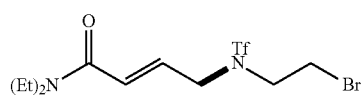
15, 85%
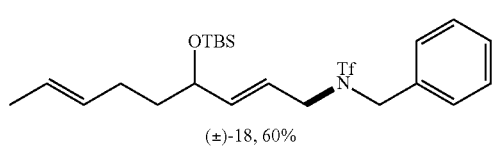
(±)-18, 60%
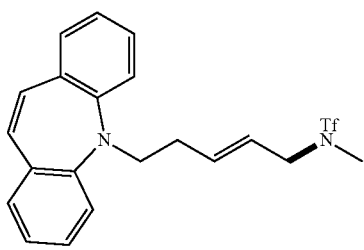
20, 60%

TABLE 4-continued
Examples of Substrate Scope.
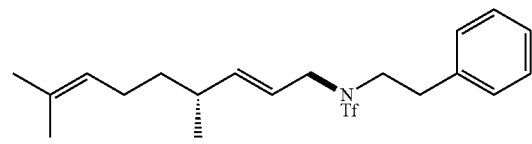
(−)-19, 68%*
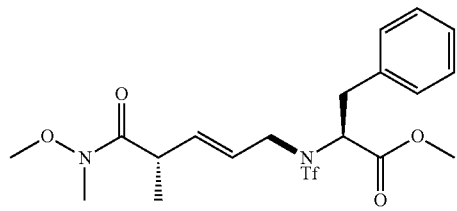
(−)-23, 62%, >20:1 dr
(L)-phenyl alanine
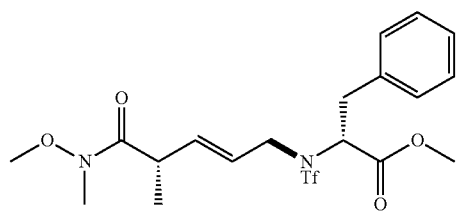
(+)-24, 60%, >20:1 dr
(D)-phenyl alanine
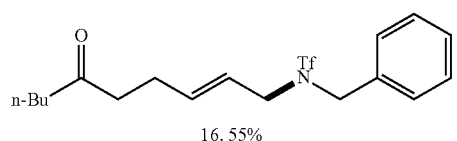
16. 55%
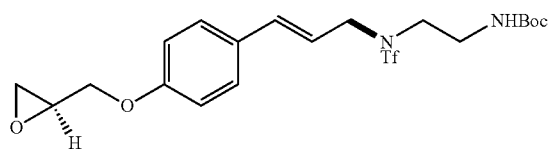
(+)-17, 90%
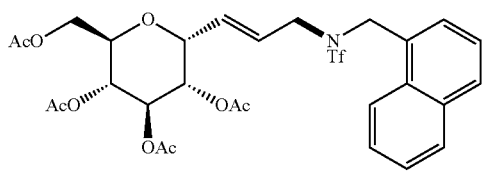
(+)-21, 70%
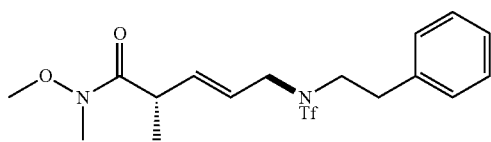
(+)-22, 62%*

TABLE 4-continued
Examples of Substrate Scope.
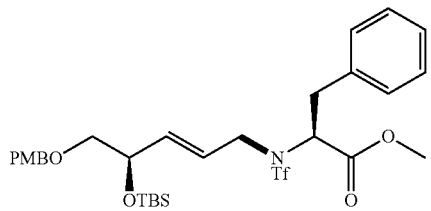
(−)-25, 75%, >20:1 dr
(L)-phenyl alanine
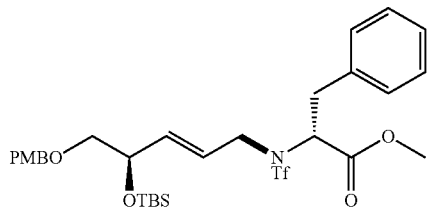
(+)-26, 78%, >20:1 dr
(D)-phenyl alanine
c. Fragment coupling to N-benzyl cinnamylamine core structure
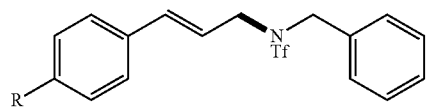
27. R = CF$_3$ 80%[†]
28. R = CO$_2$Me 95%[†]
29. R = CHO 80%[†]
30. R = Br 90%
31. R = CH$_2$OH 89%[†]
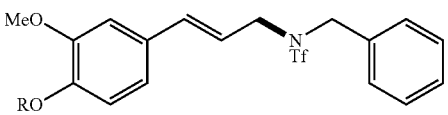
34. R = H 90%
35. R = Me 88%
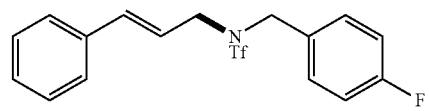
36. 89%
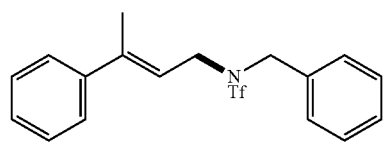
39. 65% 15:1 E/Z
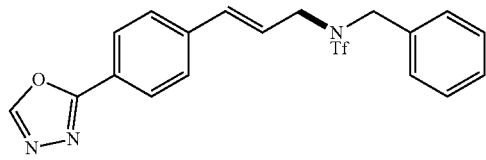
40, 64%, TABLE 4-continued Examples of Substrate Scope.

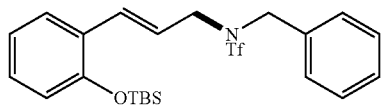

32. 81%†

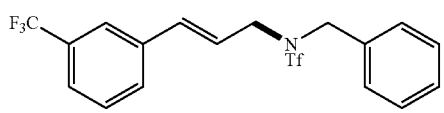

33, 85%†

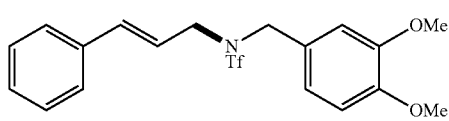

37. 87%

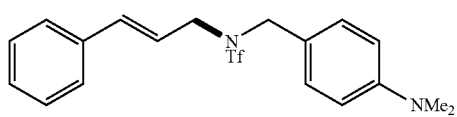

38. 85%

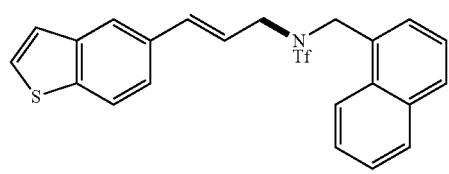

41, 89%

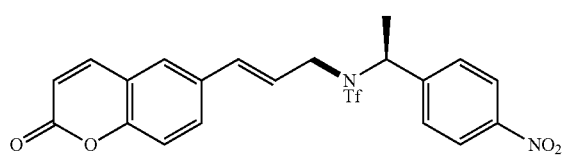

(+)-42, 90%

Isolated yields are average of three runs.
*No detectable stereoerosion, see supporting information
†5% Pd(OAc)$_2$ and (±) MeO-SOX (L5) were used.

Natural Product Diversification.

The significance of of carbon-heteroatom (C—X) linkages in joining modular building blocks in a streamlined manner is a well recognized concept inspired by nature's assembly of critical biopolymers (nucleic acids, proteins, polysaccharides). Late-stage oxidation is emerging as a powerful strategy to streamlining synthesis and/or rapidly diversify complex, bioactive molecules. However, current C—H functionalization methods are generally limited to adding heteroatom functionality that must be further manipulated to achieve fragment coupling at the newly forged C—X bond. For example, in previous allylic C—H amination reactions, the N-tosyl carbamate must be sequentially deprotected to reveal the nitrogen functionality capable of being connected via alkylation to a larger fragment. Using this allylic C—H amination method, allylated natural product derivatives can be coupled via C—N bonds with complex amines to generate both functional and structural diversity via late stage C—H amination (Scheme 5).

A range of readily available, bioactive phenolic natural products were allylated and subsequently evaluated for allyic C—H amination under fragment coupling conditions (1.0 equiv. olefin, 1.0 equiv. amine) with a medicinally important benzylamine derivative (Scheme 5a). Allylated derivatives of the steroid hormones ethinyl estradiol and estrone could be coupled to N-triflyl benzylamine in good to excellent yields (Scheme 5a, 43, 44). It is notable that an unprotected tertiary alcohol, internal alkyne, and ketone were tolerated in this C—H to C—N cross-coupling. Basic tertiary amine functionality, prevalent in many alkaloid natural products and pharmaceuticals, is well-tolerated under the allylic C—H amination coupling conditions upon in situ protonation with a dichloroacetic additive (1.0 equiv.). For example allylated dextromethorphan derivative was effectively coupled to benzylamine to afford the allylic amine compound in excellent yields and selectivities (92% yield; >20:1 E:Z) (45). In the absence of the acid additive, diminished yields of the coupled product were observed (30%), possibly because of the basic amine's capacity to bind strongly to and inactivate the electrophilic (±)-MeO—SOX ligand (L-5)/Pd(OAc)$_2$ catalyst. δ-Tocopherol, a member of vitamin E antioxidant family containing a chiral chroman core structure, was also coupled to N-triflyl benzylamine in good yield using only 5 mol % catalyst (46).

Given the broad scope of allylated natural product scaffolds demonstrated to undergo successful allylic C—H/C—N cross-coupling above, we next evaluated the effectiveness of this reaction to couple δ-tocopherol with a variety of more complex amines (Scheme 5b). N-triflyl protected amino acid, chiral α-methyl benzyl amine, and gramine indole alkaloid were all coupled to allylated δ-tocopherol to furnish amine-tocopherol hybrids in good yields with high regio- and stereoselectivities (Scheme 5b, 47-49). Even dehydroabietylamine (leelamine), a complex diterpenic amine being evalauted for chemotherapeutic activity, could be effectively coupled to allylated δ-tocopherol under fragment coupling conditions (50). It is significant to note that in all of these examples, only one equivalent of both the olefin and amine are used, underscoring the capacity for this allylic C—H amination reaction to serve an effective C—N coupling method for complex building blocks.

Scheme 5. Late-stage diversification of complex molecules via Pd(II)-sulfoxide catalyzed allylc C-H amination.

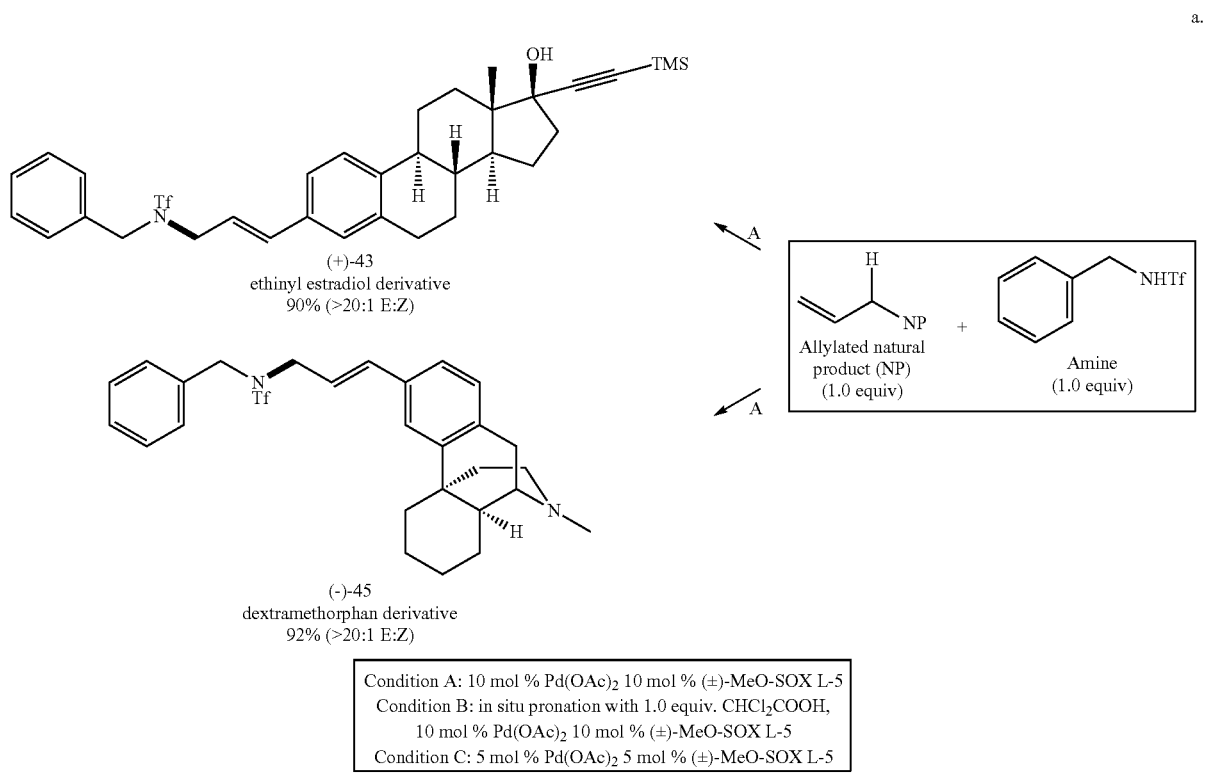

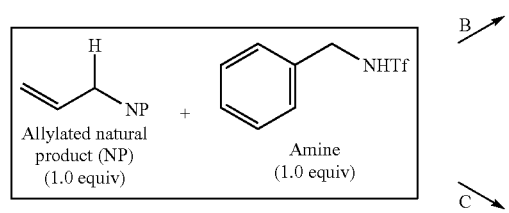

-continued
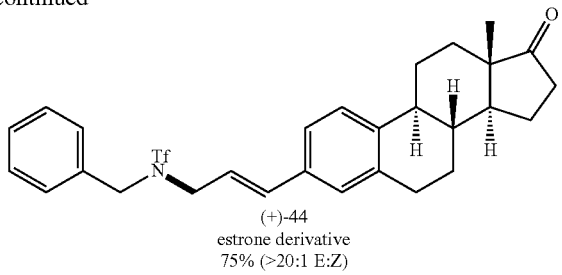
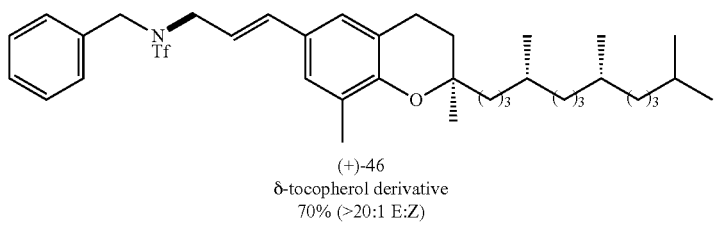
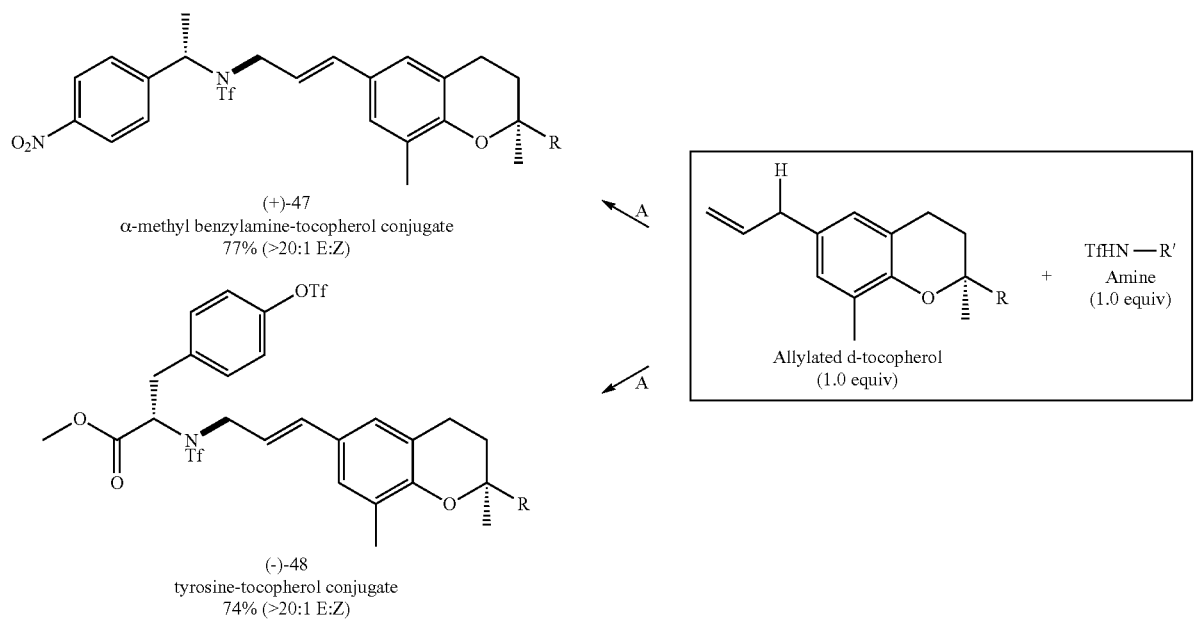
d-Tocopherol olefin coupling with complex amines
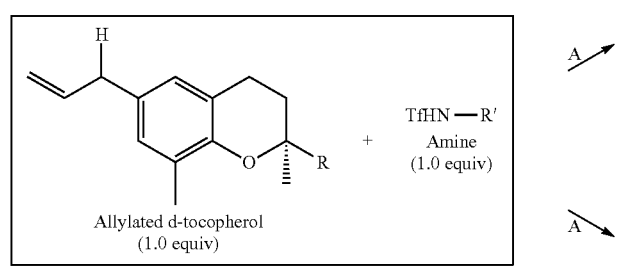

-continued

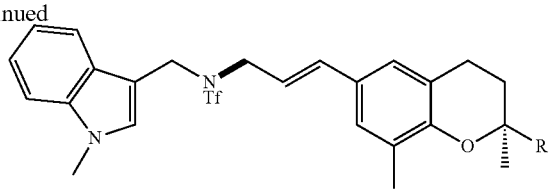

(+)-49
gramine-tocopherol conjugate
71% (>20:1 E:Z)

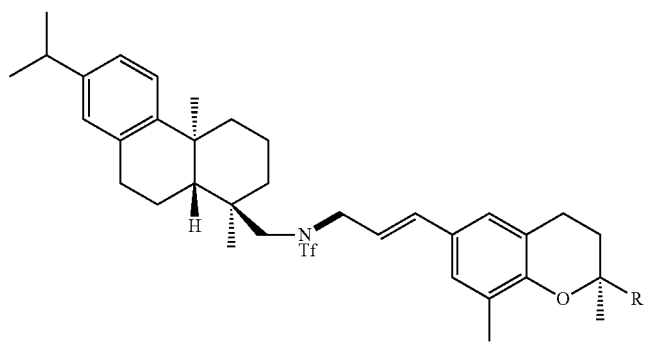

(+)-50
leelamine-tocopherol conjugate
59% (>20:1 E:Z)

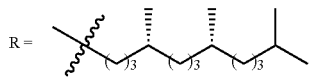

(a) Late-stage diversification of allylated ethinyl estradiol derivative, dextramethorphan derivative, estrone derivative and d-tocopherol derivative by coupling with medicinally important benzylamine. (b) Coupling of allylated d-tocopherol derivative with complex N-triflyl protected amines including a-methyl benzyl amine, dehydroabietylamine, tyrosine and gramine indole alkaloid.

Streamlining Synthesis.

A strength of this hydrocarbon amination method is the ability to cross-couple complex amines with complex olefin fragments while generating stereochemically defined E-olefin functionality. We examined the ability of these features to enable rapid generation of important allylic amine core structures as well as streamlined syntheses via the rapid build-up of molecular complexity (Scheme 6).

Abamines, small molecule inhibitors of the plant hormone abscisic acid biosynthetic pathway, are unsymmetrical N-trialkyl allylic amines. Conventional syntheses of abamines proceed from cinnamaldehydes that are generated from the corresponding cinnamic acids via a reduction/oxidation sequence. Our formal synthesis of abamines proceeds via allylic C—H amination of commercially available 1,2-dimethoxy-4-allylbenzene with N-triflyl 4-fluorobenzylamine (Scheme 6a). It is significant to note that only 2.5 mol % (±)-MeO—SOX ligand (L-5)/Pd(OAc)$_2$ catalyst was used to furnish aminated product in 86% yield as single E-isomer. The reducing agent sodium bis(2-methoxyethoxy) aluminumhydride (Red-Al) enables chemoselective cleavage of the triflate in the presence of the olefin to afford allylic amine 51 (92%), a known intermediate to abamines. Sixteen novel abamine derivatives, challenging to access via a cinnamic acid route, could be readily accessed via this method (see Table 4c).

Reboxetine, a clinically used antidepressant marketed as racemate Endronax, has been shown to be significantly more potent in many biological assays as its (S, S)-enantiomer. (S, S)-Reboxetine features a two contiguous oxygen-containing stereocenters, one found in a morpholine ring and the other in an adjacent ethoxyphenol fragment. Previous asymmetric syntheses have controlled the stereochemistry via asymmetric epoxidation of cinnamyl alcohol followed by functional group manipulations to regioselectively install the terminal amine functionality. We recognized that the allylic amines generated via this C—H amination may serve as synthons for chiral amino diols (Scheme 6b). Moreover, the remarkable ability of this reaction to tolerate electrophilic functionality on both coupling partners (e.g. 9, 14, 17, 29, Table 4) suggested the amine could be brought in containing a bromoethyl fragment that would enable direct formation of the morpholine ring. Allylic C—H amination between commercial available allylbenzene and N-triflyl 2-bromoethylamine nucleophile furnished E-allylic amine 52 in good yield and excellent stereoselectivity (86%, >20:1 E:Z) (Scheme 6b). Sharpless asymmetric dihydroxylation of allylic amine 52 furnished diol that upon exposure to sodium hydride (NaH) directly cyclized to the key morpholine intermediate 54 in 91% yield (over 2 steps). Copper-catalyzed etherification followed by lithium aluminum hydride (LAH) cleavage of the triflate furnished (S, S)-Reboxetine in 98% yield, 96% ee. Significantly, the five-step sequence furnished the desired enantioenriched compound in 48% overall yield; comparing favorably with the seven-step industrial route that proceeds 43% overall yield. Moreover, this method potentially provides expedient routes for rapidly diversifying the core structure by altering the allylated aromatic and/or amine starting materials.

Scheme 6. Streamlining synthesis of complex molecules.

a. 2-step synthesis of abamine core

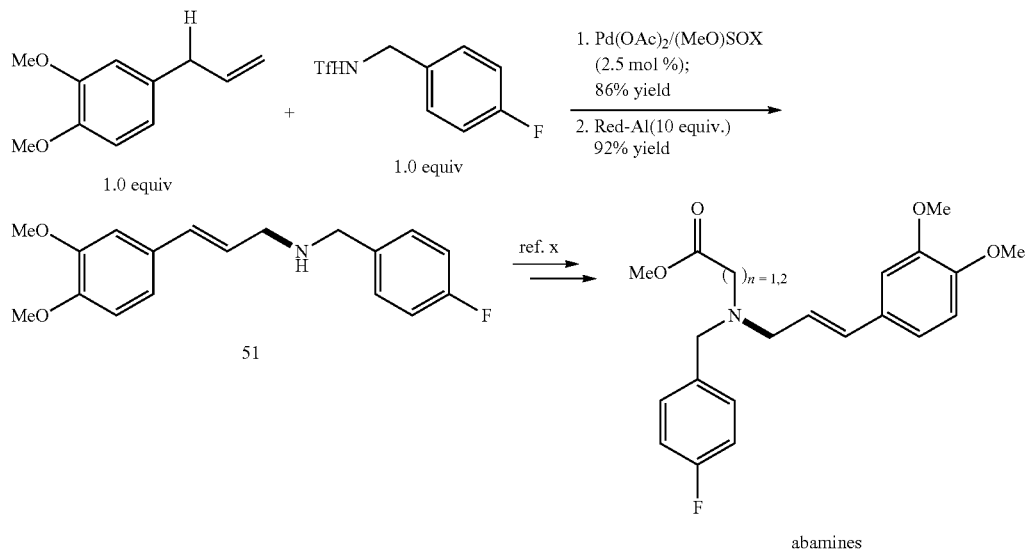

b. 5-step synthesis of (S, S)-Reboxetine

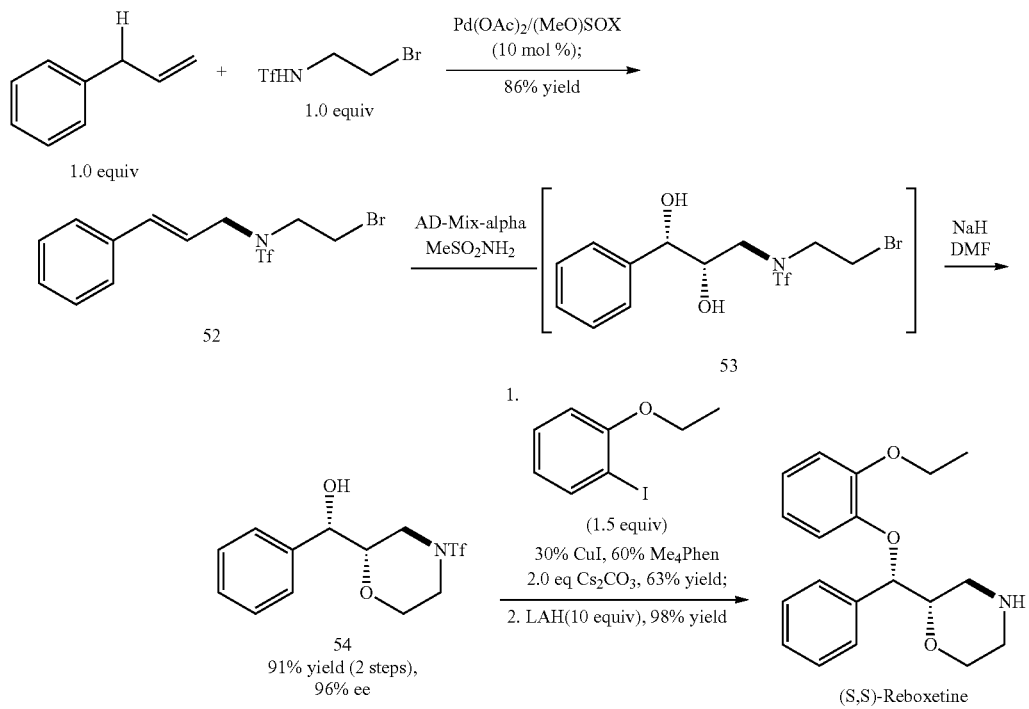

(a) 2-step streamlining synthesis of abamine core structure 51, a known precursor to abamines.
(b) 5-step streamlining synthesis of (S, S)-Reboxetine via pd-sulfoxide catalyzed allylic allylic C—H amination.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

To illustrate the invention, the following examples are included. However, it is to be understood that these examples do not limit the invention and are only meant to suggest a method of practicing the invention. Persons skilled in the art will recognize that the chemical reactions described may be readily adapted to prepare several other sulfoxide ligands of the invention are deemed to be within the scope of this invention. The preparation of a variety of compounds by the methods of this invention are also deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Example 1. Enantioselective Pd(II)/Chiral Sulfoxide Catalytic Reactions

General Information: All commercially obtained reagents were used as received; Pd(OAc)$_2$ (Johnson-Matthey Chemicals) was stored in a glove box, and weighed out in the air at room temperature prior to use. Toluene was purified prior to use by passage through a bed of activated alumina (Glass Contour, Laguna Beach, Calif.). 2,6-dimethylbenzoquinone, 1,4-benzoquinone, dibutylphosphate, diphenylphosphate, and diphenylphosphinic acid were purchased from Sigma-Aldrich and used as received. All allylic oxidation reactions were run under ambient air with no precautions taken to exclude moisture. All other reactions were run under an argon balloon unless otherwise stated. Thin-layer chromatography (TLC) was conducted with E. Merck silica gel 60 F254 precoated plates (0.25 mm) and visualized with UV and potassium permanganate stain. Flash chromatography was performed using ZEOprep 60 ECO 43-60 micron silica gel (American International Chemical, Inc.).

$^1$H NMR spectra were recorded on a Varian Unity-u400nb (500 MHz), Varian Inova-500 (500 MHz), or Varian Unity-500 (500 MHz) spectrometer and are reported in ppm using solvent as an internal standard (CDCl$_3$ at 7.26 ppm). Data reported as: s=singlet, d=doublet, t=triplet, q=quartet, quin.=quintet, sext.=sextet, sept.=septet, o=octet, m=multiplet, b=broad, ap=apparent; coupling constant(s) in Hz; integration. Proton-decoupled $^{13}$C NMR spectra were recorded on a Varian Unity-500 (125 MHz) spectrometer and are reported in ppm using solvent as an internal standard (CDCl$_3$). $^{19}$F NMR spectra were recorded on a Varian Unity-500 (470 MHz) spectrometer and are reported in ppm using solvent as an internal standard (CDCl$_3$). Chiral gas chromatographic (GC) analysis was performed on an Agilent 6890N Series instrument equipped with FID detectors using a J&W Cyclosil-B column. Chiral high pressure liquid chromatography (HPLC) analysis was performed on an Agilent 1100 Series instrument equipped with a UV detector, using a CHIRALPAK AD-RH or OJ-H column. We thank Dr. Danielle Gray at the University of Illinois George L. Clark X-Ray Facility for X-ray crystallographic analysis. Optical rotations were measured with a sodium lamp using a 1 mL cell with a 50 mm path length on a Jasco P-1020 polarimeter. High-resolution mass spectra were obtained at the University of Illinois Mass Spectrometry Laboratory.

General Procedure for Enantioselective Allylic Oxidation

To a ½ dram vial was added ligand (S,R) tBu-ArSOX (8.1 mg, 0.02 mmol) and Pd(OAc)$_2$ (4.4 mg, 0.02 mmol). Toluene (0.4 mL) was added, and the vial was capped and heated to 45° C. until all solids had dissolved. Separately, to a 1 dram vial with stir bar was added 1a (32.4 mg, 0.20 mmol), 2,6-dimethylbenzoquinone (30 mg, 0.22 mmol), and diphenylphosphinic acid (4.4 mg, 0.02 mmol), with no precautions to exclude air or moisture. The catalyst solution was subsequently added to the reaction flask, and toluene (0.9 mL) was used to rinse (total volume toluene=1.3 mL). The 1 dram vial was sealed with a Teflon cap, and allowed to stir for 8 hours at 45° C., until complete conversion of the starting material was observed by TLC. Afterward, the vial was allowed to cool to room temperature. The majority of the toluene was removed under reduced pressure, and the remaining mixture was directly subjected to flash column chromatography (10% EtOAc in hexanes) to provide the vinylisochroman as a clear oil.

Ligand Synthesis

Scheme 1-1: Ligand Intermediates S1, S2, and S3.

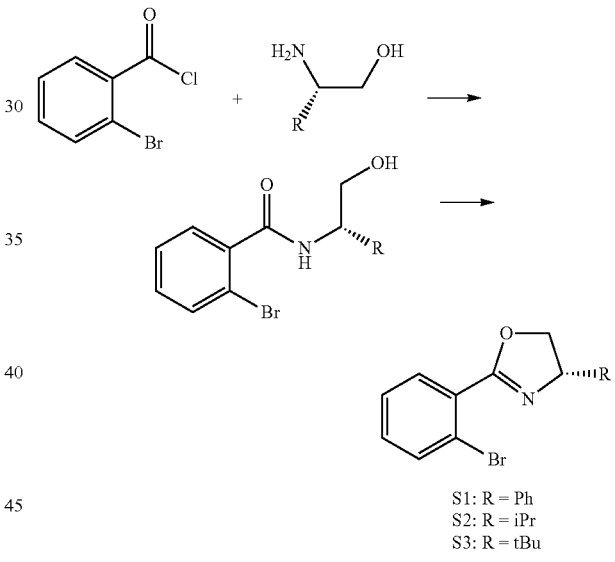

S1: R = Ph
S2: R = iPr
S3: R = tBu

Ligand intermediates S1, S2, and S3 were synthesized according to the following general procedure: The appropriate amino alcohol (10 mmol, 1.0 equiv) was dissolved in CH$_2$Cl$_2$ (33 mL). A solution of Na$_2$CO$_3$ (30 mmol, 3 equiv) in water (25 mL) was added. To the vigorously stirring biphasic mixture was added 2-bromobenzoyl chloride (11.5 mmol, 1.15 equiv) dropwise. The reaction was stirred vigorously for 12 hours at room temperature, after which the layers were separated, and the aqueous layer was extracted with CH$_2$Cl$_2$ (2×20 mL). The combined organic layers were treated with KOH (6 mL, 1M methanolic solution) for 15 minutes. The solution was neutralized with 2M HCl, and water (20 mL) was added. The layers were separated, and the aqueous layer was extracted with CH$_2$Cl$_2$ (2×30 mL). The combined organic layers were dried over anhydrous MgSO$_4$, filtered, and evaporated under reduced pressure. The crude mixture was purified via column chromatography (25→35% acetone in hexanes) to afford the desired amide, which was used for the next step.

To a solution of amide (9.2 mmol, 1 equiv) in CH$_2$Cl$_2$ (35 mL) was added tosyl chloride (11.96 mmol, 1.3 equiv) and triethylamine (46 mmol, 5 equiv). The reaction was refluxed at 55° C. for 22 hours. Water (10 mL) was added, and the reaction was refluxed at 75° C. for 2 hours. The reaction was cooled, and the layers were separated. The aqueous layer was extracted with CH$_2$Cl$_2$ (2×25 mL). The combined organic layers were dried over anhydrous MgSO$_4$, filtered, and evaporated under reduced pressure. The crude mixture was purified via column chromatography (5% EtOAc in hexanes) to afford the desired phenyloxazoline. Spectral data for phenyloxazolines S1, S2, and S3 were consistent with previously reported literature.

Scheme 1-2: Ligand Intermediates S4, S5, S6, S7, S8, and S9.

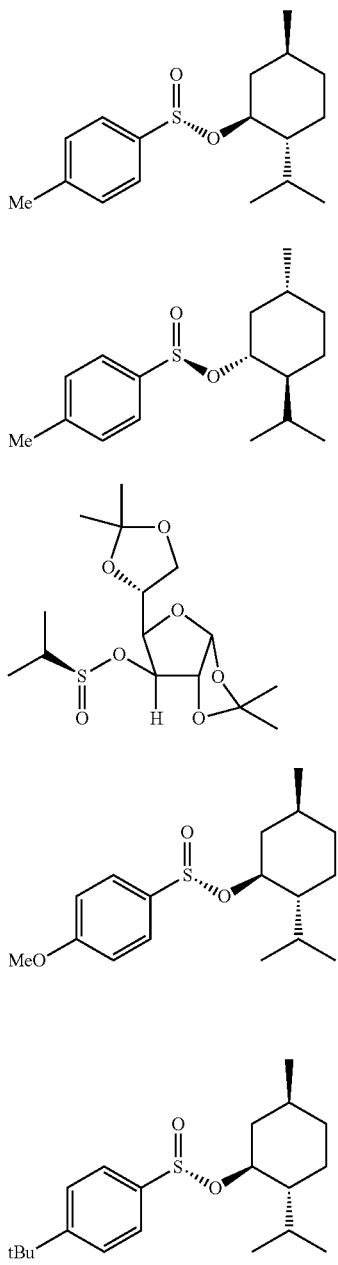

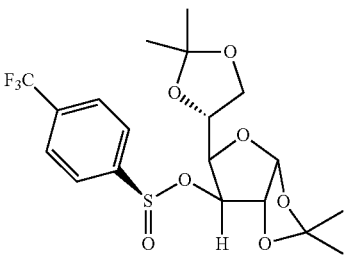

Ligand intermediates S4, S5, S6, S7 and S8 were synthesized according to reported methods, and spectral data was consistent with previously reported literature. S4, S7, and S8 use D-(+)-menthol as a chiral auxiliary, S5 uses L-(−)-menthol as a chiral auxiliary, and S6 uses diacetone-D-glucose.

Scheme 1-3: Synthesis of S9.

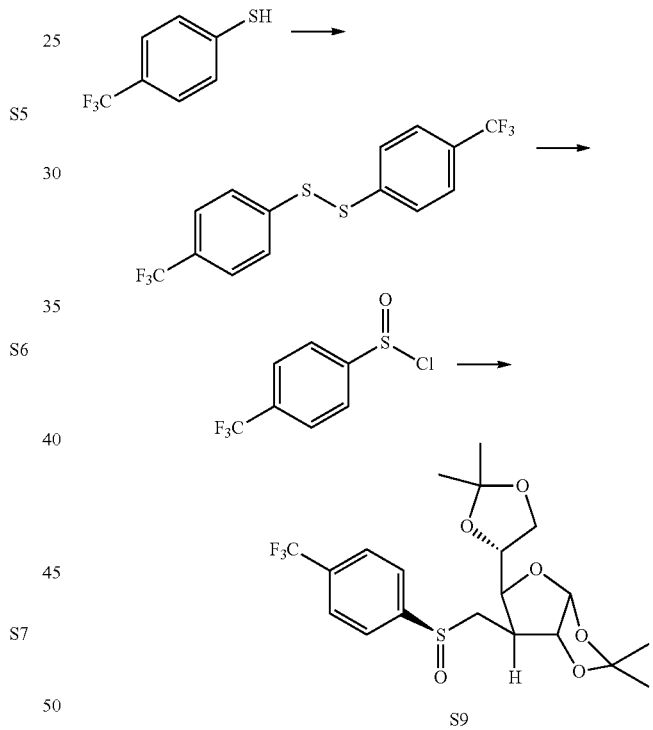

In a dried flask, 4-trifluoromethylthiophenol (5 g, 28 mmol, 1 equiv) was dissolved in DMF (20 mL). Triethylamine (3.91 mL, 28 mmol, 1 equiv) was added, and the solution was stirred at 80° C. under an atmosphere of oxygen (balloon) for 48 hours. The reaction was cooled, and the mixture was diluted with ether (100 mL). The mixture was transferred to a separatory funnel, and the organic layer was washed with water (3×40 mL). The organic layer was dried over anhydrous MgSO$_4$, filtered and concentrated to afford 1,2-bis(4-(trifluoromethyl)phenyl)disulfane as a liquid. The material was used without further purification.

To a dried flask under argon was added the disulfane (5 g, 14 mmol, 1 equiv) and glacial acetic acid (1.6 mL, 28 mmol, 2 equiv), and the mixture was cooled to −20° C. with stirring. Sulfuryl chloride (3.54 mL, 43.7 mmol, 3.1 equiv)

was added dropwise via syringe over a period of 30 minutes. The mixture was stirred for 3 hours at −20° C. and then allowed to slowly warm to room temperature over a period of 2 hours. (CAUTION: evolution of HCl gas observed) The reaction was completed by stirring for 1 hour at 35° C. Afterward, the reaction was cooled to room temperature, and the acetyl chloride and excess sulfuryl chloride was evaporated under reduced pressure to leave 4-(trifluoromethyl) benzenesulfinyl chloride as an orange liquid, used without further purification. The sulfinyl chloride was observed to be stable for up to a month if stored at 0° C.

To a dried flask under argon, diacetone-D-glucose (2.26 g, 8.67 mmol, 1 equiv) was dissolved in THF (45 mL). Pyridine (0.84 mL, 10.4 mmol, 1.2 equiv) was added via syringe, and the mixture was stirred and cooled to −78° C. 4-(trifluoromethyl)benzenesulfinyl chloride (3 g, 10.4 mmol, 1.2 equiv) was added dropwise via syringe, and the reaction was stirred 3 hours at −78° C. The reaction was quenched with dropwise addition of water, and allowed to warm to room temperature. The mixture was diluted with CH$_2$Cl$_2$ (100 mL), and the layers were separated. The organic layer was washed with 5% HCl, 2% NaHCO$_3$, and brine. The organic layer was dried over anhydrous MgSO$_4$, filtered, and concentrated under reduced pressure. The residue was purified via column chromatography (20% EtOAc in hexanes) to afford a mixture of diastereomers. This mixture was further purified via MPLC to afford S9 as a single diastereomer. S9 was observed to slowly decompose over the course of a month if stored at room temperature under air. $^1$H NMR (500 MHz, CDCl$_3$) δ 7.96 (d, J=7.9 Hz, 2H), 7.81 (d, J=8.1 Hz, 2H), 5.88 (d, J=3.4 Hz, 1H), 5.00 (d, J=2.8 Hz, 1H), 4.78 (d, J=3.6 Hz, 1H), 4.22 (dd, J=8.6, 2.8 Hz, 1H), 4.12-4.00 (m, 3H), 1.53 (s, 3H), 1.50 (s, 3H), 1.43 (s, 3H), 1.32 (s, 3H); $^{13}$C NMR (125 MHz, CDCl$_3$) δ 149.1, 134.5 (q, J=33.0 Hz), 126.3 (q, J=3.6 Hz), 125.8, 123.6 (q, J=271.1 Hz), 112.8, 109.8, 105.6, 84.1, 84.1, 81.2, 72.5, 68.0, 27.1, 27.0, 26.4, 25.6; [α]$^{22}_D$=+18.40° (c=0.25, CH$_2$Cl$_2$); $^{19}$F NMR (470 MHz, CDCl$_3$) δ −63.4; HRMS (TOF MS ES+) m/z calc'd for C$_{19}$H$_{24}$O$_7$SF$_3$ [M+H]: 453.1195; found 453.1215.

SOX Ligand Synthesis: General Procedure

To a dried flask under argon was added the phenyloxazoline (1 equiv), THF (0.1 M), and TMEDA (1.1 equiv). The reaction was cooled to −78° C. with stirring, and n-butyllithium (1.6M in hexane, 1.1 equiv) was added via syringe dropwise. The reaction was stirred 20 minutes at −78° C. Subsequently, the sulfinate (1.1 equiv) was added as a solution in THF (0.5 M) dropwise via syringe. The reaction was stirred 1 hour at −78° C., then 1 hour at 0° C., then 5 hours at room temperature. The reaction was subsequently cooled to 0° C., and quenched with water. The mixture was diluted with CH$_2$Cl$_2$, and the layers were separated. The aqueous layer was extracted with CH$_2$Cl$_2$. The combined organic layers were dried over anhydrous MgSO$_4$, filtered, and concentrated under reduced pressure. The crude residue was purified via column chromatography (20→30% EtOAc in hexanes) to afford the desired product.

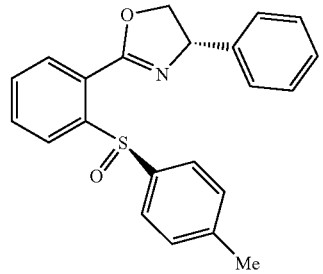

(S)-4-phenyl-2-(2-((R)-p-tolylsulfinyl) phenyl)-4,5-dihydrooxazole (L1)

Phenyloxazoline S1 (302 mg, 1 mmol, 1 equiv) was reacted according to the general procedure with sulfinate S4 (324 mg, 1.1 mmol, 1.1 equiv). Purification by flash column chromatography (20→30% EtOAc in hexanes) provided the product as a clear, viscous oil. (198 mg, 0.55 mmol, 55% Yield). $^1$H NMR (500 MHz, CDCl$_3$) δ 8.44 (d, J=7.9 Hz, 1H), 7.95 (d, J=7.5 Hz, 1H), 7.78 (t, J=7.9 Hz, 1H), 7.60-7.52 (m, 3H), 7.40-7.29 (m, 3H), 7.26 (d, J=7.1 Hz, 2H), 7.15 (d, J=8.4 Hz, 2H), 5.38 (t, J=9.6 Hz, 1H), 4.74 (dd, J=9.9, 8.4 Hz, 1H), 4.13 (t, J=8.4 Hz, 1H), 2.33 (s, 3H); $^{13}$C NMR (125 MHz, CDCl$_3$) δ 162.3, 147.3, 143.9, 142.1, 141.3, 132.4, 130.5, 130.1, 129.8, 129.1, 127.9, 127.2, 126.8, 125.3, 125.2, 74.9, 70.4, 21.6; [α]$^{21}_D$=+364.78° (c=1, CH$_2$Cl$_2$); HRMS (TOF MS ES+) m/z calc'd for C$_{22}$H$_{20}$NO$_2$S [M+H]: 362.1215; found 362.1212.

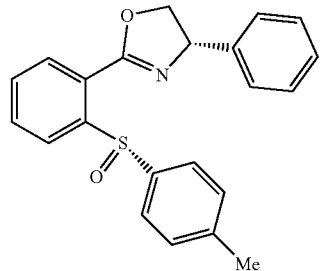

(S)-4-phenyl-2-(2-((S)-p-tolylsulfinyl)phenyl)-4,5-dihydrooxazole (L2)

Phenyloxazoline S1 (302 mg, 1 mmol, 1 equiv) was reacted according to the general procedure with sulfinate S5 (324 mg, 1.1 mmol, 1.1 equiv). Purification by flash column chromatography (20→30% EtOAc in hexanes) provided the product as a white powder. (162 mg, 0.45 mmol, 45% Yield.) $^1$H NMR (500 MHz, CDCl$_3$) δ 8.47 (d, J=8.1 Hz, 1H), 8.03 (d, J=7.7 Hz, 1H), 7.80 (t, J=7.5 Hz, 1H), 7.58 (t, J=7.7 Hz, 1H), 7.45 (d, J=7.9 Hz, 2H), 7.30-7.25 (m, 3H), 7.02 (d, J=7.5 Hz, 2H), 7.00 (d, J=8.1 Hz, 2H), 5.43 (t, J=9.6 Hz, 1H), 4.74 (ap. t, J=9.6, Hz, 1H), 4.21 (t, J=8.3 Hz, 1H), 2.32 (s, 3H); $^{13}$C NMR (125 MHz, CDCl$_3$) δ 162.0, 147.0, 143.7, 141.8, 141.0, 132.4, 130.5, 130.3, 129.7, 128.8, 127.8, 127.1, 127.1, 125.5, 125.1, 74.6, 71.0, 21.6; [α]$^{22}_D$=−195.79° (c=0.5, CH$_2$Cl$_2$); HRMS (TOF MS ES+) m/z calc'd for C$_{22}$H$_{20}$NO$_2$S [M+H]: 362.1215; found 362.1213.

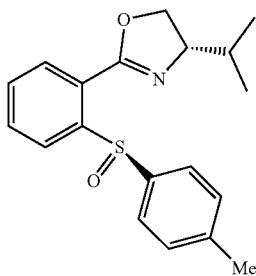

(S)-4-isopropyl-2-(2-((R)-p-tolylsulfinyl)phenyl)-4,5-dihydrooxazole (L3)

Phenyloxazoline S2 (249 mg, 0.93 mmol, 1 equiv) was reacted according to the general procedure with sulfinate S4 (300 mg, 1.02 mmol, 1.1 equiv). Purification by flash column chromatography (20→30% EtOAc in hexanes) provided the product as a clear, viscous oil. (146 mg, 0.45 mmol, 48% Yield.) $^1$H NMR (500 MHz, CDCl$_3$) δ 8.38 (dd, J=7.9, 1.1 Hz, 1H), 7.85 (dd, J=7.7, 1.3 Hz, 1H), 7.72 (td, J=7.7, 1.3 Hz, 1H), 7.62 (d, J=8.3 Hz, 2H), 7.50 (td, J=7.7, 1.3 Hz, 1H), 7.16 (d, J=7.9 Hz, 2H), 4.36-4.29 (m, 1H), 4.06-3.99 (m, 2H), 2.32 (s, 3H), 1.80-1.72 (m, 1H), 1.06 (d, J=6.6 Hz, 3H), 0.96 (d, J=6.9 Hz, 3H); $^{13}$C NMR (125 MHz, CDCl$_3$) δ 160.5, 147.4, 144.3, 141.1, 132.1, 130.4, 129.8, 129.8, 127.0, 125.6, 125.3, 73.6, 70.8, 33.5, 21.7, 19.2, 19.2; $[\alpha]^{22}_D$=+270.80° (c=0.5, CH$_2$Cl$_2$); HRMS (TOF MS ES+) m/z calc'd for C$_{19}$H$_{22}$NO$_2$S [M+H]: 328.1368; found 328.1371.

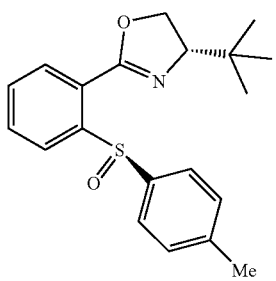

(S)-4-(tert-butyl)-2-(2-((R)-p-tolylsulfinyl)phenyl)-4,5-dihydrooxazole (L4)

Phenyloxazoline S3 (282 mg, 1 mmol, 1 equiv) was reacted according to the general procedure with sulfinate S4 (324 mg, 1.1 mmol, 1.1 equiv). Purification by flash column chromatography (20→30% EtOAc in hexanes) provided the product as a white powder. (262 mg, 0.77 mmol, 77% Yield.) $^1$H NMR (500 MHz, CDCl$_3$) δ 8.37 (dd, J=7.9, 1.1 Hz, 1H), 7.85 (dd, J=7.7, 1.3 Hz, 1H), 7.72 (td, J=7.7, 1.1 Hz, 1H), 7.65 (d, J=8.4 Hz, 2H), 7.50 (td, J=7.5, 0.9 Hz, 1H), 7.16 (d, J=8.4 Hz, 2H), 4.25 (dd, J=10.1, 8.8 Hz, 1H), 4.16 (t, J=8.1, Hz, 1H), 4.03 (dd, J=10.1, 7.9 Hz, 1H), 2.32 (s, 3H), 0.97 (s, 9H); $^{13}$C NMR (125 MHz, CDCl$_3$) δ 160.4, 147.6, 144.4, 141.0, 132.1, 130.4, 129.8, 126.8, 125.6, 125.3, 77.6, 68.9, 34.3, 26.3, 21.7; $[\alpha]^{23}_D$=+224.03° (c=0.25, CH$_2$Cl$_2$); HRMS (TOF MS ES+) m/z calc'd for C$_{20}$H$_{24}$NO$_2$S [M+H]: 342.1528; found 342.1529. Spectral data (including 15 peaks observed in the $^{13}$C NMR spectrum) is consistent with data in previous literature.

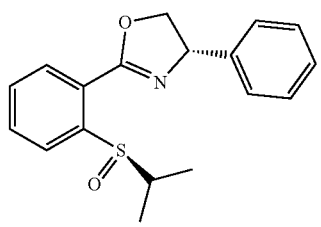

(S)-2-(2-((R)-isopropylsulfinyl)phenyl)-4-phenyl-4,5-dihydrooxazole (L5)

To a dried flask under argon was added phenyloxazoline S1 (302 mg, 1 mmol, 1 equiv), THF (10 mL), and TMEDA (0.16 mL, 1.1 mmol, 1.1 equiv). The reaction was cooled to −78° C. with stirring, and n-butyllithium (0.69 mL, 1.6M in hexane, 1.1 equiv) was added via syringe dropwise. The reaction was stirred 20 minutes at −78° C. Subsequently, sulfinate S6 (386 mg, 1.1 mmol, 1.1 equiv) was added as a solution in THF (2 mL) dropwise via syringe. The reaction was stirred 1 hour at −78° C., then 1 hour at 0° C., then 2 hours at room temperature. The reaction was subsequently cooled to 0° C., and quenched with water. The mixture was diluted with CH$_2$Cl$_2$, and the layers were separated. The aqueous layer was extracted with CH$_2$Cl$_2$. The combined organic layers were dried over anhydrous MgSO$_4$, filtered, and concentrated under reduced pressure. The crude residue was purified via column chromatography (20→30% EtOAc in hexanes) to afford the desired product along with a diacetone glucose impurity. The mixture was dissolved in 3 mL MeOH, and PTSA was added (10 mg). The reaction was stirred 10 hours at room temperature. The mixture was diluted with CH$_2$Cl$_2$ and water. The layers were separated, and the aqueous layer was extracted with CH$_2$Cl$_2$. The combined organic layers were dried over anhydrous MgSO$_4$, filtered, and concentrated under reduced pressure. The residue was purified via column chromatography (30% EtOAc in hexanes) to afford the product as a white powder. (73 mg, 0.23 mmol, 23% Yield.) $^1$H NMR (500 MHz, CDCl$_3$) δ 8.14 (dd, J=7.8, 1.0 Hz, 1H), 7.99 (dd, J=7.8, 1.0 Hz, 1H), 7.74 (td, J=7.8, 1.2 Hz, 1H), 7.56 (td, J=7.6, 1.2 Hz, 1H), 7.42-7.37 (m, 4H), 7.35-7.31 (m, 1H), 5.56 (dd, J=10.0, 8.8 Hz, 1H), 4.85 (dd, J=10.3, 8.3 Hz, 1H), 4.23 (t, J=8.3 Hz, 1H), 3.52 (sept., J=6.8 Hz, 1H), 1.43 (d, J=7.1 Hz, 3H), 0.98 (d, J=6.8 Hz, 3H); $^{13}$C NMR (125 MHz, CDCl$_3$) δ 162.3, 145.8, 142.2, 131.7, 130.0, 129.9, 129.0, 127.9, 126.6, 126.2, 124.8, 74.8, 70.8, 52.2, 18.8, 11.6; $[\alpha]^{22}_D$=+313.19° (c=0.225, CH$_2$Cl$_2$); HRMS (TOF MS ES+) m/z calc'd for C$_{18}$H$_{20}$NO$_2$S [M+H]: 314.1215; found 314.1213.

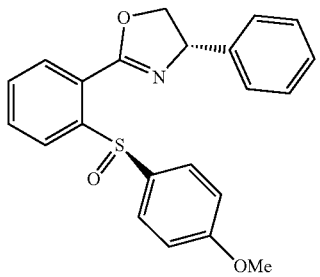

(L6)

(S)-2-(2-((R)-(4-methoxyphenyl)sulfinyl)phenyl)-4-phenyl-4,5-dihydrooxazole (L6)

Phenyloxazoline S1 (309 mg, 1.02 mmol, 1 equiv) was reacted according to the general procedure with sulfinate S7 (349 mg, 1.13 mmol, 1.1 equiv). Purification by flash column chromatography (20→30% EtOAc in hexanes) provided the product as a white powder. (182 mg, 0.48 mmol, 47% Yield.) $^1$H NMR (500 MHz, CDCl$_3$) δ 8.46 (d, J=7.9 Hz, 1H), 7.95 (d, J=7.3 Hz, 1H), 7.79 (t, J=7.3 Hz, 1H), 7.62-7.58 (m, 2H), 7.55 (t, J=7.7 Hz, 1H), 7.38-7.28 (m, 3H), 7.23 (d, J=7.5 Hz, 2H), 6.85 (d, J=8.6 Hz, 2H), 5.37 (ap. t, J=9.9 Hz, 1H), 4.73 (dd, J=10.1, 8.4 Hz, 1H), 4.11 (t, J=8.8 Hz, 1H), 3.78 (s, 3H); $^{13}$C NMR (125 MHz, CDCl$_3$) δ 162.3, 161.7, 147.3, 142.1, 138.3, 132.3, 130.4, 130.2, 129.2, 129.0, 127.9, 126.7, 125.2, 125.1, 114.5, 74.8, 70.3, 55.6; $[α]^{21}_D$=+357.55° (c=0.25, CH$_2$Cl$_2$); HRMS (TOF MS ES+) m/z calc'd for C$_{22}$H$_{20}$NO$_3$S [M+H]: 378.1164; found 378.1160.

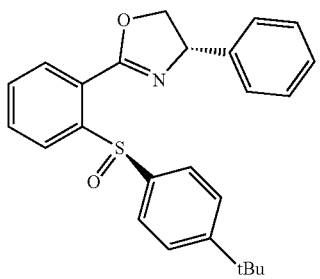

(L7)

(S,R) tBu-ArSOX (S)-2-(2-((R)-(4-(tert-butyl)phenyl)sulfinyl)phenyl)-4-phenyl-4,5-dihydrooxazole (L7)

Phenyloxazoline S1 (700 mg, 2.32 mmol, 1 equiv) was reacted according to the general procedure with sulfinate S8 (857 mg, 2.55 mmol, 1.1 equiv). Purification by flash column chromatography (20→30% EtOAc in hexanes) provided the product as a white powder (400 mg, 1 mmol, 43% Yield.) $^1$H NMR (500 MHz, CDCl$_3$) δ 8.45 (dd, J=7.9, 1.1 Hz, 1H), 7.96 (dd, J=7.7, 1.3 Hz, 1H), 7.78 (td, J=7.7, 1.3 Hz, 1H), 7.65-7.61 (m, 2H), 7.55 (td, J=7.5, 1.1 Hz, 1H), 7.38-7.30 (m, 7H), 5.41 (ap. t, J=9.6 Hz, 1H), 4.76 (dd, J=10.3, 8.4 Hz, 1H), 4.15 (t, J=8.6 Hz, 1H), 1.26 (s, 9H); $^{13}$C NMR (125 MHz, CDCl$_3$) δ 162.3, 154.2, 147.4, 143.8, 142.1, 132.4, 130.4, 130.0, 129.1, 127.9, 126.8, 126.8, 126.1, 125.3, 125.2, 74.9, 70.4, 35.1, 31.4; $[α]^{22}_D$=+371.11° (c=0.25, CH$_2$Cl$_2$); HRMS (TOF MS ES+) m/z calc'd for C$_{25}$H$_{26}$NO$_2$S [M+H]: 404.1684; found: 404.1680.

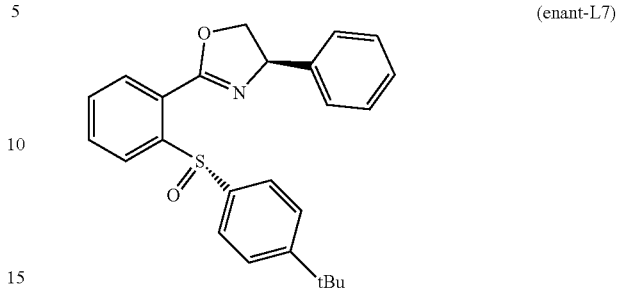

(enant-L7)

(R,S) tBu-ArSOX (R)-2-(2-((S)-(4-(tert-butyl)phenyl)sulfinyl)phenyl)-4-phenyl-4,5-dihydrooxazole (enant-L7)

Spectral data for enant-L7 matched those for L7. Rotation: $[α]^{22}_D$=−372.02° (c=0.25, CH$_2$Cl$_2$).

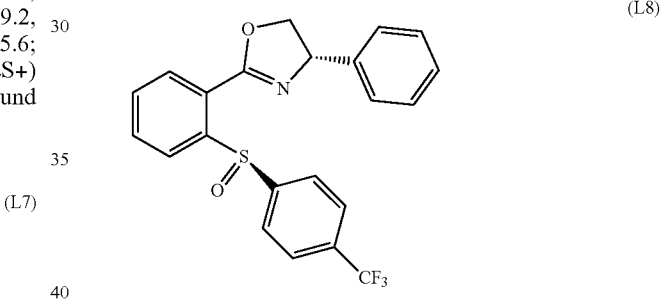

(L8)

(S,R) CF$_3$—ArSOX (S)-4-phenyl-2-(2-((R)-(4-(trifluoromethyl) phenyl)sulfinyl)phenyl)-4,5-dihydrooxazole (L8)

Phenyloxazoline S1 (387 mg, 1.28 mmol, 1 equiv) was reacted according to the general procedure with sulfinate S9 (638 mg, 1.41 mmol, 1.1 equiv). Purification by flash column chromatography (20→30% EtOAc in hexanes) provided the product as a clear, viscous oil. (132 mg, 0.32 mmol, 25% Yield.) $^1$H NMR (500 MHz, CDCl$_3$) δ 8.39 (d, J=7.9 Hz, 1H), 7.96 (d, J=7.7 Hz, 1H), 7.92 (d, J=8.4 Hz, 2H), 7.79 (t, J=7.7 Hz, 1H), 7.62-7.57 (m, 3H), 7.42-7.32 (m, 5H), 5.45 (ap. t, J=9.6 Hz, 1H), 4.80 (dd, J=10.3, 9.2 Hz, 1H), 4.21 (t, J=8.6 Hz, 1H); $^{13}$C NMR (125 MHz, CDCl$_3$) δ 162.1, 151.4, 147.0, 141.9, 132.7, 132.5 (q, J=33.0 Hz), 131.0, 130.1, 129.2, 128.1, 127.2, 126.7, 126.0 (q, J=3.8 Hz), 125.3, 125.3, 123.8 (q, J=271.1 Hz), 75.1, 70.5; $^{19}$F NMR (470 MHz, CDCl$_3$) δ −63.3; $[α]^{23}_D$=+317.47° (c=0.25, CH$_2$Cl$_2$); HRMS (TOF MS ES+) m/z calc'd for C$_{22}$H$_{17}$NO$_2$SF$_3$ [M+H]: 416.0932; found 416.0927.

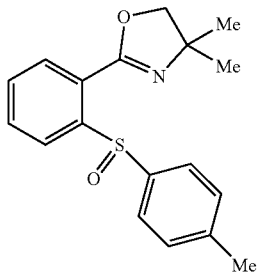

4,4-dimethyl-2-(2-(p-tolylsulfinyl)phenyl)-4,5-dihydrooxazole (S10)

Racemic product standards (2a-2k) were prepared according to analogous procedures, substituting the chiral ligands for the racemic ligand S10. $^1$H NMR (500 MHz, CDCl$_3$) δ 8.37 (d, J=7.9 Hz, 1H), 7.89 (dd, J=7.7, 1.1 Hz, 1H), 7.73 (td, J=7.7, 1.3 Hz, 1H), 7.60 (d, J=8.1 Hz, 2H), 7.52 (td, J=7.5, 1.1 Hz, 1H), 7.18 (d, J=8.1 Hz, 2H), 4.03 4.01 (ABq, J$_{AB}$=8.1 Hz, 2H), 2.34 (s, 3H), 1.33 (s, 3H), 1.28 (s, 3H); $^{13}$C NMR (125 MHz, CDCl$_3$) δ 159.5, 146.7, 143.8, 141.2, 132.0, 130.4, 129.9, 129.7, 127.1, 125.8, 125.2, 79.1, 68.8, 28.8, 28.4, 21.6; HRMS (TOF MS ES+) m/z calc'd for C$_{18}$H$_{20}$NO$_2$S [M+H]: 314.1215; found 314.1215.

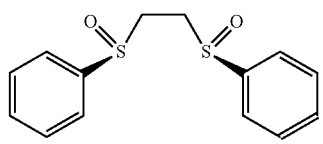
(L9)

(R,R) 1,2-bis(p-tolylsulfinyl)ethane (L9) was synthesized according to a reported method, and spectral data matched those reported (Khiar et al., *J. Org. Chem.* 2013. 78, 6510-6521).

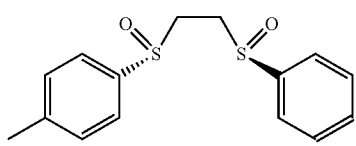
(L10)

(S)-2-(4'-(tert-butyl)-[1,1'-biphenyl]-2-yl)-4-phenyl-4,5-dihydrooxazole (L10)

$^1$H NMR (500 MHz, CDCl$_3$) δ 7.84 (dd, J=7.7, 1.4 Hz, 1H), 7.50 (td, J=7.4, 0.9 Hz, 1H), 7.44-7.31 (m, 8H), 7.30-7.26 (m, 1H), 7.24-7.21 (m, 2H), 5.30-5.26 (m, 1H), 4.53 (dd, J=10.0, 8.6 Hz, 1H), 3.98 (t, J=8.5 Hz, 1H), 1.36 (s, 9H). $^{13}$C NMR (126 MHz, CDCl$_3$) δ 166.8, 150.4, 142.5, 142.2, 138.5, 130.9, 130.7, 130.6, 128.9, 128.4, 127.7, 127.7, 127.2, 127.0, 125.3, 75.2, 70.4, 34.8, 31.7. δ −63.3; [α]$^{23}_D$=−110.11° (c=0.3, CH$_2$Cl$_2$); HRMS (TOF MS ES+) m/z calc'd for C$_{25}$H$_{25}$NO [M+H]: 356.2014; found 326.2015.

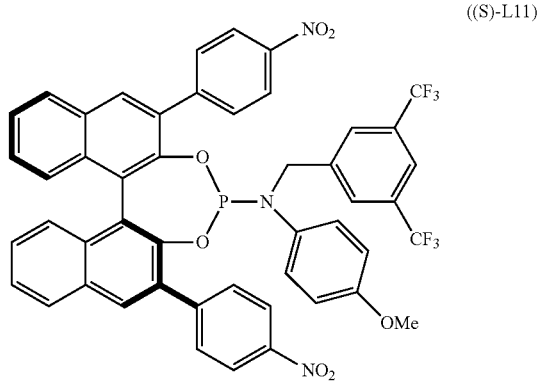
((S)-L11)

(S)-L11: was synthesized according to a reported method, and spectral data matched those reported (Miyata et al., Kitamura, *Angew. Chem. Int. Ed.* 2011. 50, 4649-4653).

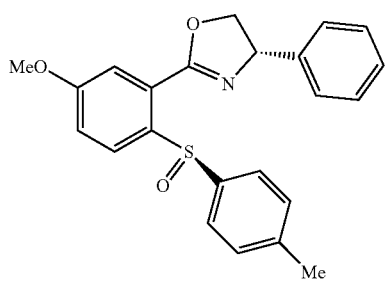
(L12)

meso-1,2-bis(phenylsulfinyl)ethane (L12) was synthesized according to a reported method, and spectral data matched those reported (Stang et al., *Nature Chem.* 2009. 1, 547-551).

(L13)

(S)-2-(5-methoxy-2-((R)-p-tolylsulfinyl)phenyl)-4-phenyl-4,5-dihydrooxazole (L13)

Product is a white powder. $^1$H NMR (500 MHz, CDCl$_3$) δ 8.30 (d, J=9.0 Hz, 1H), 7.56 (d, J=8.1 Hz, 2H), 7.45 (d, J=2.6 Hz, 1H), 7.34-7.28 (m, 3H), 7.27-7.23 (m, 3H), 7.15 (d, J=8.4 Hz, 2H), 5.34 (ap. t, J=10.0 Hz, 1H), 4.74 (dd, J=10.1, 8.4 Hz, 1H), 4.13 (t, J=8.6 Hz, 1H), 3.88 (s, 3H), 2.33 (s, 3H); $^{13}$C NMR (125 MHz, CDCl$_3$) δ 162.2, 161.3, 144.4, 142.1, 141.1, 138.1, 129.8, 129.1, 127.9, 127.3, 126.9, 126.8, 126.6, 118.0, 115.2, 74.9, 70.4, 56.0, 21.6; [α]$^{22}_D$=+284.81° (c=0.314, CH$_2$Cl$_2$); HRMS (TOF MS ES+) m/z calc'd for C$_{23}$H$_{22}$NO$_3$S [M+H]: 392.1320; found 392.1312.

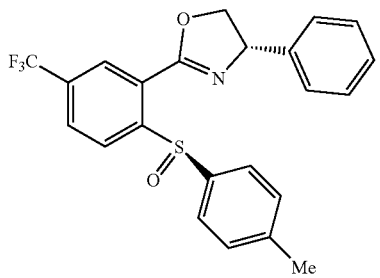

(L14)

(S)-4-phenyl-2-(2-((R)-p-tolylsulfinyl)-5-(trifluoromethyl)phenyl)-4,5-dihydrooxazole (L14)

Product is a white powder. $^1$H NMR (500 MHz, CDCl$_3$) δ 8.62 (d, J=8.3 Hz, 1H), 8.22 (s, 1H), 8.03 (d, J=8.3 Hz, 1H), 7.58 (d, J=8.1 Hz, 2H), 7.42-7.33 (m, 3H), 7.29-7.26 (m, 2H), 7.18 (d, J=8.1 Hz, 2H), 5.43 (ap. t, J=9.5 Hz, 1H), 4.79 (dd, J=10.3, 8.5 Hz, 1H), 4.19 (t, J=8.5 Hz, 1H), 2.35 (s, 3H); $^{13}$C NMR (126 MHz, CDCl$_3$) δ 161.2, 151.8, 143.2, 141.8, 141.6, 132.7 (q, J=33.2 Hz), 129.9, 129.2, 128.8 (q, J=3.7 Hz), 128.1, 127.3, 127.2 (q, J=3.6 Hz), 126.7, 126.1, 125.9, 123.5 (q, J=272.8 Hz), 75.1, 70.5, 21.7; $^{19}$F NMR (470 MHz, CDCl$_3$) δ −63.2; $[\alpha]^{24}_D$=+273.6° (c=1, CHCl$_3$); HRMS (TOF MS ES+) m/z calc'd for C$_{23}$H$_{19}$NO$_2$SF$_3$ [M+H]: 430.1089; found 430.1088.

Reaction Optimization

Entry 1:
To a ½ dram vial was added ligand L1 (7.2 mg, 0.02 mmol, 0.1 equiv) and Pd(OAc)$_2$ (4.4 mg, 0.02 mmol, 0.1 equiv). Toluene (0.4 mL) was added, and the vial was capped and heated to 45° C. until all solids had dissolved. Separately, to a 1 dram vial with stir bar was added 1a (32.4 mg, 0.20 mmol, 1 equiv), 2,6-dimethylbenzoquinone (30 mg, 0.22 mmol, 1.1 equiv). The catalyst solution was subsequently added to the reaction flask, and toluene was used to rinse up to 1.3 mL toluene. The 1 dram vial was sealed with a Teflon cap, and allowed to stir for 8 hours at 45° C. Afterward, the vial was allowed to cool to room temperature. The majority of the toluene was removed under reduced pressure, and the remaining mixture was directly subjected to flash column chromatography (10% EtOAc/hexanes) to provide vinylisochroman 2a as a clear oil. Run 1 (2.3 mg, 7% yield, 83% ee); Run 2 (3.0 mg, 9% yield, 83% ee); Average: 8% Yield, 83% ee.

Entry 2:
To a ½ dram vial was added ligand L1 (7.2 mg, 0.02 mmol, 0.1 equiv) and Pd(OAc)$_2$ (4.4 mg, 0.02 mmol, 0.1 equiv). Toluene (0.4 mL) was added, and the vial was capped and heated to 45° C. until all solids had dissolved. Separately, to a 1 dram vial with stir bar was added 1a (32.4 mg, 0.20 mmol, 1 equiv), 2,6-dimethylbenzoquinone (30 mg, 0.22 mmol, 1.1 equiv), and benzoic acid (2.5 mg, 0.02 mmol, 0.1 equiv). The catalyst solution was subsequently added to the reaction flask, and toluene was used to rinse up to 1.3 mL toluene. The 1 dram vial was sealed with a Teflon cap, and allowed to stir for 8 hours at 45° C. Afterward, the

TABLE 1-1

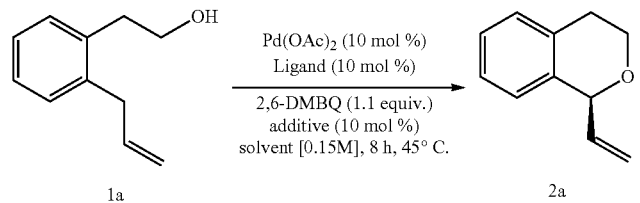

| Entry | Ligand | Additive | Solvent | % Yield[a] | % ee |
|---|---|---|---|---|---|
| 1 | L1 | none | toluene | 8 | 83 |
| 2 | L1 | benzoic acid | toluene | 13 | 84 |
| 3 | L1 | dibutyl phosphate | toluene | 54 | 87 |
| 4 | L1 | diphenyl phosphate | toluene | 47 | 82 |
| 5 | L1 | diphenylphosphinic acid | toluene | 63 | 87 |
| 6 | L2 | diphenylphosphinic acid | toluene | 32 | 19 |
| 7 | L3 | diphenylphosphinic acid | toluene | 31 | 76 |
| 8 | L4 | diphenylphosphinic acid | toluene | 8 | 25 |
| 9 | L5 | diphenylphosphinic acid | toluene | 24 | 88 |
| 10 | L6 | diphenylphosphinic acid | toleune | 60 | 86 |
| 11 | L7 | diphenylphosphinic acid | toluene | 70 | 92 |
| 12 | L8 | diphenylphosphinic acid | toluene | 49 | 93 |
| 13[b] | L9 | diphenylphosphinic acid | toluene | 31 | −6 |
| 14[b] | L10 | diphenylphosphinic acid | toluene | 13 | 12 |
| 15[c] | L11 | diphenylphosphinic acid | toluene | <5 | N.D. |
| 16[d] | L7 | diphenylphosphinic acid | toluene | 59 | 77 |
| 17 | L13 | diphenylphosphinic acid | toluene | 39 | 80 |
| 18 | L14 | diphenylphosphinic acid | toluene | 34 | 88 |

[a]Reactions run under air, average of two isolated runs.
[b]rxm run for 72 hours at [0.5M].
[c]rxmn also run under argon with conditions reported ref S9, also resulting in trace product yield.
[d]p-benzoquinone used in place of 2,6-BMBQ. 2,6-BMBQ = 2,6-dimethylbenzoquinone.
N.D. = not determined.

vial was allowed to cool to room temperature. The majority of the toluene was removed under reduced pressure, and the remaining mixture was directly subjected to flash column chromatography (10% EtOAc/hexanes) to provide vinylisochroman 2a as a clear oil. Run 1 (4.0 mg, 13% yield, 84% ee); Run 2 (4.0 mg, 13% yield, 84% ee); Average: 13% Yield, 84% ee.

Entry 3:

To a ½ dram vial was added ligand L1 (7.2 mg, 0.02 mmol, 0.1 equiv) and Pd(OAc)$_2$ (4.4 mg, 0.02 mmol, 0.1 equiv). Toluene (0.4 mL) was added, and the vial was capped and heated to 45° C. until all solids had dissolved. Separately, to a 1 dram vial with stir bar was added 1a (32.4 mg, 0.20 mmol, 1 equiv), 2,6-dimethylbenzoquinone (30 mg, 0.22 mmol, 1.1 equiv), and dibutyl phosphate (4 μL, 0.02 mmol, 0.1 equiv). The catalyst solution was subsequently added to the reaction flask, and toluene was used to rinse up to 1.3 mL toluene. The 1 dram vial was sealed with a Teflon cap, and allowed to stir for 8 hours at 45° C. Afterward, the vial was allowed to cool to room temperature. The majority of the toluene was removed under reduced pressure, and the remaining mixture was directly subjected to flash column chromatography (10% EtOAc/hexanes) to provide vinylisochroman 2a as a clear oil. Run 1 (15 mg, 47% yield, 87% ee); Run 2 (½ scale) (9.7 mg, 61% yield, 87% ee); Average: 54% Yield, 87% ee.

Entry 4:

To a ½ dram vial was added ligand L1 (7.2 mg, 0.02 mmol, 0.1 equiv) and Pd(OAc)$_2$ (4.4 mg, 0.02 mmol, 0.1 equiv). Toluene (0.4 mL) was added, and the vial was capped and heated to 45° C. until all solids had dissolved. Separately, to a 1 dram vial with stir bar was added 1a (32.4 mg, 0.20 mmol, 1 equiv), 2,6-dimethylbenzoquinone (30 mg, 0.22 mmol, 1.1 equiv), and diphenyl phosphate (5.0 mg, 0.02 mmol, 0.1 equiv). The catalyst solution was subsequently added to the reaction flask, and toluene was used to rinse up to 1.3 mL toluene. The 1 dram vial was sealed with a Teflon cap, and allowed to stir for 8 hours at 45° C. Afterward, the vial was allowed to cool to room temperature. The majority of the toluene was removed under reduced pressure, and the remaining mixture was directly subjected to flash column chromatography (10% EtOAc in hexanes) to provide vinylisochroman 2a as a clear oil. Run 1 (15.9 mg, 50% yield, 82% ee); Run 2 (½ scale) (6.9 mg, 43% yield, 82% ee); Average: 47% Yield, 82% ee.

Entry 5:

To a ½ dram vial was added ligand L1 (7.2 mg, 0.02 mmol, 0.1 equiv) and Pd(OAc)$_2$ (4.4 mg, 0.02 mmol, 0.1 equiv). Toluene (0.4 mL) was added, and the vial was capped and heated to 45° C. until all solids had dissolved. Separately, to a 1 dram vial with stir bar was added 1a (32.4 mg, 0.20 mmol, 1 equiv), 2,6-dimethylbenzoquinone (30 mg, 0.22 mmol, 1.1 equiv), and diphenylphosphinic acid (4.4 mg, 0.02 mmol, 0.1 equiv). The catalyst solution was subsequently added to the reaction flask, and toluene was used to rinse up to 1.3 mL toluene. The 1 dram vial was sealed with a Teflon cap, and allowed to stir for 8 hours at 45° C. Afterward, the vial was allowed to cool to room temperature. The majority of the toluene was removed under reduced pressure, and the remaining mixture was directly subjected to flash column chromatography (10% EtOAc in hexanes) to provide vinylisochroman 2a as a clear oil. Run 1 (20.1 mg, 63% yield, 87% ee); Run 2 (20.2 mg, 63% yield, 87% ee); Average: 63% Yield, 87% ee.

Under comparative conditions with L1 as a ligand, dibutyl phosphate ((nBnO)$_2$PO$_2$H), diphenyl phosphate ((PhO)$_2$PO$_2$H) and diphenylphosphinic acid (Ph$_2$PO$_2$H) all give major enhancements in reactivity (Entries 3, 4, 5, respectively). Between these organic phosphoric acids, it is possible the pKa of Ph$_2$PO$_2$H (2.30) is more optimal for this specific reaction than (nBuO)$_2$PO$_2$H (1.53) or (PhO)$_2$PO$_2$H (1.12)—pKa values obtained from SciFinder.cas.org, calculated using Advanced Chemistry Development (ACD/Labs) Software V11.02.

Entry 6:

General procedure: To a ½ dram vial was added ligand L2 (7.2 mg, 0.02 mmol, 0.1 equiv) and Pd(OAc)$_2$ (4.4 mg, 0.02 mmol, 0.1 equiv). Toluene (0.4 mL) was added, and the vial was capped and heated to 45° C. until all solids had dissolved. Separately, to a 1 dram vial with stir bar was added 1a (32.4 mg, 0.20 mmol, 1 equiv), 2,6-dimethylbenzoquinone (30 mg, 0.22 mmol, 1.1 equiv), and diphenylphosphinic acid (4.4 mg, 0.02 mmol, 0.1 equiv). The catalyst solution was subsequently added to the reaction flask, and toluene was used to rinse up to 1.3 mL toluene. The 1 dram vial was sealed with a Teflon cap, and allowed to stir for 8 hours at 45° C. Afterward, the vial was allowed to cool to room temperature. The majority of the toluene was removed under reduced pressure, and the remaining mixture was directly subjected to flash column chromatography (10% EtOAc in hexanes) to provide vinylisochroman 2a as a clear oil. Run 1 (11.8 mg, 37% yield, 19% ee); Run 2 (8.6 mg, 27% yield, 19% ee); Average: 32% Yield, 19% ee.

Entry 7:

Reaction proceeded according to the General procedure using ligand L3 (6.5 mg, 0.02 mmol, 0.1 equiv). Product isolated as a clear oil. Run 1 (10.4 mg, 33% yield, 78% ee); Run 2 (9.1 mg, 28% yield, 76% ee); Average: 31% Yield, 76% ee.

Entry 8:

Reaction proceeded according to the General procedure using ligand L4 (6.8 mg, 0.02 mmol, 0.1 equiv). Product isolated as a clear oil. Run 1 (3.1 mg, 10% yield, 29% ee); Run 2 (1.3 mg, 5% yield, 25% ee); Average: 8% Yield, 25% ee.

Entry 9:

Reaction proceeded according to the General procedure using ligand L5 (6.3 mg, 0.02 mmol, 0.1 equiv). Product isolated as a clear oil. Run 1 (6.1 mg, 19% yield, 88% ee); Run 2 (½ scale) (4.4 mg, 28% yield, 88% ee); Average: 24% Yield, 88% ee.

Entry 10:

Reaction proceeded according to the General procedure using ligand L6 (7.5 mg, 0.02 mmol, 0.1 equiv). Product isolated as a clear oil. Run 1 (18.6 mg, 58% yield, 88% ee); Run 2 (19.1 mg, 61% yield, 86% ee); Average: 60% Yield, 86% ee.

Entry 11:

Reaction proceeded according to the General procedure using ligand (S,R) tBu-ArSOX (L7) (8.1 mg, 0.02 mmol, 0.1 equiv). Product isolated as a clear oil. Run 1 (22.8 mg, 71% yield, 91% ee); Run 2 (22.5 mg, 70% yield, 92% ee); Average: 70% Yield, 92% ee.

Entry 12:

Reaction proceeded according to the General procedure using ligand (S,R) CF$_3$—ArSOX (L8) (8.3 mg, 0.02 mmol, 0.1 equiv). Product isolated as a clear oil. Run 1 (14.7 mg, 46% yield, 92% ee); Run 2 (16.5 mg, 52% yield, 93% ee); Average: 49% Yield, 93% ee.

Entry 13:

Reaction proceeded according to the General procedure for 72 hours at [0.5M] using ligand L9: Product isolated as a clear oil. (0.1 mmol scale) (4.9 mg, 31% yield, −6% ee). Reaction was also examined at standard [0.15M] concentration (72 h), resulting in slightly diminished reactivity: Run 1 (6.2 mg, 19% yield, −7% ee); Run 2 (½ scale) (3.0 mg, 19% yield, −6% ee); Average: 19% Yield, −6% ee.

Entry 14:

Reaction proceeded according to the General procedure for 72 hours at [0.5M] using ligand L10: Product yield determined by ¹HNMR by comparison to a nitrobenzene standard (0.1 mmol scale) (13% yield, 12% ee). Reaction was also examined at standard [0.15M] concentration (72 h): 8% Yield, 5% ee.

Entry 15:

Substrate 1a with L11 under Table 1-1 conditions: To a ½ dram vial was added ligand L11 (9.1 mg, 0.01 mmol, 0.1 equiv) and Pd(OAc)₂ (2.2 mg, 0.01 mmol, 0.1 equiv) under air. Toluene (0.2 mL) was added, and the vial was capped and heated to 45° C. until all solids had dissolved. Separately, to a ½ dram vial with stir bar was added 1a (16.2 mg, 0.10 mmol, 1 equiv), 2,6-dimethylbenzoquinone (15 mg, 0.11 mmol, 1.1 equiv) and diphenylphosphinic acid (2.2 mg, 0.01 mmol, 0.1 equiv) under air. The catalyst solution was subsequently added to the reaction flask, and toluene was used to rinse up to 0.6 mL toluene. The ½ dram vial was sealed with a Teflon cap, and allowed to stir for 8 hours at 45° C. Afterward, the vial was allowed to cool to room temperature. The majority of the toluene was removed under reduced pressure, and the remaining mixture was directly subjected to flash column chromatography (2%-10%-20% EtOAc/hexanes). Only trace product was detected, and the starting material was recovered: Run 1: (15.3 mg, 95% RSM) Run 2: (15.0 mg, 93% RSM).

Entry 15:

Substrate 1a with L11 under reported air-free conditions: A 10 ml Schlenk tube with stir bar was oven-dried and brought into glove box, where Pd(dba)₂ (2.9 mg, 0.005 mmol, 0.05 equiv.), ligand L11 (6.8 mg, 0.0075 mmol, 0.075 equiv.), DMBQ (16 mg, 0.12 mmol, 1.2 equiv.) and ortho-fluorobenzoic acid (1.4 mg, 0.01 mmol, 1 equiv.) was added. The Schlenk tube was then sealed and removed from glove box and charged with 0.4 ml MTBE under argon. The mixture was stirred at 45° C. for 15 minutes. After being cooled to room temperature, substrate (16.2 mg, 0.1 mmol, 1 equiv.) in 0.6 ml MTBE was added under argon. The resulting solution was subject to three freeze-pump-thaw cycles using liquid nitrogen to degas the solution. Then the solution was stirred at 45° C. for 12 hours. The reaction was cooled down to room temperature and concentrated under reduced pressure. The remaining mixture was directly subjected to flash column chromatography (2%-10%-20% EtOAc/hexanes). Only trace product (<5%) was detected, and the starting material was recovered (average: 79% recovered 1a; Run 1: 13.1 mg, 81% RSM; Run 2: 13.1 mg, 76% RSM).

Entry 16:

Reaction proceeded according to the General procedure using ligand (S,R) tBu-ArSOX (8.1 mg, 0.02 mmol, 0.1 equiv), and 1,4-benzoquinone (24 mg, 0.22 mmol, 1.1 equiv) (replacing 2,6-DMBQ). Product isolated as a clear oil. Run 1 (18.5 mg, 58% yield, 77% ee); Run 2 (18.8 mg, 59% yield, 77% ee); Average: 59% Yield, 77% ee.

Entry 17:

Reaction proceeded according to the General procedure using ligand L13 (7.8 mg, 0.02 mmol, 0.1 equiv). Product isolated as a clear oil. Run 1 (12.4 mg, 39% yield, 80% ee); Run 2 (12.1 mg, 38% yield, 83% ee); Average: 39% Yield, 80% ee.

Entry 18:

Reaction proceeded according to the General procedure using ligand L14 (8.6 mg, 0.02 mmol, 0.1 equiv). Product isolated as a clear oil. Run 1 (10.5 mg, 33% yield, 88% ee); Run 2 (11.3 mg, 35% yield, 87% ee); Average: 34% Yield, 88% ee.

Absolute stereochemistry for compound 2a (S-enantiomer) was assigned by matching the rotation of compound enant-2a (R-enantiomer) to the reported literature value (Miyata et al., *Angew. Chem. Int. Ed.* 2011. 50, 4649). The stereochemistry of all other compounds was assigned by analogy.

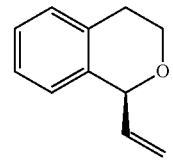

(2a)

(S)-1-vinylisochromane (2a): General Procedure

To a ½ dram vial was added ligand (S,R) tBu-ArSOX (8.1 mg, 0.02 mmol) and Pd(OAc)₂ (4.4 mg, 0.02 mmol). Toluene (0.4 mL) was added, and the vial was capped and heated to 45° C. until all solids had dissolved. Separately, to a 1 dram vial with stir bar was added 1a (32.4 mg, 0.20 mmol), 2,6-dimethylbenzoquinone (30 mg, 0.22 mmol), and diphenylphosphinic acid (4.4 mg, 0.02 mmol) with no precautions to exclude air or moisture. The catalyst solution was subsequently added to the reaction flask, and toluene was used to rinse up to 1.3 mL toluene. The 1 dram vial was sealed with a Teflon cap, and allowed to stir for 8 hours at 45° C., until complete conversion of the starting material was observed by TLC. Afterward, the vial was allowed to cool to room temperature. The majority of the toluene was removed under reduced pressure, and the remaining mixture was directly subjected to flash column chromatography (10% EtOAc in hexanes) to provide the vinylisochroman as a clear oil. Run 1 (22.8 mg, 71% yield); Run 2 (22.5 mg, 70% yield); Run 3 (22.2 mg, 70% yield). Average: 70% Yield. The enantiomeric excess was determined to be 92% by chiral GC analysis (Cyclosil-B, 100° C. isothermal, $t_R$(major)=32.78 min, $t_R$(minor)=35.08 min.) $[\alpha]^{21}_D$=+9.66 (c=1, CHCl₃). ¹H NMR (500 MHz, CDCl₃) δ 7.22-7.18 (m, 2H), 7.16-7.13 (m, 1H), 7.09-7.06 (m, 1H), 5.99 (ddd, J=17.2, 10.1, 7.3 Hz, 1H), 5.40 (d, J=17.2 Hz, 1H), 5.37 (d, J=10.1 Hz, 1H), 5.18 (d, J=7.5 Hz, 1H), 4.19 (dt, J=11.3, 4.9 Hz, 1H), 3.89 (ddd, J=11.4, 9.0, 4.1 Hz, 1H), 3.00 (ddd, J=16.5, 8.8, 5.1 Hz, 1H), 2.78 (dt, J=16.1, 4.1 Hz, 1H); ¹³C NMR (125 MHz, CDCl₃) δ 138.3, 136.4, 133.8, 129.2, 126.9, 126.3, 126.2, 118.8, 78.4, 63.4, 29.0; HRMS (EI) m/z calc'd for C₁₁H₁₂O [M]+: 160.0888; found 160.0879. Spectral data is consistent with data in previous literature. Note: at this time, 10 mol % catalyst loading is required for reactivity: A reaction run according to the general procedure (developed for 10 mol % catalyst loading) with 1 mol % Pd(OAc)₂ and 1 mol % tBuArSOX for 72 hours resulted in significantly diminished yield of 2a: 8% yield, 80% recovered starting material.

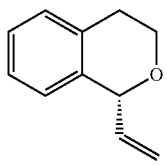

(enant-2a)

(R)-1-vinylisochromane (enant-2a)

Reaction procedure is identical to that above, except (R,S) tBu-ArSOX (enant-L7) was used as the ligand. 22.3 mg, 70% Yield. The enantiomeric excess was determined to be 92% by chiral GC analysis (Cyclosil-B, 100° C. isothermal, $t_R$(minor)=33.54 min, $t_R$(major)=34.35 min.) $[\alpha]^{21}_D$=−9.45 (c=1, CHCl$_3$). Rotation is consistent with reported literature for the (R) enantiomer:[11] (Lit: >99% ee: $[\alpha]^{22}_D$=−10.9 (c=1, CHCl$_3$)).

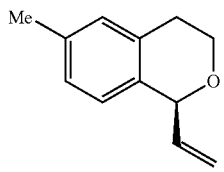

(2b)

(S)-6-methyl-1-vinylisochromane (2b)

2-(2-allyl-5-methylphenyl)ethan-1-ol (1b) (35.2 mg, 0.20 mmol) was reacted according to the general procedure. Purification by flash column chromatography (2% EtOAc in hexanes) provided the vinylisochroman as a clear oil. Run 1 (25.1 mg, 72% yield); Run 2 (23.6 mg, 68% yield); Run 3 (23.6 mg, 68% yield). Average: 69% Yield. The enantiomeric excess was determined to be 92% by chiral HPLC analysis (CHIRALPAK AD-RH column, 0.5 mL/min, 50% MeCN in H$_2$O, λ=214.4 nm): $t_R$(major)=18.263 min, $t_R$(minor)=25.081 min. $[\alpha]^{24}_D$=+20.7° (c=1, CHCl$_3$); $^1$H NMR (500 MHz, Chloroform-d) δ 7.02-6.92 (m, 3H), 5.96 (ddd, J=17.3, 10.2, 7.4 Hz, 1H), 5.38 (d, J=17.3 Hz, 1H), 5.34 (d, J=10.5 Hz, 1H), 5.13 (d, J=7.3 Hz, 1H), 4.16 (dt, J=11.5, 4.9 Hz, 1H), 3.86 (ddd, J=11.3, 9.0, 4.1 Hz, 1H), 2.95 (ddd, J=15.0, 8.9, 5.3 Hz, 1H), 2.72 (dt, J=16.5, 4.2 Hz, 1H), 2.32 (s, 3H); $^{13}$C NMR (126 MHz, CDCl$_3$) δ 138.44, 136.48, 133.64, 133.39, 129.67, 127.08, 126.24, 118.55, 78.36, 63.48, 28.99, 21.27; HRMS (EI) m/z calc'd for C$_{12}$H$_{14}$O [M]+: 174.1045; found 174.1044.

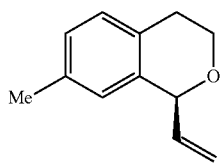

(1c)

(S)-7-methyl-1-vinylisochromane (2c)

2-(2-allyl-4-methylphenyl)ethan-1-ol (1c) (35.2 mg, 0.20 mmol) was reacted according to the general procedure. Purification by flash column chromatography (2% EtOAc in hexanes) provided the vinylisochroman as a clear oil. Run 1 (24.1 mg, 69% yield); Run 2 (23.5 mg, 68% yield); Run 3 (23.9 mg, 68% yield). Average: 68% Yield. The enantiomeric excess was determined to be 93% by chiral HPLC analysis (CHIRALPAK AD-RH column, 0.5 mL/min, 50% MeCN in H$_2$O, λ=214.4 nm): $t_R$(major)=16.639 min, $t_R$(minor)=19.879 min. $[\alpha]^{26}_D$=−6.4° (c=1, CHCl$_3$); $^1$H NMR (500 MHz, Chloroform-d) δ 7.07-6.98 (m, 2H), 6.87 (s, 1H), 5.97 (ddd, J=17.3, 10.1, 7.4 Hz, 1H), 5.40 (dt, J=17.1, 1.3 Hz, 1H), 5.35 (ddd, J=10.3, 1.8, 0.9 Hz, 1H), 5.12 (d, J=7.3 Hz, 1H), 4.16 (ddd, J=11.4, 5.3, 4.3 Hz, 1H), 3.85 (ddd, J=11.3, 8.9, 4.0 Hz, 1H), 2.94 (ddd, J=15.1, 9.0, 5.3 Hz, 1H), 2.72 (dt, J=16.2, 4.3 Hz, 1H), 2.31 (s, 3H); $^{13}$C NMR (126 MHz, CDCl$_3$) δ 138.35, 136.15, 135.75, 130.69, 129.03, 127.77, 126.76, 118.71, 78.49, 63.62, 28.64, 21.41; HRMS (EI) m/z calc'd for C$_{12}$H$_{14}$O [M]+: 174.1045; found 174.1044.

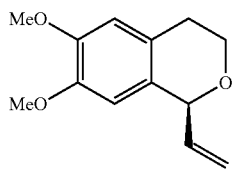

(2d)

(S)-6,7-dimethoxy-1-vinylisochromane (2d)

Reaction proceeded according to a modified procedure: To a ½ dram vial was added ligand (R,S) CF$_3$—ArSOX (8.3 mg, 0.02 mmol) and Pd(OAc)$_2$ (4.4 mg, 0.02 mmol). Toluene (0.4 mL) was added, and the vial was capped and heated to 45° C. until all solids had dissolved. Separately, to a 1 dram vial with stir bar was added 1d (44.4 mg, 0.20 mmol), 2,6-dimethylbenzoquinone (30 mg, 0.22 mmol), and diphenylphosphinic acid (4.4 mg, 0.02 mmol). The catalyst solution was subsequently added to the reaction flask, and toluene was used to rinse up to 1.3 mL toluene. The 1 dram vial was sealed with a Teflon cap, and allowed to stir for 8 hours at 45° C. Afterward, the vial was allowed to cool to room temperature. The majority of the toluene was removed under reduced pressure, and the remaining mixture was directly subjected to flash column chromatography (10% EtOAc in hexanes) to provide the vinylisochroman as a clear oil. Run 1 (26.2 mg, 59% yield); Run 2 (29.3 mg, 67% yield); Run 3 (29.0 mg, 66% yield). Average: 64% Yield. The enantiomeric excess was determined to be 95% by chiral GC analysis (Cyclosil-B, 160° C. isothermal, $t_R$(major)=23.47 min, $t_R$(minor)=24.24 min.) $[\alpha]^{22}_D$=+31.37 (c=0.26, CH$_2$Cl$_2$). $^1$H NMR (500 MHz, CDCl$_3$) δ 6.64 (s, 1H), 6.55 (s, 1H), 5.98 (ddd, J=17.1, 10.0, 7.6 Hz, 1H), 5.41 (d, J=17.1 Hz, 1H), 5.37 (d, J=10.1 Hz, 1H), 5.11 (d, J=7.3 Hz, 1H), 4.17 (dt, J=11.2, 4.4 Hz, 1H), 3.89 (s, 3H), 3.89-3.85 (m, 1H), 3.85 (s, 3H), 2.97-2.89 (m, 1H), 2.70 (dt, J=16.1, 3.7 Hz, 1H); $^{13}$C NMR (125 MHz, CDCl$_3$) δ 148.1, 147.6, 138.5, 128.1, 125.9, 118.8, 111.7, 109.2, 78.2, 63.5, 56.2, 56.1, 28.5; HRMS (EI) m/z calc'd for C$_{13}$H$_{16}$O$_3$ [M]+: 220.1099; found 220.1105.

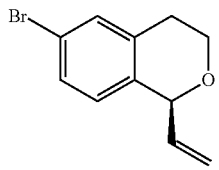

(S)-6-bromo-1-vinylisochromane (2e)

2-(2-allyl-5-bromophenyl)ethan-1-ol (1e) (48.2 mg, 0.20 mmol) was reacted according to the general procedure for 9 hours. Purification by flash column chromatography (2% EtOAc in hexanes) provided the vinylisochroman as a clear oil. Run 1 (36.1 mg, 75% yield); Run 2 (36.9 mg, 76% yield); Run 3 (37.5 mg, 78% yield). Average: 76% Yield. The enantiomeric excess was determined to be 93% by chiral HPLC analysis (CHIRALPAK OJ-H column, 1 mL/min, 0.5% isopropanol in hexane, λ=230.4 nm): $t_R$(major)=6.739 min, $t_R$(minor)=7.702 min. $[\alpha]^{22}_D$=+19.6° (c=1, CHCl$_3$); $^1$H NMR (500 MHz, Chloroform-d) δ 7.31-7.27 (m, 2H), 6.92 (d, J=8.8 Hz, 1H), 5.93 (ddd, J=16.8, 10.2, 7.3 Hz, 1H), 5.40-5.34 (m, 2H), 5.08 (d, J=7.3 Hz, 1H), 4.13 (dt, J=11.4, 4.9 Hz, 1H), 3.83 (ddd, J=11.4, 8.8, 4.1 Hz, 1H), 2.95 (ddd, J=16.7, 8.8, 5.4 Hz, 1H), 2.73 (dt, J=16.5, 4.3 Hz, 1H); $^{13}$C NMR (126 MHz, CDCl$_3$) δ 137.71, 136.15, 135.31, 131.86, 129.33, 128.13, 120.68, 119.28, 78.05, 63.01, 28.74; HRMS (EI) m/z calc'd for C$_{11}$H$_{11}$OBr [M]+: 237.9993; found 237.9990.

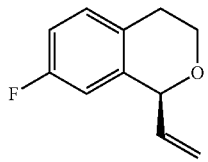

(S)-7-fluoro-1-vinylisochromane (2f)

2-(2-allyl-4-fluorophenyl)ethan-1-ol (1f) (36.0 mg, 0.20 mmol) was reacted according to the general procedure for 10 hours at 45° C. Purification by flash column chromatography (10% EtOAc in hexanes) provided the vinylisochroman as a clear oil. Run 1 (24.0 mg, 67% yield); Run 2 (21.6 mg, 61% yield); Run 3 (20.4 mg, 57% yield). Average: 61% Yield. The enantiomeric excess was determined to be 91% by chiral GC analysis (Cyclosil-B, 100° C. isothermal, $t_R$(major)=38.54 min, $t_R$(minor)=42.72 min.) $[\alpha]^{22}_D$=+10.28 (c=0.25, CH$_2$Cl$_2$). $^1$H NMR (500 MHz, CDCl$_3$) δ 7.12 (dd, J=8.3, 6.5 Hz, 1H), 6.93 (dt, J=8.5, 2.3 Hz, 1H), 6.81 (dd, J=9.5, 2.4 Hz, 1H), 5.98 (ddd, J=17.6, 10.3, 7.6 Hz, 1H), 5.44 (dt, J=17.1, 1.5 Hz, 1H), 5.42 (d, J=10.3 Hz, 1H), 5.14 (d, J=7.3 Hz, 1H), 4.20 (ddd, J=11.5, 5.4, 4.4 Hz, 1H), 3.88 (ddd, J=11.5, 9.0, 4.2 Hz, 1H), 2.98 (ddd, J=15.9, 9.0, 5.4 Hz, 1H), 2.76 (dt, J=16.1, 3.9 Hz, 1H); $^{13}$C NMR (125 MHz, CDCl$_3$) δ 161.3 (d, J=242.8 Hz), 138.2 (d, J=6.5 Hz), 137.6, 130.5 (d, J=7.3 Hz) 129.3 (d, J=2.8 Hz), 119.4, 114.1 (d, J=22.0 Hz), 112.9 (d, J=22.0 Hz), 78.3, 63.5, 28.2; $^{19}$F NMR (470 MHz, CDCl$_3$) δ -116.6; HRMS (EI) m/z calc'd for C$_{11}$H$_{11}$OF [M]+: 178.0794; found 178.0790.

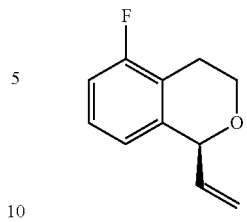

(S)-5-fluoro-1-vinylisochromane (2g)

2-(2-allyl-6-fluorophenyl)ethan-1-ol (1g) (36.0 mg, 0.20 mmol) was reacted according to the general procedure. Purification by flash column chromatography (10% EtOAc in hexanes) provided the vinylisochroman as a clear oil. Run 1 (22.1 mg, 62% yield); Run 2 (23.9 mg, 67% yield); Run 3 (22.9 mg, 64% yield). Average: 64% Yield. The enantiomeric excess was determined to be 92% by chiral GC analysis (Cyclosil-B, 100° C. isothermal, $t_R$(major)=34.44 min, $t_R$(minor)=37.65 min.) $[\alpha]^{23}_D$=+2.37 (c=0.25, CH$_2$Cl$_2$). $^1$H NMR (500 MHz, CDCl$_3$) δ 7.20-7.14 (m, 1H), 6.94 (t, J=9.0 Hz, 1H), 6.88 (d, J=7.8 Hz, 1H), 5.99 (ddd, J=17.1, 10.3, 7.1 Hz, 1H), 5.41 (d, J=18.3 Hz, 1H), 5.40 (d, J=10.3 Hz, 1H), 5.17 (d, J=7.1 Hz, 1H), 4.21 (dt, J=11.5, 5.4 Hz, 1H), 3.89 (ddd, J=11.5, 8.3, 4.4 Hz, 1H), 2.89 (ddd, J=13.7, 8.3, 5.6 Hz, 1H), 2.82 (dt, J=17.3, 4.4 Hz, 1H); $^{13}$C NMR (125 MHz, CDCl$_3$) δ 160.7 (d, J=243.6 Hz), 138.6 (d, J=5.5 Hz), 137.7, 126.9 (d, J=8.3 Hz), 121.7 (d, J=3.6 Hz), 121.5 (d, J=19.1 Hz), 119.3, 113.2 (d, J=21.1 Hz), 77.9, 62.6, 22.2; $^{19}$F NMR (470 MHz, CDCl$_3$) δ -120.1; HRMS (EI) m/z calc'd for C$_{11}$H$_{11}$OF [M]+: 178.0794; found 178.0787.

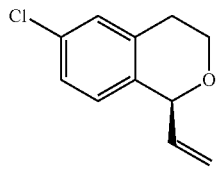

(S)-6-chloro-1-vinylisochromane (2h)

2-(2-allyl-5-chlorophenyl)ethan-1-ol (1h) (39.3 mg, 0.20 mmol) was reacted according to the general procedure for 10 hours at 45° C. Purification by flash column chromatography (10% EtOAc in hexanes) provided the vinylisochroman as a clear oil. Run 1 (20.2 mg, 52% yield); Run 2 (22.2 mg, 57% yield) Run 3 (22.1 mg, 57% yield). Average: 55% Yield. The enantiomeric excess was determined to be 92% by chiral GC analysis (Cyclosil-B, 120° C. isothermal, $t_R$(major)=49.51 min, $t_R$(minor)=54.03 min.) $[\alpha]^{22}_D$=+16.95 (c=0.25, CH$_2$Cl$_2$). $^1$H NMR (500 MHz, CDCl$_3$) δ 7.20-7.15 (m, 2H), 7.01 (d, J=8.1 Hz, 1H), 5.98 (ddd, J=17.6, 9.8, 7.3 Hz, 1H), 5.41 (d, J=17.1 Hz, 1H), 5.40 (d, J=10.7 Hz, 1H), 5.15 (d, J=7.1 Hz, 1H), 4.18 (dt, J=11.5, 4.9 Hz, 1H), 3.80 (ddd, J=11.5, 8.8, 4.1 Hz, 1H), 2.99 (ddd, J=16.6, 8.5, 5.1 Hz, 1H), 2.78 (dt, J=16.3, 4.2 Hz, 1H); $^{13}$C NMR (125 MHz, CDCl$_3$) δ 137.8, 135.8, 134.8, 132.6, 128.9, 127.8, 126.4, 119.2, 78.0, 63.0, 28.8; HRMS (EI) m/z calc'd for C$_{11}$H$_{11}$OCl [M]+: 194.0498; found 194.0499.

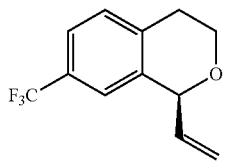

(S)-7-(trifluoromethyl)-1-vinylisochromane (2i)

Reaction proceeded according to a modified procedure: To a ½ dram vial was added ligand (S,R) CF$_3$—ArSOX (8.3 mg, 0.02 mmol) and Pd(OAc)$_2$ (4.4 mg, 0.02 mmol). Toluene (0.4 mL) was added, and the vial was capped and heated to 45° C. until all solids had dissolved. Separately, to a 1 dram vial with stir bar was added 1i (46.0 mg, 0.20 mmol), 2,6-dimethylbenzoquinone (30 mg, 0.22 mmol), and diphenylphosphinic acid (4.4 mg, 0.02 mmol). The catalyst solution was subsequently added to the reaction flask, and toluene was used to rinse up to 1.3 mL toluene. The 1 dram vial was sealed with a Teflon cap, and allowed to stir for 48 hours at 45° C. Afterward, the vial was allowed to cool to room temperature. The majority of the toluene was removed under reduced pressure, and the remaining mixture was directly subjected to flash column chromatography (10% EtOAc in hexanes) to provide the vinylisochroman as a clear oil. Run 1 (½ scale) (14.3 mg, 62% yield); Run 2 (24.9 mg, 55% yield); Run 3 (23.6 mg, 52% yield). Average: 56% Yield. The enantiomeric excess was determined to be 92% by chiral GC analysis (Cyclosil-B, 120° C. isothermal, t$_R$(major)=15.19 min, t$_R$(minor)=16.62 min.) [α]$^{22}_D$=+7.32 (c=0.25, CH$_2$Cl$_2$). $^1$H NMR (500 MHz, CDCl$_3$) δ 7.43 (d, J=7.7 Hz, 1H), 7.31-7.22 (m, 2H), 5.96 (ddd, J=17.4, 9.9, 7.5 Hz, 1H), 5.42 (d, J=15.0 Hz, 1H), 5.41 (d, J=10.7 Hz, 1H), 5.16 (d, J=7.5 Hz, 1H), 4.19 (dt, J=11.4, 5.4 Hz, 1H), 3.87 (ddd, J=11.4, 8.8, 3.9 Hz, 1H), 3.06-2.98 (m, 1H), 2.82 (d, J=16.7 Hz, 1H); $^{13}$C NMR (125 MHz, CDCl$_3$) δ 138.0, 137.3, 137.1, 129.6, 128.6 (q, J=32.9 Hz), 124.4 (q, J=271.0 Hz), 123.6 (q, J=3.6 Hz), 123.3 (q, J=3.6 Hz), 119.9, 78.3, 63.1, 28.9; $^{19}$F NMR (470 MHz, CDCl$_3$) δ −62.8; HRMS (EI) m/z calc'd for C$_{12}$H$_{10}$OF$_3$ [M−H]+: 227.0684; found 227.0685.

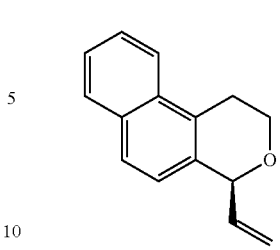

(S)-4-vinyl-1,4-dihydro-2H-benzo[f]isochromene (2j)

2-(2-allylnaphthalen-1-yl)ethan-1-ol (1j) (42.5 mg, 0.20 mmol) was reacted according to the general procedure. Purification by flash column chromatography (10% EtOAc in hexanes) provided the vinylisochroman as a clear oil. Run 1 (34.5 mg, 80% yield); Run 2 (30.7 mg, 73% yield); Run 3 (29.9 mg, 71% yield). Average: 75% Yield. The enantiomeric excess was determined to be 93% by chiral GC analysis (Cyclosil-B, 160° C. isothermal, t$_R$(major)=45.98 min, t$_R$(minor)=48.09 min.) [α]$^{23}_D$=+74.03 (c=0.25, CH$_2$Cl$_2$). $^1$H NMR (500 MHz, CDCl$_3$) δ 7.99 (d, J=8.5 Hz, 1H), 7.87 (d, J=8.1 Hz, 1H), 7.73 (d, J=8.5 Hz, 1H), 7.59 (td, J=8.3, 1.2 Hz, 1H), 7.54 (td, J=8.1, 1.0 Hz, 1H), 7.24 (d, J=8.5 Hz, 1H), 6.08 (ddd, J=17.3, 10.3, 7.3 Hz, 1H), 5.47 (d, J=17.3 Hz, 1H), 5.44 (d, J=11.7 Hz, 1H), 5.36 (d, J=7.3 Hz, 1H), 4.37 (dt, J=11.5, 5.1 Hz, 1H), 4.07 (ddd, J=11.5, 7.8, 4.6 Hz, 1H), 3.00 (dt, J=16.6, 6.3 Hz, 1H), 3.19 (dt, J=16.6, 4.6 Hz, 1H); $^{13}$C NMR (125 MHz, CDCl$_3$) δ 138.2, 133.1, 132.5, 132.2, 129.3, 128.8, 126.5, 126.4, 125.8, 124.5, 123.1, 119.2, 78.3, 62.8, 25.6; HRMS (EI) m/z calc'd for C$_{15}$H$_{14}$O [M]+: 210.1045; found 210.1042.

Catalytic Influence on Chiral Substrates Experiments

TABLE 1-2

| Entry | Ligand | % yield | d.r. (4a:4b) |
|---|---|---|---|
| 1 | meso-1,2-bis(phenylsulfinyl)ethane (L10) | 16 | 1.5:1 |
| 2 | (S,R) tBu-ArSOX | 62 | >20:1 |
| 3 | (R,S) tBu-ArSOX | 49 | 1:2.8 |

Entry 1:

To a 1 dram vial with stir bar was added (R)-1-(2-allylphenyl)propan-2-ol 3 (35.3 mg, 0.20 mmol, 1 equiv), 2,6-dimethylbenzoquinone (30 mg, 0.22 mmol, 1.1 equiv), diphenylphosphinic acid (4.4 mg, 0.02 mmol, 0.1 equiv), meso-1,2-bis(phenylsulfinyl)ethane (L10) (5.6 mg, 0.02 mmol, 0.1 equiv) and Pd(OAc)$_2$ (4.4 mg, 0.02 mmol, 0.1 equiv). Toluene (0.4 mL) was added, and the vial was sealed with a Teflon cap and allowed to stir for 72 hours at 45° C. Afterward, the vial was allowed to cool to room temperature, and the solvent was removed under reduced pressure. A crude HNMR was used for determination of the diastereomer ratio, and crude mixture was subjected directly to flash column chromatography (10% EtOAc in hexanes) to provide a mixture of cis/trans isomers as a clear oil. Run 1 (7.4 mg, 21% yield); Run 2 (4.5 mg, 13% yield) Run 3 (5.4 mg, 15% yield). Average: 16% Yield, 1.5:1 cis:trans d.r.

Entry 2:

To a ½ dram vial was added ligand (S,R) tBu-ArSOX (8.1 mg, 0.02 mmol, 0.1 equiv) and Pd(OAc)₂ (4.4 mg, 0.02 mmol, 0.1 equiv). Toluene (0.4 mL) was added, and the vial was capped and heated to 45° C. until all solids had dissolved. Separately, to a 1 dram vial with stir bar was added (R)-1-(2-allylphenyl)propan-2-ol 3 (35.3 mg, 0.20 mmol, 0.1 equiv), 2,6-dimethylbenzoquinone (30 mg, 0.22 mmol, 1.1 equiv), and diphenylphosphinic acid (4.4 mg, 0.02 mmol, 0.1 equiv). The catalyst solution was subsequently added to the reaction flask, and toluene was used to rinse up to 1.3 mL toluene. The 1 dram vial was sealed with a Teflon cap, and allowed to stir for 15 hours at 45° C. Afterward, the vial was allowed to cool to room temperature, and the solvent was removed under reduced pressure. A crude HNMR was used for determination of the diastereomer ratio, and crude mixture was subjected directly to flash column chromatography (10% EtOAc in hexanes) to provide cis-vinylisochroman 4a as a clear oil. Run 1 (21.0 mg, 60% yield); Run 2 (23.0 mg, 66% yield) Run 3 (21.4 mg, 61% yield). Average: 62% Yield, >20:1 cis:trans d.r.

Entry 3:

To a ½ dram vial was added ligand (R,S) tBu-ArSOX (8.1 mg, 0.02 mmol, 0.1 equiv) and Pd(OAc)₂ (4.4 mg, 0.02 mmol, 0.1 equiv). Toluene (0.2 mL) was added, and the vial was capped and heated to 45° C. until all solids had dissolved. Separately, to a 1 dram vial with stir bar was added (R)-1-(2-allylphenyl)propan-2-ol 3 (35.3 mg, 0.20 mmol, 0.1 equiv), 2,6-dimethylbenzoquinone (30 mg, 0.22 mmol, 1.1 equiv), and diphenylphosphinic acid (4.4 mg, 0.02 mmol, 0.1 equiv). The catalyst solution was subsequently added to the reaction flask, and toluene was used to rinse up to 0.4 mL toluene. The 1 dram vial was sealed with a Teflon cap, and allowed to stir for 48 hours at 45° C. Afterward, the vial was allowed to cool to room temperature, and the solvent was removed under reduced pressure. A crude HNMR was used for determination of the diastereomer ratio, and crude mixture was subjected directly to flash column chromatography (10% EtOAc in hexanes) to provide a mixture of cis/trans isomers as a clear oil. Run 1 (½ scale) (9.0 mg, 52% yield); Run 2 (17.0 mg, 48% yield) Run 3 (16.5 mg, 47% yield). Average: 49% Yield, 1:2.83 cis:trans d.r.

Entry 1:

To a 1 dram vial with stir bar was added (R)-2-(2-allylphenyl)propan-1-ol (5) (35.3 mg, 0.20 mmol, 1 equiv), 2,6-dimethylbenzoquinone (30 mg, 0.22 mmol, 1.1 equiv), diphenylphosphinic acid (4.4 mg, 0.02 mmol, 0.1 equiv), meso-1,2-bis(phenylsulfinyl)ethane (L10) (5.6 mg, 0.02 mmol, 0.1 equiv) and Pd(OAc)₂ (4.4 mg, 0.02 mmol, 0.1 equiv). Toluene (1.3 mL) was added, and the vial was sealed with a Teflon cap and allowed to stir for 72 hours at 45° C. Afterward, the vial was allowed to cool to room temperature, and the solvent was removed under reduced pressure. The crude mixture was subjected directly to flash column chromatography (10% EtOAc in hexanes) to provide a mixture of cis/trans isomers as a clear oil. Run 1 (21.7 mg, 62% yield); Run 2 (21.6 mg, 62% yield) Run 3 (19.9 mg, 57% yield). Average: 60% Yield, 3.6:1 cis:trans d.r.

Entry 2:

To a ½ dram vial was added ligand (S,R) tBu-ArSOX (8.1 mg, 0.02 mmol, 0.1 equiv) and Pd(OAc)₂ (4.4 mg, 0.02 mmol, 0.1 equiv). Toluene (0.4 mL) was added, and the vial was capped and heated to 45° C. until all solids had dissolved. Separately, to a 1 dram vial with stir bar was added (R)-2-(2-allylphenyl)propan-1-ol 5 (35.3 mg, 0.20 mmol, 0.1 equiv), 2,6-dimethylbenzoquinone (30 mg, 0.22 mmol, 1.1 equiv), and diphenylphosphinic acid (4.4 mg, 0.02 mmol, 0.1 equiv). The catalyst solution was subsequently added to the reaction flask, and toluene was used to rinse up to 1.3 mL toluene. The 1 dram vial was sealed with a Teflon cap, and allowed to stir for 3 hours at 45° C. Afterward, the vial was allowed to cool to room temperature, and the solvent was removed under reduced pressure. The crude mixture was subjected directly to flash column chromatography (10% EtOAc in hexanes) to provide cis-vinylisochroman 6a as a clear oil. Run 1 (23.7 mg, 68% yield); Run 2 (22.8 mg, 65% yield) Run 3 (23.5 mg, 67% yield). Average: 67% Yield, >20:1 cis:trans d.r.

Entry 3:

To a ½ dram vial was added ligand (R,S) tBu-ArSOX (8.1 mg, 0.02 mmol, 0.1 equiv) and Pd(OAc)₂ (4.4 mg, 0.02 mmol, 0.1 equiv). Toluene (0.4 mL) was added, and the vial was capped and heated to 45° C. until all solids had dissolved. Separately, to a 1 dram vial with stir bar was added (R)-2-(2-allylphenyl)propan-1-ol 5 (35.3 mg, 0.20 mmol, 0.1 equiv), 2,6-dimethylbenzoquinone (30 mg, 0.22 mmol, 1.1 equiv), and diphenylphosphinic acid (4.4 mg, 0.02 mmol, 0.1 equiv). The catalyst solution was subse-

TABLE1-3

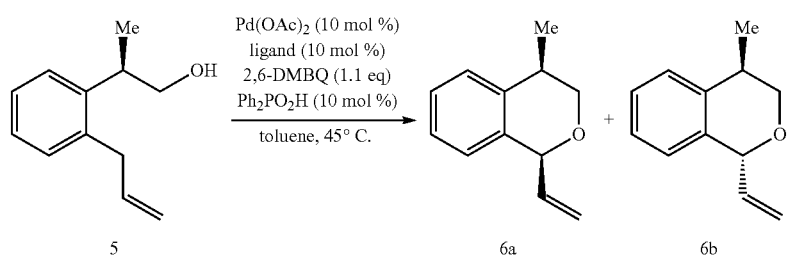

| Entry | Ligand | % Yield | d.r. (6a:6b) |
|---|---|---|---|
| 1 | meso-1,2-bis(phenylsulfinyl)ethane (L10) | 60 | 3.6:1 |
| 2 | (S,R) tBu-ArSOX | 67 | >20:1 |
| 3 | (R,S) tBu-ArSOX | 68 | 1:1.4 | quently added to the reaction flask, and toluene was used to rinse up to 1.3 mL. The 1 dram vial was sealed with a Teflon cap, and allowed to stir for 8 hours at 45° C. Afterward, the vial was allowed to cool to room temperature, and the solvent was removed under reduced pressure. The crude mixture was subjected directly to flash column chromatography (10% EtOAc in hexanes) to provide a mixture of cis/trans isomers as a clear oil. Run 1 (23.0 mg, 66% yield); Run 2 (22.9 mg, 66% yield) Run 3 (24.7 mg, 71% yield). Average: 68% Yield, 1:1.4 cis:trans d.r.

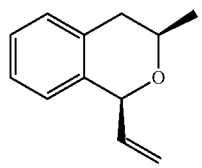

(4a)

(1S,3R)-3-methyl-1-vinylisochromane (4a)

$^1$H NMR (500 MHz, CDCl$_3$) δ 7.23-7.20 (m, 2H), 7.15-7.10 (m, 2H), 5.95 (ddd, J=17.1, 10.3, 8.3 Hz, 1H), 5.52 (dd, J=17.1, 1.7 Hz, 1H), 5.42 (dd, J=10.0, 1.7 Hz, 1H), 5.20 (d, J=8.1 Hz, 1H), 3.95 (m, 1H), 2.81 (dd, J=16.1, 10.7 Hz, 1H), 2.74 (dd, J=16.1, 2.9 Hz, 1H), 1.43 (d, J=6.1 Hz, 3H); $^{13}$C NMR (125 MHz, CDCl$_3$) δ 138.2, 136.5, 134.1, 128.9, 126.9, 126.3, 125.9, 119.2, 80.2, 70.8, 36.6, 22.1; [α]$^{23}_D$=−34.28° (c=0.25, CH$_2$Cl$_2$); HRMS (EI) m/z calc'd for C$_{12}$H$_{14}$O [M]+: 174.1045; found 174.1045. Cis-ring geometry was established by 1D $^1$HNOE spectral data:

Scheme 1-4: nOe Assignment of 4a.

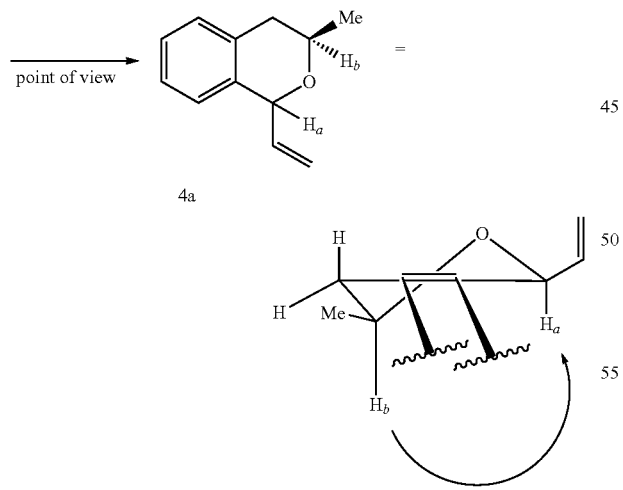

4a (500 MHz, CDCl$_3$) The ethereal proton peak at δ 3.95 (H$_b$) was irradiated, and the resulting observed relationship is illustrated above. 4a gave a characteristic nOe between the pseudo-axial ethereal proton H$_b$ and the pseudo-axial ethereal proton H$_a$ (δ 5.20), indicating a cis-relationship between H$_a$ and H$_b$ for 4a.

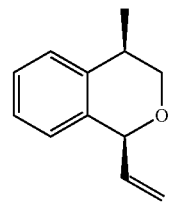

(6a)

(1S,4R)-4-methyl-1-vinylisochromane (6a)

$^1$H NMR (500 MHz, CDCl$_3$) δ 7.25-7.17 (m, 3H), 7.07 (d, J=7.5 Hz, 1H), 6.00 (ddd, J=17.6, 9.9, 7.9 Hz, 1H), 5.44 (d, J=17.2 Hz, 1H), 5.38 (d, J=10.3 Hz, 1H), 5.15 (d, J=7.5 Hz, 1H), 3.95 3.89 (ABq d, J$_{AB}$=11.4 Hz, J$_d$=3.6 Hz, 2H), 2.90-2.84 (m, 1H), 1.38 (d, J=7.1 Hz, 3H); $^{13}$C NMR (125 MHz, CDCl$_3$) δ 139.4, 138.4, 135.8, 128.5, 127.1, 126.2, 126.1, 118.9, 78.9, 69.4, 32.8, 21.0; [α]$^{23}_D$=+37.49° (c=0.25, CH$_2$Cl$_2$); HRMS (EI) m/z calc'd for C$_{12}$H$_{14}$O [M]+: 174.1045; found 174.1043. Cis-ring geometry was established by comparison with similar known structures, and by 1D NOE spectral data of the trans-diastereomer 6b.

Scheme 1-5: nOe Assignment of 6b.

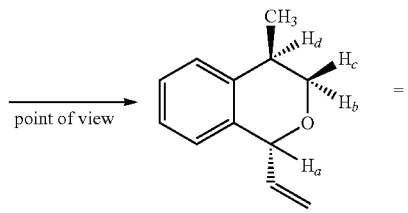

6b (500 MHz, CDCl$_3$) Unfortunately, no useful nOe data was able to be gained from 6a. Therefore, nOe data was obtained from using the inseparable mixture of 6a and 6b, and selectively irradiating protons of the trans-isomer 6b. The ethereal proton peak at δ 3.58 (H$_c$) was irradiated, and the resulting observed relationship is illustrated above. 6b gave a characteristic nOe between the pseudo-axial ethereal proton H$_c$ and the pseudo-axial ethereal proton H$_a$ (δ 5.22), indicating a cis-relationship between H$_c$ and H$_a$ for 6b. H$_c$ also gave an nOe with the geminal ethereal proton $H_b$ (δ 4.18), and the protons on the methyl group (δ 1.33). The ethereal proton peak at δ 4.18 ($H_b$) was irradiated, and did not give an nOe with $H_a$ but instead gave an nOe with the geminal ethereal proton $H_c$ (δ 3.58), the methyl protons (δ 1.33) and the methine proton at δ 3.08 ($H_d$). This data is indicative of the trans-geometry of 6b, and thus 6a has cis-geometry.

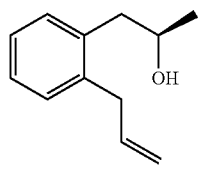

(3)

(R)-1-(2-allylphenyl)propan-2-ol (3)

Product is a clear oil. $^1$H NMR (500 MHz, Chloroform-d) δ 7.20 (s, 4H), 5.98 (ddt, J=16.6, 10.0, 6.2 Hz, 1H), 5.09 (dt, J=10.0, 1.4 Hz, 1H), 5.00 (dt, J=17.1, 1.7 Hz, 1H), 4.08-3.96 (m, 1H), 3.45 (ddd, J=6.1, 4.0, 2.1 Hz, 2H), 2.86-2.71 (m, 2H), 1.98-1.75 (br, 1H), 1.27 (d, J=6.1 Hz, 3H); $^{13}$C NMR (126 MHz, CDCl$_3$) δ 138.59, 137.52, 137.04, 130.73, 130.23, 127.03, 126.71, 116.10, 68.64, 42.69, 37.40, 23.30; $[α]^{26}_D$=−41.8° (c=1.00, CHCl$_3$) HRMS (EI) m/z calc'd for $C_{12}H_{16}O$ [M]+: 176.1201; found 176.1204.

Scheme 1-6: Synthesis of 3.

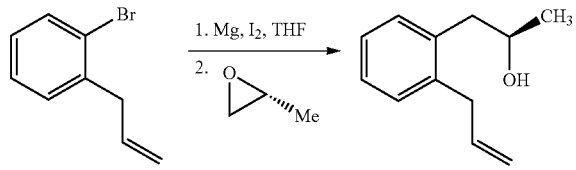

To a flamed-dried 50 mL RBF fitted with oven-dried condenser was added magnesium turnings (130 mg, 5.34 mmol, 1.2 equiv.). 0.5 mL of dry THF was added followed by the addition of a small portion of 2-bromoallylbenzene (877 mg, 4.45 mmol, 1.0 equiv.) dissolved in 3 mL of dry THF. A few crystals of iodine were added, and the deep purple solution was heated by a heat gun. Upon disappearance of the color, the rest of THF solution was added slowly, after which the reaction was heated at 70° C. for 45 min. Then the reaction was cooled in ice bath, followed by the addition of a solution of R-(+)-propylene oxide (570 mg, 9.8 mmol, 2.0 equiv.) in 3 mL of dry THF. The reaction was allowed to stir at r. t. for 90 min, followed by quenching with sat. NH$_4$Cl solution (10 mL). The layers were separated and the aqueous layer was further extracted with ethyl acetate (2×10 mL). All the organic layers were combined and dried over anhydrous MgSO$_4$. The solution was filtered and the solvent was removed under reduced pressure. The crude was purified twice via silica column chromatography (5% acetone/hexane). A colorless oil (240 mg, 1.4 mmol, 31% yield) was obtained as the final product.

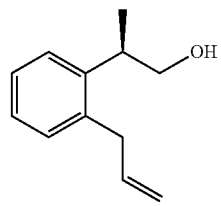

(5)

(R)-2-(2-allylphenyl)propan-1-ol (5)

Product is a clear oil. $^1$H NMR (500 MHz, CDCl$_3$) δ 7.26-7.24 (m, 2H), 7.19-7.16 (m, 2H), 5.99 (ddt, J=16.3, 10.3, 6.2 Hz, 1H), 5.06 (d, J=10.1 Hz, 1H), 5.96 (d, J=17.2 Hz, 1H), 3.71 (m, 2H), 3.52 (dd, J=16.1, 6.4 Hz, 1H), 3.42 (dd, J=15.9, 6.0 Hz, 1H), 3.27 (sex, J=6.6 Hz, 1H), 1.31 (app. t, J=6.4 Hz, 1H), 1.23 (d, J=7.1 Hz, 3H); $^{13}$C NMR (125 MHz, CDCl$_3$) δ 142.2, 138.4, 138.0, 130.5, 127.2, 126.8, 126.2, 116.0, 68.8, 37.6, 37.1, 18.4; $[α]^{23}_D$=+4.52° (c=0.25, CH$_2$Cl$_2$); HRMS (TOF MS AP+) m/z calc'd for $C_{12}H_{17}O$ [M+H]: 177.1279; found 177.1281.

Scheme 1-7: Synthesis of 5.

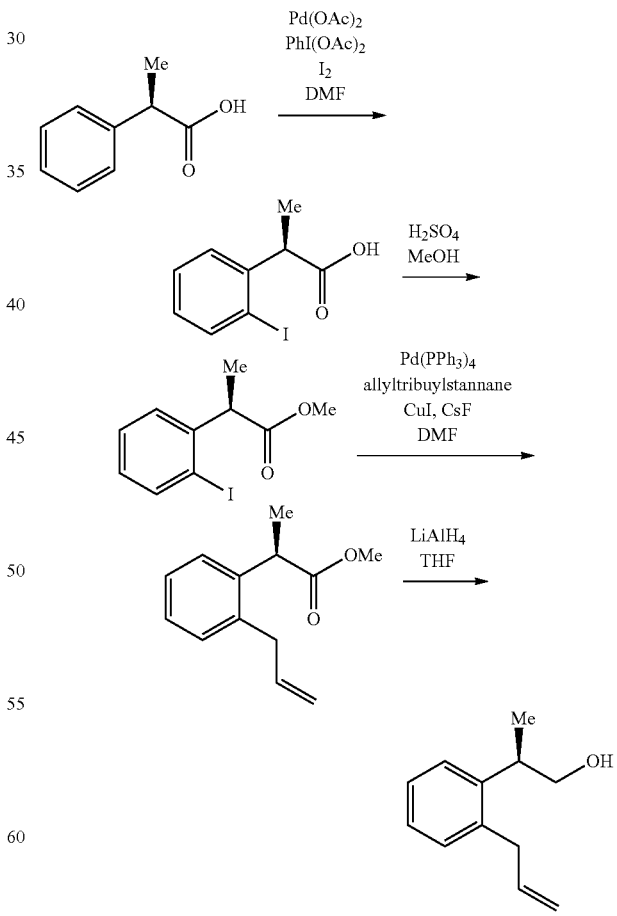

To a dried RBF was added PhI(OAc)$_2$ (0.75 equiv) and I$_2$ (0.75 equiv). The flask was wrapped in aluminum foil to protect it from light, and DMF (0.16 M) was added. The reaction was capped and stirred for 5 minutes, and then Pd(OAc)₂ (0.05 equiv) and (−)-(R)-2-Phenylpropionic acid starting material (1.0 equiv) were added quickly. The flask was sealed with a glass stopper and the seal was wrapped in Teflon tape and parafilm and subsequently covered in aluminum foil. The reaction was stirred at 60° C. for 12 hours. The solvent was subsequently evaporated under reduced pressure with the assistance of a high-vacuum, and the residue was dissolved in ether. The organic layer was extracted with sat. aq. NaHCO₃ (×3), and the combined aqueous layers were acidified with HCl. CH₂Cl₂ was added, and the aqueous layer was extracted with CH₂Cl₂ (×2) and EtOAc (×1). The combined organic layers were dried over anhydrous MgSO₄, filtered, and concentrated under reduced pressure to afford the iodinated product that was taken on directly to the next step.

To a dried RBF was added the iodinated starting material and anhydrous MeOH (0.3 M). Concentrated Sulfuric acid (5 mol %) was added, and the reaction was refluxed for three hours. After cooling to room temperature, the volatiles were evaporated under reduced pressure, and the remaining mixture was dissolved in EtOAc. The organics were washed with sat. aq. NaHCO₃ (×3), and the organic layer was dried over anhydrous MgSO₄, filtered, and concentrated under reduced pressure. The mixture was purified by column chromatography to afford the desired methyl ester (54% over two steps).

To a dried RBF in a glove box was added Pd(PPh₃)₄ (0.05 equiv), CsF (2.0 equiv), CuI (0.1 equiv), and the flask was sealed and taken out of the glovebox. DMF (0.33 M) was added followed by the corresponding methyl ester substrate (1.0 equiv) and allyltributylstannane (1.2 equiv) via syringe. The reaction was stirred at 45° C. for 6 hours under argon. After complete conversion of the starting material was observed by TLC, the flask was cooled to 0° C. and diluted slowly with water. The mixture was diluted with ether, and the layers were separated. The organic layer was washed with water (×2). The organic layer was dried over anhydrous MgSO₄, filtered, and concentrated under reduced pressure. The mixture was purified by column chromatography to afford the desired allylated methyl ester (81% yield).

To a dried RBF was added LiAlH₄ (95%, 1 equiv) under argon. THF (0.1 M) was added, and the flask was cooled to 0° C. To the mixture was added the allylated methyl ester dissolved in THF (1 M) dropwise, and the mixture was warmed to room temperature and stirred for 2 hours under argon. After complete conversion of the starting material was observed by TLC, the reaction flask was cooled to 0° C., and the reaction was quenched by dropwise addition of sat. aq. Rochelle's salt. The reaction was diluted with ether, and the biphasic mixture was stirred until both layers became homogeneous (typically 2 hours to overnight). The layers were separated, and the aqueous layer was extracted with ether (×3). The combined organic layers were washed once with brine, and dried over anhydrous MgSO₄, filtered, and concentrated under reduced pressure. The mixture was purified by column chromatography to afford the desired alcohol (77% yield).

Isotope-Labeling Study

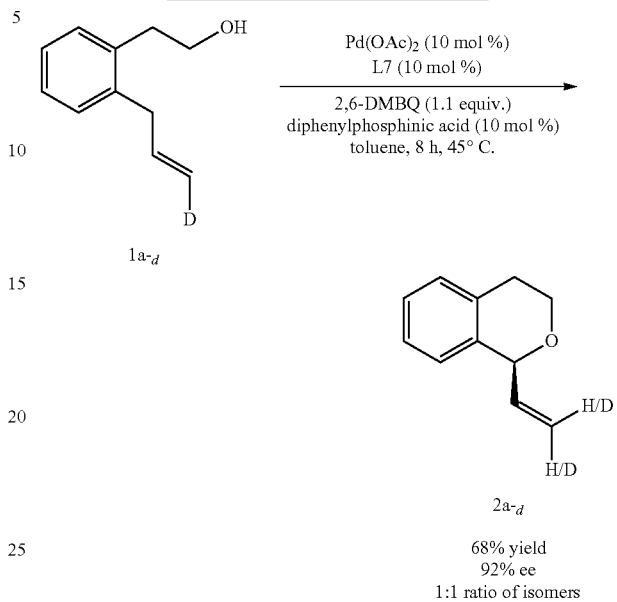

To a ½ dram vial was added ligand (S,R) tBu-ArSOX (4.1 mg, 0.01 mmol, 0.1 equiv) and Pd(OAc)₂ (2.2 mg, 0.01 mmol, 0.1 equiv). Toluene (0.2 mL) was added, and the vial was capped and allowed to stand at 45° C. until all solids had dissolved. Separately, to a ½ dram vial with stir bar was added 1a-$_d$ (16.3 mg, 0.1 mmol, 1 equiv), 2,6-dimethylbenzoquinone (15 mg, 0.11 mmol, 1.1 equiv), and diphenylphosphinic acid (2.2 mg, 0.01 mmol, 0.1 equiv.). The catalyst solution was subsequently added to the reaction flask, and toluene was used to rinse up to 0.65 mL toluene. The ½ dram vial was sealed with a Teflon cap, and allowed to stir for 8 hours at 45° C. Afterward, the vial was allowed to cool to room temperature. The majority of the toluene was removed under reduced pressure, and the remaining mixture was directly subjected to flash column chromatography (10% EtOAc in hexanes) to provide the vinylisochroman as a clear oil: 11.0 mg, 68% yield, 92% ee. Product is a 1:1 mixture of cis:trans deuterated olefin isomers.

Deuterium stereochemistry for 1a-$_d$ was determined to be >95% by ¹H NMR.

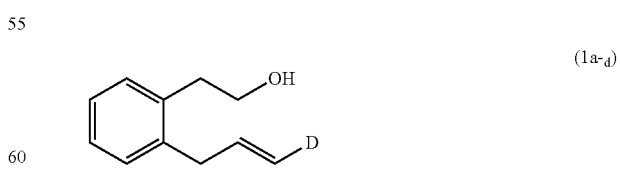

(1a-$_d$)

1a-$_d$

¹H NMR (500 MHz, CDCl₃) δ 7.26-7.21 (m, 4H), 6.01 (dt, J=17.1, 6.1 Hz, 1H), 5.02 (dt, J=17.1, 1.7 Hz, 1H), 3.89 (q, J=6.8 Hz, 2H), 3.48 (dd, J=6.3, 1.7 Hz, 2H), 2.96 (t, J=6.8 Hz, 2H), 1.42 (t, J=5.9 Hz, 1H).

Scheme 1-9: Comparison of Synthetic Routes for Compound 12

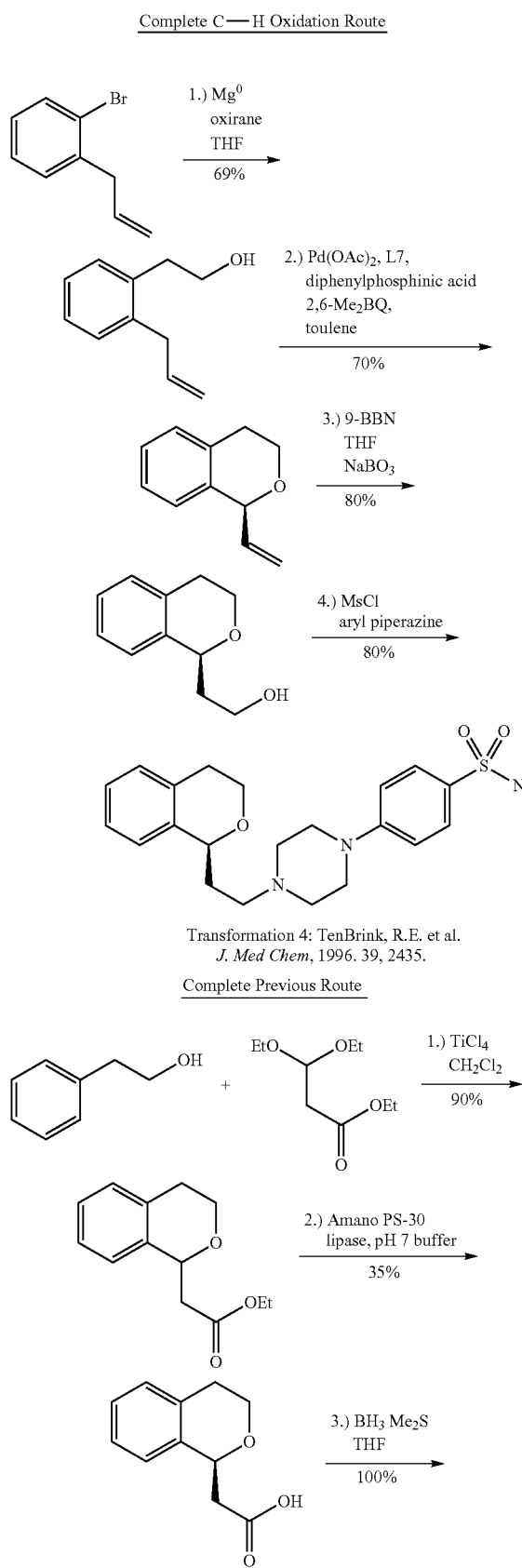

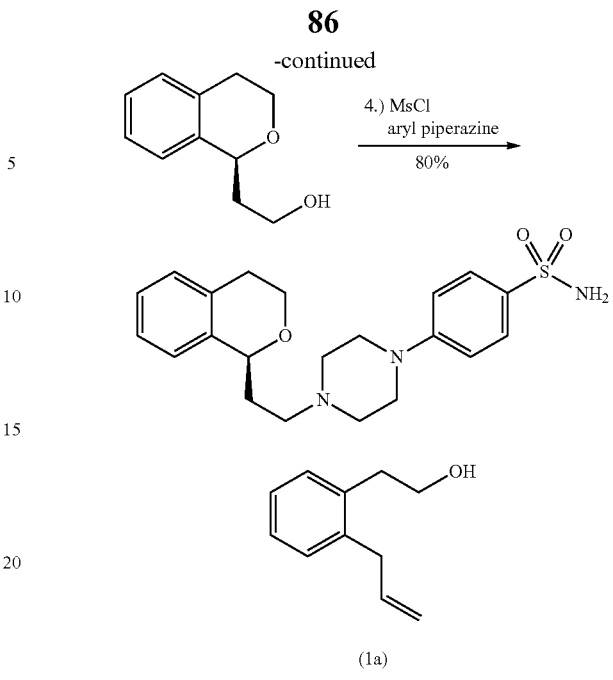

(1a)

1a:
A three-necked RBF with stirbar was charged with Mg (80 mg, 3.3 mmol, 1.3 equiv) and $I_2$ (2 crystals). The flask was equipped with a reflux condenser and an addition funnel, and the setup was flame-dried and placed under argon atmosphere. To the addition funnel was added a solution of 2-allylbromobenzene (0.5 g, 2.54 mmol, 1 equiv) and THF (0.5 M). About ¼$^{th}$ of the solution was added to the flask, and the reaction was stirred with heating until the start of the Grignard reaction, after which the remaining solution was added dropwise to the reaction. The reaction was stirred at reflux for 1 hour. The reaction was then cooled to 0° C. and ethylene oxide (5.07 mmol, 2.5 M solution in THF) was added dropwise to the reaction. The reaction was stirred at 0° C. for 30 minutes, and then at room temperature for one hour. Afterward, the reaction was cooled to 0° C. and quenched with sat. aq. $NH_4Cl$. The mixture was diluted with 30 mL ether and the layers were separated, and the aqueous layer was extracted with ethyl acetate (2×20 mL). The combined organic layers were dried over anhydrous $MgSO_4$, filtered, and concentrated under reduced pressure. The crude product was purified by column chromatography (10%→20% EtOAc in hexanes) to afford 1a. (284 mg, 69% yield).

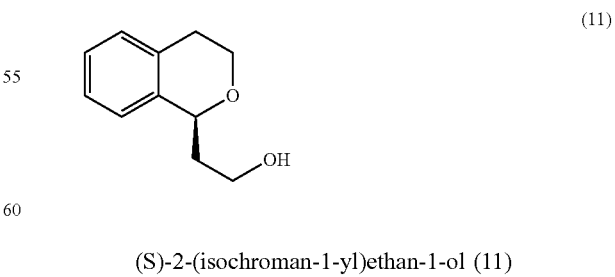

(S)-2-(isochroman-1-yl)ethan-1-ol (11)

To a dried 15 mL flask was added 1-vinylisochromane (2a) (55 mg, 0.33 mmol, 1 equiv). The flask was placed under argon, and THF (6 mL) was added. To the stirring solution was added 9-BBN (0.99 mL, 0.5M in THF, 1.5 equiv) via syringe dropwise. The solution was stirred for 3 hours until consumption of the starting olefin was observed by TLC. The solution was cooled to 0° C., and water (4 mL) was added slowly, followed by sodium perborate tetrahydrate (254 mg, 1.65 mmol, 5 equiv), and the white suspension was warmed to room temperature and stirred overnight. Afterward, the white suspension was diluted with ether, and decanted into a separatory funnel. The remaining white particulates were washed twice with 1:1 ether:water and transferred to the separatory funnel. The layers were separated, and the aqueous layer was extracted twice with ether. The combined organic phases were washed with brine, dried over anhydrous MgSO$_4$, filtered, and concentrated under reduced pressure. Purification by flash column chromatography (10%→20% EtOAc in hexanes) provided the alcohol as a clear oil: (47.3 mg, 0.265 mmol, 80% Yield). The enantiomeric excess was determined to be 92% by chiral GC analysis (Cyclosil-B, 150° C. isothermal, $t_R$(major)=23.82 min, $t_R$(minor)=25.39 min.) $[\alpha]^{21}_D$=−134.2° (c=0.2, CH$_2$Cl$_2$); $^1$H NMR (500 MHz, CDCl$_3$) δ 7.23-7.18 (m, 2H), 7.16-7.12 (m, 1H), 7.10-7.05 (m, 1H), 5.02 (d, J=7.3 Hz, 1H), 4.21 (ddd, J=11.1, 5.4, 3.0 Hz, 1H), 3.90-3.84 (m, 1H), 3.80 (td, J=10.9, 3.4 Hz, 1H), 3.07 (ddd, J=16.1, 10.1, 5.4 Hz, 1H), 2.81 (t, J=4.5 Hz, 1H), 2.71 (dt, J=16.3, 3.0 Hz, 1H), 2.26 (ddt, J=14.8, 6.6, 3.6 Hz, 1H), 2.08 (dddd, J=15.7, 8.8, 7.1, 4.1 Hz, 1H); $^{13}$C NMR (125 MHz, CDCl$_3$) δ 137.6, 134.0, 129.3, 126.7, 126.5, 124.8, 76.8, 64.0, 61.4, 37.8, 29.3; HRMS (TOF MS EI+) m/z calc'd for C$_{11}$H$_{14}$O [M]+: 178.0994; found 178.0990. A rotation of $[\alpha]^{21}_D$=+71.4° (c=0.2, CH$_2$Cl$_2$) is reported in the literature for the R-enantiomer. All other spectral data is consistent with data in previous literature.

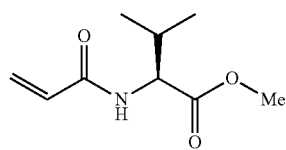

methyl acryloyl-L-valinate (S11) was prepared according to literature precedent, and spectral data matched reported literature.

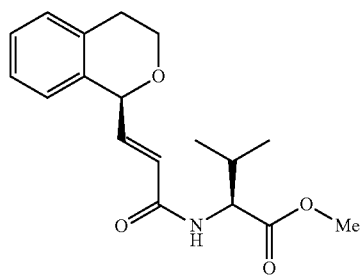

methyl ((E)-3-((S)-isochroman-1-yl)acryloyl)-L-valinate (9)

To a flame-dried 15 mL round-bottom flask was added 2$^{nd}$ generation Hoveyda-Grubbs catalyst (15.3 mg, 0.024 mmol, 0.075 equiv) and CH$_2$Cl$_2$ (2 mL) under argon. To a separate dried flask was added 2a (52 mg, 0.325 mmol, 1 equiv) and S11$^{14}$ (120 mg, 0.65 mmol, 2 equiv), and the flask was placed under argon. The mixture was dissolved with CH$_2$Cl$_2$ (4 mL), and was cannulated to the reaction vessel. A reflux condenser was quickly added, and the reaction was stirred 48 hours at reflux. The flask was cooled to room temperature, and the solvent was evaporated under reduced pressure. Purification by flash column chromatography (20%→50% EtOAc/hexanes) provided 9 as an off-white solid. (75 mg, 0.24 mmol, 73% Yield) $[\alpha]^{22}_D$=−31.97° (c=0.25, CH$_2$Cl$_2$); $^1$H NMR (500 MHz, CDCl$_3$) δ 7.23-7.19 (m, 2H), 7.18-7.14 (m, 1H), 7.13-7.09 (m, 1H), 7.06 (dd, J=15.7, 5.6 Hz, 1H), 6.15 (d, J=15.2 Hz, 1H), 6.09 (d, J=7.5 Hz, 1H), 5.41 (d, J=4.9 Hz, 1H), 4.67 (dd, J=8.6, 4.7 Hz, 1H), 4.13 (dt, J=11.6, 5.4 Hz, 1H), 3.93 (ddd, J=11.6, 7.3, 4.3 Hz, 1H), 3.75 (s, 3H), 2.93 2.84 (ABq t, J$_{AB}$=17.6 Hz, J$_t$=5.4 Hz, 2H), 2.20 (o, J=7.3 Hz, 1H), 0.97 (d, J=6.9 Hz, 3H), 0.93 (d, J=6.9 Hz, 3H); $^{13}$C NMR (125 MHz, CDCl$_3$) δ 172.7, 165.4, 143.6, 134.9, 133.8, 129.4, 127.2, 126.5, 126.1, 124.7, 75.2, 63.1, 57.3, 52.5, 31.7, 28.9, 19.2, 18.1; HRMS (TOF MS ES+) m/z calc'd for C$_{18}$H$_{24}$NO$_4$ [M+H]: 318.1705; found 318.1701.

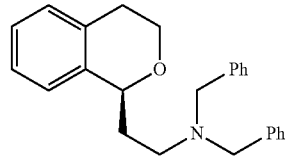

(S)—N,N-dibenzyl-2-(isochroman-1-yl)ethan-1-amine (10)

In a glove box, to a dried 8 mL dram vial with stir bar was added Cu(OAc)$_2$ (2.7 mg, 0.0147 mmol, 0.04 equiv) and (R)-DTBM-SEGPHOS (19.1 mg, 0.0162 mmol, 0.044 equiv). The vial was taken out of the glove box, and THF (0.2 mL) was added under argon. The mixture was stirred for 15 minutes, and then diethoxymethylsilane (0.12 mL, 0.736 mmol, 2 equiv) was added via syringe, and the solution was stirred for 10 minutes. A mixture of 2a (59 mg, 0.368 mmol, 1 equiv) and O-benzoyl-N,N-dibenzylhydroxylamine (140 mg, 0.442 mmol, 1.2 equiv) dissolved in THF (0.6 mL) was added via syringe. The reaction was stirred at 40° C. for 36 hours. After cooling to room temperature, the reaction was diluted with EtOAc and quenched with 2 mL Na$_2$CO$_3$ solution. The layers were separated, and the aqueous layer extracted with EtOAc (3×6 mL). The combined organic layers were dried over anhydrous MgSO$_4$, filtered, and concentrated under reduced pressure. Purification by flash column chromatography (10%→20% EtOAc/hexanes) provided the amine as a clear oil: (85.7 mg, 0.24 mmol, 65% Yield). The enantiomeric excess was determined to be 92% by chiral HPLC analysis (CHIRALPAK OJ-H column, 1 mL/min, 2% isopropanol in hexane, λ=214.4 nm): $t_R$(minor) =8.93 min, $t_R$(major)=10.53 min. $[\alpha]^{22}_D$=−55.95° (c=0.25, CH$_2$Cl$_2$); $^1$H NMR (500 MHz, CDCl$_3$) δ 7.39 (d, J=7.9 Hz, 4H), 7.32 (t, J=7.3 Hz, 4H), 7.25 (t, J=7.1 Hz, 2H), 7.16-7.08 (m, 3H), 6.95 (d, J=6.4 Hz, 1H), 4.81 (d, J=8.8 Hz, 1H), 4.01 (dt, J=15.0, 3.9 Hz, 1H), 3.71 (d, J=13.7 Hz, 2H), 3.70-3.64 (m, 1H), 3.55 (d, J=13.9 Hz, 2H), 2.93 (ddd, J=15.4, 10.6, 6.0 Hz, 1H), 2.80 (dt, J=13.1, 7.1 Hz, 1H), 2.67 (d, J=15.6 Hz, 1H), 2.61 (ddd, J=12.9, 8.6, 4.5 Hz, 1H), 2.17-2.10 (m, 1H), 1.97-1.90 (m, 1H); $^{13}$C NMR (125 MHz, CDCl$_3$) δ 140.2, 138.8, 134.1, 129.1, 129.1, 128.4, 127.0, 126.3, 126.3, 124.9, 74.4, 63.2, 58.9, 50.4, 34.0, 29.3; HRMS (TOF MS ES+) m/z calc'd for C$_{25}$H$_{28}$NO [M+H]: 358.2171; found 358.2167.

Scheme 1-10: Comparison of Synthetic Routes for Compound 8.
Complete Previous Route
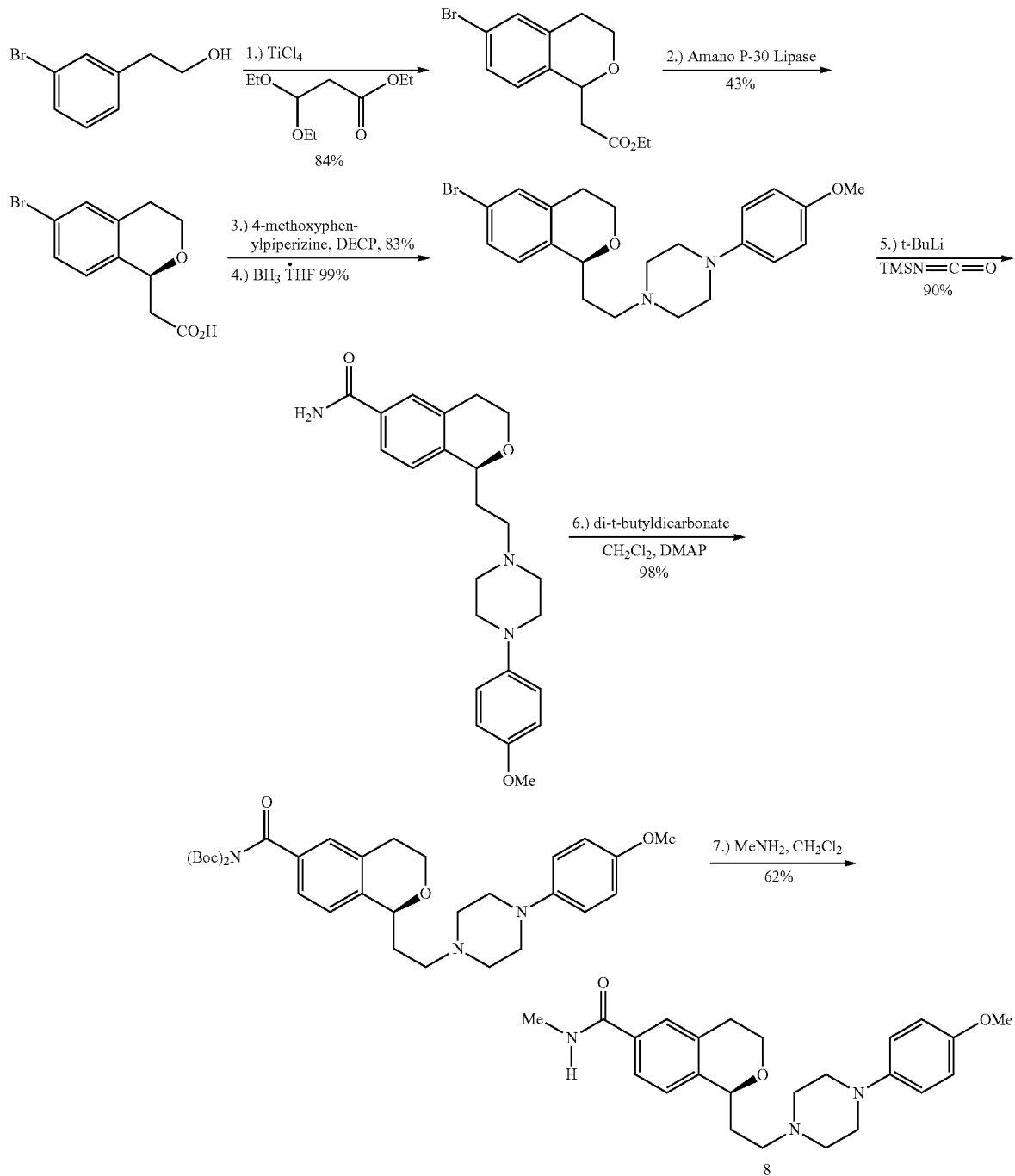
Complete C—H Oxidation Route
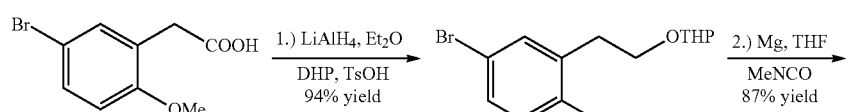

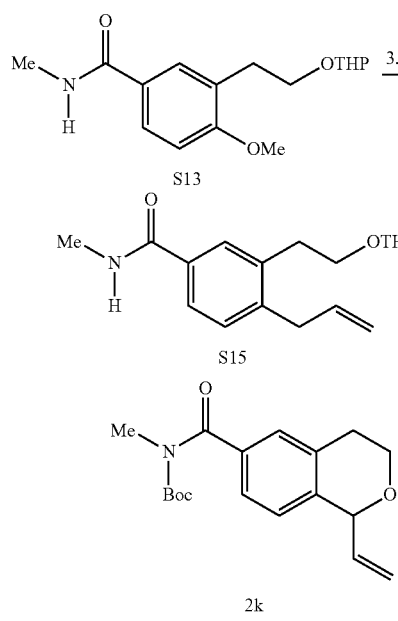
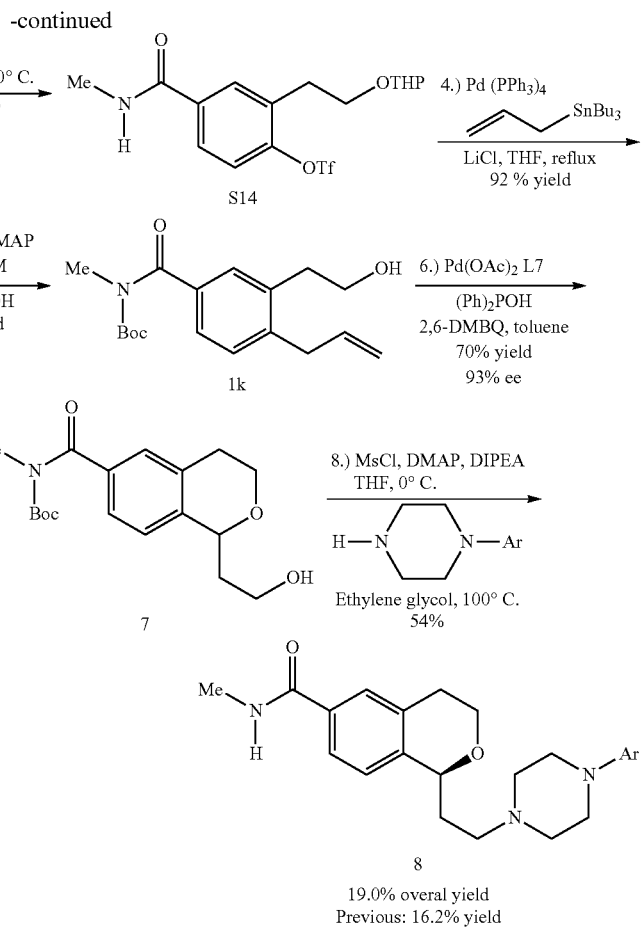

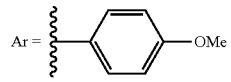

2-(5-bromo-2-methoxyphenethoxy)tetrahydro-2H-pyran (S12)

To a 200 mL flamed-dried RBF, fitted with an oven-dried condenser, was added 2-(5-bromo-2-methoxyphenyl)acetic acid (5 g, 20.4 mmol, 1 equiv) and 50 mL dry $Et_2O$ under $N_2$. The solution was stirred at 0° C. and $LiAlH_4$ (0.78 g, 20.4 mmol, 1 equiv) was added in 5 portions over 5 minutes (CAUTION: gas evolution!). Then, the reaction was heated at 45° C. to reflux for 1 hour. After the solution was cooled to 0° C., 0.78 mL of water was added, followed by 0.78 mL of 15% NaOH aqueous solution and at last 2.4 mL of $H_2O$. After the slurry was stirred for 30 minutes at RT, several spatulas of anhydrous $MgSO_4$ were added and stirred for 30 minutes. The solid was filtered off and the solvent was removed under reduced pressure. The crude was continued to next step without purification.

To a 100 mL flame-dried RBF was added the above crude starting material, a few crystals of p-toluenesulfonic acid monohydrate, and 20 mL dry THF. After cooling to 0° C., 3,4-Dihydro-2H-pyran (1.95 mL, 21.4 mmol, 1.05 equiv) was added dropwise. After the reaction was stirred at RT overnight, all the volatiles were removed under reduced pressure and the crude was applied directly to silica column chromatography (10% EtOAc in hexanes). A colorless oil (5.91 g, 18.7 mmol, 94% yield) was obtained. $^1$H NMR (500 MHz, Chloroform-d) δ 7.32 (d, J=2.5 Hz, 1H), 7.29-7.24 (m, 1H), 6.70 (d, J=8.7 Hz, 1H), 4.60 (t, J=3.7 Hz, 1H), 3.88 (dt, J=9.7, 7.2 Hz, 1H), 3.83-3.72 (m, 4H), 3.59 (dt, J=9.7, 7.0 Hz, 1H), 3.46 (ddd, J=12.7, 7.1, 3.4 Hz, 1H), 2.89 (t, J=7.1 Hz, 2H), 1.82 (dtd, J=15.7, 8.1, 7.4, 3.6 Hz, 1H), 1.70 (ddt, J=13.0, 9.7, 3.4 Hz, 1H), 1.63-1.44 (m, 4H); $^{13}$C NMR (126 MHz, $CDCl_3$) δ 156.94, 133.55, 130.19, 129.93, 112.67, 112.07, 98.78, 66.66, 62.31, 55.73, 30.90, 30.69, 25.73, 19.70; HRMS (ESI) m/z calc'd for $C_{14}H_{19}O_3BrNa$ [M+Na]+: 337.0415; found 337.0414. Spectral data is consistent with data in previous literature.

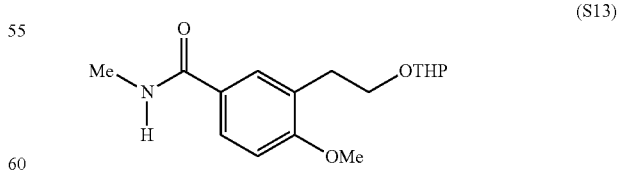

4-methoxy-N-methyl-3-(2-((tetrahydro-2H-pyran-2-yl)oxy)ethyl)benzamide (S13)

To a 100 mL RBF fitted with a condenser was added magnesium turnings (0.28 g, 11.57 mmol, 1.2 equiv). The apparatus was flamed-dried under vacuum with vigorous stirring for 20 minutes. After cooling to RT, 2 mL of dry THF was added followed by the addition of a small portion of S12 (3.04 g, 9.64 mmol, 1 equiv) dissolved in 8 mL of dry THF under $N_2$. A few crystals of iodine were added, and the deep purple solution was heated by a heat gun. Upon disappearance of the color, the rest of the THF solution was added slowly, after which the reaction was heated to 70° C. with vigorous stirring for 2 hours. The color of the solution was changed from light yellow to dark brown. Then, the reaction was cooled to 0° C., after which methyl isocyanate (500 mg, 8.76 mmol, 0.91 equiv) dissolved in 24 mL of dry $Et_2O$ was added dropwise. (NOTE: A fresh new bottle of methyl isocyanate was opened and used immediately.) After the reaction was stirred at RT for 30 mins, 30 mL of saturated $NH_4Cl$ solution was added to quench the reaction and the resulting solution was partitioned in a 150 mL separatory funnel. The aqueous layer was extracted with EtOAc (50 mL×3). The organic layers were combined and dried over anhydrous $Na_2SO_4$. The solid was filtered off and the solvent was removed under reduced pressure. The crude was purified via silica column chromatography (40%→50% EtOAc in hexanes). A colorless oil (2.46 g, 8.39 mmol, 87% yield) was obtained. $^1$H NMR (500 MHz, Chloroform-d) δ 7.66-7.61 (m, 2H), 6.81 (d, J=8.5 Hz, 1H), 6.33 (d, J=4.6 Hz, 1H), 4.57 (dd, J=4.6, 2.7 Hz, 1H), 3.89 (dt, J=9.5, 7.4 Hz, 1H), 3.82 (s, 3H), 3.76 (ddd, J=11.1, 8.0, 3.3 Hz, 1H), 3.60 (dt, J=9.5, 7.1 Hz, 1H), 3.47-3.40 (m, 1H), 2.96 (d, J=4.8 Hz, 3H), 2.91 (t, J=7.2 Hz, 2H), 1.84-1.73 (m, 1H), 1.67 (ddt, J=12.3, 8.8, 3.2 Hz, 1H), 1.58-1.42 (m, 4H); $^{13}$C NMR (126 MHz, CDCl₃) δ 168.16, 160.33, 129.47, 127.49, 127.12, 126.66, 109.96, 99.09, 66.78, 62.68, 55.70, 30.98, 30.83, 27.02, 25.70, 19.92; HRMS (ESI) m/z calc'd for $C_{16}H_{23}NO_4Na$ [M+Na]+: 316.1525; found 316.1522.

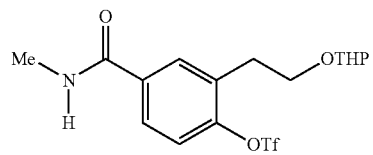

4-(methylcarbamoyl)-2-(2-((tetrahydro-2H-pyran-2-yl)oxy)ethyl)phenyl trifluoro methanesulfonate (S14)

To a 200 ml flamed-dried RBF was added NaH (200 mg, 8.36 mmol, 1.1 equiv) and 9 mL dry DMF under $N_2$. After the solution was cooled to 0° C., ethanethiol (0.66 mL, 9.12 mmol, 1.2 equiv) in 9 mL dry DMF was added dropwise. The reaction was stirred at RT for 20 mins to result in a homogeneous solution. Then S13 (2.23 g, 7.60 mmol, 1 equiv) dissolved in 19 mL dry DMF was added to the above solution. The flask was fitted with an oven-dried condenser and heated in 110° C. oil bath for 6 hours under $N_2$. After cooling down to RT, the reaction was quenched with 20 mL of saturated $NH_4Cl$ solution and transferred to a 150 mL separatory funnel. The aqueous layer was extracted with EtOAc (80 mL×4), and all the organic layers were combined and dried over $Na_2SO_4$. The solid was filtered off and the volatiles were removed under reduced pressure including most of the residual DMF. A sticky yellow oil (2 g) was obtained and carried forward to next step without further purification.

To a 100 mL flamed-dried RBF was added the above crude, 22 mL dry DCM, triethylamine (3 mL, 21.5 mmol) and 4-dimethylaminopyridine (87.5 mg, 0.72 mmol). The solution was stirred at RT and then N-phenyl-bis(trifluoromethanesulfonimide) (3.8 g, 10.7 mmol) was added in one portion. The reaction was stirred at RT for 80 mins under $N_2$, after which all the solution was directly loaded onto a silica column flushed with acetone/hexane (10%→15%→20%). The product (2.8 g, 6.81 mmol, 90% yield) was isolated as a pale yellow oil. $^1$H NMR (500 MHz, Chloroform-d) δ 7.90 (d, J=2.3 Hz, 1H), 7.69 (dd, J=8.6, 2.3 Hz, 1H), 7.28 (d, J=8.6 Hz, 1H), 6.58 (d, J=7.7 Hz, 1H), 4.55 (dd, J=4.6, 2.5 Hz, 1H), 3.97 (dt, J=9.7, 6.8 Hz, 1H), 3.69 (ddt, J=22.3, 12.6, 5.0 Hz, 2H), 3.45 (ddd, J=9.6, 5.2, 2.9 Hz, 1H), 3.07-2.92 (m, 5H), 1.76 (dq, J=10.8, 4.6, 3.4 Hz, 1H), 1.70-1.62 (m, 1H), 1.58-1.41 (m, 4H); $^{13}$C NMR (126 MHz, CDCl₃) δ 166.95, 150.06, 134.71, 132.83, 130.88, 127.11, 121.57, 118.74 (q, J=320.1 Hz), 99.36, 66.19, 62.84, 30.83, 30.27, 27.17, 25.60, 19.82; $^{19}$F NMR (470 MHz, CDCl₃) δ −74.18; HRMS (ESI) m/z calc'd for $C_{16}H_{20}F_3NO_6S$ [M+H]+: 412.1042; found 412.1036.

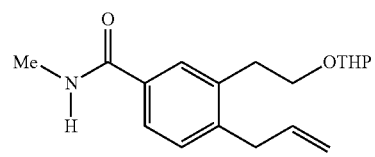

4-allyl-N-methyl-3-(2-((tetrahydro-2H-pyran-2-yl)oxy)ethyl)benzamide (S15)

To a 300 mL flamed-dried RBF was added S14 (2.8 g, 6.81 mmol, 1 equiv), lithium chloride (1.44 g, 34 mmol, 5 equiv), 70 mL of dry THF and finally allyltributylstannane (2.3 mL, 7.49 mmol, 1.1 equiv). The solution was stirred and degassed under dry argon for 15 mins. Then, $Pd(PPh_3)_4$ (0.79 g, 0.68 mmol, 0.1 equiv) was added as a solid and the reaction flask was fitted with an oven-dried condenser. The reaction was heated in 80° C. oil bath for 22 hours under argon. After cooled down to RT, the reaction was diluted with 50 mL of water, which was then partition into a 150 mL separatory funnel. The aqueous layer was extracted with EtOAc (3×50 mL). The organic layers were combined and dried over anhydrous $Na_2SO_4$. The solid was filtered off and the solvent was removed under reduced pressure. The crude was purified via silica column chromatography (10%→15%→20% acetone/hexane). A colorless oil (1.90 g, 6.25 mmol, 92% yield) was obtained. $^1$H NMR (500 MHz, Chloroform-d) δ 7.65 (d, J=2.1 Hz, 1H), 7.54 (dd, J=7.9, 2.0 Hz, 1H), 7.15 (d, J=7.9 Hz, 1H), 6.54 (s, 1H), 5.91 (ddt, J=16.6, 10.1, 6.2 Hz, 1H), 5.04 (dd, J=10.1, 1.7 Hz, 1H), 4.94 (dd, J=17.1, 1.8 Hz, 1H), 4.53 (dd, J=4.5, 2.7 Hz, 1H), 3.90 (dt, J=9.7, 7.3 Hz, 1H), 3.71 (ddd, J=11.3, 8.1, 3.2 Hz, 1H), 3.57 (dt, J=9.7, 7.2 Hz, 1H), 3.47-3.38 (m, 3H), 2.95 (d, J=4.8 Hz, 3H), 2.91 (t, J=7.3 Hz, 2H), 1.76 (dddd, J=15.7, 12.1, 7.2, 3.4 Hz, 1H), 1.66 (ddt, J=12.1, 8.7, 3.2 Hz, 1H), 1.59-1.38 (m, 4H); $^{13}$C NMR (126 MHz, CDCl₃) δ 168.44, 142.05, 137.75, 136.69, 132.82, 129.96, 128.67, 125.14, 116.46, 99.19, 67.81, 62.64, 37.21, 33.06, 30.90, 27.01, 25.64, 19.85; HRMS (ESI) m/z calc'd for $C_{18}H_{25}NO_3Na$ [M+Na]+: 326.1732; found 326.17302.

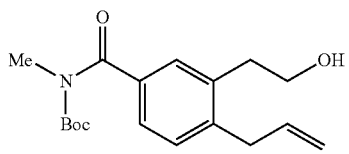

Tert-butyl (4-allyl-3-(2-hydroxyethyl)benzoyl)(methyl)carbamate (1k)

To a 25 mL flame-dried RBF was added S15 (1.90 g, 6.25 mmol, 1 equiv), 6.3 mL of dry DCM, Et$_3$N (0.88 mL, 6.25 mmol, 1 equiv) and (Boc)$_2$O (4.3 mL, 18.8 mmol, 3 equiv) under N$_2$. Then, DMAP (1.53 g, 12.5 mmol, 2 equiv) was added as a solid in one portion. After the reaction was stirred at RT for 6 h, another portion of (Boc)$_2$O (2.2 mL, 9.58 mmol) was added. After stirring for 8 more hours, another portion of (Boc)$_2$O (2.2 mL, 9.58 mmol) was further added and the reaction was allowed to stir for 6 more hours. The volatiles were removed under reduced pressure and the resulting crude was flushed through a silica gel plug with 10% EtOAc/Hexane. After removal of the solvents under reduced pressure, the oil obtained was diluted with 35 mL of EtOH, followed by the addition of pyridinium p-toluenesulfonate (150 mg, 0.6 mmol, 0.1 equiv). The solution was stirred in a 45° C. oil bath for 24 hours. All the volatiles were removed by reduced pressure and the crude was applied directly to silica column chromatography (10%→15%→20%→25%→30% EtOAc in hexanes). A colorless oil (1.89 g, 5.92 mmol, 95% yield) was obtained as pure product. $^1$H NMR (500 MHz, Chloroform-d) δ 7.34 (d, J=1.9 Hz, 1H), 7.31 (dd, J=7.9, 1.9 Hz, 1H), 7.18 (d, J=7.9 Hz, 1H), 5.91 (ddt, J=16.5, 10.0, 6.2 Hz, 1H), 5.06 (dd, J=10.3, 1.7 Hz, 1H), 4.97 (dd, J=17.1, 1.8 Hz, 1H), 3.78 (t, J=6.9 Hz, 2H), 3.44 (d, J=6.1 Hz, 2H), 3.27 (s, 3H), 2.88 (t, J=6.9 Hz, 2H), 2.00 (br, 1H), 1.18 (s, 9H); $^{13}$C NMR (126 MHz, CDCl$_3$) δ 173.84, 153.90, 141.88, 136.79, 136.74, 135.99, 129.82, 129.32, 126.14, 116.49, 83.17, 63.11, 37.27, 35.91, 32.89, 27.72; HRMS (ESI) m/z calc'd for C$_{18}$H$_{25}$NO$_4$Na [M+Na]+: 342.1681; found 342.1678.

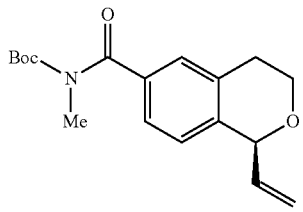

(S)-tert-butyl methyl(1-vinylisochromane-6-carbonyl)carbamate (2k)

tert-butyl (4-allyl-3-(2-hydroxyethyl)benzoyl)(methyl) carbamate (1k) (640 mg, 2.0 mmol) was reacted according to the general procedure for 7 hours. Purification by flash column chromatography (5%→8% EtOAc in hexanes) provided the vinylisochroman as a clear oil. Run 1 (440 mg, 70% yield); Run 2 (0.4 mmol scale, 85.7 mg, 68% yield); Run 3 (0.73 mmol scale, 165.6 mg, 71% yield). Average: 70% Yield. The enantiomeric excess was determined to be 93% by chiral HPLC analysis (CHIRALPAK AD-RH column, 0.5 mL/min, 50% MeCN in H$_2$O, λ=254.4 nm): t$_R$(major)=10.882 min, t$_R$(minor)=14.043 min. [α]$^{26}_D$=+13.2° (c=0.84, CHCl$_3$); $^1$H NMR (500 MHz, Chloroform-d) δ 7.32-7.27 (m, 2H), 7.06 (d, J=8.0 Hz, 1H), 5.92 (ddd, J=17.3, 10.2, 7.3 Hz, 1H), 5.40-5.33 (m, 2H), 5.16 (dd, J=7.2, 1.5 Hz, 1H), 4.14 (dt, J=11.4, 4.9 Hz, 1H), 3.84 (ddd, J=11.4, 8.7, 4.1 Hz, 1H), 3.28 (s, 3H), 2.95 (dddd, J=15.3, 9.1, 5.5, 1.3 Hz, 1H), 2.76 (dt, J=16.4, 4.3 Hz, 1H), 1.17 (s, 9H); $^{13}$C NMR (126 MHz, CDCl$_3$) δ 173.53, 153.82, 139.36, 137.67, 136.39, 133.68, 128.22, 126.10, 125.34, 119.32, 83.17, 78.23, 63.15, 32.81, 28.84, 27.69; HRMS (ESI) m/z calc'd for C$_{18}$H$_{23}$NO$_4$Na [M+Na]+: 340.1525; found 340.1522.

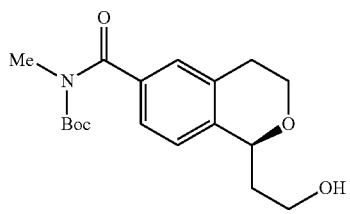

Tert-butyl (1-(2-hydroxyethyl)isochromane-6-carbonyl)(methyl)carbamate (7)

To an oven-dried 2 dram vial, fitted with PTFE/silicone septum and screw cap, was added 9-BBN (1.44 mL, 0.72 mmol, 0.5 M in THF, fresh new bottle, 1.2 equiv) under argon. The solution was cooled to 0° C., after which 2k (190 mg, 0.6 mmol, 1 equiv) dissolved in 0.85 mL of dry THF was added dropwise. The reaction was stirred at 0° C. under argon for 12 hours. Then, 1.44 mL of H2O was added, followed by the addition of sodium perborate tetrahydrate (462 mg, 3 mmol, 5 equiv). The reaction was warmed to RT and stirred overnight. The white suspension was transferred to a 60 mL separatory funnel by 10 mL of H$_2$O and 20 mL of EtOAc. The aqueous layer was separated and extracted carefully with EtOAc (10 mL×4). The organic layers were combined together and dried over anhydrous Na$_2$SO$_4$. The solid was filtered off and the solvent was removed under reduced pressure. The crude was purified via silica column chromatography (30% EtOAc in hexanes). A sticky colorless oil (162 mg, 0.48 mmol, 80% yield) was obtained. [α]$^{26}_D$=−50.6° (c=1.00, CHCl$_3$) $^1$H NMR (500 MHz, Chloroform-d) δ 7.31 (dd, J=8.1, 1.8 Hz, 1H), 7.26 (s, 1H), 7.07 (d, J=8.0 Hz, 1H), 5.00-4.95 (m, 1H), 4.16 (ddd, J=11.4, 5.5, 3.2 Hz, 1H), 3.82 (td, J=5.1, 4.3, 1.4 Hz, 2H), 3.74 (ddd, J=11.3, 10.1, 3.6 Hz, 1H), 3.27 (s, 3H), 3.06-2.96 (m, 1H), 2.80 (br. s, 1H), 2.69 (dt, J=16.5, 3.5 Hz, 1H), 2.21 (dddd, J=14.7, 6.8, 5.1, 3.3 Hz, 1H), 2.07-1.94 (m, 1H), 1.17 (s, 9H); $^{13}$C NMR (126 MHz, CDCl$_3$) δ 173.45, 153.79, 140.87, 136.20, 133.83, 128.29, 125.66, 124.56, 83.21, 76.17, 63.72, 60.89, 37.94, 32.81, 29.16, 27.68. HRMS (ESI) m/z calc'd for C$_{18}$H$_{25}$NO$_5$Na [M+Na]+: 358.1630; found 358.1628.

(8)

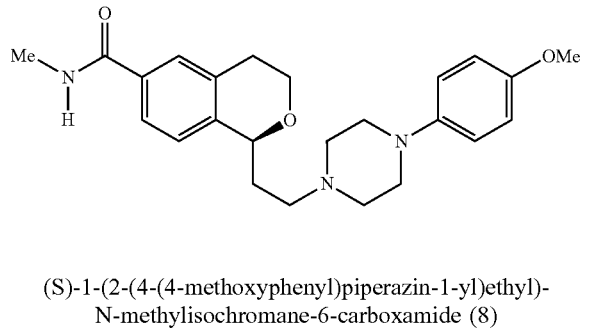

(S)-1-(2-(4-(4-methoxyphenyl)piperazin-1-yl)ethyl)-
N-methylisochromane-6-carboxamide (8)

To an oven-dried ½ dram vial, fitted with PTFE/silicone septum and screw cap, was added 7 (68 mg, 0.2 mmol, 1 equiv), DMAP (1.2 mg, 0.01 mmol, 0.05 equiv), DIPEA (88 µL, 0.51 mmol, 2.5 equiv) and 0.23 mL of dry THF under $N_2$. After the reaction was cooled to 0° C., MsCl (17 µL, 0.21 mmol, 1.05 equiv; NOTE: MsCl was distilled over $P_2O_5$ under high vacuum prior to use) was added slowly under $N_2$. The reaction was stirred at 0° C. for 35 minutes, after which 1-(4-methoxyphenyl)piperazine (55 mg, 0.29 mmol, 1.5 equiv) and 0.23 mL of ethylene glycol was added. The reaction was heated in 110° C. oil bath and the residual THF was distilled off under $N_2$. After 12 h reaction, 0.5 mL of water was added to the reaction. By using 2 mL of water and 4 mL of DCM, the solution was transferred to a 10 mL test tube, where extraction of the layers was performed. The mixing of layers was carefully performed by Pasteur pipette with bulb and the aqueous layer was extracted with DCM (4 mL×5). The organic layers were combined and dried over anhydrous $Na_2SO_4$. The solid was filtered off and the solvent was removed under reduced pressure. The crude was purified via silica column chromatography (1%%→2%→5% MeOH in DCM). A sticky colorless oil (45 mg, 0.11 mmol, 54% yield) was obtained initially. Upon trituration with $Et_2O$, a white solid was obtained as pure product. $[\alpha]^{23}_D$=−44.7° (c=0.93, MeOH/CHCl$_3$=1:1). The enantiomeric excess was determined to be 93% by correlating optical rotation to the literature reported value of $[\alpha]_D$=−48° (c=0.93, MeOH:CHCl$_3$=1:1) for enantiopure product. $^1$H NMR (500 MHz, Chloroform-d) δ 7.57-7.51 (m, 2H), 7.13 (d, J=8.4 Hz, 1H), 6.88 (d, J=9.1 Hz, 2H), 6.82 (d, J=9.1 Hz, 2H), 6.36 (d, J=5.3 Hz, 1H), 4.84 (dd, J=8.5, 3.2 Hz, 1H), 4.11 (ddd, J=11.5, 5.3, 3.7 Hz, 1H), 3.74 (s, 3H), 3.74 (dd, J=20.7, 3.8 Hz, 1H), 3.09 (t, J=5.0 Hz, 4H), 2.98 (d, J=4.9 Hz, 3H), 3.02-2.92 (m, 1H), 2.75-2.59 (m, 6H), 2.54 (ddd, J=12.4, 10.3, 4.9 Hz, 1H), 2.23-2.11 (m, 1H), 2.02 (tq, J=13.9, 4.8 Hz, 1H). $^{13}$C NMR (126 MHz, CDCl$_3$) δ 168.24, 154.01, 145.87, 141.73, 134.64, 132.89, 127.93, 125.20, 124.70, 118.40, 114.65, 74.73, 63.19, 55.80, 54.89, 53.70, 50.78, 33.30, 29.27, 27.08. HRMS (EI) m/z calc'd for $C_{24}H_{32}N_3O_3$ [M]+: 410.2444; found 410.2437. The spectral data is consistent with the literature.

Scheme 1-11: Resubjection of racemic 2a to the reaction.

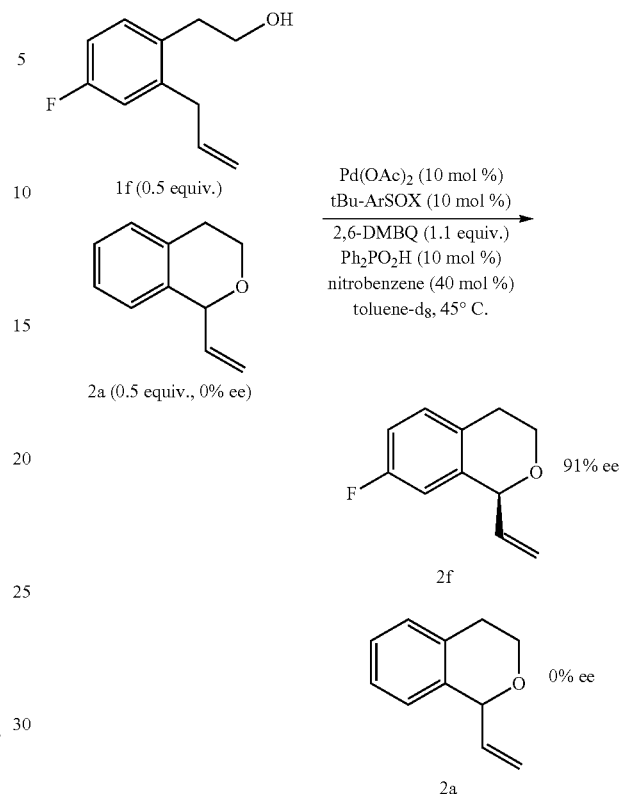

To a ½ dram vial was added ligand (S,R) tBu-ArSOX (8.1 mg, 0.02 mmol, 0.1 equiv) and Pd(OAc)$_2$ (4.4 mg, 0.02 mmol, 0.1 equiv). Toluene-d$_8$ (0.3 mL) was added, and the vial was capped and allowed to stand at 45° C. until all solids had dissolved. Separately, to a 1 dram vial with stir bar was added racemic 2a (16.2 mg, 0.1 mmol, 0.5 equiv), 1f (18 mg, 0.1 mmol, 0.5 equiv), 2,6-dimethylbenzoquinone (30 mg, 0.22 mmol, 1.1 equiv), diphenylphosphinic acid (4.4 mg, 0.02 mmol, 0.1 equiv.) and nitrobenzene (4.1 µL, 0.04 mmol). The catalyst solution was subsequently added to the reaction flask, and toluene was used to rinse up to 1.3 mL toluene-d$_8$. The 1 dram vial was sealed with a Teflon cap, and allowed to stir for 2 hours at 45° C., at which point an aliquot was taken and passed through a silica gel plug with ether as an eluent before being subjected to chiral GC analysis. The enantiomeric excess for 2f was determined to be 91% (Cyclosil-B, 100° C. isothermal, t$_R$(major)=37.13 min, t$_R$(minor)=41.06 min.) and the enantiomeric excess for 2a was determined to be 0% (Cyclosil-B, 100° C. isothermal, t$_R$=32.55 min, t$_R$=34.03 min.). A separate aliquot was taken from the reaction flask at the same time, and diluted with CDCl$_3$ to determine the conversion of 2f versus the nitrobenzene internal standard by $^1$HNMR (50% conversion).

Enantiomeric Excess Over Time

To a ½ dram vial was added ligand (S,R) tBu-ArSOX (8.1 mg, 0.02 mmol, 0.1 equiv) and Pd(OAc)$_2$ (4.4 mg, 0.02 mmol, 0.1 equiv). Toluene (0.3 mL) was added, and the vial was capped and allowed to stand at 45° C. until all solids had dissolved. Separately, to a 1 dram vial with stir bar was added 1a (32.4 mg, 0.2 mmol, 1 equiv), 2,6-dimethylbenzoquinone (30 mg, 0.22 mmol, 1.1 equiv), and diphenylphosphinic acid (4.4 mg, 0.02 mmol, 0.1 equiv.). The catalyst solution was subsequently added to the reaction flask, and toluene was used to rinse up to 1.3 mL toluene. The 1 dram vial was sealed with a Teflon cap, and allowed to stir at 45° C. Aliquots were taken and passed through a silica gel plug with ether as an eluent before being subjected to chiral GC analysis (FIG. 1).

Scheme 1-12: Internal olefin study

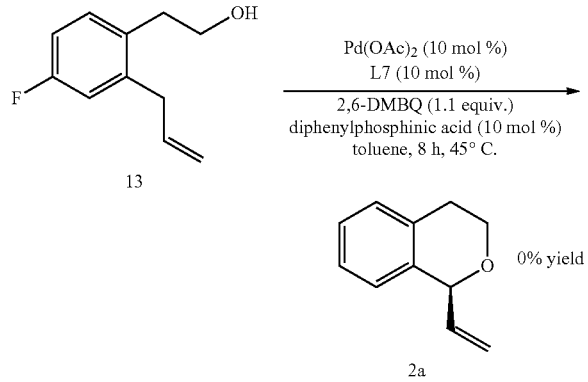

To a ½ dram vial was added ligand (S,R) tBu-ArSOX (L7, 4.1 mg, 0.01 mmol, 0.1 equiv) and Pd(OAc)$_2$ (2.2 mg, 0.01 mmol, 0.1 equiv). Toluene (0.2 mL) was added, and the vial was capped and allowed to stand at 45° C. until all solids had dissolved. Separately, to a ½ dram vial with stir bar was added 13 (16.2 mg, 0.1 mmol, 1 equiv), 2,6-dimethylbenzoquinone (15 mg, 0.11 mmol, 1.1 equiv), and diphenylphosphinic acid (2.2 mg, 0.01 mmol, 0.1 equiv.). The catalyst solution was subsequently added to the reaction flask, and toluene was used to rinse up to 0.65 mL toluene. The vial was sealed with a Teflon cap, and allowed to stir for 8 hours at 45° C. The vial was allowed to cool to room temperature, and solvent was evaporated under reduced pressure. The crude residue was examined by $^1$HNMR, and 2a was not observed. 13 $^1$H NMR (500 MHz, CDCl$_3$) δ 7.45 (dd, J=8.4, 1.7 Hz, 1H) 7.24-7.17 (m, 3H), 6.68 (dd, J=15.7, 1.7 Hz, 1H), 6.14 (dq, J=15.6, 6.6 Hz, 1H), 3.84 (t, J=6.9 Hz, 2H), 2.98 (t, J=6.9 Hz, 2H), 1.93 (dd, J=6.6, 1.7 Hz, 3H), 1.5 (br. s, 1H); $^{13}$C NMR (125 MHz, CDCl$_3$) δ 137.6, 135.2, 130.5, 128.6, 128.2, 127.2, 127.1, 126.5, 63.4, 36.7, 19.1; HRMS (EI) m/z calc'd for C$_{11}$H$_{14}$O [M]+: 162.1045; found 162.1047.

Scheme 1-13: Aliphatic olefin study

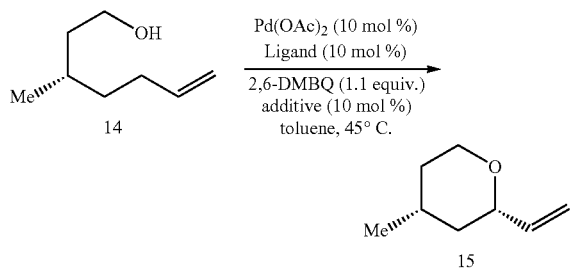

| Entry | Ligand | % Yield | d.r. (cis:trans) |
|---|---|---|---|
| 1 | (R,S) tBu-ArSOX | 78 | 19:1 |
| 2 | meso - 1,2-bis(phenylsulfinyl)ethane | 76 | 8:1 |
| 3 | (S,R) tBu-ArSOX | 85 | 1.3:1 |

Entry 1:

To a ½ dram vial was added ligand (R,S) tBu-ArSOX (4.1 mg, 0.01 mmol, 0.1 equiv) and Pd(OAc)$_2$ (2.2 mg, 0.01 mmol, 0.1 equiv). Toluene-d$_8$ (0.2 mL) was added, and the vial was capped and heated to 45° C. until all solids had dissolved. Separately, to a ½ dram vial with stir bar was added (S)-3-methylhept-6-en-1-ol (14) (12.8 mg, 0.10 mmol, 1 equiv), 2,6-dimethylbenzoquinone (15 mg, 0.11 mmol, 1.1 equiv), and diphenylphosphinic acid (2.2 mg, 0.01 mmol, 0.1 equiv). The catalyst solution was subsequently added to the reaction flask, and toluene-d$_8$ was used to rinse up to 0.65 mL. The ½ dram vial was sealed with a Teflon cap, and allowed to stir for 48 hours at 45° C. Afterward, the vial was allowed to cool to room temperature, and nitrobenzene (4.1 μL, 0.04 mmol, 0.4 equiv) was added as an internal standard. The diasteromeric ratio (19:1 cis:trans) was determined by subjecting a crude aliquot to GC analysis (HP-5 (5%-Phenyl)-methylpolysiloxane column (30 m, 0.32 mm, 0.25 mm). Because of the low boiling point of 15, the yield was determined by $^1$HNMR, compared to the nitrobenzene internal standard. The yield was determined to be 78%. For purposes of isolation, the reaction mixture was directly subjected to column chromatography (97:3 pentane:Et$_2$O), and the fractions collected from the column were concentrated under reduced pressure at 0° C.

Entry 2:

To a ½ dram vial with stir bar was added (S)-3-methylhept-6-en-1-ol (14) (12.8 mg, 0.10 mmol, 1 equiv), 2,6-dimethylbenzoquinone (15 mg, 0.11 mmol, 1.1 equiv), diphenylphosphinic acid (2.2 mg, 0.01 mmol, 0.1 equiv), meso-1,2-bis(phenylsulfinyl)ethane (L12) (2.8 mg, 0.01 mmol, 0.1 equiv) and Pd(OAc)$_2$ (2.2 mg, 0.01 mmol, 0.1 equiv). Toluene-d$_8$ (0.65 mL) was added, and the vial was sealed with a Teflon cap and allowed to stir for 24 hours at 45° C. Afterward, the vial was allowed to cool to room temperature, and nitrobenzene (4.1 μL, 0.04 mmol, 0.4 equiv) was added as an internal standard. The diasteromeric ratio (8:1 cis:trans) was determined by subjecting a crude aliquot to GC analysis. The yield was determined by $^1$HNMR, compared to the nitrobenzene internal standard. The yield was determined to be 76%.

Entry 3:

To a ½ dram vial was added ligand (S,R) tBu-ArSOX (4.1 mg, 0.01 mmol, 0.1 equiv) and Pd(OAc)$_2$ (2.2 mg, 0.01 mmol, 0.1 equiv). Toluene-d$_8$ (0.2 mL) was added, and the vial was capped and heated to 45° C. until all solids had dissolved. Separately, to a ½ dram vial with stir bar was added (S)-3-methylhept-6-en-1-ol (14) (12.8 mg, 0.10 mmol, 1 equiv), 2,6-dimethylbenzoquinone (15 mg, 0.11 mmol, 1.1 equiv), and diphenylphosphinic acid (2.2 mg, 0.01 mmol, 0.1 equiv). The catalyst solution was subsequently added to the reaction flask, and toluene-d$_8$ was used to rinse up to 0.65 mL. The ½ dram vial was sealed with a Teflon cap, and allowed to stir for 48 hours at 45° C. Afterward, the vial was allowed to cool to room temperature, and nitrobenzene (4.1 μL, 0.04 mmol, 0.4 equiv) was added as an internal standard. The diasteromeric ratio (1.3:1 cis:trans) was determined by subjecting a crude aliquot to GC analysis. The yield was determined by $^1$HNMR, compared to the nitrobenzene internal standard. The yield was determined to be 85%.

(14)

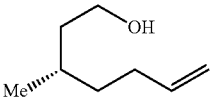

(S)-3-methylhept-6-en-1-ol (14)

¹H NMR (500 MHz, CDCl₃) δ 5.83 (ddt, J=16.7, 10.1, 6.6 Hz, 1H), 5.02 (d, J=17.1, 1H), 4.96 (d, J=10.3 Hz 1H), 3.78-3.68 (m, 2H), 2.16-2.02 (m, 2H), 1.69-1.59 (m, 2H), 1.48-1.38 (m, 2H), 1.30-1.23 (m, 1H), 0.93 (d, J=6.4 Hz, 3H); ¹³C NMR (125 MHz, CDCl₃) δ 139.3, 114.5, 61.4, 40.1, 36.5, 31.5, 29.2, 19.7; $[\alpha]^{23}_D$=-4.06° (c=0.45, hexane); HRMS (EI+) m/z calc'd for $C_8H_{15}$ [M−OH]+: 111.1174; found 111.1178. Spectral data is consistent with previous literature.

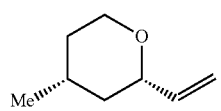

(cis-15)

(2S,4R)-4-methyl-2-vinyltetrahydro-2H-pyran (cis-15)

Product is a clear oil. ¹H NMR (500 MHz, CDCl₃) δ 5.89 (ddd, J=16.4, 10.7, 5.6 Hz, 1H), 5.27 (d, J=17.3 Hz, 1H), 5.12 (d, J=10.7 Hz, 1H), 4.07 (ddd, J=11.5, 4.6, 1.2 Hz, 1H), 3.81 (ddd, J=11.0, 5.4, 1.0 Hz, 1H), 3.51 (td, J=12.2, 2.2 Hz, 1H), 1.74-1.65 (m, 2H), 1.60-1.55 (m, 1H) 1.32-1.22 (m, 1H), 1.10-1.02 (m, 1H), 0.99 (d, J=6.3 Hz, 3H); ¹³C NMR (125 MHz, CDCl₃) δ 139.6, 114.7, 78.3, 68.2, 40.7, 34.6, 30.5, 22.5; $[\alpha]^{23}_D$=-19.88° (c=0.2, CH₂Cl₂); HRMS (EI+) m/z calc'd for $C_8H_{14}O$ [M]+: 126.1045; found 126.1046.

Scheme 1-14: nOe Assignment of 6b.

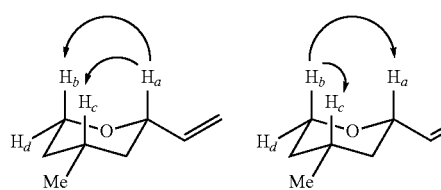

(6b)

(500 MHz, CDCl₃) The ethereal proton peak at δ 4.07 ($H_a$) was irradiated, and the resulting observed relationship is illustrated above. cis-15 gave a characteristic nOe between the axial ethereal proton $H_a$, and both the axial proton $H_c$ (δ 1.27, multiplet) and the axial ethereal proton $H_b$ (δ 3.51). Additionally, the ethereal proton peak at δ 3.51 ($H_b$) was irradiated, and an nOe between the axial ethereal proton $H_b$, and both the and axial ethereal proton $H_a$ (δ 4.07) and the axial proton $H_c$ (δ 1.27, multiplet) was observed. This indicates a cis-relationship between $H_a$, $H_b$, and $H_c$ for cis-15.

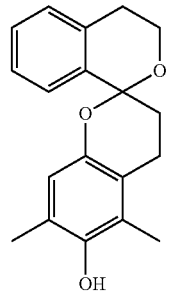

(S16)

Under the optimized reaction conditions, small amounts (approx. 10%) of an adduct from the reaction of the isochroman product (2a) and the 2,6-dimethylquinone oxidant were isolated as a side product. The quantity of this side product (S16) was observed to increase if the reaction was allowed to stir past the reaction's completion. S16 ¹H NMR (500 MHz, CDCl₃) δ 7.39 (d, J=7.9 Hz, 1H), 7.31-7.27 (m, 2H), 7.21 (d, J=7.7 Hz, 1H), 6.57 (s, 1H), 4.28 (br. s, 1H), 4.16 (t, J=11.6 Hz, 1H), 3.93 (dd, J=11.1, 6.0 Hz, 1H), 3.21-3.10 (m, 1H), 2.99-2.90 (m, 1H), 2.76 (dd, J=16.1, 6.0 Hz, 1H), 2.68 (d, J=15.9 Hz, 1H), 2.40 (td, J=13.1, 6.2 Hz, 1H), 2.22 (s, 3H), 2.20 (s, 3H), 2.13 (dd, J=13.5, 6.6 Hz, 1H); ¹³C NMR (125 MHz, CDCl₃) δ 146.6, 146.2, 137.2, 134.8, 128.9, 128.4, 127.0, 126.8, 122.2, 122.0, 119.5, 116.6, 95.8, 59.4, 32.3, 29.1, 20.5, 16.3, 11.7; HRMS (EI+) m/z calc'd for $C_{19}H_{20}O_3$ [M]+: 296.1413; found 296.1419.

Figure 2:
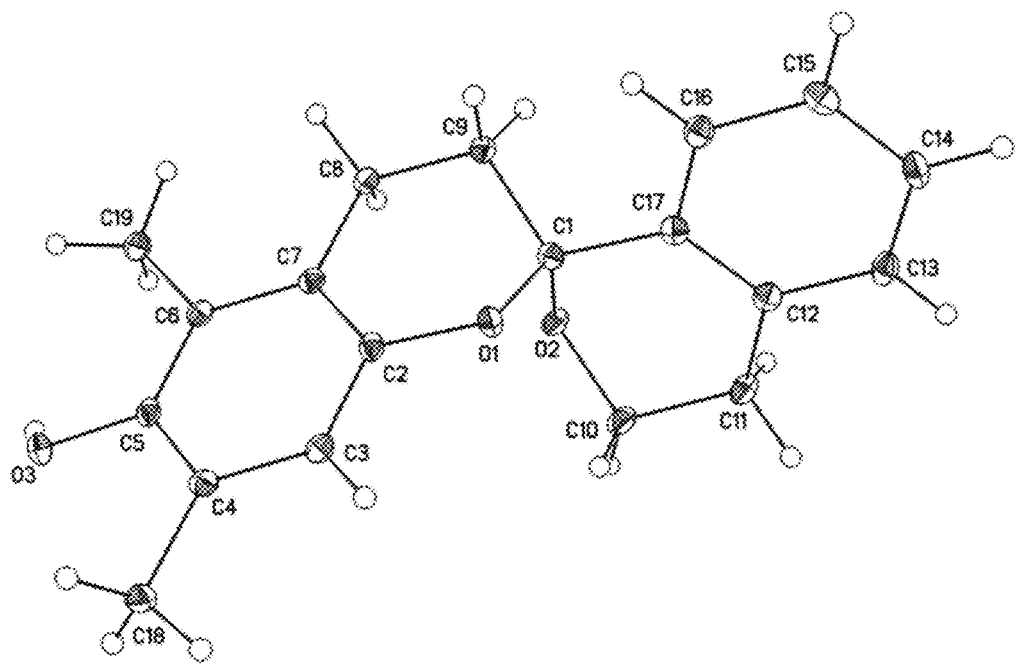
FIG. 2. X-ray crystal structure for compound S16.

A (racemic) crystal structure was obtained of S16, produced from a reaction run with racemic ligand S10. This crystal was spectroscopically identical (¹HNMR) to S16 produced from reactions run with chiral ligand (FIG. 2, Table 1-4).

TABLE 1-4

| Crystal data and structure refinement for S16. | |
|---|---|
| Identification code | cd89zsa |
| Empirical formula | C19 H20 O3 |
| Formula weight | 296.35 |
| Temperature | 100(2)K |
| Wavelength | 1.54178 Å |
| Crystal system | Monoclinic |
| Space group | P2₁/n |
| Unit cell dimensions | a = 7.6306(2) Å   a = 90°. |
| | b = 7.6652(2) Å   b = 90.5414(12)°. |
| | c = 24.7258(8) Å   g = 90°. |
| Volume | 1446.15(7) Å³ |
| Z | 4 |
| Density (calculated) | 1.361 Mg/m3 |
| Absorption coefficient | 0.728 mm−1 |
| F(000) | 632 |
| Crystal size | 0.287 × 0.153 × 0.114 mm3 |
| Theta range for data collection | 3.575 to 68.369°. |
| Index ranges | −9 <= h <= 9, −8 <= k <= 9, −29 <= l <= 28 |
| Reflections collected | 39068 |
| Independent reflections | 2633 [R(int) = 0.0434] |
| Completeness to theta = 67.679° | 99.7% |
| Absorption correction | Integration |
| Max. and min. transmission | 0.95969 and 0.91376 |
| Refinement method | Full-matrix least-squares on F2 |
| Data/restraints/parameters | 2633/0/204 |
| Goodness-of-fit on F2 | 1.080 |
| Final R indices [l > 2sigma(l)] | R1 = 0.0382, wR2 = 0.0941 |
| R indices (all data) | R1 = 0.0439, wR2 = 0.0978 |
| Extinction coefficient | n/a |
| Largest diff. peak and hole | 0.218 and −0.283 e.Å−3 |

Starting Materials

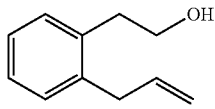

2-(2-allylphenyl)ethan-1-ol (1a)

Product is a clear oil $^1$H NMR (500 MHz, CDCl$_3$) δ 7.20-7.18 (m, 4H), 5.98 (ddt, J=16.9, 10.1, 6.2 Hz, 1H), 5.07 (d, J=10.1 Hz, 1H), 4.99 (d, J=16.9 Hz, 1H), 3.84 (app. q, J=6.4 Hz, 2H), 3.44 (d, J=6.2 Hz, 2H), 2.91 (t, J=6.9 Hz, 2H), 1.46 (br. s, 1H); $^{13}$C NMR (125 MHz, CDCl$_3$) δ 138.6, 137.6, 136.7, 130.3, 130.3, 127.1, 126.9, 116.1, 63.5, 37.4, 36.2; HRMS (EI) m/z calc'd for C$_{11}$H$_{13}$O [M]+: 161.0966; found 161.0969. Spectral data is consistent with data in previous literature.

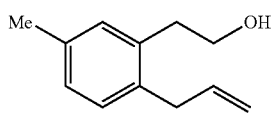

2-(2-allyl-5-methylphenyl)ethan-1-ol (1b)

Product is a clear oil. $^1$H NMR (500 MHz, Chloroform-d) δ 7.07 (d, J=7.5 Hz, 1H), 7.01 (d, J=8.1 Hz, 2H), 5.95 (ddt, J=17.1, 10.1, 6.3 Hz, 1H), 5.05 (dq, J=10.1, 1.4 Hz, 1H), 4.98 (ddd, J=17.1, 2.3, 1.3 Hz, 1H), 3.83 (t, J=6.9 Hz, 2H), 3.39 (d, J=6.3 Hz, 2H), 2.87 (t, J=6.8 Hz, 2H), 2.31 (s, 3H); $^{13}$C NMR (126 MHz, CDCl$_3$) δ 137.79, 136.42, 136.24, 135.41, 130.99, 130.17, 127.76, 115.84, 63.48, 37.00, 36.11, 21.24; HRMS (EI) m/z calc'd for C$_{12}$H$_{16}$O [M]+: 176.1201; found 176.1209.

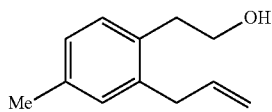

2-(2-allyl-4-methylphenyl)ethan-1-ol (1c)

Product is a clear oil. $^1$H NMR (500 MHz, Chloroform-d) δ 7.09 (d, J=8.2 Hz, 1H), 7.04-6.98 (m, 2H), 5.96 (ddt, J=17.2, 10.1, 6.3 Hz, 1H), 5.06 (dq, J=10.1, 1.6 Hz, 1H), 5.00 (dq, J=17.1, 1.8 Hz, 1H), 3.82 (t, J=6.9 Hz, 2H), 3.40 (dt, J=6.4, 1.6 Hz, 2H), 2.87 (t, J=6.9 Hz, 2H), 2.31 (s, 3H), 1.45 (br, 1H); $^{13}$C NMR (126 MHz, CDCl$_3$) δ 138.31, 137.64, 136.54, 133.47, 130.94, 130.18, 127.50, 115.98, 63.53, 37.38, 35.71, 21.25; HRMS (EI) m/z calc'd for C$_{12}$H$_{16}$O [M]+: 176.1201; found 176.1201.

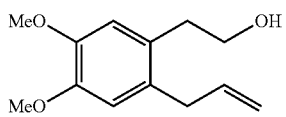

2-(2-allyl-4,5-dimethoxyphenyl)ethan-1-ol (1d)

Product is a clear oil $^1$H NMR (500 MHz, CDCl$_3$) δ 6.72 (s, 1H), 6.69 (s, 1H), 5.95 (ddt, J=16.3, 10.1, 6.2 Hz, 1H), 5.06 (dq, J=10.1, 1.7 Hz, 1H), 4.98 (dq, J=17.1, 1.7 Hz, 1H), 3.86 (s, 3H), 3.85 (s, 3H), 3.81 (app. q, J=6.6 Hz, 2H), 3.36 (d, J=6.2 Hz, 2H), 2.84 (t, J=6.9 Hz, 2H), 1.42 (t, J=5.6 Hz, 1H); $^{13}$C NMR (125 MHz, CDCl$_3$) δ 147.9, 147.7, 137.9, 130.6, 128.6, 116.0, 113.6, 113.5, 63.8, 56.3, 56.3, 37.1, 36.0; HRMS (EI) m/z calc'd for C$_{13}$H$_{18}$O$_3$ [M]+: 222.1256; found 222.1259.

2-(2-allyl-5-bromophenyl)ethan-1-ol (1e)

Product is a clear oil. $^1$H NMR (500 MHz, Chloroform-d) δ 7.38-7.28 (m, 2H), 7.04 (d, J=8.2 Hz, 1H), 5.92 (ddt, J=16.4, 9.9, 6.1 Hz, 1H), 5.08 (dd, J=9.9, 1.8 Hz, 1H), 4.96 (dd, J=17.2, 1.9 Hz, 1H), 3.80 (t, J=6.8 Hz, 2H), 3.37 (d, J=5.7 Hz, 2H), 2.84 (t, J=6.8 Hz, 2H), 1.91 (br, 1H); $^{13}$C NMR (126 MHz, CDCl$_3$) δ 139.22, 137.47, 136.83, 132.87, 131.84, 129.95, 120.38, 116.49, 63.07, 36.81, 35.80; HRMS (EI) m/z calc'd for C$_{11}$H$_{13}$OBr [M]+: 240.1050; found 240.1050.

2-(2-allyl-4-fluorophenyl)ethan-1-ol (1f)

Product is a clear oil $^1$H NMR (500 MHz, CDCl$_3$) δ 7.18 (dd, J=8.3, 5.9 Hz, 1H), 6.94-6.87 (m, 2H), 5.97 (ddt, J=16.4, 10.0, 6.1 Hz, 1H), 5.14 (dq, J=10.0, 1.5 Hz, 1H), 5.04 (dq, J=17.1, 1.7 Hz, 1H), 3.84 (app. q, J=6.6 Hz, 2H), 3.44 (d, J=6.1 Hz, 2H), 2.89 (t, J=6.8 Hz, 2H), 1.51 (br. s, 1H); $^{13}$C NMR (125 MHz, CDCl$_3$) δ 161.9 (d, J=244.1 Hz), 140.8 (d, J=6.8 Hz), 136.6, 132.3 (d, J=2.8 Hz), 131.6, 131.5, 116.3 (d, J=21.0 Hz), 113.4 (d, J=20.5 Hz), 63.4, 37.3, 35.4; $^{19}$F NMR (470 MHz, CDCl$_3$) δ −117.1; HRMS (EI) m/z calc'd for C$_{11}$H$_{13}$OF [M]+: 180.0950; found 180.0948.

2-(2-allyl-6-fluorophenyl)ethan-1-ol (1g)

Product is a clear oil $^1$H NMR (500 MHz, CDCl$_3$) δ 7.15 (dt, J=7.9, 5.8 Hz, 1H), 6.97 (d, J=7.7 Hz, 1H), 6.92 (t, J=9.6

Hz, 1H), 5.96 (ddt, J=16.5, 10.1, 6.2 Hz, 1H), 5.08 (dq, J=10.1, 1.5 Hz, 1H), 4.98 (dq, J=17.2, 1.7 Hz, 1H), 3.81 (app. q, J=7.1 Hz, 2H), 3.46 (dt, J=6.2, 1.5 Hz, 2H), 2.96 (td, J=7.1, 1.9 Hz, 2H), 1.44 (br. s, 1H); $^{13}$C NMR (125 MHz, CDCl$_3$) δ 162.2 (d, J=244.0 Hz), 141.3, 137.2, 128.0 (d, J=9.2 Hz), 125.7 (d, J=2.8 Hz), 124.2 (d, J=14.7), 116.5, 113.6 (d, J=23.0 Hz), 62.7, 37.3, 29.3; $^{19}$F NMR (470 MHz, CDCl$_3$) δ −117.4; HRMS (EI) m/z calc'd for C$_{11}$H$_{13}$FO [M]+: 180.0950; found 180.0955.

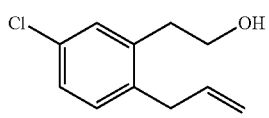

2-(2-allyl-5-chlorophenyl)ethan-1-ol (1h)

Product is a clear oil $^1$H NMR (500 MHz, CDCl$_3$) δ 7.20 (d, J=1.9 Hz, 1H), 7.16 (dd, J=8.1, 1.9 Hz, 1H), 7.10 (d, J=8.1 Hz, 1H), 5.93 (ddt, J=16.3, 10.1, 5.6 Hz, 1H), 5.08 (d, J=10.3 Hz, 1H), 4.96 (d, J=17.1 Hz, 1H), 3.84 (app. q, J=6.4 Hz, 2H), 3.38 (d, J=6.2 Hz, 2H), 2.87 (t, J=6.6 Hz, 2H), 1.46 (t, J=5.6 Hz, 1H); $^{13}$C NMR (125 MHz, CDCl$_3$) δ 138.8, 137.0, 132.4, 131.6, 130.1, 127.1, 127.1, 116.5, 63.2, 36.9, 35.9; HRMS (EI) m/z calc'd for C$_{11}$H$_{13}$OCl [M]+: 196.0655; found 196.0652.

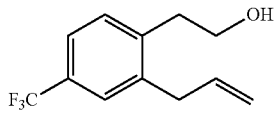

2-(2-allyl-4-(trifluoromethyl)phenyl)ethan-1-ol (1i)

Product is a clear oil $^1$H NMR (500 MHz, CDCl$_3$) δ 7.48-7.45 (m, 2H), 7.36 (d, J=8.3 Hz, 1H), 5.99 (ddt, J=16.4, 10.0, 6.1 Hz, 1H), 5.16 (dq, J=10.3, 1.5 Hz, 1H), 5.03 (dq, J=17.1, 1.7 Hz, 1H), 3.90 (t, J=6.8 Hz, 2H), 3.52 (d, J=6.1 Hz, 2H), 2.99 (t, J=6.6 Hz, 2H); $^{13}$C NMR (125 MHz, CDCl$_3$) δ 141.1, 139.3, 136.4, 130.5, 129.2 (q, J=32.1 Hz), 126.8 (q, J=3.6 Hz), 124.5 (q, J=270.1 Hz), 123.5 (q, J=3.6 Hz), 117.0, 63.0, 37.2, 35.9; $^{19}$F NMR (470 MHz, CDCl$_3$) δ −62.8; HRMS (EI) m/z calc'd for C$_{12}$H$_{13}$OF$_3$ [M]+: 230.0918; found 230.0925.

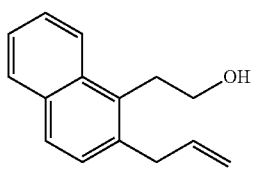

2-(2-allylnaphthalen-1-yl)ethan-1-ol (1j)

Product is a clear oil $^1$H NMR (500 MHz, CDCl$_3$) δ 8.12 (d, J=8.5 Hz, 1H), 7.85 (d, J=8.1 Hz, 1H), 7.74 (d, J=8.5 Hz, 1H), 7.55 (t, J=6.8 Hz, 1H), 7.48 (t, J=7.8 Hz, 1H), 7.36 (d, J=8.5 Hz, 1H), 6.07 (ddt, J=16.1, 10.0, 6.1 Hz, 1H), 5.12 (dq, J=10.0, 1.7 Hz, 1H), 5.03 (dq, J=17.1, 1.7 Hz, 1H), 3.97 (t, J=7.1 Hz, 2H), 3.68 (dt, J=6.1, 1.7 Hz, 2H), 3.45 (t, J=7.3 Hz, 2H), 1.48 (br. s, 1H); $^{13}$C NMR (125 MHz, CDCl$_3$) δ 137.6, 136.2, 133.0, 132.9, 131.5, 128.9, 128.8, 127.4, 126.4, 125.3, 124.1, 116.0, 63.2, 38.2, 31.8; HRMS (EI) m/z calc'd for C$_{15}$H$_{16}$O [M]+: 212.1201; found 212.1207.

General Synthesis of Starting Materials

General Route A was Used for 1a, 1f, 1h, 1i. General Route B was Used for 1b, 1c, 1d, 1e, 1g, 1j.

Scheme 1-15: General Starting Material Synthesis A.

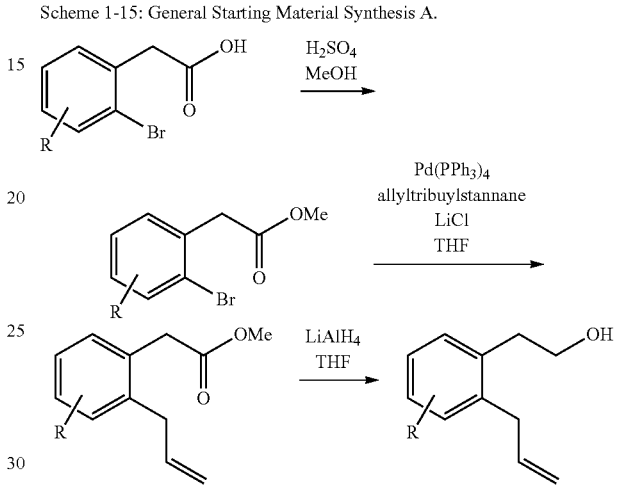

General Route A:

To a dried round-bottom flask (RBF) was added the 2-bromophenylacetic acid starting material and anhydrous MeOH (0.3 M). Concentrated Sulfuric acid (5 mol %) was added, and the reaction was refluxed for three hours. After cooling to room temperature, the volatiles were evaporated under reduced pressure, and the remaining mixture was dissolved in EtOAc. The organics were washed with sat. aq. NaHCO$_3$ (×3), and the organic layer was dried over anhydrous MgSO$_4$, filtered, and concentrated under reduced pressure. The mixture was purified by column chromatography to afford the desired methyl ester.

To a dried RBF in a glove box was added Pd(PPh$_3$)$_4$ (0.1 equiv), LiCl (5.0 equiv), and the flask was sealed and taken out of the glovebox. THF (0.1 M) was added followed by the corresponding methyl ester substrate (1.0 equiv) and allyltributylstannane (1.2 equiv) via syringe. The reaction was refluxed under argon overnight. After complete conversion of the starting material was observed by TLC, the flask was cooled to 0° C. and diluted slowly with water. The layers were separated, and the aqueous layer was extracted with EtOAc (×2). The combined organic layers were dried over anhydrous MgSO$_4$, filtered, and concentrated under reduced pressure. The mixture was purified by column chromatography to afford the desired allylated methyl ester.

To a dried RBF was added LiAlH$_4$ (95%, 1 equiv) under argon. THF (0.1 M) was added, and the flask was cooled to 0° C. To the mixture was added the allylated methyl ester (1.4 equiv) dissolved in THF (1 M) dropwise, and the mixture was warmed to room temperature and stirred for 2 hours under argon. After complete conversion of the starting material was observed by TLC, the reaction flask was cooled to 0° C., and the reaction was quenched by dropwise addition of sat. aq. Rochelle's salt. The reaction was diluted with ether, and the biphasic mixture was stirred until both layers became homogeneous (typically 2 hours to overnight). The layers were separated, and the aqueous layer was extracted with ether (×3). The combined organic layers were washed once with brine, and dried over anhydrous MgSO₄, filtered, and concentrated under reduced pressure. The mixture was purified by column chromatography to afford the desired alcohol.

Scheme 1-16: General Starting Material Synthesis B.

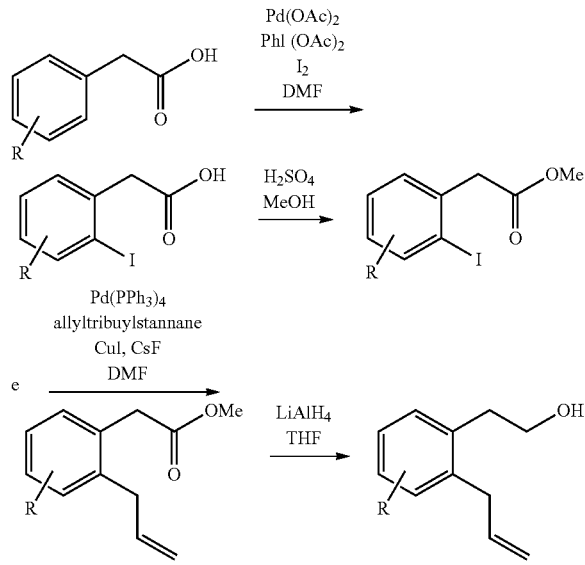

General Route B:

Under the conditions of Yu[13], to a dried RBF was added PhI(OAc)₂ (0.75 equiv) and I₂ (0.75 equiv). The flask was wrapped in aluminum foil to protect it from light, and DMF (0.16 M) was added. The reaction was capped and stirred for 5 minutes, and then Pd(OAc)₂ (0.05 equiv) and the phenylacetic acid starting material (1.0 equiv) were added quickly. The flask was sealed with a glass stopper and the seal was wrapped in Teflon tape and parafilm and subsequently covered in aluminum foil. The reaction was stirred at 60° C. for 12 hours. The solvent was subsequently evaporated under reduced pressure with the assistance of a high-vacuum, and the residue was dissolved in ether. The organic layer was extracted with sat. aq. NaHCO₃ (×3), and the combined aqueous layers were acidified with HCl. CH₂Cl₂ was added, and the aqueous layer was extracted with CH₂Cl₂ (×2) and EtOAc (×1). The combined organic layers were dried over anhydrous MgSO₄, filtered, and concentrated under reduced pressure to afford the iodinated phenylacetic acid substrate that was taken on directly to the next step.

To a dried RBF was added the 2-iodophenylacetic acid starting material and anhydrous MeOH (0.3 M). Concentrated Sulfuric acid (5 mol %) was added, and the reaction was refluxed for three hours. After cooling to room temperature, the volatiles were evaporated under reduced pressure, and the remaining mixture was dissolved in EtOAc. The organics were washed with sat. aq. NaHCO₃ (×3), and the organic layer was dried over anhydrous MgSO₄, filtered, and concentrated under reduced pressure. The mixture was purified by column chromatography to afford the desired methyl ester.

To a dried RBF in a glove box was added Pd(PPh₃)₄ (0.05 equiv), CsF (2.0 equiv), CuI (0.1 equiv), and the flask was sealed and taken out of the glovebox. DMF (0.33 M) was added followed by the corresponding methyl ester substrate (1.0 equiv) and allyltributylstannane (1.2 equiv) via syringe. The reaction was stirred at 45° C. for 6 hours under argon. After complete conversion of the starting material was observed by TLC, the flask was cooled to 0° C. and diluted slowly with water. The mixture was diluted with ether, and the layers were separated. The organic layer was washed with water (×2). The organic layer was dried over anhydrous MgSO₄, filtered, and concentrated under reduced pressure. The mixture was purified by column chromatography to afford the desired allylated methyl ester.

To a dried RBF was added LiAlH₄ (95%, 1 equiv) under argon. THF (0.1 M) was added, and the flask was cooled to 0° C. To the mixture was added the allylated methyl ester dissolved in THF (1 M) dropwise, and the mixture was warmed to room temperature and stirred for 2 hours under argon. After complete conversion of the starting material was observed by TLC, the reaction flask was cooled to 0° C., and the reaction was quenched by dropwise addition of sat. aq. Rochelle's salt. The reaction was diluted with ether, and the biphasic mixture was stirred until both layers became homogeneous (typically 2 hours to overnight). The layers were separated, and the aqueous layer was extracted with ether (×3). The combined organic layers were washed once with brine, and dried over anhydrous MgSO₄, filtered, and concentrated under reduced pressure. The mixture was purified by column chromatography to afford the desired alcohol.

Example 2. Pd(II) Sulfoxide Catalytic Coupling_Reactions

General Information: The following commercially obtained reagents were used as received: Pd(OAc)₂ (Johnson Mattey Chemicals) was stored in a glove box, and weighted out in the air at room temperature prior to use. Trifluoromethanesulfonic anhydride (Oakwood Chemicals) was stored in 5° C. fridge under N₂. 1,4-benzoquinone, 2,6-dimethylbenzoquinone and 2,5-dimethylbenzoquinone was purchased from Sigma-Aldrich and used as received. All allylic amination reactions were run under ambient air with no precautions taken to exclude moisture. All other reactions were run in flame- or oven-dried glassware under an atmosphere of N₂ or Ar gas with dry solvents unless otherwise stated. All products were filtered through a glass wool plug prior to obtaining a final weight. Anhydrous solvents were purified by passage through a bed of activated alumina immediately prior to use (Glass Countour, Laguna Beach, Calif.). Chloroform-d was stored over 3 Å molecular sieves in a secondary container with drierite. Thin-layer chromatography (TLC) was conducted with E. Merck silica gel 60 F254 precoated plates (0.25 mm) and visualized with UV and Cerium-ammonium-molybdate and potassium permanganate stains. Flash chromatography was performed using American International ZEOprep 60 ECO silica gel (230-400 mesh).

¹H-NMR spectra were recorded on a Varian Inova-500 (500 MHz), Varian Unity-500 (500 MHz) or Carver-Bruker 500 (500 MHz) spectrometer and are reported in ppm using solvent as an internal standard (CDCl₃ at 7.26 ppm). Data reported as: s=singlet, d=doublet, t=triplet, q=quartet, p=pentet, sxt=sextet, hept=septet, m=multiplet, br=broad, app=apparent; coupling constant(s) in Hz; integration. Proton-decoupled ¹³C-NMR spectra were recorded on a Varian Unity-500 (125 MHz) or Carver-Bruker 500 (125 MHz) spectrometer and are reported in ppm using solvent as an internal standard (CDCl₃ at 77.16 ppm). Chiral gas chromatographic (GC) analysis was performed on an Agilent 6890N Series instrument equipped with FID detectors using a J&W Cyclosil-B column. Chiral high pressure liquid chromatography (HPLC) analysis was performed on an Agilent 1100 Series instrument equipped with a UV detector, using a CHIRALPAK AD-RH or OJ-H column. Optical rotations were measured using a 1 mL cell with a 50 mm path length on a Jasco P-1020 polarimeter. Optical rotations were obtained with a sodium lamp and are reported as follows: $[\alpha]_\lambda T°$ C. (c=g/100 mL solvent). High-resolution mass spectra were obtained at the University of Illinois Mass Spectrometry Laboratory. Electrospray ionization (ESI) spectra were performed on a Waters Q-Tof μLtima spectrometer, and electron ionization (EI) and field desorption (FD) spectra were performed on a Micromass 70-VSE spectrometer.

General Procedure for the Cross-Coupling of Amines with Olefins

To a half dram screw-cap vial equipped a magnetic stir bar was added Pd(OAc)₂ (5 or 10 mol %), (±)-MeO—SOX ligand (L5) (5 or 10 mol %), 2,5-dimethylbenzoquinone (0.22 mmol, 1.1 equiv), olefin (0.2 mmol, 1.0 equiv) and N-triflyl protected amine (0.2 mmol, 1.0 equiv). Toluene (0.2 mL, 1.0M) was added and the vial was capped and heated to 45° C. for 24-72 hours. After the reaction was complete, the reaction mixture was allowed to cool to room temperature, diluted with acetone and was directly filtered through a short pad of silica gel (pipette plug using acetone) into a 20 mL vial. The mixture was concentrated under reduced pressure, trifluorotoluene (14.6 mg, 0.1 mmol, 0.5 equiv) was added as internal standard for ¹H NMR analysis of the crude material. The product was purified by flash chromatography on silica gel.

Synthesis of (±)-SOX Ligands: The General Procedure for Phenyloxazoline Synthesis.

Scheme 2-1: Ligand intermediate S1, S2, S3, S4, S5 and S6

General procedure A

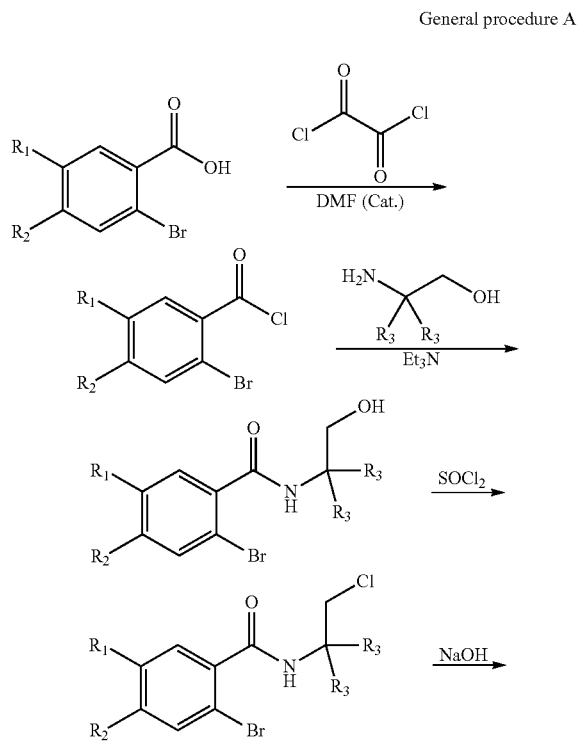

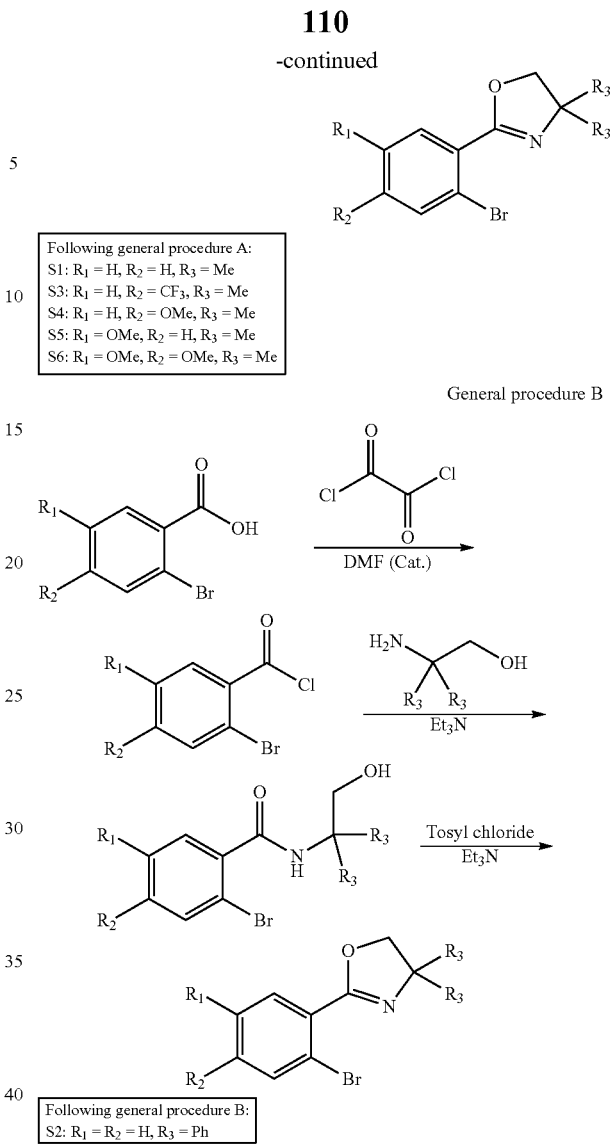

General Procedure A

Ligand intermediate S1, S3, S4, S5 and S6 were synthesized according the following general procedure: To a 100 mL oven-dried round-bottom flask was added the benzoic acid (10 mmol, 1.0 equiv) and CH₂Cl₂ (20 mL, 0.5 M). The solution was cooled to 0° C., oxalyl chloride (15 mmol, 1.5 equiv) was then added, followed by slowly addition of DMF (1.0 mmol, 0.1 equiv). The reaction was slowly warmed to room temperature and stirred overnight. The reaction was diluted with CH₂Cl₂ (300 mL), the organic layer was washed by 5% NaHCO₃ (200 mL×2) and dried over anhydrous Na₂SO₄, filtered, and concentrated under reduced pressure. The crude 2-bromobenzoyl chloride was carried through to the next step without further purification.

To a 100 mL oven-dried round-bottom flask was added commercial 2-amino-2-methyl-1-propanol (10 mmol, 1.0 equiv, Sigma Aldrich), Et₃N (20 mmol, 2.0 equiv) and 1,4 dioxane (14 mL). The solution was cooled to 0° C., and the 2-bromobenzoyl chloride from the previous step in 12 ml of 1,4 dioxane was added slowly. The reaction was allowed to warm up to room temperature and stirred for another 1 hour. The reaction mixture was filtered through a silica plug with ethyl acetate and concentrated under reduced pressure. The crude amide was carried through to the next step without further purification.

An oven-dried 300 mL round-bottom flask equipped with condenser was added the crude amide and toluene (70 mL). After cooled to 0° C., thionyl chloride (2.2 mL, 30 mmol, 3.0 equiv) was added dropwise and the reaction was heated to reflux for 3 hours. The solution and thionyl chloride was removed by repeated rotary evaporation with ethyl acetate (3 times). The crude product was carried through without further purification.

To the same round-bottom flask was added NaOH (15 mmol, 1.5 equiv) and MeOH (80 mL), and the mixture was heated to reflux open to air for 1 hour. After cooling to room temperature, diethyl ether (200 mL) was added. The resulting solution was washed 3 times with brine. The organic layer was dried over anhydrous $MgSO_4$, filtered, and concentrated under reduced pressure. The crude mixture was purified via flash column chromatography (0%=>10% acetone in hexanes) to afford the desired phenyloxazoline.

General Procedure B

Ligand intermediate S2 was synthesized according to the following general procedure: To a 100 mL oven-dried round-bottom flask was added the benzoic acid (10 mmol, 1.0 equiv) and $CH_2Cl_2$ (20 mL, 0.5 M). The solution was cooled to 0° C., oxalyl chloride (15 mmol, 1.5 equiv) was then added, followed by slow addition of DMF (1.0 mmol, 0.1 equiv). The reaction was slowly warmed to room temperature and stirred overnight. The reaction was diluted with $CH_2Cl_2$ (300 mL), the organic layer was washed by 5% $NaHCO_3$ (200 mL×2) and dried over anhydrous $NaSO_4$, filtered, and concentrated under reduced pressure. The crude 2-bromobenzoyl chloride was carried through to the next step without further purification.

To a 100 mL oven-dried round-bottom flask was added 2-amino-2,2-diphenylethanol[3] (10 mmol, 1.0 equiv), $Et_3N$ (20 mmol, 2.0 equiv) and 1,4 dioxane (14 mL). The solution was cooled to 0° C., and the crude 2-bromobenzoyl chloride from previous step in 12 ml of 1,4 dioxane was added slowly. The reaction was allowed to warm up to room temperature and stirred for another 1 hour. The reaction mixture was filtered through a silica plug with ethyl acetate and concentrated under reduced pressure. The crude amide was carried through next step without further purification.

To a solution of amide in $CH_2Cl_2$ (30 mL) was added tosyl chloride (13 mmol, 1.3 equiv) and $Et_3N$ (50 mmol, 5 equiv). The reaction was refluxed at 55° C. for 22 hours. After $H_2O$ (10 mL) was added, the reaction was refluxed at 75° C. for another 2 hours. The reaction was cooled, and the layers were separated. The aqueous layer was extracted with $CH_2Cl_2$ (30 mL×2). The combined organic layers were dried over anhydrous $MgSO_4$, filtered and concentrated under reduced pressure. The crude mixture was purified via flash column chromatography (0%=>10% acetone in hexanes) to afford the desired phenyloxazoline.

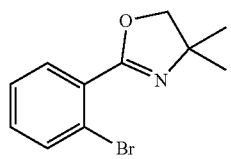

(S1)

Phenyloxazoline S1 was synthesized following the general procedure A in 73% yield (1.857 g, 7.340 mmol) as a colorless oil. $^1$H NMR (500 MHz, Chloroform-d) δ 7.64 (dd, J=7.7, 1.8 Hz, 1H), 7.62 (dd, J=8.0, 1.3 Hz, 1H), 7.33 (ddd, J=7.5, 7.5, 1.3 Hz, 1H), 7.27 (ddd, J=7.7, 7.5, 1.8 Hz, 1H), 4.14 (s, 2H), 1.41 (s, 6H). These data are in agreement with that previously reported in the literature.

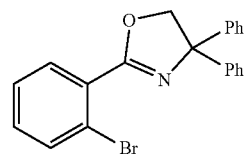

(S2)

Phenyloxazoline S2 was synthesized following the general procedure B in 53% yield (2.009 g, 5.311 mmol) as a colorless oil. $^1$H NMR (500 MHz, Chloroform-d) δ 7.81 (dd, J=7.7, 1.8 Hz, 1H), 7.69 (dd, J=8.0, 1.3 Hz, 1H), 7.52-7.49 (m, 4H), 7.41-7.36 (m, 5H), 7.34-7.28 (m, 3H), 5.03 (s, 2H). $^{13}$C NMR (125 MHz, $CDCl_3$) 162.5, 145.9, 134.0, 131.9, 131.7, 129.8, 128.6, 127.3, 127.2, 126.8, 122.2, 80.2, 79.9. HRMS (ESI) m/z calculated for $C_{21}H_{17}NOBr$ $[M+H]^+$: 378.0494, found 378.0492.

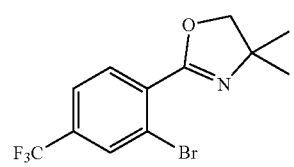

(S3)

Phenyloxazoline S3 was synthesized following the general procedure A in 51% yield (1.652 g, 5.129 mmol) as a colorless oil. $^1$H NMR (500 MHz, Chloroform-d) δ 7.91-7.87 (m, 1H), 7.78 (dd, J=8.1, 1.0 Hz, 1H), 7.59 (ddd, J=8.1, 1.7, 0.8 Hz, 1H), 4.16 (s, 2H), 1.42 (s, 6H). $^{13}$C NMR (126 MHz, Chloroform-d) δ 160.7, 133.5 (q, J=33.2 Hz), 131.8, 130.8 (q, J=3.8 Hz), 124.1 (q, J=3.6 Hz), 122.9 (q, J=273.1 Hz), 122.4, 79.8, 68.6, 28.4. $^{19}$F NMR (470 MHz, Chloroform-d) δ −63.09. HRMS (ESI) m/z calculated for $C_{12}H_{12}NOF_3Br$ $[M+H]^+$: 322.0054, found 322.0044.

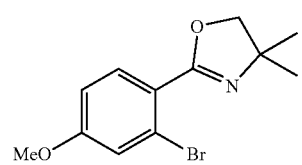

(S4)

Phenyloxazoline S4 was synthesized following the general procedure A in 59% yield (1.673 g, 5.887 mmol) as a white solid. $^1$H NMR (500 MHz, Chloroform-d) δ 7.57 (dd, J=8.6, 0.6 Hz, 1H), 7.10 (d, J=2.5 Hz, 1H), 6.80 (ddd, J=8.7, 2.6, 0.6 Hz, 1H), 4.05 (s, 2H), 3.75 (s, 3H), 1.34 (s, 6H). $^{13}$C NMR (125 MHz, $CDCl_3$) δ 161.47, 161.27, 132.30, 122.54, 122.31, 118.90, 113.04, 79.12, 67.84, 55.58, 28.26. HRMS (ESI) m/z calculated for $C_{12}H_{15}NO_2Br$ $[M+H]^+$: 284.0268, found 284.0293.

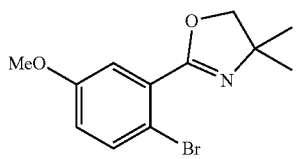

(S5)

Phenyloxazoline S5 was synthesized following the general procedure A in 79% yield (2.251 g, 7.920 mmol) as a white solid. $^1$H NMR (500 MHz, Chloroform-d) δ 7.48 (d, J=8.8 Hz, 1H), 7.16 (d, J=3.1 Hz, 1H), 6.83 (dd, J=8.8, 3.1 Hz, 1H), 4.14 (s, 2H), 3.81 (s, 3H), 1.41 (s, 6H). These data are in agreement with that previously reported in the literature.

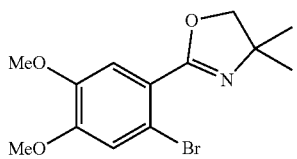

(S6)

Phenyloxazoline S6 was synthesized following the general procedure A in 62% yield (1.954 g, 6.219 mmol) as a white solid. $^1$H NMR (500 MHz, Chloroform-d) δ 7.12 (s, 1H), 6.99 (s, 1H), 4.04 (s, 2H), 3.82 (s, 3H), 3.82 (s, 3H), 1.33 (s, 6H). $^{13}$C NMR (125 MHz, CDCl$_3$) δ 161.5, 150.8, 147.8, 121.8, 116.2, 113.4, 112.7, 79.1, 67.8, 56.1, 56.1, 28.2. HRMS (ESI) m/z calculated for C$_{13}$H$_{17}$NO$_3$Br [M+H]$^+$: 314.0392, found 314.0385.

The General Procedure for the Synthesis of Methyl Sulfinates

Scheme 2-2: Ligand intermediate S7, S8 and S9

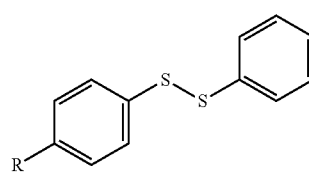

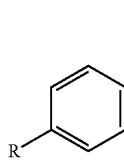

S7: R = Me,
S8: R = OMe,
S9: R = CF$_3$

Ligand intermediates (methyl sulfinates) S7, S8 and S9 was synthesize according the following general procedure. To a solution of the corresponding disulfide (10 mmol, 1.0 equiv) in MeOH (25 mL, 0.4 M) was slowly added NBS (15 mmol, 1.5 equiv) at room temperature. The reaction mixture was stirred and monitored by TLC. Upon completion, the reaction was diluted with CH$_2$Cl$_2$ (25 mL), washed with sat. aq. NaHSO$_3$ (10 mL) and sat. aq. NaHCO$_3$ (4×10 mL). The organic layer was dried over anhydrous Na$_2$SO$_4$, filtered and the solvent was removed under reduced pressure.

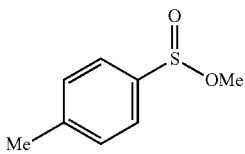

(S7)

Methyl sulfinate S7 was synthesize according to the general procedure in 95% yield (3.236 g, 19.01 mmol) as a colorless oil. $^1$H NMR (500 MHz, Chloroform-d) δ 7.59 (d, J=8.2 Hz, 2H), 7.34 (d, J=7.8 Hz, 2H), 3.46 (s, 3H), 2.43 (s, 3H). These data are in agreement with that previously reported in the literature.

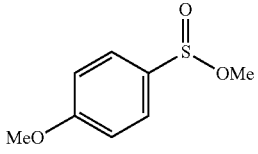

(S8)

Methyl sulfinate S8 was synthesized according to the general procedure in 91% yield (3.396 g, 18.24 mmol) as a colorless oil. $^1$H NMR (500 MHz, Chloroform-d) δ 7.64 (d, J=8.8, 2H), 7.03 (d, J=8.8, 2H), 3.87 (s, 3H), 3.46 (s, 3H). These data are in agreement with that previously reported in the literature.

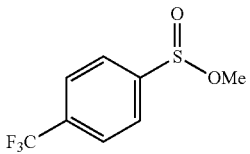

(S9)

Methyl sulfinate S9 was synthesized according to the general procedure in 94% yield (4.215 g, 18.80 mmol) as a colorless oil. $^1$H NMR (500 MHz, Chloroform-d) δ 7.90-7.72 (m, 4H), 3.52 (s, 3H). These data are in agreement with that previously reported in the literature.

The General Procedure for (±)-SOX Ligand Synthesis

Scheme 2-3: Synthesis of (±)-SOX ligands

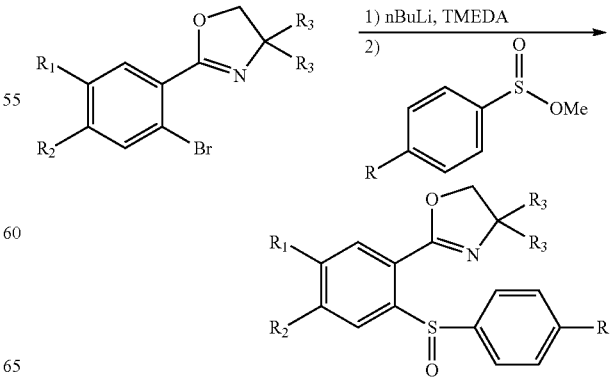

To an oven-dried round-bottom flask was added a stir bar, phenyloxazoline (5.0 mmol, 1.0 equiv), THF (25 ml, 0.2 M), and tetramethylethylenediamine (TMEDA, 5.5 mmol, 1.1 equiv). The reaction flask was cooled to −78° C. and n-butyllithium (1.6 M in hexane, 5.5 mmol, 1.1 equiv) was added dropwise. The reaction was stirred 20 minutes at −78° C. Subsequently, the methyl sulfinate (6.0 mmol, 1.2 equiv) was added as a solution in THF (12 ml, 0.5 M) dropwise. The reaction was stirred 1 hour at −78° C., then 1 hour at 0° C., then 1 hour at room temperature. The reaction was quenched with water. The mixture was diluted with diethyl ether, and the layers were separated. The aqueous layer was extracted with diethyl ether (20 mL×3). The combined organic layers were dried over anhydrous MgSO$_4$, filtered, and concentrated under reduced pressure. The crude residue was purified via flash column chromatography (0%=>20% acetone in hexanes) to afford the (±)-SOX ligand.

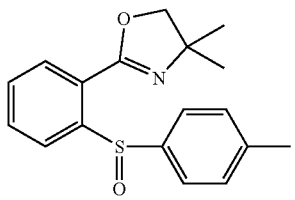

(L1)

(±)-SOX-Ligand 1 (L1) was synthesized following the general procedure. 1.27 g of phenyloxazoline S1 (5.0 mmol, 1.0 equiv) was used, along with 1.02 g of sulfinate S7 (6.0 mmol, 1.2 equiv). The crude residue was purified via flash column chromatography (0%=>20% acetone in hexanes) to afford 1.176 g (3.76 mmol) of pure product as a white solid (75% yield). $^1$H NMR (500 MHz, CDCl$_3$) δ 8.37 (dd, J=7.9, 1.1 Hz, 1H), 7.85 (dd, J=7.7, 1.3 Hz, 1H), 7.72 (ddd, J=7.7, 7.7, 1.1 Hz, 1H), 7.65 (d, J=8.4 Hz, 2H), 7.50 (ddd, J=7.5, 7.5, 0.9 Hz, 1H), 7.16 (d, J=8.4 Hz, 2H), 4.25 (dd, J=10.1, 8.8 Hz, 1H), 4.16 (t, J=8.1, Hz, 1H), 4.03 (dd, J=10.1, 7.9 Hz, 1H), 2.32 (s, 3H), 0.97 (s, 9H). These data are in agreement with that previously reported in the literature.

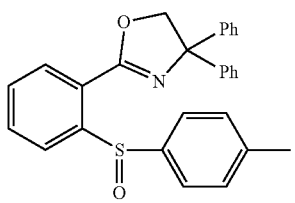

(L2)

(±)-SOX-Ligand 2 (L2) was synthesized following the general procedure. Phenyloxazoline S2 (1.89 g, 5.0 mmol, 1.0 equiv) and sulfinate S7 (1.02 g, 6.0 mmol, 1.2 equiv) were used. The crude residue was purified via flash column chromatography (0%=>20% acetone in hexanes) to afford 1.597 g (3.64 mmol) of pure product as a white solid (73% yield). $^1$H NMR (500 MHz, Chloroform-d) δ 8.46 (dd, J=8.0, 1.3 Hz, 1H), 8.01 (dd, J=7.7, 1.4 Hz, 1H), 7.77 (ddd, J=7.7, 7.7, 1.4 Hz, 1H), 7.55 (ddd, J=7.5, 7.5, 1.3 Hz, 1H), 7.51-7.47 (m, 4H), 7.38 (dd, J=8.5, 7.0 Hz, 2H), 7.31-7.27 (m, 1H), 7.23-7.16 (m, 3H), 7.04 (dd, J=8.0, 1.7 Hz, 2H), 7.00 (d, J=8.1 Hz, 2H), 4.95 (d, J=8.6 Hz, 1H), 4.85 (d, J=8.7 Hz, 1H), 2.29 (s, 3H). $^{13}$C NMR (125 MHz, CDCl$_3$) δ 159.9, 146.7, 145.6, 145.4, 143.5, 140.7, 132.2, 130.3, 129.9, 129.5, 128.6, 128.28, 127.3, 127.05 126.7, 126.7, 126.6, 125.4, 125.1, 81.0, 79.5, 21.4. HRMS (ESI) m/z calculated for C$_{28}$H$_{24}$NO$_2$S [M+H]$^+$: 438.1528, found 438.1519.

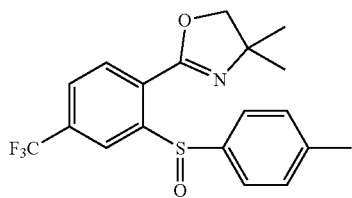

(L3)

(±)-SOX-Ligand 3 (L3) was synthesized according to the following modified procedure. To an oven-dried flask was added a stir bar, phenyloxazoline S3 (322.1 mg, 1.0 mmol, 1.0 equiv), THF (5 ml, 0.2M), and TMEDA (168 μL, 1.1 mmol, 1.1 equiv). The reaction flask was cooled to −94° C. and n-butyllithium (688 μL, 1.6 M in hexane, 1.1 mmol, 1.1 equiv) was added dropwise. The reaction was stirred 20 minutes at −94° C. and then the reaction was warmed up to −78° C., the methyl sulfinate S7 (1.02 g, 1.2 mmol, 1.2 equiv) was added as a solution in THF (5 mL, 0.2M) dropwise. The reaction was stirred 1 hour at −78° C., then 1 hour at 0° C., then 1 hour at room temperature. The reaction was then quenched with water. The mixture was diluted with diethyl ether, and the layers were separated. The aqueous layer was extracted with diethyl ether (25 mL×3). The combined organic layers were dried over anhydrous MgSO$_4$, filtered, and concentrated under reduced pressure. The crude residue was purified via flash column chromatography (0%=>20% acetone in hexanes) to afford 171.6 mg (0.450 mmol) of pure product as a white solid (45% yield). $^1$H NMR (500 MHz, Chloroform-d) δ 8.68 (d, J=1.8 Hz, 1H), 7.99 (d, J=8.0 Hz, 1H), 7.74 (dd, J=8.1, 1.8 Hz, 1H), 7.56 (d, J=8.3 Hz, 2H), 7.16 (d, J=8.0 Hz, 2H), 4.03 (d, J=8.1 Hz, 1H) 4.00 (d J=8.1 Hz, 1H), 2.31 (s, 3H), 1.32 (s, 3H), 1.26 (s, 3H). $^{13}$C NMR (126 MHz, Chloroform-d) δ 158.2, 148.4, 142.9, 141.6, 133.6 (q, J=33.4 Hz), 130.4, 129.6, 128.7, 127.1, 127.0 (q, J=3.7 Hz), 123.5 (q, J=273.2 Hz), 122.3 (q, J=3.8 Hz), 79.1, 69.0, 28.6, 28.1, 21.4. $^{19}$F NMR (470 MHz, Chloroform-d) δ −63.20. HRMS (ESI) m/z calculated for C$_{19}$H$_{19}$NO$_2$SF$_3$ [M+H]$^+$: 382.1089, found 382.1092.

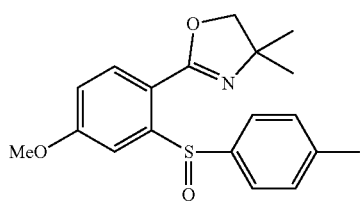

(L4)

(±)-SOX-Ligand 4 (L4) was synthesized following the general procedure. Phenyloxazoline S4 (1.42 g, 5.0 mmol, 1.0 equiv) and sulfinate S7 (1.02 g, 6.0 mmol, 1.2 equiv) were used. The crude residue was purified via flash column chromatography (0%=>30% acetone in hexanes) to afford 1.371 g (3.99 mol) of pure product as a white solid (80% yield). $^1$H NMR (500 MHz, CDCl$_3$) δ 7.89 (d, J=2.6 Hz, 1H), 7.78 (d, J=8.6 Hz, 1H), 7.54 (d, J=8.2 Hz, 2H), 7.12 (d, J=8.0 Hz, 2H), 6.94 (ddd, J=8.6, 2.7, 0.7 Hz, 1H), 3.91 (s, 2H), 3.90 (s, 3H), 2.27 (s, 3H), 1.25 (s, 3H), 1.18 (s, 3H). $^{13}$C NMR (125 MHz, CDCl$_3$) δ 162.5, 159.0, 148.3, 143.5, 141.0, 131.5, 129.4, 127.0, 117.7, 116.3, 109.3, 78.6, 77.4, 77.2, 76.9, 68.29, 55.8, 28.6, 28.1, 21.3. HRMS (ESI) m/z calculated for C$_{19}$H$_{22}$NO$_3$S [M+H]$^+$: 344.1320, found 344.1322.

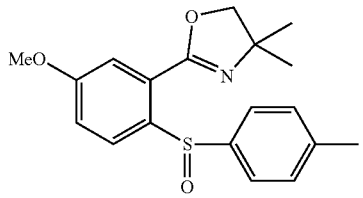

(L5)

(±)-MeO—SOX-Ligand 5 (L5) was synthesized following the general procedure. Phenyloxazoline S5 (1.42 g, 5.0 mmol, 1.0 equiv) and methyl sulfinate S7 (1.02 g, 6.0 mmol, 1.2 equiv). The crude residue was purified via flash column chromatography (0%=>30% acetone in hexanes) to afford 1.371 g (3.99 mmol) of pure product as a white solid (80% yield). $^1$H NMR (500 MHz, Chloroform-d) δ 8.18 (d, J=8.8 Hz, 1H), 7.54 (d, J=8.2 Hz, 2H), 7.34 (d, J=2.8 Hz, 1H), 7.15 (dd, J=8.9, 2.7 Hz, 1H), 7.12 (d, J=8.3 Hz, 2H), 3.96 (d, J=1.5 Hz, 2H), 3.81 (s, 3H), 2.27 (s, 3H), 1.27 (s, 3H), 1.22 (s, 3H). $^{13}$C NMR (126 MHz, CDCl$_3$) δ 161.0, 159.1, 144.0, 140.7, 137.3, 129.3, 127.0, 126.9, 126.5, 117.4, 114.6, 78.9, 68.5, 55.7, 28.5, 28.1, 21.3. HRMS (ESI) m/z calculated for C$_{19}$H$_{22}$NO$_3$S [M+H]$^+$: 344.1320, found 344.1318.

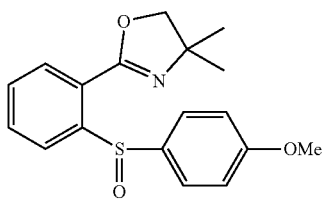

(L6)

(±)-SOX-Ligand 6 (L6) was synthesized following the general procedure. Phenyloxazoline S1 (1.27 g, 5.0 mmol, 1.0 equiv) and methyl sulfinate S8 (1.12 g, 6.0 mmol, 1.2 equiv). The crude residue was purified via flash column chromatography (0%=>20% acetone in hexanes) to afford 1.381 g (4.19 mmol) of pure product as a white solid (84% yield). $^1$H NMR (500 MHz, Chloroform-d) δ 8.37 (dd, J=8.0, 1.3 Hz, 1H), 7.86 (dd, J=7.7, 1.4 Hz, 1H), 7.70 (ddd, J=8.0, 7.4, 1.4 Hz, 1H), 7.61-7.57 (m, 2H), 7.49 (td, J=7.5, 1.3 Hz, 1H), 6.86-6.82 (m, 2H), 3.98 (d, J=1.9 Hz, 2H), 3.75 (s, 3H), 1.29 (s, 3H), 1.24 (s, 3H). $^{13}$C NMR (125 MHz, CDCl$_3$) δ 161.5, 159.3, 146.5, 138.1, 131.7, 130.2, 129.8, 129.0, 125.5, 124.9, 114.2, 78.9, 68.6, 55.5, 28.7, 28.2. HRMS (ESI) m/z calculated for C$_{18}$H$_{20}$NO$_3$S [M+H]$^+$: 330.1164, found 330.1160.

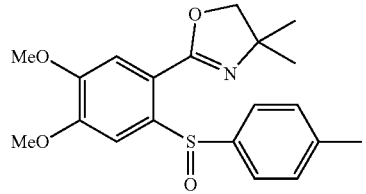

(L7)

(±)-SOX-Ligand 7 (L7) was synthesized following the general procedure. Phenyloxazoline S6 (1.57 g, 5.0 mmol, 1.0 equiv) and methyl sulfinate S7 (1.02 g, 6.0 mmol, 1.2 equiv) were used. The crude residue was purified via flash column chromatography (0%=>30% acetone in hexanes) to afford 1.438 g (3.85 mmol) of pure product as a white solid (77% yield). $^1$H NMR (500 MHz, Chloroform-d) δ 7.80 (s, 1H), 7.51 (d, J=8.2 Hz, 2H), 7.34 (s, 1H), 7.12 (d, J=8.0 Hz, 2H), 3.98 (s, 3H), 3.95-3.91 (m, 2H), 3.89 (s, 3H), 2.27 (s, 3H), 1.24 (s, 3H), 1.19 (s, 3H). $^{13}$C NMR (125 MHz, CDCl$_3$) δ 159.0, 151.7, 149.9, 143.9, 140.8, 138.6, 129.4, 126.6, 118.1, 112.0, 107.1, 78.8, 68.3, 56.4, 56.3, 28.5, 28.1, 21.3. HRMS (ESI) m/z calculated for C$_{20}$H$_{24}$NO$_4$S [M+H]$^+$: 374.1426, found 374.1426.

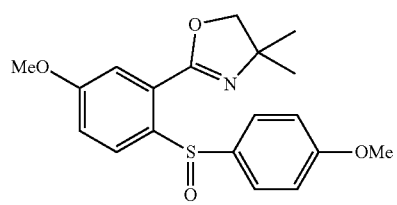

(L8)

(±)-SOX-Ligand 8 (L8) was synthesized following the general procedure. Phenyloxazoline S5 (1.42 g, 5.0 mmol, 1.0 equiv) and methyl sulfinate S8 (1.12 g, 6.0 mmol, 1.2 equiv). The crude residue was purified via flash column chromatography (0%=>30% acetone in hexanes) to afford 1.350 g (3.75 mmol) of pure product as a white solid (75% yield). $^1$H NMR (500 MHz, Chloroform-d) δ 8.21 (d, J=8.8 Hz, 1H), 7.60-7.54 (m, 2H), 7.35 (d, J=2.7 Hz, 1H), 7.18 (dd, J=8.8, 2.7 Hz, 1H), 6.84-6.81 (m, 2H), 3.96 (s, 2H), 3.83 (s, 3H), 3.74 (s, 3H), 1.28 (s, 3H), 1.22 (s, 3H). $^{13}$C NMR (125 MHz, CDCl$_3$) δ 161.3, 161.0, 159.1, 138.5, 137.3, 128.6, 126.9, 126.9, 117.4, 114.8, 114.1, 78.9, 68.6, 55.7, 55.4, 28.6, 28.2. HRMS (ESI) m/z calculated for C$_{19}$H$_{22}$NO$_4$S [M+H]$^+$: 360.1270, found 360.1268.

Preparation of N-Triflyl Protected Amine Nucleophiles:
General Procedure for N-Triflyl Protected Amine Nucleophiles Procedure A (from Amines)

An oven dried round-bottom flask equipped with a stir bar was charged with amine (5.0 mmol, 1.0 equiv), CH$_2$Cl$_2$ (10 ml, 0.5M) and Et$_3$N (767 μL, 5.5 mmol, 1.1 equiv). The flask was cooled to −78° C., and trifluoromethanesulfonic anhydride (840 μL, 1.41 g, 5.0 mmol, 1.0 equiv) was added dropwise. The reaction was stirred vigorously at −78° C. for 30 min and allowed to gradually warm up to room temperature. The reaction was then quenched with 20 mL H$_2$O. The reaction mixture was partitioned between H$_2$O and CH$_2$Cl$_2$ and layers were separated. The aqueous layer was extracted with CH$_2$Cl$_2$ (20 ml×3). The organic layers were combined, dried over NaSO$_4$, filtered, and concentrated under reduced pressure. The reaction mixture was applied directly to a flash silica column for purification (acetone/hexanes).

Procedure B (from Amine Hydrochlorides)

An oven dried round-bottom flask equipped with a stir bar was charged with amine hydrochloride (5.0 mmol, 1.0 equiv), CH$_2$Cl$_2$ (10 ml, 0.5M) and Et$_3$N (1.53 mL, 11 mmol, 2.2 equiv). The flask was cooled to −78° C., and Trifluoromethanesulfonic anhydride (840 μL, 1.41 g, 5.0 mmol, 1.0 equiv) was added dropwise. The reaction was stirred vigorously at −78° C. for 30 min and allowed to gradually warm up to r.t. The reaction was then quenched with 20 mL H$_2$O. The reaction mixture was partitioned between H$_2$O and CH$_2$Cl$_2$ and layers were separated. The aqueous layer was extracted with CH$_2$Cl$_2$ (20 ml×3). The organic layers were combined, dried over NaSO$_4$, filtered, and concentrated under reduced pressure. The reaction mixture was applied directly to a flash silica column for purification (Acetone/Hexanes). NOTE: Most N-trifyl protected amines are bench stable for at least one year. (Some of them exhibited color change and suboptimal reactivity (10-15% drop in yield) after storing on bench for over 12 months, repurification by flash column usually restored reactivity in these cases.

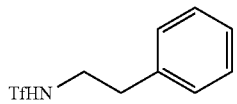

(S10)

N-(2-Phenylethyl)trifluoromethanesulfonamide (S10)

The reaction was performed according general procedure A with distilled 2-phenylethylamine (630 μL, 5.0 mmol). The reaction mixture was purified by flash column chromatography on silica (100 mL silica gel, 2.5% acetone/hexanes=>10% acetone/hexanes) to give 1.192 g (4.71 mmol) pure N-triflyl protected amine (S10) as a white solid in 94% yield. $^1$H NMR (500 MHz, CDCl$_3$) δ 7.36 (m, 2H), 7.29 (m, 1H), 7.20 (dd, J=7.9 Hz, 1.1 Hz, 1H), 4.67 (br s, 1H), 3.58 (q, J=6.3 Hz, 2H), 2.92 (t, J=6.8 Hz, 2H). These data are in agreement with that previously reported in the literature.

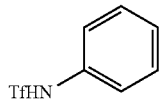

(S11)

1,1,1-trifluoro-N-phenylmethanesulfonamide (S11)

The reaction was performed according to general procedure A with aniline (460 μL, 5.0 mmol). The reaction mixture was purified by flash column chromatography on silica (100 mL silica gel, 2.5% acetone/hexanes=>10% acetone/hexanes) to give 1.079 g (4.79 mmol) pure N-triflyl protected amine (S11) as a white solid in 96% yield. $^1$H NMR (500 MHz, CDCl$_3$) δ 7.40 (dd, J=8.4 Hz, 6.9 Hz, 2H), 7.33 (m, 1H), 7.27 (m, 2H), 6.68 (br s, 1H). These data are in agreement with that previously reported in the literature.

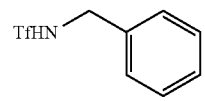

(S12)

N-benzyl-1,1,1-trifluoromethanesulfonamide (S12)

The reaction was performed according to general procedure A with distilled benzylamine (516 μL, 5.0 mmol). The reaction mixture was purified by flash column chromatography on silica (100 mL silica gel, 2.5% acetone/hexanes=>10% acetone/hexanes) to give 1.103 g (4.61 mmol) pure N-triflyl protected amine (S12) as a white solid in 92% yield. $^1$H NMR (500 MHz, CDCl$_3$) δ 7.44-7.30 (m, 5H), 4.94 (br s, 1H), 4.46 (d, J=5.8 Hz, 2H). These data are in agreement with that previously reported in the literature.

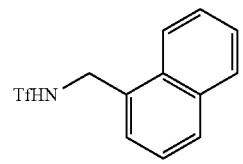

(S13)

1,1,1-trifluoro-N-(naphthalen-1-ylmethyl)methanesulfonamide (S13)

The reaction was performed according to general procedure A with 1-naphthylmethylamine (733 μL, 786 mg, 5.0 mmol). The reaction mixture was purified by flash column chromatography on silica (100 ml silica gel, 5% acetone/hexanes=>10% acetone/hexanes) to give 1.298 g (4.49 mmol) pure N-triflyl protected amine (S13) as a white solid in 90% yield. $^1$H NMR (500 MHz, Chloroform-d) δ 8.01 (dd, J=8.4, 1.0 Hz, 1H), 7.94-7.90 (m, 1H), 7.89 (dt, J=7.9, 1.1 Hz, 1H), 7.62 (ddd, J=8.4, 6.8, 1.4 Hz, 1H), 7.56 (ddd, J=8.1, 6.9, 1.2 Hz, 1H), 7.51-7.45 (m, 2H), 4.98 (t, J=5.3 Hz, 1H), 4.90 (d, J=5.1 Hz, 2H). $^{13}$C NMR (125 MHz, CDCl$_3$) δ 134.1, 131.0, 130.3, 130.1, 129.3, 127.4, 127.4, 126.6, 125.5, 122.6, 119.9 (q, J=321.4 Hz), 46.5. $^{19}$F NMR (470 MHz, Chloroform-d) δ −76.84. HRMS (ESI) m/z calculated for C$_{12}$H$_{10}$NO$_2$SF$_3$Na [M+Na]$^+$: 312.0282, found 312.0293.

TfHN-Me (S14)

1,1,1-trifluoro-N-methylmethanesulfonamide (S14)

The reaction was performed according to general procedure B with methylamine hydrochloride (378 mg, 5.0 mmol). The reaction mixture was purified by flash column chromatography on silica (100 mL silica gel, 5% acetone/hexanes)=>give 698 mg (4.28 mmol) pure N-triflyl protected amine (S14) as a colorless oil in 86% yield. $^1$H NMR (500 MHz, Chloroform-d) δ 4.99 (s, 1H), 2.98 (q, J=1.2 Hz, 3H). $^{13}$C NMR (125 MHz, Chloroform-d) δ 119.9 (q, J=321.2 Hz), 30.2. $^{19}$F NMR (470 MHz, Chloroform-d) δ −76.90. HRMS (EI) m/z calculated for C$_2$H$_4$NO$_2$SF$_3$ [M]$^+$: 162.9915, found 162.9915.

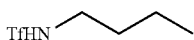

N-butyl-1,1,1-trifluoromethanesulfonamide (S15)

The reaction was performed according to general procedure A with butylamine (494 µL, 366 mg, 5.0 mmol). The reaction mixture was purified by flash column chromatography on silica (100 mL silica gel using 2.5% acetone/hexanes=>5% acetone/hexanes as eluent) to give 864 mg (4.21 mmol) pure N-triflyl protected amine (S15) as a white solid in 84% yield. $^1$H NMR (500 MHz, Chloroform-d) δ 5.11 (br s, 1H), 3.35-3.16 (m, 2H), 1.57 (tt, J=7.8, 6.5 Hz, 2H), 1.45-1.28 (m, 2H), 0.93 (t, J=7.4 Hz, 3H). These data are in agreement with that previously reported in the literature.

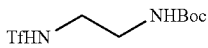

tert-Butyl (2-(((trifluoromethyl)sulfonamido)ethyl)carbamate (S16)

The reaction was performed according to general procedure A with N-boc-ethylenediamine (792 µL, 801 mg, 5.0 mmol). The reaction mixture was purified by flash column chromatography on silica (100 mL silica gel, 5% acetone/hexanes=>10% acetone/hexanes) to give 1.388 g (4.75 mmol) pure N-triflyl protected amine (S16) as a white solid in 95% yield. $^1$H NMR (500 MHz, Chloroform-d) δ 6.80 (br s, 1H), 5.05 (br s, 1H), 3.36 (t, J=5.6 Hz, 2H), 3.31 (q, J=5.8 Hz, 2H), 1.44 (s, 9H). $^{13}$C NMR (125 MHz, CDCl$_3$) δ 157.5, 120.0 (q, J=321.3), 80.9, 45.3, 40.6, 28.4. $^{19}$F NMR (470 MHz, Chloroform-d) δ −77.85. HRMS (EI) m/z calculated for C$_8$H$_{16}$N$_2$O$_4$SF$_3$ [M+H]$^+$: 293.0783, found 293.0786.

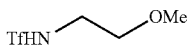

1,1,1-trifluoro-N-(2-methoxyethyl)methanesulfonamide (S17)

The reaction was performed according to general procedure A with 2-methoxyethylamine (435 µL, 376 mg, 5.0 mmol). The reaction mixture was purified by flash column chromatography on silica (100 ml silica gel, 5% acetone/hexanes=>10% acetone/hexanes) to give 999 mg (4.82 mmol) pure N-triflyl protected amine (S17) as a white solid in 96% yield. $^1$H NMR (500 MHz, Chloroform-d) δ 5.35 (br s, 1H), 3.53 (m, 2H), 3.48-3.43 (m, 2H), 3.39 (s, 3H). $^{13}$C NMR (125 MHz, Chloroform-d) δ 119.8 (q, J=321.0 Hz), 71.0, 59.1, 44.1. $^{19}$F NMR (470 MHz, Chloroform-d) δ −77.87. HRMS (EI) m/z calculated for C$_4$H$_8$NO$_3$SF$_3$ [M+H]$^+$: 208.02553, found 208.02523.

N-(2-bromoethyl)-1,1,1-trifluoromethanesulfonamide (S18)

An oven dried 100 mL round-bottom flask equipped with a stir was charged with 2-bromoethylamine hydrobromide (2.05 g, 10.0 mmol, 1.0 equiv), CH$_2$Cl$_2$ (20 mL, 0.5 M). The flask was cooled to −78° C., and anhydrous K$_2$CO$_3$ (1.38 g, 10.0 mmol, 2.0 equiv) was added in one batch followed by slowly addition of trifluoromethanesulfonic anhydride (1.68 mL, 2.82 g, 10.0 mmol, 1.0 equiv). The reaction was stirred vigorously at −78° C. for 30 min. After warmed up to 0° C., the reaction was quenched with 20 mL cold H$_2$O. The reaction mixture was partitioned between H$_2$O and CH$_2$Cl$_2$ and the layers were separated. The aqueous layer was then extracted with CH$_2$Cl$_2$ (20 ml×3). The organic layers were combined, dried over NaSO$_4$, filtered, and concentrated under reduced pressure.). The reaction mixture was purified by flash column chromatography on silica (100 mL silica gel, 2.5% acetone/hexanes=>5% acetone/hexanes) to give 1.213 g (4.74 mmol) pure N-triflyl protected amine (S18) as a colorless oil in 47% yield. $^1$H NMR (500 MHz, Chloroform-d) δ 5.52 (br s, 1H), 3.70 (q, J=5.9 Hz, 2H), 3.51 (t, J=5.8 Hz, 2H). $^{13}$C NMR (125 MHz, Chloroform-d) δ 119.6 (q, J=320.5 Hz), 45.7, 31.4. $^{19}$F NMR (470 MHz, Chloroform-d) δ −77.90. HRMS (EI) m/z calculated for C$_3$H$_6$NO$_2$BrSF$_3$ [M+H]$^+$: 255.92546, found 255.92546.

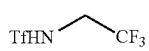

1,1,1-Trifluoro-N-(2,2,2-trifluoroethyl)methanesulfonamide (S19)

An oven dried round-bottom flask equipped with a stir bar was charged with 2,2,2-trifluoroethylamine hydrochloride (677.6 mg, 5.0 mmol, 1.0 equiv), CH$_2$Cl$_2$ (10 mL, 0.5M) and Et$_3$N (1.53 mL, 11 mmol, 2.2 equiv). The flask was cooled to −78° C., and Trifluoromethanesulfonic anhydride (840 µL, 1.41 g, 5.0 mmol, 1.0 equiv) was added dropwise. The reaction was stirred vigorously at −78° C. for 30 min and allowed to gradually warm up to r.t. The reaction mixture was concentrated under reduced pressure, the remaining mixture was dissolve in 20 mL 3 M NaOH, extracted with CH$_2$Cl$_2$ (20 mL×3), the aqueous layer was neutralized by 3 M HCl, and extracted with 3×20 mL CH$_2$Cl$_2$. The combined organic layers were concentrated to afford 982 mg (4.25 mmol) pure N-triflyl protected amine (S19) as a colorless oil in 85% yield. $^1$H NMR (500 MHz, Chloroform-d) δ 5.27 (br s, 1H), 3.91-3.84 (m, 2H). $^{13}$C NMR (125 MHz, Chloroform-d) δ 122.8 (q, J=278.1 Hz), 122.0 (q, J=320.1 Hz), 45.4 (q, J=36.7 Hz). $^{19}$F NMR (470 MHz, Chloroform-d) δ −73.50, −77.64. HRMS (ESI) m/z calculated for C$_3$H$_2$NO$_2$SF$_6$ [M−H]$^+$: 229.9710, found 229.9705.

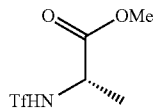

Methyl ((trifluoromethyl)sulfonyl)-L-alaninate (S20)

The reaction was performed according to general procedure B with L-alanine methyl ester hydrochloride (698 mg, 5.0 mmol). The reaction mixture was purified by flash column chromatography on silica (100 mL silica gel, 5% acetone/hexanes=>10% acetone/hexanes) to give 1.069 g (4.55 mmol) pure N-triflyl protected amine (S20) as a white solid in 91% yield. $^1$H NMR (500 MHz, Chloroform-d) δ 5.53 (s, 1H), 4.32 (q, J=7.2 Hz, 1H), 3.83 (s, 3H), 1.54 (d, J=7.2 Hz, 3H). These data are in agreement with that previously reported in the literature.

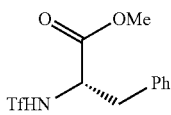

(+)-Methyl ((trifluoromethyl)sulfonyl)-L-phenylalaninate (S21)

The reaction was performed according to general procedure B with L-phenylalanine methyl ester hydrochloride (1.08 g, 5.0 mmol). The reaction mixture was purified by flash column chromatography on silica (100 mL silica gel, 5% acetone/hexanes=>10% acetone/hexanes) to give 1.442 g (4.63 mmol) pure N-triflyl protected amine (S21) as a white solid in 93% yield. $^1$H NMR (500 MHz, Chloroform-d) δ 7.39-7.28 (m, 3H), 7.16-7.10 (m, 2H), 5.33 (br s, 1H), 4.53 (dt, J=9.3, 5.5 Hz, 1H), 3.79 (s, 3H), 3.24-3.10 (m, 2H). $^{13}$C NMR (125 MHz, Chloroform-d) δ 170.8, 134.3, 129.5, 128.8, 127.7, 119.5 (q, J=320.7 Hz), 58.2, 53.0, 39.5. These data are in agreement with that previously reported in the literature.[10] $[\alpha]^{23}_D$=28.4° (c=1.01, CHCl$_3$).

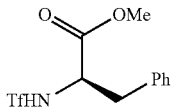

(−)-Methyl ((trifluoromethyl)sulfonyl)-D-phenylalaninate (S22)

The reaction was performed under general procedure B with D-phenylalanine methyl ester hydrochloride (1.08 g, 5.0 mmol). The reaction mixture was purified by flash column chromatography on silica (100 ml silica gel, 5% acetone/hexanes=>10% acetone/hexanes) to give 1.424 g (4.57 mmol) pure N-triflyl protected amine (S22) as a white solid in 91% yield. $^1$H NMR (500 MHz, Chloroform-d) δ 7.37-7.27 (m, 3H), 7.17-7.15 (m, 2H), 5.91 (br s, 1H), 4.51 (t, J=6.0 Hz, 1H), 3.76 (s, 3H), 3.14 (d, J=6.0 Hz, 2H). $^{13}$C NMR (126 MHz, CDCl$_3$) δ 170.7, 134.2, 129.5, 128.9, 127.8, 119.5 (q, J=320.8 Hz), 58.1, 53.1, 39.6. $^{19}$F NMR (470 MHz, Chloroform-d) δ −77.72. HRMS (ESI) m/z calculated for C$_{11}$H$_{13}$NO$_4$F$_3$S [M+H]$^+$: 312.0517, found 312.0506. $[\alpha]^{23}_D$=−28.3° (c=1.00, CHCl$_3$).

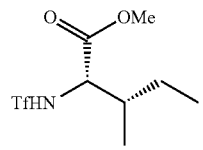

Methyl ((trifluoromethyl)sulfonyl)-L-isoleucinate (S23)

The reaction was performed according to general procedure B with L-isoleucine methyl ester hydrochloride (909 mg, 5.0 mmol). The reaction mixture was purified by flash column chromatography on silica (100 mL silica gel, 5% acetone/hexanes=>10% acetone/hexanes) to give 1.221 g (4.40 mmol) pure N-triflyl protected amine (S23) as a colorless oil in 88% yield. $^1$H NMR (500 MHz, Chloroform-d) δ 5.51 (br s, 1H), 4.13 (d, J=4.7 Hz, 1H), 3.81 (s, 3H), 1.94 (dqd, J=9.3, 4.6, 2.4 Hz, 1H), 1.49-1.33 (m, 1H), 1.19 (dtd, J=13.7, 7.3, 2.0 Hz, 1H), 0.99 (d, J=6.8 Hz, 3H), 0.94 (t, J=7.4 Hz, 3H). These data are in agreement with that previously reported in the literature.

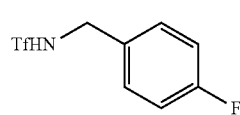

1,1,1-Trifluoro-N-(4-fluorobenzyl)methanesulfonamide (S24)

The reaction was performed under general procedure B with 4-fluorobenzylamine (568 µL, 626 mg, 5.0 mmol). The reaction mixture was purified by flash column chromatography on silica (100 mL silica gel, 5% acetone/hexanes=>10% acetone/hexanes) to give 1.203 g (4.68 mmol) pure N-triflyl protected amine (S24) as a colorless oil in 93% yield. $^1$H NMR (500 MHz, Chloroform-d) δ 7.31 (dd, J=8.7, 5.2 Hz, 2H), 7.11-7.04 (m, 2H), 5.11 (s, 1H), 4.42 (s, 2H). $^{13}$C NMR (125 MHz, Chloroform-d) δ 163.0 (d, J=248.0 Hz), 131.1 (d, J=3.3 Hz), 129.0 (d, J=8.4 Hz), 119.8 (q, J=321.0 Hz), 116.2 (d, J=21.8 Hz), 47.7. $^{19}$F NMR (470 MHz, Chloroform-d) δ −77.61, −113.30. HRMS (ESI) m/z calculated for C$_8$H$_7$NO$_2$NaSF$_4$ [M+Na]$^+$: 280.0031, found 280.0026.

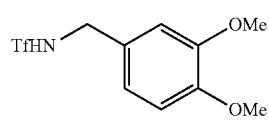

N-(3,4-dimethoxybenzyl)-1,1,1-trifluoromethanesulfonamide (S25)

The reaction was performed according to general procedure A with 3,4-Dimethoxyphenyl)methanamine (745 µL, 836 mg, 5.0 mmol). The reaction mixture was purified by flash column chromatography on silica (100 mL silica gel, 5% acetone/hexanes=>20% acetone/hexanes) to give 1.373 g (4.59 mmol) pure N-triflyl protected amine (S25) as a white solid in 92% yield. $^1$H NMR (500 MHz, Chloroform-d) δ 6.80 (dd, J=8.2, 2.0 Hz, 1H), 6.76 (d, J=8.2 Hz, 1H), 6.72 (d, J=2.0 Hz, 1H), 5.71 (br d, J=5.2 Hz, 1H), 4.32 (d, J=4.3 Hz, 2H), 3.80 (s, 3H), 3.77 (s, 3H). $^{13}$C NMR (125 MHz, CDCl$_3$) δ 149.1, 149.0, 128.0, 120.6, 119.9 (q, J=321.2 Hz) 111.5, 111.1, 56.0, 55.8, 48.1. $^{19}$F NMR (470 MHz, CDCl$_3$) δ −77.22. HRMS (ESI) m/z calculated for C$_{10}$H$_{12}$NO$_4$F$_3$SNa [M+Na]$^+$: 322.0337, found 322.0349.

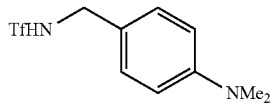

(S26)

N-(4-(dimethylamino)benzyl)-1,1,1-trifluoromethanesulfonamide (S26)

The reaction was performed according to general procedure A with 4-(aminomethyl)-N,N-dimethylaniline (745 μL, 836 mg, 5.0 mmol). The reaction mixture was purified by flash column chromatography on silica (100 mL silica gel, 5% acetone/hexanes=>20% acetone/hexanes) to give 1.158 g (4.10 mmol) pure N-triflyl protected amine (S26) as a white solid in 82% yield. $^1$H NMR (500 MHz, Chloroform-d) δ 7.15 (d, J=8.8 Hz, 2H), 6.69 (d, J=8.8 Hz, 2H), 5.13 (br s, 1H), 4.32 (s, 2H), 2.95 (s, 6H). $^{13}$C NMR (125 MHz, CDCl$_3$) δ 150.8, 129.3, 122.7, 119.9 (q, J=321.3 Hz), 113.0, 48.3, 40.7. $^{19}$F NMR (470 MHz, CDCl$_3$) δ −77.15. HRMS (ESI) m/z calculated for C$_{10}$H$_{14}$N$_2$O$_2$F$_3$S [M+H]$^+$: 283.0728, found 283.0739.

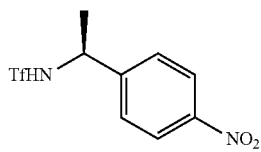

(S27)

(−)-(S)-1,1,1-trifluoro-N-(1-(4-nitrophenyl)ethyl) methanesulfonamide (−)-S27

The reaction was performed according to general procedure A with (S)-α-methyl-4-nitrobenzylamine hydrochloride (1.01 g, 5.0 mmol). The reaction mixture was purified by flash column chromatography on silica (100 mL silica gel, 5% acetone/hexanes=>20% acetone/hexanes) to give 1.425 g (4.78 mmol) pure N-triflyl protected amine (−)-S27 as a light yellow solid in 95% yield. $^1$H NMR (500 MHz, Chloroform-d) δ 8.24 (d, J=8.7 Hz, 2H), 7.51 (d, J=8.7 Hz, 2H), 5.55 (d, J=8.5 Hz, 1H), 4.90 (app p, J=7.2 Hz, 1H), 1.66 (d, J=7.0 Hz, 3H). 13C NMR (125 MHz, Chloroform-d) δ 148.7, 147.6, 127.0, 124.4, 119.5 (q, J=320.8 Hz), 54.7, 23.4. $^{19}$F NMR (470 MHz, Chloroform-d) δ −78.0. HRMS (ESI) m/z calculated for C$_9$H$_8$N$_2$O$_4$F$_3$S [M−H]$^+$: 297.0157, found 297.0151. [α]$^{22}_D$=−54.7° (c=1.00, CHCl$_3$).

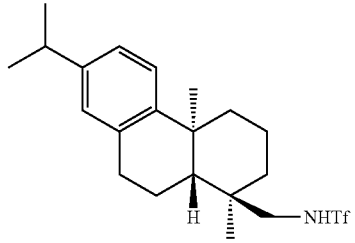

(S28)

(+)-N-triflyl protected dihydroabietylamine (+)-S28

(−)-(N-nitroisoindolyl) dihydroabietylamine (1.15 g, 2.5 mmol) was dissolved in hot ethanol (20 mL 0.125 M), treated with hydrazine monohydrate (0.72 mL, 15 mmol) and heated at reflux for 3 hours. Then, without cooling a white solid was filtered off and washed with fresh ethanol to give the crude dihydroabietylamine. Triflyl protection was performed directly on the crude dihydroabietylamine under general procedure A. The reaction mixture was purified by flash column chromatography on silica (100 mL silica gel, 5% acetone/hexanes=>10% acetone/hexanes) to give 868 mg (2.08 mmol) pure N-triflyl protected amine (+)-S28 as a white solid in 83% yield over two steps. $^1$H NMR (500 MHz, Chloroform-d) δ 7.27 (d, J=8.6 Hz, 1H), 7.10 (dd, J=8.2, 2.0 Hz, 1H), 7.00 (d, J=2.0 Hz, 1H), 5.32 (br s, 1H), 3.25 (d, J=13.2 Hz, 1H), 3.17 (d, J=13.2 Hz, 1H), 3.04-2.95 (m, 2H), 2.93 (hept, J=6.9 Hz, 1H), 2.44-2.38 (m, 1H), 1.89-1.75 (m, 4H), 1.61-1.43 (m, 3H), 1.37 (dd, J=13.2, 4.6 Hz, 1H), 1.33 (d, J=7.0 Hz, 6H), 1.33 (s, 3H), 1.06 (s, 3H). $^{13}$C NMR (125 MHz, CDCl$_3$) δ 146.8, 145.9, 134.5, 127.0, 124.2, 124.0, 119.9 (q, J=321.7 Hz), 55.1, 45.2, 38.2, 37.5, 37.1, 35.7, 33.6, 29.9, 25.3, 24.1, 24.0, 18.9, 18.4, 18.1. $^{19}$F NMR (470 MHz, Chloroform-d) δ −77.17. HRMS (ESI) m/z calculated for C$_{21}$H$_{30}$NO$_2$F$_3$SNa [M+Na]$^+$: 440.1847, found 440.1846. [α]$^{23}_D$=+25.3° (c=0.50, CHCl$_3$).

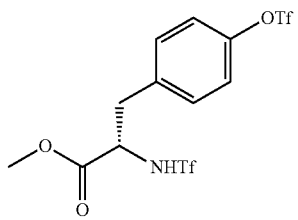

(S29)

Methyl-(S)-2-((trifluoromethyl)sulfonamido)-3-(4-(((trifluoromethyl)sulfonyl) oxy) phenyl) propanoate (S29)

The reaction was performed according to reported procedure (Newcombe et al., Org. Biomol. Chem. 2013, 11, 3255) with L-tyrosine methyl ester hydrochloride (1.16 g, 5 mmol) affording 1.035 g (2.25 mmol) pure N-triflyl protected amine (S29) as a white solid in 45% yield. $^1$H NMR (500 MHz, Chloroform-d) δ 7.33-7.18 (m, 4H), 5.39 (br s, 1H), 4.51 (t, J=5.9 Hz, 1H), 3.79 (d, J=1.0 Hz, 3H), 3.25-3.12 (m, 2H). These data are in agreement with that previously reported in the literature.

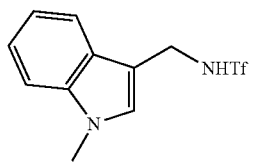

1,1,1-trifluoro-N-((1-methyl-1H-indol-3-yl) methyl) methanesulfonamide (S30)

The reaction was performed according to general procedure A with 3-(aminomethyl)-1-methylindole (730 mL, 801 mg, 5.0 mmol). The reaction mixture was purified by flash column chromatography on silica (100 mL silica gel, 20% $CH_2Cl_2$/hexanes=>50% $CH_2Cl_2$/hexanes) to give 1.180 g (4.04 mmol) pure N-triflyl protected amine (S30) as a white solid in 81% yield. $^1H$ NMR (500 MHz, Chloroform-d) δ 7.67 (d, J=7.9 Hz, 1H), 7.39-7.29 (m, 2H), 7.22 (ddd, J=8.0, 6.7, 1.2 Hz, 1H), 7.07 (s, 1H), 5.03 (br s, 1H), 4.60 (s, 2H), 3.77 (s, 3H). 13C NMR (125 MHz, Chloroform-d) δ 137.2, 128.7, 126.5, 122.5, 120.0, 119.9 (q, J=321.3 Hz), 118.5, 109.8, 108.3, 40.0, 32.8. $^{19}F$ NMR (470 MHz, Chloroform-d) δ −77.50. HRMS (ESI) m/z calculated for $C_{11}H_{12}N_2O_2F_3S$ $[M+H]^+$: 293.0572, found 293.0563.

Preparation of Olefins

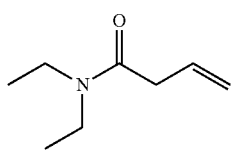

N, N-diethylbut-3-enamide (S31)

An oven-dried round-bottom flask was charged with a stir bar and vinyl acetic acid (426 μL, 5 mmol, 1.0 equiv). Oxalyl chloride (465 μL, 5.5 mmol, 1.1 equiv) was added dropwise to the reaction mixture at 0° C. and the reaction was warmed up to room temperature and stirred for 3 hours. The acid chloride was carried through to the next step without purification. To a solution of $Et_3N$ (730 μL, 5.25 mmol, 1.05 equiv) and $Et_2NH$ (517 μL, 5 mmol) in $CH_2Cl_2$ (25 mL, 0.2 M) at 0° C. was slowly added the acid chloride (1.0 equiv) and the reaction was allowed to warm to room temperature and stirred overnight. The reaction was quenched by addition of sat. aq. $NH_4Cl$, extracted with $CH_2Cl_2$, dried over anhydrous $Na_2SO_4$ and concentrated under reduced pressure. The crude mixture was purified by flash column chromatography (100 mL silica gel, 10% ethyl acetate/hexanes=>20% ethyl acetate/hexanes) to give 593 mg (4.20 mmol) product in 84% yield as a colorless oil. $^1H$ NMR (500 MHz, Chloroform-d) δ 5.98 (ddt, J=16.9, 10.2, 6.5, 1H), 5.22-5.01 (m, 2H), 3.37 (q, J=7.1, 2H), 3.30 (q, J=7.2, 2H), 3.11 (m, 2H), 1.17 (td, J=7.2, 1.1 Hz, 3H), 1.11 (td, J=7.2, 1.2 Hz, 3H). $^{13}C$ NMR (125 MHz, $CDCl_3$) δ 170.1, 132.3, 117.4, 42.2, 40.2, 38.7, 14.5, 13.2. HRMS (ESI) m/z calculated for $C_8H_{16}NO$ $[M+H]^+$: 142.1232, found 142.1230.

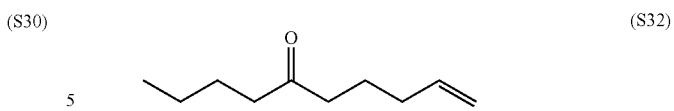

Dec-9-en-5-one (S32)

An oven-dried round-bottom flask was charged with a stir bar, N-methoxy-N-methylhex-5-enamide (786 mg, 5 mmol) and THF (20 mL, 0.25 M). The reaction mixture was cooled to −78° C. and n-BuLi (1.6 M in hexanes, 3.75 mL, 6.0 mmol, 1.2 equiv) was added dropwise. The reaction was stirred for 30 min and quenched with sat. aq. $NH_4Cl$. Layers were separated, aqueous layer was extracted with $Et_2O$, dried over anhydrous $MgSO_4$ and concentrated under reduced pressure. The crude mixture was purified by flash column chromatography (100 mL silica gel, 5% ethyl acetate/hexanes=>10% ethyl acetate/hexanes) to give 625 mg (4.05 mmol) product in 81% yield as a colorless oil. $^1H$ NMR (500 MHz, Chloroform-d) δ 5.76 (ddt, J=17.0, 10.2, 6.7 Hz, 1H), 5.05-4.94 (m, 2H), 2.39 (q, J=7.5 Hz, 4H), 2.10-2.02 (m, 2H), 1.67 (p, J=7.3 Hz, 2H), 1.60-1.49 (m, 2H), 1.36-1.22 (m, 2H), 0.90 (t, J=7.4 Hz, 3H). $^{13}C$ NMR (125 MHz, $CDCl_3$) δ 211.4, 138.2, 115.3, 42.8, 42.0, 33.3, 26.1, 23.0, 22.5, 14.0. HRMS (EI) m/z calculated for $C_{10}H_{17}O$ $[M−H]^+$: 153.12795, found 153.12766.

Scheme 2-4: Synthesis of olefin S35

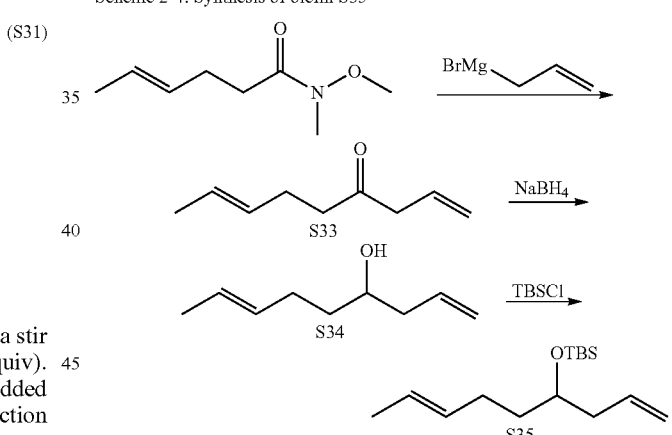

(±)-(E)-tert-butyldimethyl(nona-1,7-dien-4-yloxy) silane (S35)

An oven-dried round-bottom flask was charged with a stir bar, Weinreb amide ((4E)-N-methoxy-N-methyl-4-hexenamide)[18] (786 mg, 5 mmol, 1.0 equiv) and THF (20 mL, 0.25 M). The reaction mixture was cooled to −10° C. and allylmagnesium bromide (1.0 M in $Et_2O$, 6.5 mL, 6.5 mmol, 1.3 equiv) was added dropwise. The reaction was stirred for 30 min at −10° C. and poured onto a mixture of crushed ice (40 mL), sat. aq. $NH_4Cl$ (70 mL) and 1M HCl (15 mL). Layers were separated, aqueous layer was extracted with $Et_2O$, dried over anhydrous $MgSO_4$ and concentrated under reduced pressure. The crude mixture was purified by flash column chromatography (5% ethyl acetate/hexanes=>10% ethyl acetate/hexanes) to give 622 mg (4.05 mmol) product (S33) in 90% yield as a colorless oil.

An oven-dried round-bottom flask was charged with a stir bar, ketone (S33) (622 mg, 4.05 mmol, 1.0 equiv) and MeOH (8.0 mL, 0.5 M). The reaction was cooled to 0° C. and NaBH$_4$ (613 mg, 16.2 mmol, 4.0 equiv) was added in one portion. The reaction was allowed to warm up to room temperature and stirred overnight. The reaction was quenched with water. The resulting layers were separated and the aqueous layer was extracted by ethyl acetate (20 mL×3). The crude mixture was purified by flash column chromatography (10% ethyl acetate/hexanes=>20% ethyl acetate/hexanes) to give 495 mg (3.52 mmol) product (S34) in 87% yield as a colorless oil.

To an oven-dried round-bottom flask with a stir bar was added alcohol (S34) (495 mg, 3.52 mmol, 1.0 equiv), CH$_2$Cl$_2$ (18 mL, 0.2 M), TBSCl (583 mg, 5.87 mmol, 1.1 equiv) and imidazole (359 mg, 5.28 mmol, 1.5 equiv). The reaction mixture was cooled to 0° C. and DMAP (43 mg, 0.1 equiv) was added in one portion. The reaction was allowed to warm up to room temperature and stirred overnight. The reaction was quench with water. The resulting layers were separated and the aqueous layer was extracted by CH$_2$Cl$_2$ (20 mL×3). Organic layers were combined, dried with anhydrous MgSO$_4$ and concentrated under reduced pressure. The crude mixture was purified by flash column chromatography (5% ethyl acetate/hexanes=>10% ethyl acetate/hexanes) to give 769 mg (3.02 mmol) product (S35) in 86% yield as a colorless oil. $^1$H NMR (500 MHz, Chloroform-d) δ 5.81 (ddt, J=16.8, 10.4, 7.2 Hz, 1H), 5.42 (m, 2H), 5.08-4.97 (m, 2H), 3.70 (p, J=5.8 Hz, 1H), 2.21 (dddt, J=6.8, 5.3, 4.0, 1.3 Hz, 2H), 2.11-1.92 (m, 2H), 1.64 (dd, J=3.5, 1.3 Hz, 3H), 1.54-1.42 (m, 2H), 0.89 (s, 9H), 0.05 (d, J=0.9 Hz, 6H). $^{13}$C NMR (125 MHz, CDCl$_3$) δ 135.5, 131.4, 124.9, 116.8, 71.7, 42.1, 36.9, 28.7, 26.1, 18.3, 18.1, −4.2, −4.4. HRMS (EI) m/z calculated for C$_{15}$H$_{29}$OSi [M−H]$^+$: 253.1988, found 253.1982.

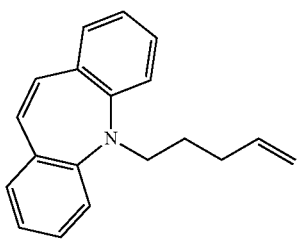

(S36)

5-(pent-4-en-1-yl)-5H-dibenzo[b]azepine (S36)

To an oven-dried round-bottom flask with a stir bar was added 5H-dibenzo[b,f]azepine (193 mg, 1.0 mmol), 1,2-dichloroethane (5 mL, 0.2M), acetic acid (172 μL, 3.0 mmol, 3.0 equiv) and 4-pentenal (197 μL, 2.0 mmol, 2.0 equiv). The reaction was stirred under room temperature for 30 min. Then NaBH(OAc)$_3$ (423 mg, 2.0 mmol, 2.0 equiv) was added, the reaction was stirred for 2 hours. Upon completion, the reaction mixture was poured into a separatory funnel with sat. aq. NaHCO$_3$. Layers were separated, and aqueous layers was extracted with ethyl acetate (10 mL×3). The crude mixture was purified by flash column chromatography (pure pentane) to give 238 mg (0.91 mmol) product (S36) in 91% yield as a bright yellow oil. $^1$H NMR (500 MHz, Chloroform-d) δ 7.25 (ddd, J=8.1, 7.2, 1.7 Hz, 2H), 7.06 (dd, J=7.6, 1.7 Hz, 2H), 7.01 (dd, J=8.2, 1.1 Hz, 2H), 6.98 (td, J=7.4, 1.2 Hz, 2H), 6.73 (s, 2H), 5.76 (ddt, J=17.0, 10.2, 6.7 Hz, 1H), 5.03-4.83 (m, 2H), 3.72 (t, J=6.9 Hz, 2H), 2.19-2.09 (m, 2H), 1.72-1.57 (m, 2H). $^{13}$C NMR (125 MHz, Chloroform-d) δ 151.2, 138.5, 134.1, 132.3, 129.3, 128.9, 123.3, 120.6, 115.0, 49.9, 31.1, 26.9. HRMS (ESI) m/z calculated for C$_{19}$H$_{20}$N [M+H]$^+$: 262.1596, found 262.1594.

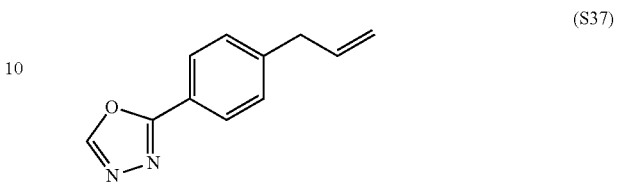

2-(4-allylphenyl)-1,3,4-oxadiazole (S37)

To an oven-dried round-bottom-flask equipped with a condenser was added a stir bar, LiCl (1.06 g, 25 mmol, 5.0 equiv), THF (50 mL, 0.1 M), allyltributylstannane (1.7 mL, 5.5 mmol, 1.1 equiv), 2-(4-bromophenyl)-1,3,4-oxadiazole (1.13 g, 5.0 mmol, 1.0 equiv) and Pd(PPh$_3$)$_4$ (578 mg, 0.50 mmol, 0.1 equiv). The reaction was heated to reflux and stirred overnight. Upon completion, the reaction was cooled to room temperature, transferred into a separatory funnel with ice cold 10% NH$_4$OH solution (50 mL, diluted from 30% NH$_4$OH solution) and shaken vigorously. Layers were separated, aqueous layer was extracted with ethyl acetate (30 mL×3). Organic layers were combined and concentrated under reduced pressure. The crude mixture was purified by flash column chromatography (acetone/hexanes) to give 884 mg (4.75 mmol) product (S37) in 95% yield as a white solid. $^1$H NMR (500 MHz, Chloroform-d) δ 8.45 (s, 1H), 8.01 (d, J=8.0 Hz, 2H), 7.34 (d, J=8.0 Hz, 2H), 6.05-5.85 (m, 1H), 5.17-5.05 (m, 2H), 3.46 (dd, J=6.7, 1.6 Hz, 2H). $^{13}$C NMR (125 MHz, CDCl$_3$) δ 164.6, 152.5, 144.4, 136.2, 129.3, 127.1, 121.3, 116.7, 40.0. HRMS (ESI) m/z calculated for C$_{11}$H$_{11}$N$_2$O [M+H]$^+$: 187.0871, found 187.0871.

General Procedure to Form Olefin Substrates from Phenolic Compounds.

Scheme 2-5: General Procedure for olefin substrates from phenolic compounds

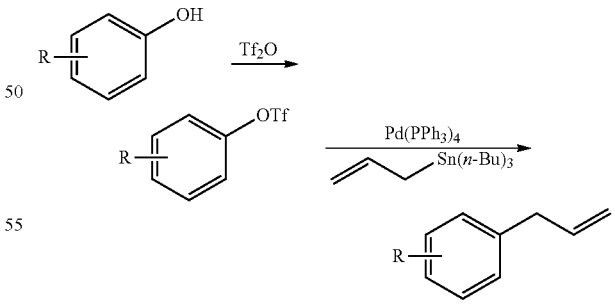

To an oven-dried round-bottom flask with a stir bar was added phenol starting material (5.0 mmol, 1.0 equiv), CH$_2$Cl$_2$ (25 mL, 0.2 M), Et$_3$N (1.39 mL, 10 mmol, 2.0 equiv). The reaction was cooled to 0° C. Trifluoromethanesulfonic anhydride (Tf$_2$O, 1.0 mL, 6.0 mmol, 1.2 equiv) was added dropwise and the reaction was stirred at 0° C. for 30 min. After warming up to room temperature, the reaction was quenched with addition of cold water. The layers were separated, and the aqueous layer was extracted with CH₂Cl₂ (20 mL×3). The organic layers were combined and concentrated under reduced pressure. The crude mixture was purified by flash column chromatography to the phenol triflate compound.

To an oven-dried round bottom flask equipped with condenser was added a stir bar, LiCl (4.0 equiv), DMF (0.25 M), allyltributylstannane (1.1 equiv), phenol triflate (1.0 equiv) and Pd(PPh₃)₄ (0.03 equiv). The reaction was heated to 100° C. and stirred for 12 hours. Upon completion, the reaction was cooled to room temperature, transferred into a separatory funnel with iced 10% NH₄OH solution (1:1 to DMF) and shake vigorously. Layers were separated, aqueous layer was extracted with ethyl acetate (30 mL×3). The organic layers were combined and concentrated under reduced pressure. The crude mixture was purified by flash column chromatography to give allylated olefin product.

(S38)

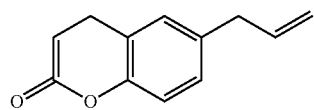

6-allyl-2H-chromen-2-one (S38) was synthesized according to the general procedure from 6-hydroxycoumarin (811 mg, 5.0 mmol) in 60% yield (550.2 mg, 3.0 mmol) over two steps as a white solid. ¹H NMR (500 MHz, Chloroform-d) δ 7.67 (d, J=9.6 Hz, 1H), 7.35 (dd, J=8.4, 2.1 Hz, 1H), 7.28 (d, J=2.1 Hz, 1H), 7.26 (d, J=8.4 Hz, 1H), 6.40 (d, J=9.5 Hz, 1H), 5.95 (ddt, J=16.9, 10.1, 6.7 Hz, 1H), 5.20-4.98 (m, 2H), 3.43 (dt, J=6.6, 1.5 Hz, 2H). ¹³C NMR (126 MHz, CDCl₃) δ 161.1, 152.7, 143.5, 136.7, 136.5, 132.5, 127.5, 118.9, 117.0, 116.8, 116.8, 39.4. HRMS (ESI) m/z calculated for C₁₂H₁₁O₂ [M+H]⁺: 187.0759, found 187.0764.

(S39)

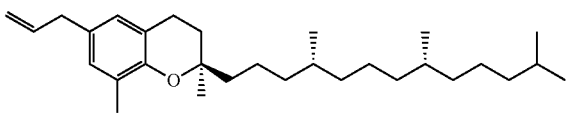

(+)-Allylated-δ-Tocopherol derivative (S39) was synthesized according to the general procedure from (+)-δ-Tocopherol (2.01 g, 5.0 mmol) in 75% yield (1.602 g, 3.7 mmol) over two steps as a colorless oil. ¹H NMR (500 MHz, Chloroform-d) δ 6.80 (d, J=2.2 Hz, 1H), 6.73 (d, J=2.1 Hz, 1H), 5.97 (ddt, J=16.8, 10.0, 6.8 Hz, 1H), 5.13-4.95 (m, 2H), 3.28 (d, J=6.8 Hz, 2H), 2.80-2.61 (m, 2H), 2.16 (s, 3H), 1.86-1.71 (m, 2H), 1.64-1.03 (m, 24H), 0.91-0.84 (m, 12H). ¹³C NMR (125 MHz, CDCl₃) δ 150.5, 138.5, 130.2, 128.6, 126.8, 126.3, 120.4, 115.2, 75.96, 40.3, 39.7, 39.5, 37.6, 37.6, 37.4, 33.0, 32.9, 31.4, 28.1, 25.0, 24.6, 24.4, 22.9, 22.8, 22.5, 21.1, 19.9, 19.8, 16.2. HRMS (ESI) m/z calculated for C₃₀H₅₀O [M]⁺: 426.3862, found 426.3851. [α]²²_D=+5.6° (c=1.05, CHCl₃).

Scheme 2-6: Synthesis of olefin S41

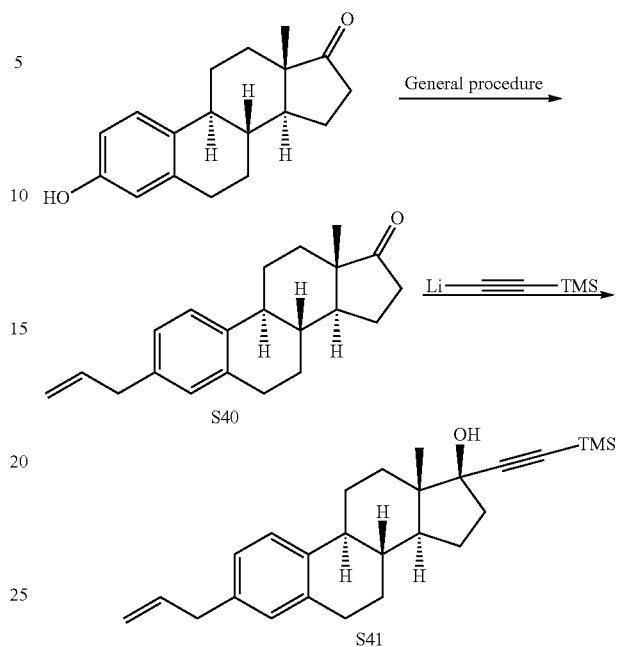

(−)-Allylated ethinyl estradiol derivative (S41). Allylated estrone (S40) was synthesized according to general procedure to form olefin substrates from phenolic compounds from estrone (1.35 g, 5.0 mmol, 1.0 equiv) in 73% yield (1.07 g, 3.64 mmol) over 2 steps as a light yellow solid. Then, t-BuLi (8.8 mL, 1.7 M in pentane, 5.0 equiv) was carefully added dropwise to a solution of ethynyltrimethylsilane (2.22 mL, 15.0 mmol, 5.0 equiv) in THF (60 mL) at −78° C. After stirring at this temperature for 30 min the reaction was warmed up to 0° C. and then a solution of allylated estrone (883 mg, 3.0 mmol, 1.0 equiv) was added. The reaction was allowed to reach room temperature and stirred for 2 hours. Upon completion (monitored by TLC). The reaction mixture was cooled to 0° C. and quenched by sat. aq. NH₄Cl. The layers were separated, and the aqueous layer was extracted with ethyl acetate (30 mL×3). The combined organic layers were washed with brine, dried over anhydrous Na₂SO₄ and concentrated under reduced pressure. The crude mixture was purified by flash column chromatography (0=>5% ethyl acetate/hexanes, 100 mL silica gel) to give allylated ethinyl estradiol derivative (S41) in 93% yield (1.104 g, 2.81 mmol) as a colorless gel. ¹H NMR (500 MHz, Chloroform-d) δ 7.26 (d, J=8.1 Hz, 1H), 6.99 (d, J=8.1 Hz, 1H), 6.92 (s, 1H), 5.96 (ddt, J=16.8, 10.1, 6.8, 1H), 5.15-5.00 (m, 2H), 3.34 (d, J=6.8 Hz, 2H), 2.86 (dd, J=7.7, 3.1 Hz, 2H), 2.40 (dq, J=13.1, 4.0 Hz, 1H), 2.31 (ddd, J=13.5, 9.6, 5.6 Hz, 1H), 2.27-2.19 (m, 1H), 2.00 (ddd, J=13.6, 11.9, 3.9 Hz, 1H), 1.94-1.75 (m, 4H), 1.74-1.66 (m, 2H), 1.55-1.34 (m, 4H), 0.87 (s, 3H), 0.18 (s, 9H). ¹³C NMR (125 MHz, CDCl₃) δ 138.0, 137.7, 137.3, 136.8, 129.2, 126.0, 125.6, 115.7, 109.7, 90.1, 80.2, 49.8, 47.3, 44.2, 39.9, 39.4, 39.0, 33.0, 29.7, 27.4, 26.4, 23.0, 12.9, 0.2. HRMS (EI) m/z calculated for C₂₆H₃₆OSi [M]⁺: 392.2536, found 392.2533. [α]²²_D=−9.0° (c=0.51, CHCl₃).

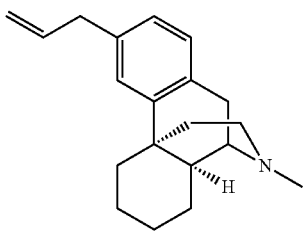

(S42)

(+)-Allylated dextromethorphan derivative (S42) was synthesized from 3-(OTf) dextromethorphan[20] (1.95 g, 5.0 mmol, 1.0 equiv) under the allylation condition from general procedure. The crude mixture was purified by flash column chromatography (5%=>20%, 100 mL Act II basic $Al_2O_3$) to give allylated olefin product (S42) in 88% yield (1.239 g, 4.40 mmol) as a colorless gel. $^1$H NMR (500 MHz, Chloroform-d) δ 7.05 (s, 1H), 7.03 (d, J=7.8 Hz, 1H), 6.93 (dd, J=7.7, 1.8 Hz, 1H), 5.97 (ddt, J=16.8, 10.1, 6.7 Hz, 1H), 5.12-5.00 (m, 2H), 3.35 (d, J=6.7 Hz, 2H), 3.00 (d, J=18.4 Hz, 1H), 2.81 (dd, J=5.8, 3.1 Hz, 1H), 2.61 (dd, J=18.4, 5.8 Hz, 1H), 2.46-2.37 (m, 2H), 2.40 (s, 3H) 2.07 (td, J=12.3, 3.3 Hz, 1H), 1.83 (dt, J=12.8, 3.2 Hz, 1H), 1.74 (td, J=12.6, 4.8 Hz, 1H), 1.67-1.61 (m, 1H), 1.54-1.48 (m, 1H), 1.44-1.22 (m, 5H), 1.18-1.08 (m, 1H). $^{13}$C NMR (126 MHz, $CDCl_3$) δ 140.5, 138.0, 137.8, 135.5, 127.8, 125.7, 125.6, 115.6, 58.1, 47.4, 45.7, 42.9, 42.3, 40.3, 37.2, 36.7, 26.9, 26.8, 24.0, 22.3. HRMS (EI) m/z calculated for $C_{20}H_{28}N$ $[M+H]^+$: 282.2222, found 282.2213. $[\alpha]^{21}_D$=+59.5° (c=0.51, $CHCl_3$).

TABLE 2-1

Reaction development of Pd-Sulfoxide catalyzed allylic C—H Amination

| entry | Pd(II) | Ligand | quinone | % yield |
| --- | --- | --- | --- | --- |
| 1* | Pd(OAc)$_2$ | bis-sulfoxide | BQ | <5 |
| 2† | Pd(OAc)$_2$ | bis-sulfoxide | BQ | <5 |
| 3 | Pd(OAc)$_2$ | L-1 | 2,6 DMBQ | 30 |
| 4 | Pd(OAc)$_2$ | L-1 | BQ | 24 |
| 5 | Pd(OAc)$_2$ | L-1 | 2,5 DMBQ | 52 |
| 6 | Pd(OAc)$_2$ | L-2 | 2,5 DMBQ | 21 |
| 7 | Pd(OAc)$_2$ | L-3 | 2,5 DMBQ | 32 |
| 8 | Pd(OAc)$_2$ | L-4 | 2,5 DMBQ | 55 |
| 9 | Pd(OAc)$_2$ | L-5 | 2,5 DMBQ | 75 |
| 10 | Pd(OAc)$_2$ | L-6 | 2,5 DMBQ | 62 |
| 11 | Pd(OAc)$_2$ | L-7 | 2,5 DMBQ | 55 |
| 12 | Pd(OAc)$_2$ | L-8 | 2,5 DMBQ | 74 |
| 13‡ | Pd(OAc)$_2$ | L-5 | 2,5 DMBQ | 73 |
| 14 | Pd(OAc)$_2$ (5%) | L-5 (5%) | 2,5 DMBQ | 53 |
| 15§ | Pd(OAc)$_2$ | none | 2,5 DMBQ | ND |

Bis-sulfoxide: Ph-S(O)-CH$_2$CH$_2$-S(O)-Ph

SOX ligands:

L-1: $R_1$ = H, $R_2$ = H, $R_3$ = Me, $R_4$ = Me;
L-2: $R_1$ = H, $R_2$ = H, $R_3$ = Ph, $R_4$ = Ph;
L-3: $R_1$ = H, $R_2$ = $CF_3$, $R_3$ = Me, $R_4$ = Me;
L-4: $R_1$ = H, $R_2$ = OMe, $R_3$ = Me, $R_4$ = Me;
L-5: $R_1$ = OMe, $R_2$ = H, $R_3$ = Me, $R_4$ = Me;
L-6: $R_1$ = H, $R_2$ = H, $R_3$ = Me, $R_4$ = OMe;
L-7: $R_1$ = OMe, $R_2$ = OMe, $R_3$ = Me, $R_4$ = Me;
L-8: $R_1$ = OMe, $R_2$ = H, $R_3$ = Me, $R_4$ = OMe;

Isolated yields are average of two runs.
*Conditions: 0.2 mmol (1.0 equiv.) olefin, 0.2 mmol amine nucleophile, 10 mol% Pd(OAc)$_2$/bis-sulfoxide, 2.0 equiv. BQ, 6% Cr(salen)Cl, 0.66M TBME, 45° C., 72 h
†Conditions: 0.2 mmol (1.0 equiv.) olefin, 0.2 mmol amine nucleophile, 10 mol% Pd(OAc)$_2$/bis-sulfoxide, 2.0 equiv. BQ, 6% DIPEA, 0.66M TBME, 45° C., 72 h
‡10% Ph$_2$P(O)OH was added.
§96% recovered amine nucleophile.

Entry 1:

Reaction proceeded according to reported procedure using Pd(OAc)$_2$/bissulfoxide (10 mg, 0.02 mmol, 0.1 equiv), Cr(salen)Cl (7.6 mg, 0.012 mmol, 0.06 equiv), 1,4 benzoquinone (43.2 mg, 0.4 mmol, 2.0 equiv), allylcyclohexane (30.9 mg, 0.2 mmol, 1.0 equiv), N-(2-Phenylethyl)trifluoromethanesulfonamide (50.6 mg, 0.2 mmol, 1.0 equiv) and 0.3 mL TBME (0.66 M). The mixture was concentrated under reduced pressure, the remaining mixture was diluted with 2 mL CDCl$_3$ and crude $^1$H NMR was taken with internal standard (trifluorotoluene 14.6 mg, 0.1 mmol, 0.5 equiv). Trace amount of product was observed by crude $^1$H NMR. The mixture was concentrated under reduced pressure and subjected to flash column chromatography (0%=>10% acetone in hexanes). No product was isolated by flash column chromatography.

Entry 2:

Reaction proceeded according to reported procedure using Pd(OAc)$_2$/bissulfoxide (10 mg, 0.02 mmol, 0.1 equiv), DIPEA (2.1 µL, 0.012 mmol, 0.06 equiv), BQ, (1,4 benzoquinone) (43.2 mg, 0.4 mmol, 2.0 equiv), allylcyclohexane (30.9 mg, 0.2 mmol, 1.0 equiv), N-(2-Phenylethyl)trifluoromethanesulfonamide (50.6 mg, 0.2 mmol, 1.0 equiv) and 0.3 mL TBME (0.66 M). Trace amount of product was observed by crude $^1$H NMR. No product was isolated by flash column chromatography.

Entry 3:

To a ½ dram vial was added a stir bar, Pd(OAc)$_2$ (4.4 mg, 0.02 mmol, 0.1 equiv), ligand 1 (6.3 mg, 0.02 mmol, 0.1 equiv), 2,6 DMBQ (2,6-dimethylbenzoquinone) (30 mg, 0.22 mmol, 1.1 equiv), allylcyclohexane (30.9 mg, 0.2 mmol, 1.0 equiv) and N-(2-Phenylethyl)trifluoromethanesulfonamide (50.6 mg, 0.2 mmol, 1.0 equiv). Toluene (0.2 mL, 1.0 M) was added and the vial was capped and heated to 45° C. for 72 hours. The vial was allowed to cool to room temperature and diluted with 1 mL acetone. The reaction mixture was filtered through a pipette silica plug into a 20 mL vial with acetone. The mixture was concentrated under reduced pressure, diluted with 2 mL CDCl$_3$ and analyzed by crude $^1$H NMR with internal standard (trifluorotoluene 14.6 mg, 0.1 mmol, 0.5 equiv). The mixture was then concentrated under reduced pressure and subjected to flash column chromatography (0%=>10% acetone in hexanes) to provide allylic amine product 1 as a clear oil. Run 1 (22.1 mg, 29.4% yield); Run 2 (22.9 mg, 30.5% yield); Average: 30% yield.

Entry 4:

The same conditions used in Entry 3 were used except using BQ (benzoquinone) (23.8 mg, 0.22 mmol, 1.1 equiv). Run 1 (17.9 mg, 23.8% yield); Run 2 (18.2 mg, 24.2% yield); Average: 24% yield.

Entry 5:

General Procedure:

The following procedure was used with no effort to exclude air or moisture. To a ½ dram vial was added a stir bar, Pd(OAc)$_2$ (4.4 mg, 0.02 mmol, 0.1 equiv), (±)-SOX-Ligand 1 (L1) (6.3 mg, 0.02 mmol, 0.1 equiv), 2,5 DMBQ (2,5-dimethylbenzoquinone) (30 mg, 0.22 mmol, 1.1 equiv), allylcyclohexane (30.9 mg, 0.2 mmol, 1.0 equiv) and N-(2-Phenylethyl)trifluoromethanesulfonamide (50.6 mg, 0.2 mmol, 1.0 equiv). Toluene (0.2 mL, 1.0 M) was added and the vial was capped and heated to 45° C. for 72 hours. The vial was allowed to cool to room temperature and diluted with 1 mL acetone. The reaction mixture was filtered through a pipette silica plug into a 20 mL vial with acetone. The mixture was concentrated under reduced pressure, diluted with 2 mL CDCl$_3$ and analyzed by crude $^1$H NMR with internal standard (trifluorotoluene 14.6 mg, 0.1 mmol, 0.5 equiv). The mixture was then concentrated under reduced pressure and subjected to flash column chromatography (0%=>10% acetone in hexanes) to provide allylic amine 1 as a clear oil. Run 1 (38.8 mg, 51.7% yield); Run 2 (39.4 mg, 52.5% yield); Average: 52% yield.

Entry 6:

The general procedure was followed using (±)-SOX-Ligand 2 (L2) (8.7 mg, 0.02 mmol, 0.1 equiv). Run 1 (15.7 mg, 20.9% yield); Run 2 (16.0 mg, 21.3% yield); Average: 21% yield.

Entry 7:

The general procedure was followed using (±)-SOX-Ligand 3 (L3) (7.6 mg, 0.02 mmol, 0.1 equiv). Run 1 (23.8 mg, 31.7% yield); Run 2 (23.7 mg, 31.6% yield); Average: 32% yield.

Entry 8:

The general procedure was followed using (±)-SOX-Ligand 4 (L4) (6.9 mg, 0.02 mmol, 0.1 equiv). Run 1 (41.3 mg, 54.9% yield); Run 2 (41.8 mg, 55.7% yield); Average: 55% yield.

Entry 9:

The general procedure was followed using (±)-MeO—SOX Ligand (L5) (6.9 mg, 0.02 mmol, 0.1 equiv). Run 1 (56.9 mg, 75.8% yield); Run 2 (56.1 mg, 74.7% yield); Run 3 (56.6 mg, 75.3% yield); Average: 75% yield.

Entry 10:

The general procedure was followed using (±)-SOX-Ligand 6 (L6) (6.6 mg, 0.02 mmol, 0.1 equiv). Run 1 (46.6 mg, 62.1% yield); Run 2 (47.2 mg, 62.9% yield); Average: 63% yield.

Entry 11:

The general procedure was followed using (±)-SOX-Ligand 7 (L7) (7.4 mg, 0.02 mmol, 0.1 equiv). Run 1 (41.7 mg, 55.5% yield); Run 2 (41.2 mg, 54.8% yield); Average: 55% yield.

Entry 12:

The general procedure was followed using (±)-SOX-Ligand 8 (L8) (7.2 mg, 0.02 mmol, 0.1 equiv). Run 1 (55.2 mg, 73.5% yield); Run 2 (55.4 mg, 73.7% yield); Average: 74% yield.

Entry 13:

The reaction proceeded under general procedure using (±)-MeO—SOX Ligand (L5) (6.9 mg, 0.02 mmol, 0.1 equiv) and Ph$_2$P(O)OH (4.4 mg, 0.02 mmol, 0.1 equiv) was added as additive. Run 1 (54.9 mg, 73.1% yield); Run 2 (55.3 mg, 73.6% yield); Average: 73% yield.

Entry 14:

The reaction proceeded under general procedure using Pd(OAc)$_2$ (2.2 mg, 0.01 mmol, 0.05 equiv) (±)-MeO—SOX Ligand (L5) (3.4 mg, 0.01 mmol, 0.05 equiv). Run 1 (39.9 mg, 53.1% yield); Run 2 (40.1 mg, 53.4% yield); Average: 53% yield.

Entry 15:

The general procedure was followed without any ligand. No product was detected by crude $^1$H NMR. No product or allylcyclohexene (volatile under reduced pressure) could be isolated by flash column chromatography, but 96% N-triflyl protected phenylethylamine was recovered.

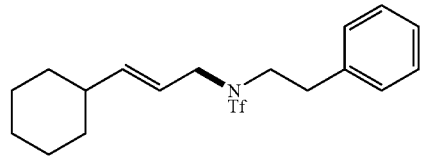

(1)

(E)-N-(3-cyclohexylallyl)-1,1,1-trifluoro-N-phenethylmethanesulfonamide (1)

$^1$H NMR (500 MHz, Chloroform-d) δ 7.35 (dd, J=8.1, 6.7 Hz, 2H), 7.30-7.25 (m, 1H), 7.22-7.18 (m, 2H), 5.69 (dd, J=15.4, 6.8 Hz, 1H), 5.37 (dt, J=15.4, 7.0, 1H), 3.92 (d, J=7.0 Hz, 2H), 3.55 (br s, 2H), 2.94 (t, J=8.0 Hz, 2H), 2.09-2.00 (m, 1H), 1.77 (m, 4H), 1.72-1.67 (m, 1H), 1.37-1.26 (m, 2H), 1.24-1.07 (m, 3H). $^{13}$C NMR (126 MHz, Chloroform-d) δ 144.0, 137.6, 128.9, 127.0, 120.6 120.2 (q, J=323.3 Hz). 51.2, 48.8, 40.5, 35.5, 32.7, 26.1, 26.0. (one carbon missing probably due to overlapping) 19F NMR (470 MHz, Chloroform-d) δ −76.42. HRMS (ESI) m/z calculated for $C_{18}H_{24}NO_2F_3SNa$ [M+Na]$^+$: 398.1378, found 398.1377.

Reaction Scope

General Procedure:

The following procedure was used with no effort to exclude air or moisture. To a ½ dram vial was added a stir bar, Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), olefin (0.2 mmol, 1.0 equiv) and N-trifyl protected amine (0.2 mmol, 1.0 equiv). Toluene (0.2 mL, 1.0 M) was added and the vial was capped and heated to 45° C. for 24-72 hours (monitored by TLC). The vial was allowed to cool to room temperature and diluted with 1 mL acetone. The reaction mixture was filtered through a pipette silica plug into a 20 mL vial with acetone. The mixture was concentrated under reduced pressure, diluted with 2 mL CDCl$_3$ and analyzed by crude $^1$H NMR with internal standard (trifluorotoluene 14.6 mg, 0.1 mmol, 0.5 equiv). The mixture was then concentrated under reduced pressure and subjected to flash column chromatography.

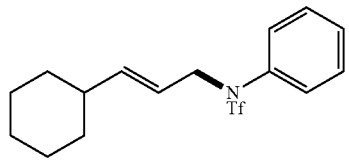

(2)

(E)-N-(3-cyclohexylallyl)-1,1,1-trifluoro-N-phenylmethanesulfonamide (2)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and 1,1,1-trifluoro-N-phenylmethanesulfonamide (S11) (45.0 mg, 0.2 mmol, 1.0 equiv) were reacted according to the general procedure for 72 hours. Purification by flash column chromatography (50 mL silica gel, 0%=>30% CH$_2$Cl$_2$ in hexanes) provided pure product 2 as a colorless oil. Run 1: (48.1 mg, 69.2% yield); Run 2: (49.1 mg, 70.6% yield); Run 3: (49.2 mg, 70.8% yield). Average: 70% yield±0.9%. $^1$H NMR (500 MHz, Chloroform-d) δ 7.42-7.34 (m, 3H), 7.29-7.23 (m, 2H), 5.43-5.33 (m, 2H), 4.27 (d, J=5.2 Hz, 2H), 1.92-1.82 (m, 1H), 1.69-1.51 (m, 5H), 1.28-1.15 (m, 2H), 1.14-1.05 (m, 1H), 0.98-0.87 (m, 2H). $^{13}$C NMR (125 MHz, CDCl$_3$) δ 144.2, 136.9, 129.8, 129.4, 129.2, 120.5 (q, J=323.7), 120.4, 56.1, 40.3, 32.5, 26.1, 25.9. $^{19}$F NMR (470 MHz, CDCl$_3$) δ −76.67. HRMS (ESI) m/z calculated for $C_{16}H_{20}NO_2F_3SNa$ [M+Na]$^+$: 370.1065, found 370.1074.

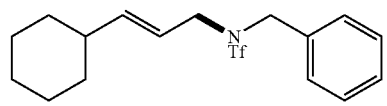

(3)

(E)-N-benzyl-N-(3-cyclohexylallyl)-1,1,1-trifluoromethanesulfonamide (3)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and N-benzyl-1,1,1-trifluoromethanesulfonamide (S12) (47.8 mg, 0.2 mmol, 1.0 equiv) were reacted according to the general procedure. Purification by flash column chromatography (50 mL silica gel, 0%=>30% CH$_2$Cl$_2$ in hexanes) provided pure product 3 as a colorless oil. Run 1: (58.9 mg, 81.5% yield); Run 2: (59.4 mg, 82.2% yield); Run 3: (59.6 mg, 82.4% yield). Average: 82% yield±0.5%. $^1$H NMR (500 MHz, Chloroform-d) δ 7.41-7.33 (m, 3H), 7.32-7.28 (m, 2H), 5.50 (dd, J=15.4, 6.8 Hz, 1H), 5.29 (dt, J=14.8, 7.0 Hz, 1H), 4.49 (br s, 2H), 3.81 (br s, 2H), 2.05-1.92 (m, 1H), 1.78-1.62 (m, 5H), 1.33-1.22 (m, 2H), 1.22-1.12 (m, 1H), 1.10-1.00 (m, 2H). $^{13}$C NMR (126 MHz, Chloroform-d) δ 144.6, 134.3, 129.0, 128.7, 128.5, 120.2 (q, J=322.8 Hz), 119.7, 50.4, 49.6, 40.6, 32.7, 26.2, 26.0. $^{19}$F NMR (470 MHz, Chloroform-d) δ −76.40. HRMS (EI) m/z calculated for $C_{17}H_{22}NO_2F_3S$ [M]$^+$: 361.1323, found 361.1322.

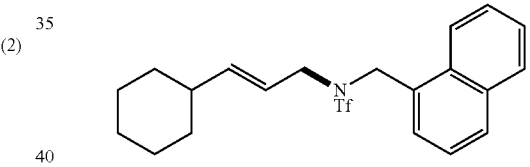

(4)

(E)-N-(3-cyclohexylallyl)-1,1,1-trifluoro-N-(naphthalen-1-ylmethyl)methane sulfonamide (4)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and 1,1,1-trifluoro-N-(naphthalen-1-ylmethyl)methane sulfonamide (S13) (57.9 mg, 0.2 mmol, 1.0 equiv) were reacted according to the general procedure. Purification by flash column chromatography (50 mL silica gel, 0%=>30% CH$_2$Cl$_2$ in hexanes) provided pure product 4 as a colorless oil. Run 1: (57.9 mg, 70.4% yield); Run 2: (57.0 mg, 69.3% yield); Run 3: (58.5 mg, 71.1% yield). Average: 70% yield±0.9%. $^1$H NMR (500 MHz, Chloroform-d) δ 8.12 (dd, J=8.4, 1.1 Hz, 1H), 7.91-7.88 (m, 1H), 7.86 (d, J=7.4 Hz, 1H), 7.60-7.45 (m, 4H), 5.36-5.19 (m, 2H), 5.01 (br s, 2H), 3.83 (br s, 2H), 1.90-1.76 (m, 1H), 1.70-1.59 (m, 3H), 1.57-1.50 (m, 2H), 1.29-1.15 (m, 2H), 1.14-1.03 (m, 1H), 0.94-0.82 (m, 2H). $^{13}$C NMR (126 MHz, CDCl$_3$) δ 144.0, 134.0, 131.6, 129.5, 129.4, 129.0, 127.3, 126.9, 126.2, 125.3, 122.9, 120.4 (q, J=323.8 Hz), 119.9, 50.2, 48.8, 40.4, 32.5, 26.1, 25.9. $^{19}$F NMR (470 MHz, Chloroform-d) δ −75.47. HRMS (ESI) m/z calculated for $C_{21}H_{24}NO_2F_3SNa$ [M+Na]$^+$: 434.1378, found 434.1388.

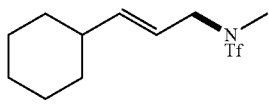

(5)

(E)-N-(3-cyclohexylallyl)-1,1,1-trifluoro-N-methyl-methanesulfonamide (5)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and 1,1,1-trifluoro-N-methylmethanesulfonamide (S14) (32.6 mg, 0.2 mmol, 1.0 equiv) were reacted according to the general procedure. Purification by flash column chromatography (50 mL silica gel, 0%=>30% CH$_2$Cl$_2$ in hexanes) provided pure product 5 as a colorless oil. Run 1: (41.7 mg, 73.1% yield); Run 2: (41.4 mg, 72.6% yield); Run 3: (41.9 mg, 73.6% yield). Average: 73% yield±0.5%. $^1$H NMR (500 MHz, Chloroform-d) δ 5.68 (dd, J=15.4, 6.7 Hz, 1H), 5.34 (dt, J=15.3, 6.9 Hz, 1H), 3.87 (br s, 2H), 2.94 (s, 3H), 2.07-1.90 (m, 1H), 1.76-1.61 (m, 5H), 1.33-1.22 (m, 2H), 1.20-1.12 (m, 1H), 1.12-1.02 (m, 2H). 13C NMR (126 MHz, Chloroform-d) δ 144.0, 120.3 (q, J=323.6 Hz), 120.2, 53.2, 40.5, 34.3, 32.8, 26.2, 26.0. $^{19}$F NMR (470 MHz, Chloroform-d) δ -75.77. HRMS (EI) m/z calculated for C$_{11}$H$_{18}$NO$_2$F$_3$S [M]$^+$: 285.1010, found 285.1012.

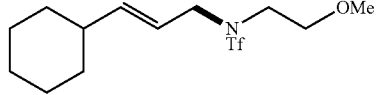

(6)

(E)-N-butyl-N-(3-cyclohexylallyl)-1,1,1-trifluoromethanesulfonamide (6)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and N-butyl-1,1,1-trifluoromethanesulfonamide (S15) (41.0 mg, 0.2 mmol, 1.0 equiv) were reacted according to the general procedure. Purification by flash column chromatography (50 mL silica gel, 0%=>30% CH$_2$Cl$_2$ in hexanes) provided pure product 6 as a colorless oil. Run 1: (33.1 mg, 50.5% yield); Run 2: (33.6 mg, 51.3% yield); Run 3: (33.4 mg, 51.0% yield). Average: 51% yield±0.4%. $^1$H NMR (500 MHz, Chloroform-d) δ 5.66 (dd, J=15.4, 6.7 Hz, 1H), 5.34 (dt, J=15.4, 7.0, 1H), 3.91 (d, J=7.0 Hz, 2H), 3.30 (br s, 2H), 2.06-1.95 (m, 1H), 1.77-1.67 (m, 5H), 1.57 (p, J=7.7 Hz, 2H), 1.36-1.21 (m, 4H), 1.21-1.13 (m, 1H), 1.12-1.02 (m, 2H), 0.92 (t, J=7.4 Hz, 3H). 13C NMR (125 MHz, CDCl$_3$) δ 143.6, 120.7, 120.18 (q, J=323.4 Hz), 50.5, 47.2, 40.5, 32.7, 30.1, 26.2, 26.0, 19.7, 13.8. HRMS (ESI) m/z calculated for C$_{14}$H$_{23}$NO$_3$F$_3$S [M-H]$^+$: 342.1351, found: 342.1345.

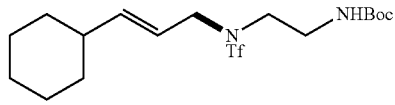

(7)

tert-Butyl-(E)-(2-((N-(3-cyclohexylallyl)-1,1,1-trifluoromethyl)sulfonamido)ethyl) carbamate (7)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and tert-butyl (2-((trifluoromethyl)sulfonamido)ethyl)carbamate (S16) (58.4 mg, 0.2 mmol, 1.0 equiv) were reacted according to the general procedure. Purification by flash column chromatography (50 mL silica gel, 0%=>5% acetone in hexanes) and preparative TLC (10% ethyl acetate in hexanes) provided pure product 7 as a colorless oil. Run 1: (52.3 mg, 63.1% yield); Run 2: (51.9 mg, 62.6% yield); Run 3: (52.9 mg, 63.9% yield). Average: 63% yield±0.7%. $^1$H NMR (500 MHz, Chloroform-d) δ 5.73 (dd, J=15.5, 6.7 Hz, 1H), 5.38-5.28 (m, 1H), 4.74 (d, J=6.4 Hz, 1H), 3.97 (d, J=7.1 Hz, 2H), 3.41 (br s, 2H), 3.30 (br q, J=6.2 Hz, 2H), 2.05-1.93 (m, 1H), 1.77-1.61 (m, 5H), 1.44 (s, 9H), 1.31-1.21 (m, 2H), 1.19-1.12 (m, 1H), 1.12-1.02 (m, 2H). $^{13}$C NMR (125 MHz, CDCl$_3$) δ 156.0, 144.7, 120.11 (q, J=120.11), 120.1, 79.9, 51.0, 46.6, 40.5, 38.4, 32.6, 28.4, 26.1, 26.0. $^{19}$F NMR (470 MHz, CDCl$_3$) δ -76.28. HRMS (ESI) m/z calculated for C$_{17}$H$_{30}$N$_2$O$_4$F$_3$S [M+H]$^+$: 415.1878, found 415.1866.

(8)

(E)-N-(3-cyclohexylallyl)-1,1,1-trifluoro-N-(2-methoxyethyl)methanesulfonamide (8)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and 1,1,1-trifluoro-N-(2-methoxyethyl)methanesulfonamide (S17) (41.4 mg, 0.2 mmol, 1.0 equiv) were reacted according to the general procedure. Purification by flash column chromatography (50 mL silica gel, 0%=>20% acetone in hexanes) provided pure product 8 as a colorless oil. Run 1: (40.9 mg, 62.1% yield); Run 2: (41.6 mg, 63.1% yield); Run 3: (42.2 mg, 64.1% yield). Average: 63% yield±1.0%. $^1$H NMR (500 MHz, Chloroform-d) δ 5.68 (dd, J=15.5, 6.6 Hz, 1H), 5.34 (dt, J=15.3, 7.0, 1H), 4.00 (d, J=6.9 Hz, 2H), 3.54 (t, J=5.7 Hz, 2H), 3.48 (br s, 2H), 3.34 (s, 3H), 2.04-1.95 (m, 1H), 1.75-1.68 (m, 4H), 1.68-1.63 (m, 1H), 1.31-1.05 (m, 5H). $^{13}$C NMR (125 MHz, CDCl$_3$) δ 144.0, 121.4, 121.4 (q, J=321.3 Hz), 71.3, 59.0, 52.0, 46.4, 40.5, 32.7, 26.2, 26.0. $^{19}$F NMR (470 MHz, CDCl$_3$) δ -76.43. HRMS (ESI) m/z calculated for C$_{13}$H$_{22}$NO$_3$F$_3$SNa [M+Na]$^+$: 352.1170, found 352.1169.

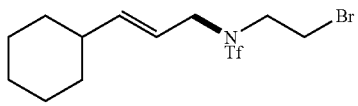

(9)

(E)-N-(2-bromoethyl)-N-(3-cyclohexylallyl)-1,1,1-trifluoromethanesulfonamide (9)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and N-(2-bromoethyl)-1,1,1-trifluoromethanesulfonamide (S18). (51.2 mg, 0.2 mmol, 1.0 equiv) were reacted according to the general procedure. Purification by flash column chromatography (50 mL silica gel, 0%=>30% CH$_2$Cl$_2$ in hexanes) provided pure product 9 as a colorless oil. Run 1: (44.9 mg, 59.4% yield); Run 2: (45.7 mg, 60.5% yield); Run 3: (45.6 mg, 60.3% yield). Average: 60% yield±0.6%. $^1$H NMR (500 MHz, Chloroform-d) δ 5.82-5.60 (m, 1H), 5.36 (dtd, J=15.4, 7.1, 1.3 Hz, 1H), 4.09-3.90 (br s, 2H), 3.66 (br s, 2H), 3.44 (t, J=7.5 Hz, 2H), 2.11-1.95 (m, 1H), 1.85-1.58 (m, 4H), 1.33-1.22 (m, 2H), 1.21-1.14 (m, 1H), 1.13-1.03 (m, 2H). 13C NMR (126 MHz, Chloroform-d) δ 144.8, 120.3, 120.0 (q, J=323.0 Hz), 52.2, 48.7, 40.5, 32.6, 27.9, 26.1, 26.0. $^{19}$F NMR (470 MHz, Chloroform-d) δ −76.20. HRMS (ESI) m/z calculated for C$_{12}$H$_{19}$NO$_2$F$_3$SNa [M+Na]$^+$: 400.0170, found 400.0179.

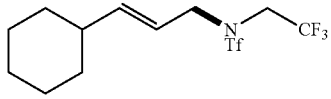

(10)

(E)-N-(3-cyclohexylallyl)-1,1,1-trifluoro-N-(2,2,2-trifluoroethyl)methanesulfonamide (10)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and 1,1,1-trifluoro-N-(2,2,2-trifluoroethyl)methanesulfonamide (S19) (46.2 mg, 0.2 mmol, 1.0 equiv) were reacted according to the general procedure for 24 hours. Purification by flash column chromatography (50 mL silica gel, 0%=>30% CH$_2$Cl$_2$ in hexanes) provided pure product 10 as a colorless oil. Run 1: (63.2 mg, 89.5% yield); Run 2: (64.1 mg, 90.7% yield); Run 3: (63.5 mg, 89.8% yield). Average: 90% yield±0.6%. $^1$H NMR (500 MHz, Chloroform-d) δ 5.77 (dd, J=15.5, 6.8 Hz, 1H), 5.38-5.23 (m, 1H), 4.06 (d, J=7.3 Hz, 2H), 3.89 (q, J=8.4 Hz, 2H), 2.04 (dtt, J=10.8, 6.9, 3.5 Hz, 1H), 1.79-1.63 (m, 5H), 1.34-1.22 (m, 2H), 1.22-1.14 (m, 1H), 1.14-1.05 (m, 2H). $^{13}$C NMR (126 MHz, Chloroform-d) δ 146.9, 123.58 (q, J=280.3 Hz), 119.83 (q, J=322.2 Hz), 118.5, 52.0, 46.22 (q, J=35.8 Hz), 40.6, 32.6, 26.0, 25.9. $^{19}$F NMR (470 MHz, Chloroform-d) δ −69.96, −76.32. HRMS (EI) m/z calculated for C$_{12}$H$_{17}$NO$_2$F$_6$S$_2$ [M]$^+$: 353.0884, found 353.0871.

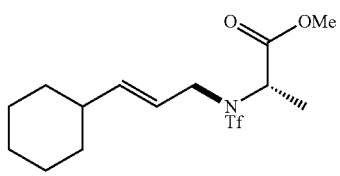

(11)

(−)-Methyl (E)-N-(3-cyclohexylallyl)-N-((trifluoromethyl)sulfonyl)-L-alaninate (11)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and methyl ((trifluoromethyl)sulfonyl)-L-alaninate (S20) (47.0 mg, 0.2 mmol, 1.0 equiv) were reacted according to the general procedure. Purification by flash column chromatography (50 mL silica gel, 0%=>30% CH$_2$Cl$_2$ in hexanes) provided pure product (−)-11 as a colorless oil. Run 1: (57.3 mg, 80.2% yield); Run 2: (57.0 mg, 79.7% yield); Run 3: (57.8 mg, 80.9% yield). Average: 80% yield±0.6%. $^1$H NMR (500 MHz, Chloroform-d) δ 5.61 (dd, J=15.5, 6.6, 1H), 5.41 (dt, J=14.8, 6.8 Hz, 1H), 4.56 (q, J=7.3 Hz, 1H), 4.01 (d, J=6.6 Hz, 2H), 3.76 (s, 3H), 1.99-1.90 (m, 1H), 1.77-1.61 (m, 5H), 1.53 (d, J=7.4 Hz, 3H), 1.31-1.21 (m, 2H), 1.20-1.12 (m, 1H), 1.10-0.99 (m, 2H). $^{13}$C NMR (125 MHz, CDCl$_3$) δ 170.8, 142.6, 122.3, 119.9 (q, J=323.0), 56.5, 52.7, 50.0, 41.4, 32.5, 26.2, 26.0, 16.6. $^{19}$F NMR (470 MHz, CDCl$_3$) δ −76.61. HRMS (ESI) m/z calculated for C$_{14}$H$_{22}$NO$_4$F$_3$SNa [M+Na]$^+$: 380.1119, found 380.1120.

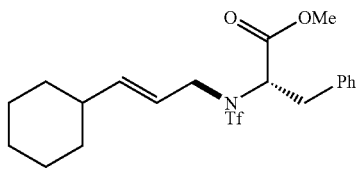

(12)

(−)-methyl (E)-N-(3-cyclohexylallyl)-N-((trifluoromethyl)sulfonyl)-L-phenylalaninate (12)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and methyl ((trifluoromethyl)sulfonyl)-L-phenylalaninate (S21) (62.2 mg, 0.2 mmol, 1.0 equiv) were reacted according to the general procedure. Purification by flash column chromatography (50 mL silica gel, 0%=>30% CH$_2$Cl$_2$ in hexanes) provided pure product (−)-12 as a colorless oil. Run 1: (60.0 mg, 69.2% yield); Run 2: (60.9 mg, 70.2% yield); Run 3: (61.4 mg, 70.8% yield). Average: 70% yield±0.8%. $^1$H NMR (500 MHz, Chloroform-d) δ 7.34-7.30 (m, 2H), 7.28-7.22 (m, 3H), 5.68 (dd, J=15.5, 6.5, 1H), 5.42 (dt, J=15.4, 6.9, 1H), 4.71 (t, J=7.4 Hz, 1H), 4.06 (dd, J=7.0, 3.7 Hz, 2H), 3.71 (s, 3H), 3.44 (dd, J=14.1, 8.0 Hz, 1H), 3.04 (dd, J=14.1, 6.8 Hz, 1H), 2.06-1.89 (m, 1H), 1.84-1.58 (m, 5H), 1.34-1.22 (m, 2H), 1.22-1.14 (m, 1H), 1.14-1.02 (m, 2H). 13C NMR (126 MHz, CDCl$_3$) δ 169.9, 143.0, 136.3, 129.4, 128.9, 127.4, 122.2, 119.9 (q, J=323.5 Hz) 62.3, 52.7, 50.3, 40.5, 37.3, 32.6, 26.3, 26.1. $^{19}$F NMR (470 MHz, Chloroform-d) δ− 75.98. HRMS (ESI) m/z calculated for C$_{20}$H$_{26}$NO$_4$F$_3$SNa [M+Na]$^+$: 454.1432, found 454.1422. Complete stereoretention was proven by chiral HPLC analysis. The enantiomeric excess was determined to be >99% ee by chiral HPLC analysis (against mixture of (−)-12 (52%) and (+)-12 (48%)) (CHIRALPAK AD-RH column, 0.25 mL/min, 80% EtOH in H$_2$O, λ=220 nm (4 nm). tR(major)=20.177 min).

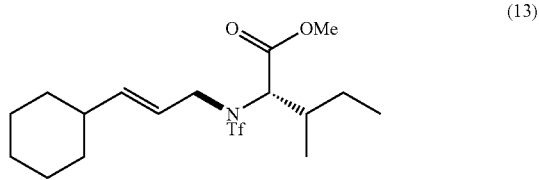

(−)-methyl N-((E)-3-cyclohexylallyl)-N-((trifluoromethyl)sulfonyl)-L-alloisoleucinate (13)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allyl cyclohexane (24.8 mg, 0.2 mmol, 1.0 equiv) and Methyl ((trifluoromethyl)sulfonyl)-L-isoleucinate (S23) (55.5 mg, 0.2 mmol, 1.0 equiv) were reacted according to the general procedure. Purification by flash column chromatography (50 mL silica gel, 0%=>30% CH$_2$Cl$_2$ in hexanes) provided pure product (−)-13 as a colorless oil. Run 1: (60.0 mg, 75.1% yield); Run 2: (60.4 mg, 75.6% yield); Run 3: (59.7 mg, 74.7% yield). Average: 75% yield±0.5%. $^1$H NMR (500 MHz, Chloroform-d) δ 5.64 (dd, J=15.5, 6.5 Hz, 1H), 5.52-5.43 (m, 1H), 4.24 (dd, J=16.0, 8.4 Hz, 1H), 4.16-4.05 (m, 2H), 3.74 (s, 3H), 2.05-1.90 (m, 2H), 1.75-1.62 (m, 6H), 1.31-0.98 (m, 6H), 0.93-0.86 (m, 6H). 13C NMR (125 MHz, CDCl$_3$) δ 170.7, 141.8, 123.0, 119.9 (q, J=323.2 Hz), 65.7, 52.1, 49.3, 40.4, 34.4, 32.5, 26.2, 26.0, 25.2, 15.4, 10.7. $^{19}$F NMR (470 MHz, CDCl$_3$) δ −75.45. HRMS (ESI) m/z calculated for C$_{17}$H$_{28}$NO$_4$F$_3$SNa [M+Na]$^+$: 422.1589, found 422.1587.

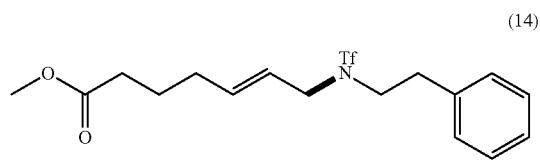

Methyl-(E)-7-((1,1,1-trifluoro-N-phenethylmethyl)sulfonamido)hept-5-enoate (14)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), 6-Heptenoic acid methyl ester (28.4 mg, 0.2 mmol, 1.0 equiv) and N-(2-Phenylethyl)trifluoromethanesulfonamide (S10) (50.6 mg, 0.2 mmol, 1.0 equiv) were reacted according to the general procedure. Purification by flash column chromatography (50 mL silica gel, 0%=>10% acetone in hexanes) and preparative TLC provided pure product 14 as a colorless oil. Run 1: (46.6 mg, 59.2% yield); Run 2: (47.4 mg, 60.3% yield); Run 3: (47.8 mg, 60.8% yield). Average: 60% yield±0.8%. $^1$H NMR (500 MHz, Chloroform-d) δ 7.37-7.29 (m, 2H), 7.27-7.23 (m, 1H), 7.21-7.14 (m, 2H), 5.72-5.62 (m, 1H), 5.41 (dt, J=15.3, 6.9, 1H), 3.88 (d, J=6.9 Hz, 2H), 3.67 (s, 3H), 3.52 (br s, 2H), 2.91 (t, J=7.9 Hz, 2H), 2.32 (t, J=7.4 Hz, 2H), 2.18-2.08 (m, 2H), 1.74 (p, J=7.5 Hz, 2H). $^{13}$C NMR (126 MHz, Chloroform-d) δ 173.8, 137.5, 136.8, 128.9, 128.9, 127.0, 124.2, 120.1 (q, J=323.2 Hz), 51.7, 50.8, 48.9, 35.5, 33.4, 31.6, 24.2. $^{19}$F NMR (470 MHz, Chloroform-d) δ −76.45. HRMS (ESI) m/z calculated for C$_{17}$H$_{22}$NO$_4$F$_3$SNa [M+Na]$^+$: 416.1119, found 416.1116.

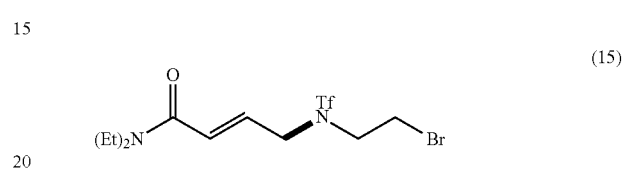

(E)-4-((N-(2-bromoethyl)-1,1,1-trifluoromethyl)sulfonamido)-N,N-diethylbut-2-enamide (15)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), N, N-diethylbut-3-enamide (S31). (28.2 mg, 0.2 mmol, 1.0 equiv) and N-(2-bromoethyl)-1,1,1-trifluoromethanesulfonamide (S18). (51.2 mg, 0.2 mmol, 1.0 equiv) were reacted according to the general procedure. Purification by flash column chromatography (column 1: 50 mL silica gel, 0%=>10% acetone in hexanes) and preparative TLC provided pure product 15 as colorless oil. Run 1: (67.4 mg, 85.3% yield); Run 2: (66.7 mg, 84.4% yield); Run 3: (68.0 mg, 86.0% yield). Average: 85% yield±0.8%. $^1$H NMR (500 MHz, Chloroform-d) δ 6.74 (dt, J=15.1, 6.3 Hz, 1H), 6.45 (d, J=15.1, 1H), 4.22 (d, J=6.3 Hz, 2H), 3.72 (br s, 2H), 3.46 (t, J=7.1 Hz, 2H), 3.42 (q, J=7.2 Hz, 2H), 3.36 (q, J=7.2 Hz, 2H), 1.19 (t, J=7.2 Hz, 3H), 1.14 (t, J=7.1 Hz, 3H). $^{13}$C NMR (126 MHz, Chloroform-d) δ 164.1, 136.4, 125.9, 119.8 (q, J=322.9 Hz), 50.6, 49.6, 42.4, 42.1, 27.9, 15.0, 13.1. $^{19}$F NMR (470 MHz, Chloroform-d) δ −76.19. HRMS (ESI) m/z calculated for C$_{11}$H$_{19}$N$_2$O$_3$F$_3$SBr [M+H]$^+$: 395.0252, found 395.0251.

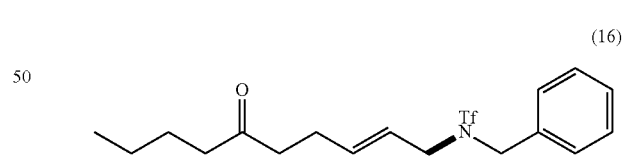

(E)-N-benzyl-1,1,1-trifluoro-N-(6-oxodec-2-en-1-yl)methane sulfonamide (16)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), Dec-9-en-5-one (S32) (30.9 mg, 0.2 mmol, 1.0 equiv) and 1,1,1-trifluoro-N-phenylmethanesulfonamide (S12) (47.8 mg, 0.2 mmol, 1.0 equiv) were reacted according to the general procedure. Purification by flash column chromatography (50 mL silica gel, 0%=>5% acetone in hexanes) and preparative TLC (40% CH$_2$Cl$_2$ in hexanes)

provided pure product 16 as a colorless oil. Run 1: (42.5 mg, 54.3% yield); Run 2: (43.1 mg, 55.0% yield); Run 3: (43.4 mg, 55.5% yield). Average: 55% yield±0.6%. $^1$H NMR (500 MHz, Methylene Chloride-d$_2$) δ 7.39-7.30 (m, 3H), 7.30-7.26 (m, 2H), 5.59-5.45 (m, 1H), 5.37-5.27 (m, 1H), 4.45 (br s, 2H), 3.78 (br s, 2H), 2.41 (t, J=7.2 Hz, 2H), 2.35 (t, J=7.5 Hz, 2H), 2.27-2.19 (m, 2H), 1.49 (p, J=7.5 Hz, 2H), 1.32-1.21 (m, 2H), 0.87 (t, J=7.4 Hz, 3H). $^{13}$C NMR (126 MHz, Chloroform-d) δ 210.3, 137.7, 135.2, 129.6, 129.3, 129.1, 123.8, 122.2 (q, J=323.8 Hz), 51.4, 50.2, 43.2, 42.1, 26.9, 26.7, 23.1, 14.4. $^{19}$F NMR (470 MHz, Methylene Chloride-d$_2$) δ −76.87. HRMS (ESI) m/z calculated for C$_{18}$H$_{25}$NO$_3$F$_3$S [M+H]$^+$: 392.1507, found 392.1524.

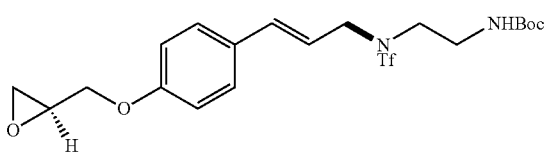

(17)

(+)-tert-butyl-(S,E)-(2-((1,1,1-trifluoro-N-(3-(4-(oxiran-2-ylmethoxy) phenyl) allyl) methyl) sulfonamido) ethyl)carbamate (17)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (S)-2-((4-allylphenoxy)methyl)oxirane$^{22}$ (30.9 mg, 0.2 mmol, 1.0 equiv) and 1,1,1-trifluoro-N-phenylmethanesulfonamide (S16). (47.8 mg, 0.2 mmol, 1.0 equiv) were reacted according to the general procedure. Purification by flash column chromatography (column 1: 50 mL silica gel, 0%=>15% acetone in hexanes) provided pure product 17 as a white solid. Run 1: (86.9 mg, 90.4% yield); Run 2: (85.6 mg, 89.1% yield); Run 3: (87.7 mg, 91.3% yield). Average: 90% yield±1.1%. $^1$H NMR (500 MHz, Chloroform-d) δ 7.33 (d, J=8.7 Hz, 2H), 6.88 (d, J=8.7 Hz, 2H), 6.61 (d, J=15.7 Hz, 1H), 5.97 (dt, J=15.7, 7.2 Hz, 1H), 4.81-4.75 (m, 1H), 4.24 (dd, J=11.0, 3.1 Hz, 1H), 4.18 (d, J=7.2 Hz, 2H), 3.95 (dd, J=11.1, 5.8 Hz, 1H), 3.47 (br s, 2H), 3.38-3.30 (m, 3H), 2.91 (t, J=4.5 Hz, 1H), 2.76 (dd, J=4.9, 2.6 Hz, 1H), 1.44 (s, 9H). $^{13}$C NMR (126 MHz, Chloroform-d) δ 158.9, 156.1, 136.0, 129.0, 128.2, 120.11 (q, J=323.0 Hz), 119.8, 114.9, 80.0, 68.9, 51.1, 50.2, 46.9, 44.8, 38.4, 28.5. $^{19}$F NMR (470 MHz, Chloroform-d) δ −76.29. HRMS (ESI) m/z calculated for C$_{20}$H$_{27}$N$_2$O$_6$F$_3$SNa [M+Na]$^+$: 503.1434, found 503.1441. [α]$^{22}_D$=+2.5° (c=0.58, CHCl$_3$).

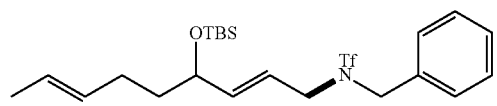

(18)

(±)-N-benzyl-N-((2E,7E)-4-((tert-butyldimethylsilyl)oxy)nona-2,7-dien-1-yl)-1,1,1-trifluoromethanesulfonamide (18)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (±)-(E)-tert-butyldimethyl(nona-1,7-dien-4-yloxy)silane (S35) (50.9 mg, 0.2 mmol, 1.0 equiv) and 1,1,1-trifluoro-N-phenylmethanesulfonamide (S12) (47.8 mg, 0.2 mmol, 1.0 equiv) were reacted according to the general procedure. Purification by flash column chromatography (column 1: 50 mL silica gel, 0%=>5% acetone in hexanes) provided pure product (±)-18 as a colorless oil. Run 1: (58.7 mg, 59.7% yield); Run 2: (59.7 mg, 60.7% yield); Run 3: (59.4 mg, 60.4% yield). Average: 60% yield±0.5%. $^1$H NMR (500 MHz, Chloroform-d) δ 7.42-7.33 (m, 3H), 7.32-7.29 (m, 2H), 5.64-5.50 (m, 2H), 5.48-5.36 (m, 2H), 4.48 (br s, 2H), 4.14 (q, J=5.7 Hz, 1H), 3.85 (br s, 2H), 2.07-1.97 (m, 2H), 1.66 (d, J=4.9 Hz, 3H), 1.61-1.42 (m, 2H), 0.92 (s, 9H), 0.07 (s, 3H), 0.04 (s, 3H). $^{13}$C NMR (126 MHz, Chloroform-d) δ 141.1, 134.1, 130.8, 129.1, 128.7, 128.6, 125.4, 121.5, 120.19 (q, J=322.7 Hz), 71.7, 50.5, 48.7, 38.0, 28.3, 25.9, 18.3, 18.1, −4.3, −4.7. $^{19}$F NMR (470 MHz, Chloroform-d) δ −76.53. HRMS (ESI) m/z calculated for C$_{23}$H$_{36}$NO$_3$F$_3$SiSNa [M+Na]$^+$: 514.2035, found 514.2032.

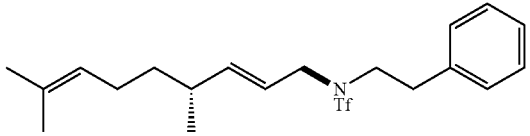

(19)

(−)-(R,E)-N-(4,8-dimethylnona-2,7-dien-1-yl)-1,1,1-trifluoro-N-phenethylmethane sulfonamide (19)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (R)-4,8-dimethylnona-1,7-diene (30.5 mg, 0.2 mmol, 1.0 equiv) and N-(2-Phenylethyl)trifluoromethanesulfonamide (S10) (50.6 mg, 0.2 mmol, 1.0 equiv) were reacted according to the general procedure. Purification by flash column chromatography (50 mL silica gel, 0%=>30% CH$_2$Cl$_2$ in hexanes) provided pure product 14 as colorless oil. Run 1: (54.4 mg, 67.4% yield); Run 2: (55.1 mg, 68.3% yield); Run 3: (55.7 mg, 69.0% yield). Average: 68% yield±0.8%. $^1$H NMR (500 MHz, Chloroform-d) δ 7.35-7.29 (m, 2H), 7.29-7.22 (m, 1H), 7.20-7.16 (m, 2H), 5.59 (dd, J=15.3, 7.8, 1H), 5.36 (dt, J=14.6, 7.0, 1H), 5.12-5.05 (m, 1H), 3.96-3.85 (m, 2H), 3.55 (br s, 2H), 2.92 (t, J=8.0 Hz, 2H), 2.21 (hept, J=7.0 Hz, 1H), 1.96 (q, J=7.6 Hz, 2H), 1.69 (s, 3H), 1.58 (s, 3H), 1.35 (q, J=7.3 Hz, 2H), 1.02 (d, J=6.7, 3H). $^{13}$C NMR (126 MHz, Chloroform-d) δ 144.0, 137.6, 131.9, 128.9, 128.9, 127.1, 124.2, 121.5, 120.1 (q, J=323.3 Hz), 51.0, 48.8, 36.8, 36.2, 35.4, 25.9, 25.9, 20.4, 17.8. $^{19}$F NMR (470 MHz, Chloroform-d) δ −76.47. HRMS (ESI) m/z calculated for C$_{20}$H$_{28}$NO$_2$F$_3$SNa [M+Na]$^+$: 426.1691, found 426.1700. [α]$^{23}_D$=−16.9° (c=0.50, CHCl$_3$). Complete stereoretention was determined by chiral HPLC analysis. The enantiomeric excess was determined to be >99% ee (from pure chiral olefin starting material) by chiral HPLC analysis (CHIRALPAK AD-RH column, 0.25 mL/min, 80% EtOH in H$_2$O, λ=214 nm (4 nm). tR(major)= 14.804 min).

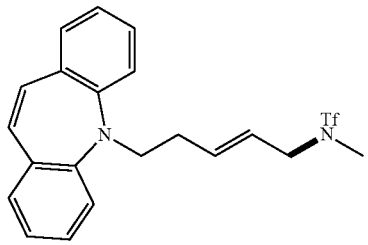

(20)

(E)-N-(5-(5H-dibenzo[b,f]azepin-5-yl)pent-2-en-1-yl)-1,1,1-trifluoro-N-methyl methanesulfonamide (20)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), 5-(pent-4-en-1-yl)-5H-dibenzo[b,f]azepine (S36) (52.3 mg, 0.2 mmol, 1.0 equiv) and 1,1,1-trifluoro-N-methylmethanesulfonamide (S14) (32.6 mg, 0.2 mmol, 1.0 equiv) were reacted according to the general procedure. Purification by flash column chromatography (50 mL silica gel, 0%=>30% CH$_2$Cl$_2$ in hexanes) provided pure product 20 as a yellow oil. Run 1: (50.3 mg, 59.5% yield); Run 2: (51.1 mg, 60.5% yield); Run 3: (51.3 mg, 60.7% yield). Average: 60% yield±0.6%. $^1$H NMR (500 MHz, Methanol-d$_4$) δ 7.23 (ddd, J=8.2, 7.2, 1.7 Hz, 2H), 7.02 (m, 4H), 6.95 (ddd, J=7.4, 7.4, 1.1 Hz, 2H), 6.66 (s, 2H), 5.74 (dt, J=15.1, 6.9, 1H), 5.23 (dt, J=15.1, 6.8, 1H), 3.88-3.68 (m, 4H), 2.84 (s, 3H), 2.24 (q, J=6.6, 2H). $^{13}$C NMR (126 MHz, Methanol-d$_4$) δ 152.0, 136.1, 135.4, 133.1, 130.2, 130.0, 125.4, 124.4, 121.6, 121.6 (q, J=323.0 Hz), 53.6, 51.0, 34.9, 31.2. $^{19}$F NMR (470 MHz, Methanol-d$_4$) δ 77.66. HRMS (ESI) m/z calculated for C$_{21}$H$_{22}$N$_2$O$_2$F$_3$S [M+H]$^+$: 423.1354, found 423.1335.

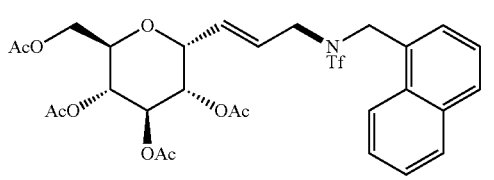

(21)

(+)-(2R,3R,4R,5S,6R)-2-(acetoxymethyl)-6-((E)-3-((1,1,1-trifluoro-N-(naphthalen-1-ylmethyl)methyl)sulfonamido)prop-1-en-1-yl)tetrahydro-2H-pyran-3,4,5-triyl triacetate (21)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), 1-allyl-2,3,4,6-tetra-O-acetyl-α-D-glucopyranoside[24] (74.5 mg, 0.2 mmol, 1.0 equiv) and 1,1,1-trifluoro-N-(naphthalen-1-ylmethyl)methanesulfonamide (S13) (57.9 mg, 0.2 mmol, 1.0 equiv) were reacted according to the general procedure. Purification by flash column chromatography (50 mL silica gel, 0%=>20% Acetone in hexanes) and preparative TLC (66% Et$_2$O in hexanes) provided pure product (+)-21 as a white solid. Run 1: (91.4 mg, 69.3% yield); Run 2: (93.5 mg, 70.9% yield); Run 3: (92.7 mg, 70.3% yield). Average: 70% yield±0.8%. $^1$H NMR (500 MHz, Chloroform-d) δ 8.17-8.14 (m, 1H), 7.90 (td, J=7.7, 7.2, 1.8 Hz, 2H), 7.61 (ddd, J=8.5, 6.8, 1.4 Hz, 1H), 7.55 (ddd, J=8.1, 6.8, 1.1 Hz, 1H), 7.52-7.48 (m, 2H), 5.68 (dt, J=14.3, 6.4 Hz, 1H), 5.48 (dd, J=15.8, 5.1 Hz, 1H), 5.40-4.60 (br s, 2H), 5.11 (dd, J=10.1, 9.1 Hz, 1H), 5.01-4.92 (m, 2H), 4.50 (s, 1H), 4.11 (dd, J=12.3, 5.1 Hz, 1H), 4.03-3.98 (m, 1H), 3.94-3.83 (m, 2H), 3.59 (s, 1H), 2.07 (s, 3H), 2.02 (s, 3H), 2.01 (s, 3H), 1.97 (s, 3H). $^{13}$C NMR (126 MHz, CDCl$_3$) δ 170.8, 170.2, 169.5, 169.5, 133.9, 131.6, 130.2, 130.0, 129.2, 128.8, 128.0, 127.9, 127.3, 126.6, 125.2, 122.8, 120.3 (q, J=323.6 Hz), 72.0, 70.5, 70.1, 69.6, 68.8, 62.3, 50.1, 49.3, 20.8, 20.8, 20.7, 20.7. $^{19}$F NMR (470 MHz, Chloroform-d) δ -75.25. HSQC and DEPT 135 please see supporting information. HRMS (ESI) m/z calculated for C$_{29}$H$_{32}$NO$_{11}$F$_3$SNa [M+Na]$^+$: 682.1546, found 682.1552. [α]$^{22}_D$=+65.3° (c=0.56, CHCl$_3$).

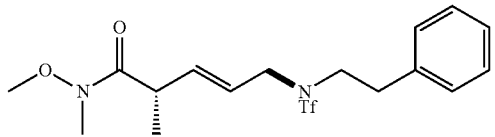

(22)

(+)-(S,E)-N-methoxy-N,2-dimethyl-5-((1,1,1-trifluoro-N-phenethylmethyl)sulfonamido)pent-3-enamide (22)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (S)—N-methoxy-N,2-dimethylpent-4-enamide[21] (31.44 mg, 0.2 mmol, 1.0 equiv) and 1,1,1-trifluoro-N-phenethylmethanesulfonamide (S10) (50.6 mg, 0.2 mmol, 1.0 equiv) were reacted according to the general procedure. Purification by flash column chromatography (column 1: 50 mL silica gel, 0%=>20% Acetone in hexanes; column 2: 50 mL silica gel, 100% CH$_2$Cl$_2$=>0.5% MeOH in CH$_2$Cl$_2$) provided pure product (+)-22 as a colorless oil. Run 1: (49.9 mg, 61.1% yield); Run 2: (50.8 mg, 62.2% yield); Run 3: (51.8 mg, 63.4% yield). Average: 62% yield±1.2%. $^1$H NMR (500 MHz, Chloroform-d) δ 7.33-7.29 (m, 2H), 7.26-7.22 (m, 1H), 7.17 (dd, J=8.1, 1.3 Hz, 2H), 5.85 (dd, J=15.5, 8.0, 1H), 5.50 (dt, J=15.3, 7.0, 1H), 3.91 (d, J=7.0 Hz, 2H), 3.69 (s, 3H), 3.67-3.61 (m, 1H), 3.53 (m, 2H), 3.18 (s, 3H), 2.90 (t, J=8.0 Hz, 2H), 1.27 (d, J=6.9 Hz, 3H). $^{13}$C NMR (126 MHz, CDCl$_3$) δ 174.8, 137.4, 137.4, 128.9, 128.9, 127.1, 124.4, 120.1 (q, J=323.3 Hz), 61.7, 50.8, 49.2, 38.8, 35.5, 32.4, 17.7. $^{19}$F NMR (470 MHz, CDCl$_3$) δ -76.40. HRMS (ESI) m/z calculated for C$_{17}$H$_{24}$N$_2$O$_4$F$_3$S [M+H]$^+$: 409.1409, found 409.1399. [α]$^{23}_D$=+5.4° (c=0.57, CHCl$_3$). Complete stereoretention was proven by chiral GC and HPLC analysis. Olefin starting material was determined by chiral GC analysis to be 94% ee. The allylic amine product 22 was determined by chiral HPLC analysis to be 94% ee. (CHIRALPAK AD-RH column, 0.3 mL/min, 50% EtOH in H$_2$O, λ=210 nm (4 nm). tR(major)=61.526 min, tR(major)=67.559 min.) See HPLC trace for product 22 and GC trace for the chiral olefin starting material.

(23)

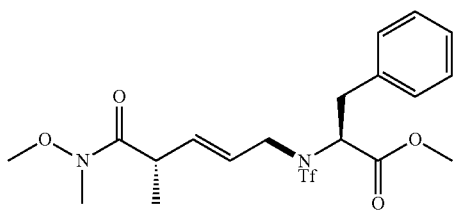

(−)-methyl N—((S,E)-5-(methoxy(methyl)amino)-4-methyl-5-oxopent-2-en-1-yl)-N-((trifluoromethyl)sulfonyl)-L-phenylalaninate (23)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (S)—N-methoxy-N,2-dimethylpent-4-enamide[21] (31.44 mg, 0.2 mmol, 1.0 equiv) and (+)-methyl ((trifluoromethyl)sulfonyl)-L-phenylalaninate (S21) (62.3 mg, 0.2 mmol, 1.0 equiv) were reacted according to the general procedure. Purification by flash column chromatography (column 1: 50 mL silica gel, 0%=>20% Acetone in hexanes; column 2: 50 mL silica gel, 100% CH$_2$Cl$_2$=>1% MeOH in CH$_2$Cl$_2$) provided pure product (−)-23 as a colorless oil. Run 1: (58.0 mg, 62.1% yield); Run 2: (57.6 mg, 61.7% yield); Run 3: (58.7 mg, 62.9% yield). Average: 62% yield±0.6%. $^1$H NMR (500 MHz, Chloroform-d) δ 7.33-7.28 (m, 2H), 7.26-7.21 (m, 3H), 5.86 (dd, J=15.6, 7.7 Hz, 1H), 5.59 (dt, J=16.0, 6.8 Hz, 1H), 4.71 (t, J=7.5 Hz, 1H), 4.08 (qd, J=16.0, 6.8 Hz, 2H), 3.69 (s, 3H), 3.69 (s, 3H), 3.63-3.57 (m, 1H), 3.42 (dd, J=14.2, 8.0 Hz, 1H), 3.17 (s, 3H), 3.03 (dd, J=14.2, 7.0 Hz, 1H), 1.24 (d, J=6.9 Hz, 3H). $^{13}$C NMR (125 MHz, CDCl$_3$) δ 174.8, 169.7, 136.1, 136.0, 129.3, 128.8, 127.4, 125.9, 119.8 (q, J=323.4 Hz), 62.4, 61.7, 52.7, 49.7, 38.6, 37.3, 32.5, 17.3. $^{19}$F NMR (470 MHz, CDCl$_3$) δ −75.93. HRMS (ESI) m/z calculated for C$_{19}$H$_{26}$N$_2$O$_6$F$_3$S [M+H]$^+$: 467.1481, found 467.1480. [α]$^{23}_D$=−26.4° (c=0.50, CHCl$_3$).

(24)

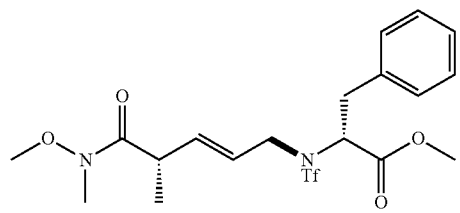

(+)-methyl N—((S,E)-5-(methoxy(methyl)amino)-4-methyl-5-oxopent-2-en-1-yl)-N-((trifluoromethyl)sulfonyl)-D-phenylalaninate (24)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (S)—N-methoxy-N,2-dimethylpent-4-enamide[21] (31.44 mg, 0.2 mmol) and (−)-methyl ((trifluoromethyl)sulfonyl)-D-phenylalaninate (S22) (62.3 mg, 0.2 mmol) were reacted according to the general procedure. Purification by flash column chromatography (column 1: 50 mL silica gel, 0%=>20% Acetone in hexanes; column 2: 50 mL silica gel, 100% CH$_2$Cl$_2$=>1% MeOH in CH$_2$Cl$_2$) provided pure product (+)-24 as a colorless oil. Run 1: (55.3 mg, 59.3% yield); Run 2: (56.4 mg, 60.4% yield); Run 3: (57.2 mg, 61.3% yield). Average: 60% yield±1.0%. $^1$H NMR (500 MHz, Chloroform-d) δ 7.33-7.28 (m, 2H), 7.26-7.20 (m, 3H), 5.85 (dd, J=15.5, 7.8, 1H), 5.58 (dt, J=15.3, 6.9, 1H), 4.72 (t, J=7.5 Hz, 1H), 4.09 (t, J=6.3 Hz, 2H), 3.71 (s, 3H), 3.69 (s, 3H), 3.58 (q, J=6.3, 5.4 Hz, 1H), 3.41 (dd, J=14.2, 7.8 Hz, 1H), 3.17 (s, 3H), 3.03 (dd, J=14.2, 7.2 Hz, 1H), 1.24 (d, J=6.9 Hz, 3H). $^{13}$C NMR (125 MHz, CDCl$_3$) δ 174.8, 169.8, 136.1, 136.0, 129.3, 128.8, 127.4, 126.1, 119.8 (q, J=323.7 Hz), 62.4, 61.7, 52.7, 49.7, 38.8, 37.1, 32.5, 17.5. $^{19}$F NMR (470 MHz, CDCl$_3$) δ −75.92. HRMS (ESI) m/z calculated for C$_{19}$H$_{26}$N$_2$O$_6$F$_3$S [M+H]$^+$: 467.1464, found 464.1460. [α]$^{23}_D$=+25.9° (c=0.59, CHCl$_3$).

(25)

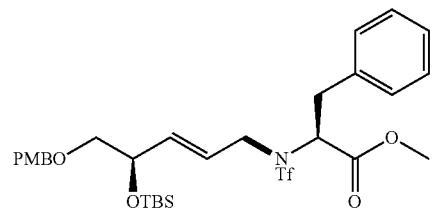

(−)-methyl N—((R,E)-4-((tert-butyldimethylsilyl)oxy)-5-((4-methoxybenzyl)oxy)pent-2-en-1-yl)-N-((trifluoromethyl)sulfonyl)-L-phenylalaninate (25)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (R)-tert-butyl((1-((4-methoxybenzyl)oxy)pent-4-en-2-yl)oxy)dimethylsilane[21] (67.3 mg, 0.2 mmol, 1.0 equiv) and (+)-methyl ((trifluoromethyl)sulfonyl)-L-phenylalaninate (S21) (62.3 mg, 0.2 mmol, 1.0 equiv) were reacted according to the general procedure. Purification by flash column chromatography (column 1: 50 mL silica gel, 0%=>20% Acetone in hexanes; column 2: 50 mL silica gel, 100% CH$_2$Cl$_2$=>2% MeOH in CH$_2$Cl$_2$) provided pure product (−)-25 as a colorless oil. Run 1: (96.7 mg, 74.9% yield); Run 2: (97.9 mg, 75.8% yield); Run 3: (95.6 mg, 74.0% yield). Average: 75% yield±0.9%. $^1$H NMR (500 MHz, Chloroform-d) δ 7.33 (dd, J=8.1, 6.5 Hz, 2H), 7.30-7.20 (m, 5H), 6.88 (d, J=8.6 Hz, 2H), 5.90-5.77 (m, 2H), 4.72 (t, J=7.5 Hz, 1H), 4.50 (br s, 2H), 4.38-4.32 (m, 1H), 4.14 (d, J=5.2 Hz, 2H), 3.82 (s, 3H), 3.70 (s, 3H), 3.47-3.34 (m, 3H), 3.04 (dd, J=14.0, 6.7 Hz, 1H), 0.93 (s, 9H), 0.09 (s, 3H), 0.07 (s, 3H). $^{13}$C NMR (126 MHz, CDCl$_3$) δ 169.7, 159.3, 136.8, 136.0, 130.4, 129.4, 129.3, 128.8, 127.3, 124.8, 119.7 (q, J=323.8 Hz), 113.8, 74.3, 73.2, 71.2, 62.1, 55.4, 52.7, 49.3, 37.4, 25.9, 18.3, −4.6, −4.7. $^{19}$F NMR (470 MHz, Chloroform-d) δ −75.93. HRMS (ESI) m/z calculated for C$_{30}$H$_{42}$NO$_7$F$_3$SSiNa [M+Na]$^+$: 668.2301, found 668.2304. [α]$^{23}_D$=−8.4° (c=1.02, CHCl$_3$).

(26)

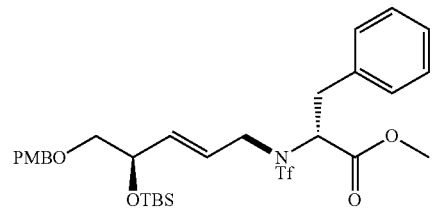

(+)-methyl N—((R,E)-4-((tert-butyldimethylsilyl)oxy)-5-((4-methoxybenzyl)oxy)pent-2-en-1-yl)-N-((trifluoromethyl)sulfonyl)-D-phenylalaninate (26)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (R)-tert-butyl((1-((4-methoxybenzyl)oxy)pent-4-en-2-yl)oxy)dimethylsilane[21] (67.3 mg, 0.2 mmol, 1.0 equiv) and (−)-methyl ((trifluoromethyl)sulfonyl)-D-phenylalaninate (S22) (62.3 mg, 0.2 mmol, 1.0 equiv) were reacted according to the general procedure. Purification by flash column chromatography (column 1: 50 mL silica gel, 0%=>20% Acetone in hexanes; column 2: 50 mL silica gel, 100% CH$_2$Cl$_2$=>2% MeOH in CH$_2$Cl$_2$) provided pure product (+)-26 as a colorless oil. Run 1: (101.3 mg, 78.4% yield); Run 2: (100.0 mg, 77.4% yield); Run 3: (101.5 mg, 78.6% yield). Average: 78% yield±0.6%. $^1$H NMR (500 MHz, Chloroform-d) δ 7.35 (dd, J=8.0, 6.4 Hz, 2H), 7.32-7.24 (m, 5H), 6.88 (d, J=8.6 Hz, 2H), 5.85 (s, 2H), 4.74 (t, J=7.6 Hz, 1H), 4.55-4.46 (m, 2H), 4.41-4.35 (m, 1H), 4.27-4.19 (m, 1H), 4.13 (s, 1H), 3.84 (s, 3H), 3.71 (s, 3H), 3.48-3.37 (m, 3H), 3.09 (dd, J=13.9, 6.6 Hz, 1H), 0.95 (s, 9H), 0.12 (s, 3H), 0.10 (s, 3H). 13C NMR (126 MHz, CDCl$_3$) δ 169.7, 159.3, 136.4, 135.9, 130.4, 129.3, 129.3, 128.8, 127.3, 125.3, 119.7 (q, J=324.0 Hz), 113.8, 74.4, 73.2, 71.4, 62.6, 55.4, 52.7, 49.4, 37.7, 25.9, 18.4, −4.6, −4.7. $^{19}$F NMR (470 MHz, Chloroform-d) δ −75.90. HRMS (ESI) m/z calculated for C$_{30}$H$_{42}$NO$_7$F$_3$SSiNa [M+Na]$^+$: 668.2301, found 668.2284. [α]$^{23}_D$=+31.3° (c=1.06, CHCl$_3$).

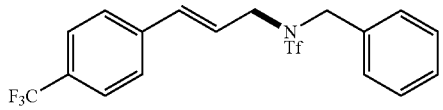

(27)

(E)-N-benzyl-1,1,1-trifluoro-N-(3-(4-(trifluoromethyl)phenyl)allyl)methanesulfonamide (27)

Pd(OAc)$_2$ (2.2 mg, 0.01 mmol, 0.05 equiv), (±)-MeO—SOX ligand (L-5) (3.4 mg, 0.01 mmol, 0.05 equiv), 2,5 DMBQ (2,5-dimethylbenzoquinone) (30 mg, 0.22 mmol, 1.1 equiv), 1-allyl-4-(trifluoromethyl)benzene (37.2 mg, 0.2 mmol) and 1,1,1-trifluoro-N-phenylmethanesulfonamide (S12) (47.8 mg, 0.2 mmol) were reacted according to the general procedure. Purification by flash column chromatography (50 mL silica gel, 10%=>30% CH$_2$Cl$_2$ in hexanes) provided pure product 27 as a colorless oil. Run 1: (67.9 mg, 80.1% yield); Run 2: (68.0 mg, 80.3% yield); Run 3: (67.6 mg, 79.8% yield). Average: 80% yield±0.3%. $^1$H NMR (500 MHz, Chloroform-d) δ 7.59 (d, J=8.1 Hz, 2H), 7.43-7.37 (m, 5H), 7.37-7.34 (m, 2H), 6.44 (d, J=15.8 Hz, 1H), 6.10 (dt, J=15.8, 7.0 Hz, 1H), 4.57 (br s, 2H), 4.07 (br s, 2H). $^{13}$C NMR (126 MHz, Chloroform-d) δ 139.2, 134.6, 134.1, 130.33 (q, J=32.4 Hz), 129.2, 128.8, 128.7, 126.9, 125.9 (d, J=260.2 Hz), 125.8 (q, J=3.8 Hz), 124.9, 120.2 (q, J=322.7 Hz), 51.6, 49.7. $^{19}$F NMR (470 MHz, Chloroform-d) δ −63.02, −76.20. HRMS (ESI) m/z calculated for C$_{18}$H$_{15}$NO$_2$F$_6$SNa [M+Na]$^+$: 446.0625, found 446.0649.

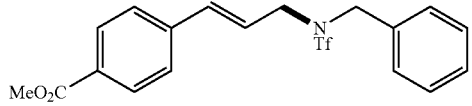

(28)

Methyl-(E)-4-(3-((N-benzyl-1,1,1-trifluoromethyl)sulfonamido)prop-1-en-1-yl) benzoate (28)

Pd(OAc)$_2$ (2.2 mg, 0.01 mmol, 0.05 equiv), (±)-MeO—SOX ligand (L-5) (3.4 mg, 0.01 mmol, 0.05 equiv), 2,5 DMBQ (2,5-dimethylbenzoquinone) (30 mg, 0.22 mmol, 1.1 equiv), Methyl 4-allylbenzoate (35.2 mg, 0.2 mmol, 1.0 equiv) and 1,1,1-trifluoro-N-phenylmethanesulfonamide (S12) (47.8 mg, 0.2 mmol, 1.0 equiv) were reacted according to the general procedure. Purification by flash column chromatography (column 1: 50 mL silica gel, 2.5%=>15% acetone in hexanes, column 2: 50 mL silica gel, 10%=>50% CH$_2$Cl$_2$ in hexanes) provided pure product 28 as a colorless oil. Run 1: (78.0 mg, 94.3% yield); Run 2: (78.6 mg, 95.1% yield); Run 3: (79.1 mg, 95.7% yield). Average: 95% yield±0.7%. $^1$H NMR (500 MHz, Chloroform-d) δ 8.00 (d, J=8.1 Hz, 2H), 7.43-7.31 (m, 7H), 6.43 (d, J=15.8 Hz, 1H), 6.11 (dt, J=15.8, 7.0 Hz, 1H), 4.56 (br s, 2H), 4.06 (br s, 2H), 3.93 (s, 3H). $^{13}$C NMR (126 MHz, Chloroform-d) δ 166.9, 140.2, 135.2, 134.2, 130.3, 130.1, 129.3, 128.9, 128.9, 126.7, 124.8, 120.33 (q, J=322.9 Hz), 52.4, 51.6, 49.9. $^{19}$F NMR (470 MHz, Chloroform-d) δ −76.19. HRMS (ESI) m/z calculated for C$_{19}$H$_{19}$NO$_4$F$_3$S [M+H]$^+$: 414.0987, found 414.0974.

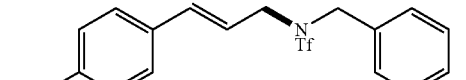

(29)

(E)-N-benzyl-1,1,1-trifluoro-N-(3-(4-formylphenyl)allyl)methanesulfonamide (29)

Pd(OAc)$_2$ (2.2 mg, 0.01 mmol, 0.05 equiv), (±)-MeO—SOX ligand (L-5) (3.4 mg, 0.01 mmol, 0.05 equiv), 2,5 DMBQ (2,5-dimethylbenzoquinone) (30 mg, 0.22 mmol, 1.1 equiv), 4-allylbenzaldehyde (29.2 mg, 0.2 mmol, 1.0 equiv) and 1,1,1-trifluoro-N-phenylmethanesulfonamide (S12) (47.8 mg, 0.2 mmol, 1.0 equiv) were reacted according to the general procedure. Purification by flash column chromatography (column 1: 50 mL silica gel, 2.5%=>15% acetone in hexanes, column 2: 50 mL silica gel, 10%=>50% CH$_2$Cl$_2$ in hexanes) provided pure product 29 as a colorless oil. Run 1: (62.0 mg, 80.9% yield); Run 2: (60.9 mg, 79.4% yield); Run 3: (61.5 mg, 80.2% yield). Average: 80% yield±0.8%. $^1$H NMR (500 MHz, Chloroform-d) δ 10.00 (s, 1H), 7.87-7.82 (m, 2H), 7.48-7.32 (m, 7H), 6.44 (d, J=15.8 Hz, 1H), 6.15 (dt, J=15.8, 7.0, 1H), 4.56 (br s, 2H), 4.07 (br s, 2H). 13C NMR (126 MHz, Chloroform-d) δ 191.8, 141.7, 136.2, 134.2, 130.4, 129.3, 129.0, 128.9, 127.4, 125.9, 120.3 (q, J=322.7 Hz), 51.8, 49.9. $^{19}$F NMR (470 MHz, Chloroform-d) δ −76.16. HRMS (ESI) m/z calculated for C$_{18}$H$_{17}$NO$_3$F$_3$S [M+H]$^+$: 383.0881, found 384.0880.

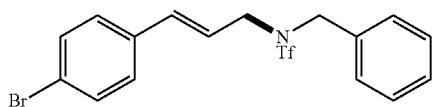

(30)

(E)-N-benzyl-N-(3-(4-bromophenyl)allyl)-1,1,1-trifluoromethanesulfonamide (30)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), 1-allyl-4-bromobenzene (39.4 mg, 0.2 mmol) and 1,1,1-trifluoro-N-phenylmethanesulfonamide (S12) (47.8 mg, 0.2 mmol) were reacted according to general procedure. Purification by flash column chromatography (50 mL silica gel, 2.5%=>15% acetone in hexanes) provided pure product 30 as a colorless oil. Run 1: (78.2 mg, 90.0% yield); Run 2: (79.0 mg, 91.0% yield); Run 3: (61.5 mg, 79.0% yield). Average: 90% yield±0.6%. $^1$H NMR (500 MHz, Chloroform-d) δ 7.46 (d, J=8.4 Hz, 2H), 7.43-7.35 (m, 3H), 7.35-7.31 (m, 2H), 7.17 (d, J=8.4 Hz, 2H), 6.34 (d, J=15.8 Hz, 1H), 6.00 (dt, J=15.8, 7.0 Hz, 1H), 4.55 (br s, 2H), 4.02 (br s, 2H). $^{13}$C NMR (126 MHz, Chloroform-d) δ 135.0, 134.7, 134.1, 132.0, 129.1, 128.8, 128.7, 128.2, 122.8, 122.5, 120.2 (q, J=322.8 Hz), 51.3, 49.8. $^{19}$F NMR (470 MHz, Chloroform-d) δ -76.23. HRMS (EI) m/z calculated for C$_{17}$H$_{15}$NO$_2$F$_3$SBr [M]$^+$: 432.9959, found 432.9951.

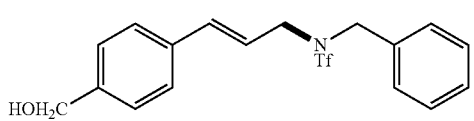

(31)

(E)-N-benzyl-1,1,1-trifluoro-N-(3-(4-(hydroxymethyl)phenyl)allyl)methanesulfon amide (31)

Pd(OAc)$_2$ (2.2 mg, 0.01 mmol, 0.05 equiv), (±)-MeO—SOX ligand (L-5) (3.4 mg, 0.01 mmol, 0.05 equiv), 2,5 DMBQ (2,5-dimethylbenzoquinone) (30 mg, 0.22 mmol, 1.1 equiv), (4-allylphenyl)methanol (29.6 mg, 0.2 mmol, 1.0 equiv) and 1,1,1-trifluoro-N-phenylmethanesulfonamide (S12) (47.8 mg, 0.2 mmol, 1.0 equiv) were reacted according to the general. Purification by flash column chromatography (column 1: 50 mL silica gel, 2.5%=>15% acetone in hexanes, column 2: 50 mL silica gel, 10%=>50% CH$_2$Cl$_2$ in hexanes) provided pure product 29 as a white solid. Run 1: (68.1 mg, 88.3% yield); Run 2: (67.5 mg, 87.6% yield); Run 3: (69.6 mg, 90.3% yield). Average: 89% yield±1.4%. $^1$H NMR (500 MHz, Chloroform-d) δ 7.44-7.30 (m, 9H), 6.41 (d, J=15.8 Hz, 1H), 6.02 (dt, J=15.7, 7.1 Hz, 1H), 4.70 (s, 2H), 4.56 (br s, 2H), 4.03 (br s, 2H), 1.77 (s, 1H). $^{13}$C NMR (126 MHz, Chloroform-d) δ 141.3, 136.0, 135.1, 134.2, 129.1, 128.7, 128.7, 127.4, 126.9, 121.8, 120.2 (q, J=322.7 Hz), 65.0, 51.1, 49.8. $^{19}$F NMR (470 MHz, Chloroform-d) δ -76.26. HRMS (EI) m/z calculated for C$_{18}$H$_{18}$NO$_3$F$_3$S [M]$^+$: 385.0960, found 385.0959.

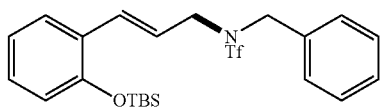

(32)

(E)-N-benzyl-N-(3-(2-((tert-butyldimethylsilyl)oxy)phenyl)allyl)-1,1,1-trifluoro methanesulfonamide (32)

Pd(OAc)$_2$ (2.2 mg, 0.01 mmol, 0.05 equiv), (±)-MeO—SOX ligand (L-5) (3.4 mg, 0.01 mmol, 0.05 equiv), 2,5 DMBQ (2,5-dimethylbenzoquinone) (30 mg, 0.22 mmol, 1.1 equiv), (2-allylphenoxy)(tert-butyl)dimethylsilane (49.7 mg, 0.2 mmol, 1.0 equiv) and 1,1,1-trifluoro-N-phenylmethanesulfonamide (S12) (47.8 mg, 0.2 mmol, 1.0 equiv) were reacted according to the general procedure. Purification by flash column chromatography (column 1: 50 mL silica gel, 10%=>30% CH$_2$Cl$_2$ in hexanes) provided pure product 32 as a colorless oil. Run 1: (79.0 mg, 81.3% yield); Run 2: (78.7 mg, 81.0% yield); Run 3: (79.3 mg, 81.7% yield). Average: 81% yield±0.4%. $^1$H NMR (500 MHz, Chloroform-d) δ 7.48-7.32 (m, 6H), 7.24-7.17 (m, 1H), 6.97 (td, J=7.5, 1.3 Hz, 1H), 6.90-6.79 (m, 2H), 6.04 (ddd, J=15.9, 7.9, 6.4 Hz, 1H), 4.57 (br s, 2H), 4.07 (br s, 2H), 1.02 (s, 9H), 0.25 (s, 6H). 13C NMR (126 MHz, Chloroform-d) δ 153.2, 134.3, 131.5, 129.5, 129.0, 128.7, 128.6, 127.0, 126.7, 121.6, 121.4, 120.2 (q, J=322.9 Hz), 119.7, 50.7, 50.0, 25.9, 18.5, 4.0. $^{19}$F NMR (470 MHz, Chloroform-d) δ -76.33. HRMS (EI) m/z calculated for C$_{23}$H$_{31}$NO$_3$F$_3$SSi [M+H]$^+$: 486.1746, found 486.1732.

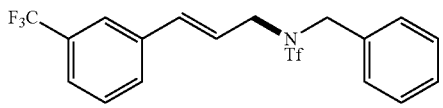

(33)

(E)-N-benzyl-1,1,1-trifluoro-N-(3-(3-(trifluoromethyl)phenyl)allyl)methanesulfonamide (33)

Pd(OAc)$_2$ (2.2 mg, 0.01 mmol, 0.05 equiv), (±)-MeO—SOX ligand (L-5) (3.4 mg, 0.01 mmol, 0.05 equiv), 2,5 DMBQ (2,5-dimethylbenzoquinone) (30 mg, 0.22 mmol, 1.1 equiv), 1-allyl-3-(trifluoromethyl)benzene (37.2 mg, 0.2 mmol, 1.0 equiv) and 1,1,1-trifluoro-N-phenylmethanesulfonamide (S12) (47.8 mg, 0.2 mmol, 1.0 equiv) were reacted according to the general procedure. Purification by flash column chromatography (column 1: 50 mL silica gel, 10%=>30% CH$_2$Cl$_2$ in hexanes) provided pure product 33 as a colorless oil. Run 1: (71.4 mg, 84.3% yield); Run 2: (72.5 mg, 85.7% yield); Run 3: (72.2 mg, 85.3% yield). Average: 85% yield±0.7%. $^1$H NMR (500 MHz, Chloroform-d) δ 7.54 (d, J=6.9 Hz, 1H), 7.52-7.45 (m, 3H), 7.43-7.33 (m, 5H), 6.43 (d, J=15.8 Hz, 1H), 6.06 (dt, J=15.7, 7.0 Hz, 1H), 4.56 (br s, 2H), 4.07 (br s, 2H). 13C NMR (126 MHz, Chloroform-d) δ 136.6, 134.5, 134.2, 131.3 (q, J=32.3 Hz), 129.8, 129.3, 129.2, 128.8, 128.8, 125.1 (q, J=3.8 Hz), 124.2, 124.1 (q, J=272.3 Hz), 123.5 (q, J=3.8 Hz), 120.2 (q, J=322.7 Hz), 51.7, 49.8. $^{19}$F NMR (470 MHz, Chloroform-d) δ -63.20, -76.18. HRMS (ESI) m/z calculated for C$_{18}$H$_{15}$NO$_2$F$_6$SNa [M+Na]$^+$: 446.0625, found 446.0618.

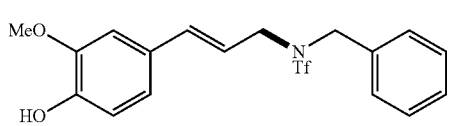

(34)

(E)-N-benzyl-1,1,1-trifluoro-N-(3-(4-hydroxy-3-methoxyphenyl)allyl)methanesulfon amide (34)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5-DMBQ (2,5-dimethylbenzoquinone) (30 mg, 0.22 mmol, 1.1 equiv), eugenol (32.8 mg, 0.2 mmol, 1.0 equiv) and 1,1,1-trifluoro-N-phenylmethanesulfonamide (S12) (47.8 mg, 0.2 mmol) were reacted according to the general procedure. Purification by flash column chromatography (column 1: 50 mL silica gel, 2.5%=>10% acetone in hexanes; column 2: 50 mL silica gel, 10%=>30% CH$_2$Cl$_2$ in hexanes) provided pure product 34 as a yellow oil. Run 1: (72.4 mg, 90.2% yield); Run 2: (71.7 mg, 89.3% yield); Run 3: (72.8 mg, 90.7% yield). Average: 90% yield±0.7%. $^1$H NMR (500 MHz, Chloroform-d) δ 7.44-7.31 (m, 5H), 6.89 (d, J=8.0 Hz, 1H), 6.86-6.81 (m, 2H), 6.33 (d, J=15.7 Hz, 1H), 5.85 (dt, J=15.7, 7.2 Hz, 1H), 5.74 (s, 1H), 4.56 (br s, 2H), 4.02 (br s, 2H), 3.92 (s, 3H). $^{13}$C NMR (126 MHz, Chloroform-d) δ 146.8, 146.3, 136.3, 134.3, 129.1, 128.7, 128.6, 128.3, 120.8, 120.2 (q, J=322.8 Hz), 119.3, 116.4, 114.6, 56.0, 51.0, 50.0. $^{19}$F NMR (470 MHz, Chloroform-d) δ −76.25. HRMS (ESI) m/z calculated for C$_{18}$H$_{19}$NO$_4$F$_3$S [M+H]$^+$: 402.0987, found 402.0998.

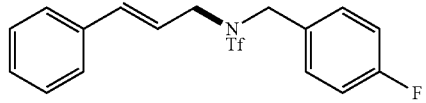

(36)

N-cinnamyl-1,1,1-trifluoro-N-(4-fluorobenzyl)methanesulfonamide (36)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5-DMBQ (2,5-dimethylbenzoquinone) (30 mg, 0.22 mmol, 1.1 equiv), allylbenzene (23.6 mg, 0.2 mmol, 1.0 equiv) and 1,1,1-trifluoro-N-(4-fluorobenzyl)methanesulfonamide (S24) (51.4 mg, 0.2 mmol, 1.0 equiv) were reacted according to the general procedure. Purification by flash column chromatography (50 mL silica gel, 10%=>20% CH$_2$Cl$_2$ in hexanes) provided pure product 36 as a colorless oil. Run 1: (66.1 mg, 88.5% yield); Run 2: (66.8 mg, 89.4% yield); Run 3: (66.6 mg, 89.2% yield). Average: 89% yield±0.5%. $^1$H NMR (500 MHz, Chloroform-d) δ 7.40-7.29 (m, 7H), 7.09 (t, J=8.6 Hz, 2H), 6.43 (d, J=15.8 Hz, 1H), 6.03 (dt, J=15.8, 7.1 Hz, 1H), 4.51 (br s, 2H), 4.03 (br s, 2H). $^{13}$C NMR (126 MHz, Chloroform-d) δ 162.9 (d, J=247.7 Hz), 136.5, 135.6, 130.6 (d, J=8.3 Hz), 130.0 (d, J=3.2 Hz), 128.9, 128.7, 126.7, 121.7, 120.2 (q, J=322.6 Hz), 116.1 (d, J=21.6 Hz), 50.3, 49.8. $^{19}$F NMR (470 MHz, Chloroform-d) δ −76.30, −113.45. HRMS (EI) m/z calculated for C$_{17}$H$_{15}$NO$_2$F$_4$SNa [M+Na]$^+$: 396.0657, found 396.0647.

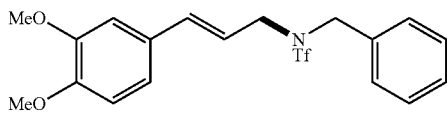

(35)

(E)-N-benzyl-N-(3-(3,4-dimethoxyphenyl)allyl)-1,1,1-trifluoromethanesulfonamide (35)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5-DMBQ (2,5-dimethylbenzoquinone) (30 mg, 0.22 mmol, 1.1 equiv), 4-allyl-1,2-dimethoxybenzene (35.6 mg, 0.2 mmol, 1.0 equiv) and 1,1,1-trifluoro-N-phenylmethanesulfonamide (S12) (47.8 mg, 0.2 mmol, 1.0 equiv) were reacted according to the general procedure. Purification by flash column chromatography (column 1: 50 mL silica gel, 2.5%=>10% acetone in hexanes; column 2: 50 mL silica gel, 30%=>60% CH$_2$Cl$_2$ in hexanes) provided pure product 35 as a colorless oil. Run 1: (71.9 mg, 86.5% yield); Run 2: (74.9 mg, 90.1% yield); Run 3: (73.9 mg, 89.0% yield). Average: 88% yield±1.8%. $^1$H NMR (500 MHz, Chloroform-d) δ 7.44-7.32 (m, 5H), 6.88 (dd, J=8.2, 2.0 Hz, 1H), 6.83 (d, J=8.4 Hz, 2H), 6.34 (d, J=15.7 Hz, 1H), 5.86 (dt, J=15.7, 7.1 Hz, 1H), 4.56 (br s, 2H), 4.03 (br s, 2H), 3.91 (s, 3H), 3.90 (s, 3H). $^{13}$C NMR (126 MHz, Chloroform-d) δ 149.6, 149.2, 136.1, 134.3, 129.0, 128.8, 128.7, 128.6, 120.2 (q, J=322.8 Hz), 120.1, 119.7, 111.2, 108.9, 56.0, 56.0, 51.0, 50.0. $^{19}$F NMR (470 MHz, Chloroform-d) δ −76.25. HRMS (EI) m/z calculated for C$_{19}$H$_{20}$NO$_4$F$_3$S [M]$^+$: 415.10651, found 415.10649.

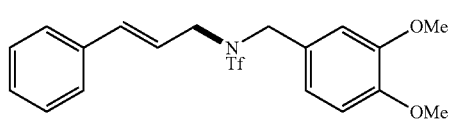

(37)

N-cinnamyl-N-(3,4-dimethoxybenzyl)-1,1,1-trifluoromethanesulfonamide (37)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5-DMBQ (2,5-dimethylbenzoquinone) (30 mg, 0.22 mmol, 1.1 equiv), allylbenzene (23.6 mg, 0.2 mmol, 1.0 equiv) and N-(3,4-dimethoxybenzyl)-1,1,1-trifluoromethanesulfonamide (S25) (59.9 mg, 0.2 mmol, 1.0 equiv) were reacted according to the general procedure. Purification by flash column chromatography (50 mL silica gel, 2.5%=>5% acetone in hexanes) provided pure product 37 as a colorless oil. Run 1: (71.6 mg, 86.2% yield); Run 2: (72.6 mg, 87.4% yield); Run 3: (73.3 mg, 88.2% yield). Average: 87% yield±1.0%. $^1$H NMR (500 MHz, Chloroform-d) δ 7.38-7.27 (m, 5H), 6.87 (app s, 1H), 6.85 (app s, 2H), 6.43 (d, J=15.7, 1H), 6.04 (dt, J=15.7, 7.1 Hz, 1H), 4.48 (br s, 2H), 4.10-3.93 (m, 2H), 3.89 (s, 3H), 3.86 (s, 3H). $^{13}$C NMR (126 MHz, Chloroform-d) δ 149.5, 149.3, 136.2, 135.7, 128.9, 128.6, 126.7, 126.4, 121.9, 121.5, 120.2 (q, J=322.7 Hz), 111.5, 111.1, 56.0, 56.0, 50.9, 49.5. $^{19}$F NMR (470 MHz, Chloroform-d) δ −76.30. HRMS (ESI) m/z calculated for C$_{19}$H$_{21}$NO$_4$F$_3$S [M+H]$^+$: 416.1143, found 416.1130.

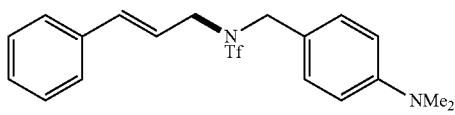

N-cinnamyl-N-(4-(dimethylamino)benzyl)-1,1,1-trifluoromethanesulfonamide (38)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allylbenzene (23.6 mg, 0.2 mmol, 1.0 equiv) and N-(4-(dimethylamino)benzyl)-1,1,1-trifluoromethanesulfonamide (S26) (56.5 mg, 0.2 mmol, 1.0 equiv) were reacted according to general procedure. Purification by flash column chromatography (50 mL silica gel, 2%=>4% Ethyl acetate in hexanes) provided pure product 38 as a white solid. Run 1: (68.0 mg, 85.3% yield); Run 2: (68.7 mg, 86.2% yield); Run 3: (67.5 mg, 84.7% yield). Average: 85% yield±0.8%. $^1$H NMR (500 MHz, Chloroform-d) δ 7.34 (app d, J=4.3 Hz, 4H), 7.32-7.27 (m, 1H), 7.20 (d, J=8.2 Hz, 2H), 6.73 (app s, 2H), 6.43 (d, J=15.8, 1H), 6.02 (dt, J=15.8, 7.0 Hz, 1H), 4.44 (br s, 2H), 4.00 (br s, 2H), 2.97 (s, 6H). $^{13}$C NMR (126 MHz, Chloroform-d) δ 150.7, 136.0, 135.9, 130.1, 128.8, 128.4, 126.7, 122.3, 121.1, 120.3 (q, J=322.8 Hz), 112.6, 50.8, 49.1, 40.6. $^{19}$F NMR (470 MHz, Chloroform-d) δ −76.42. HRMS (ESI) m/z calculated for C$_{19}$H$_{22}$N$_2$O$_2$F$_3$S [M+H]$^+$: 399.1354, found 399.1349.

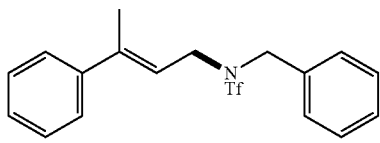

(E)-N-benzyl-1,1,1-trifluoro-N-(3-phenylbut-2-en-1-yl)methanesulfonamide (39)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), but-3-en-2-ylbenzene[25] (26.4 mg, 0.2 mmol) and 1,1,1-trifluoro-N-phenylmethanesulfonamide (S12) (47.8 mg, 0.2 mmol) were reacted according to the general procedure. Purification by flash column chromatography (column 1: 50 mL silica gel, 2.5%=>5% acetone in hexanes; column 2: 50 mL silica gel, 10%=>20% CH$_2$Cl$_2$ in hexanes) provided product 39 as a colorless oil (E:Z=15:1). E:Z selectivity was measured by $^1$H NMR: triplet of doublet at 5.65 ppm (E isomer) and triplet at 5.46 (Z isomer). Run 1: (51.9 mg, 70.2% yield, 15:1 E:Z, 66.2% yield for E); Run 2: (51.2 mg, 69.3% yield, 15:1 E:Z, 64.8% yield for E isomer); Run 3: (51.7 mg, 70.0% yield, 15:1 E:Z, 65.4% yield for E isomer). Average: 65% yield±0.7%. Further purification column chromatography was applied to afford pure E isomer (>20:1 E:Z). For E isomer: $^1$H NMR (500 MHz, Chloroform-d) δ 7.43-7.27 (m, 10H), 5.65 (td, J=7.1, 1.6 Hz, 1H), 4.57 (br s, 2H), 4.10 (br s, 2H), 1.82 (d, J=1.3 Hz, 3H). $^{13}$C NMR (126 MHz, CDCl$_3$) δ 142.5, 141.2, 134.4, 129.1, 128.7, 128.6, 128.5, 127.9, 125.9, 120.4, 120.3 (q, J=322.8 Hz), 51.5, 45.9, 16.2. $^{19}$F NMR (470 MHz, Chloroform-d) δ −76.22. HRMS (ESI) m/z calculated for C$_{18}$H$_{18}$NO$_2$F$_3$SNa [M+Na]$^+$: 392.0908, found 392.0910. E/Z configuration assignment is based on $^{13}$C NMR analogy to similar compounds (the chemical shifts of the methyl group attached to olefin, geranyl acetate (E, 16.4 ppm) and neryl acetate (Z, 23.5 ppm)) from previous literature[26,27]. In addition to $^{13}$C NMR, in NOESY-1D, no NOE to the olefin proton was observed when irradiating the methyl group; larger NOE observed between olefin proton and the aryl proton and the neighboring methylene, but not to the methyl group (tiny peak), which are consistent with an E isomer.

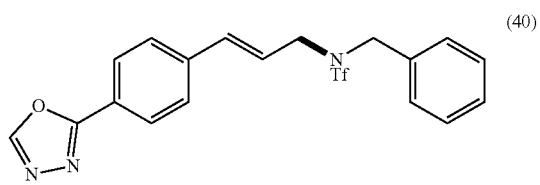

(E)-N-(3-(4-(1,3,4-oxadiazol-2-yl)phenyl)allyl)-N-benzyl-1,1,1-trifluoromethane sulfonamide (40)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), 2-(4-allylphenyl)-1,3,4-oxadiazole (S37) (37.2 mg, 0.2 mmol, 1.0 equiv) and 1,1,1-trifluoro-N-phenylmethanesulfonamide (S12) (47.8 mg, 0.2 mmol, 1.0 equiv) were reacted according to the general procedure. Purification by flash column chromatography (column 1: 50 mL silica gel, 2.5%=>15% acetone in hexanes) provided pure product 40 as white solid. Run 1: (53.7 mg, 63.4% yield); Run 2: (54.8 mg, 64.7% yield); Run 3: (54.6 mg, 64.5% yield). Average: 64% yield±0.7%. $^1$H NMR (500 MHz, Chloroform-d) δ 8.48 (s, 1H), 8.04 (d, J=8.3 Hz, 2H), 7.45-7.33 (m, 7H), 6.43 (d, J=15.8 Hz, 1H), 6.12 (dt, J=15.8, 7.0 Hz, 1H), 4.56 (br s, 2H), 4.07 (br s, 2H). 13C NMR (126 MHz, CDCl$_3$) δ 164.5, 152.8, 139.3, 134.7, 134.1, 129.1, 128.8, 128.7, 127.6, 127.3, 124.8, 123.2, 120.2 (q, J=322.8 Hz), 51.6, 49.8. $^{19}$F NMR (470 MHz, Chloroform-d) δ −76.17. HRMS (ESI) m/z calculated for C$_{19}$H$_{17}$N$_3$O$_3$F$_3$S [M+H]$^+$: 424.0943, found 424.0945.

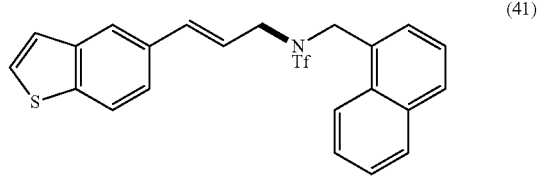

(E)-N-(3-(benzo[b]thiophen-5-yl)allyl)-1,1,1-trifluoro-N-(naphthalen-1-ylmethyl) methane Sulfonamide (41)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), 5-allylbenzo[b]thiophene (34.9 mg, 0.2 mmol, 1.0 equiv) and and 1,1,1-trifluoro-N-(naphthalen-1-ylmethyl)methanesulfonamide (S13) (57.9 mg, 0.2 mmol, 1.0 equiv) were reacted according to the general procedure. Purification by flash column chromatography (50 mL silica gel, 0%=>30% CH$_2$Cl$_2$ in hexanes) provided pure product (3) as a colorless oil. Run 1: (81.1 mg, 87.9% yield); Run 2: (83.0 mg, 89.9% yield); Run 3: (82.5 mg, 89.4% yield). Average: 89% yield±1.0%. $^1$H NMR (500 MHz, Chloroform-d) δ 8.17 (d, J=8.5 Hz, 1H), 7.90 (t, J=9.2 Hz, 2H), 7.80 (d, J=8.4 Hz, 1H), 7.62-7.50 (m, 5H), 7.47 (d, J=5.4 Hz, 1H), 7.31 (dd, J=5.5, 0.8 Hz, 1H), 7.19 (dd, J=8.4, 1.7 Hz, 1H), 6.29 (d, J=15.7 Hz, 1H), 6.00 (dt, J=15.7, 7.0 Hz, 1H), 5.11 (br s, 2H), 4.09 (br s, 2H). $^{13}$C NMR (126 MHz, CDCl$_3$) δ 140.0, 139.7, 136.2, 134.0, 132.1, 131.6, 129.7, 129.2, 129.1, 127.5, 127.3, 127.1, 126.3, 125.3, 124.0, 123.0, 122.7, 122.5, 122.1, 121.4, 120.4 (q, J=323.6 Hz), 50.2, 49.3. $^{19}$F NMR (470 MHz, CDCl$_3$) δ -75.4. HRMS (ESI) m/z calculated for C$_{23}$H$_{18}$NO$_2$F$_3$S$_2$ [M]$^+$: 461.0731, found 461.0721.

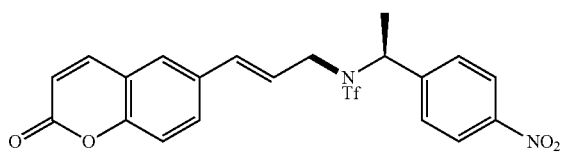

(42)

(+)-(S,E)-1,1,1-trifluoro-N-(1-(4-nitrophenyl)ethyl)-N-(3-(2-oxo-2H-chromen-6-yl)allyl)methanesulfonamide (42)

Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), 6-allyl-2H-chromen-2-one (S38) (37.2 mg, 0.2 mmol, 1.0 equiv) and (S)-1,1,1-trifluoro-N-(1-(4-nitrophenyl)ethyl)methanesulfonamide (S27) (59.6 mg, 0.2 mmol, 1.0 equiv) were reacted according to the general procedure. Purification by flash column chromatography (column 1: 50 mL silica gel, 2.5%=>30% acetone in hexanes provided pure product (+)-42 as a yellow oil. Run 1: (85.8 mg, 88.9% yield); Run 2: (87.3 mg, 90.5% yield); Run 3: (88.2 mg, 91.4% yield). Average: 88% yield±1.3%. $^1$H NMR (500 MHz, Chloroform-d) δ 8.19 (d, J=8.0 Hz, 2H), 7.70-7.53 (m, 3H), 7.34-7.11 (m, 3H), 6.41 (d, J=9.4 Hz, 1H), 6.23 (d, J=15.7 Hz, 1H), 5.78 (br s, 1H), 5.39 (q, J=7.1 Hz, 1H), 4.08-3.93 (m, 2H), 1.82 (d, J=7.0 Hz, 3H). $^{13}$C NMR (126 MHz, Chloroform-d) δ 160.4, 153.8, 147.9, 145.7, 143.1, 132.5, 132.2, 129.5, 129.0, 125.6, 125.2, 123.9, 119.9 (q, J=322.9 Hz), 119.0, 117.3, 56.9, 47.7, 17.1. $^{19}$F NMR (470 MHz, Chloroform-d) δ -76.13. HRMS (ESI) m/z calculated for C$_{21}$H$_{18}$N$_2$O$_6$F$_3$S [M+H]$^+$: 483.0838, found 483.0834. [α]$^{22}_D$=+8.2° (c=0.55, CHCl$_3$).

Natural Product Derivatizations

General procedure: No effort to exclude air or moisture is required. To a ½ dram vial was added a stir bar, Pd(OAc)$_2$ (4.4 mg, 0.02 mmol, 0.1 equiv), ligand (0.02 mmol, 0.1 equiv), 2,5 DMBQ (2,5-dimethylbenzoquinone) (30 mg, 0.22 mmol, 1.1 equiv), olefin (0.2 mmol, 1.0 equiv) and N-triflyl protected amine (0.2 mmol, 1.0 equiv). Toluene (0.2 mL, 1.0M) was added and the vial was capped and heated to 45° C. for 24-72 hours (monitored by TLC). The vial was allowed to cool to room temperature and diluted with acetone. The reaction mixture was filtered through a ½ inch pipette silica plug into a 20 mL vial with acetone. The mixture was concentrated under reduced pressure, diluted with 2 mL CDCl$_3$ and an internal standard (trifluorotoluene 14.6 mg, 0.1 mmol, 0.5 equiv) for crude $^1$HNMR analysis, the mixture was concentrated under reduced pressure and subjected to flash column chromatography for purification.

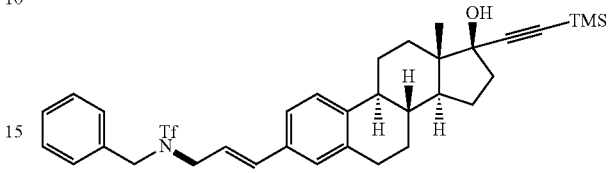

(43)

Ethinyl Estradiol Derivative (+)-43

The reaction was performed according to the general procedure using Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (−)-Allylated ethinyl estradiol derivative (S41) (78.5 mg, 0.2 mmol, 1.0 equiv) and 1,1,1-trifluoro-N-phenylmethanesulfonamide (S12) (47.8 mg, 0.2 mmol, 1.0 equiv) for 24 hours. The reaction mixture was purified by flash column chromatography (50 mL silica gel, 0%=>30% CH$_2$Cl$_2$ in hexanes) to provide pure desired product (+)-43 as a colorless oil. Run 1: (113.8 mg, 90.3% yield); Run 2: (113.2 mg, 89.9% yield); Run 3: (114.4 mg, 90.8% yield). Average: 90% yield±0.5%. $^1$H NMR (500 MHz, Chloroform-d) δ 7.39 (m, 3H), 7.35-7.32 (m, 2H), 7.31 (d, J=8.2 Hz, 1H), 7.14 (d, J=8.0 Hz, 1H), 7.06 (s, 1H), 6.37 (d, J=15.7 Hz, 1H), 5.99 (dt, J=15.1, 7.2 Hz, 1H), 4.54 (br s, 2H), 4.01 (br s, 2H), 2.88 (dd, J=8.8, 4.1 Hz, 2H), 2.45-2.37 (m, 1H), 2.32 (ddd, J=13.6, 9.5, 5.6 Hz, 1H), 2.30-2.21 (m, 1H), 2.01 (ddd, J=13.6, 11.9, 3.8 Hz, 1H), 1.91 (td, J=12.8, 3.8 Hz, 2H), 1.86-1.77 (m, 2H), 1.77-1.65 (ddt, J=18.9, 11.0, 5.4 Hz, 2H), 1.57-1.35 (m, 4H), 0.88 (s, 3H), 0.19 (s, 9H). $^{13}$C NMR (125 MHz, CDCl$_3$) δ 141.10, 137.28, 136.50, 134.24, 133.12, 129.10, 128.74, 128.65, 127.39, 125.98, 124.06, 120.79, 120.24 (q, 321.0 Hz), 109.54, 90.33, 80.22, 50.82, 49.85, 49.74, 47.33, 44.38, 39.32, 39.09, 33.02, 29.68, 27.32, 26.39, 23.01, 12.91, 0.20. $^{19}$F NMR (470 MHz, CDCl$_3$) δ -76.33. HRMS (ESI) m/z calculated for C$_{34}$H$_{41}$NO$_2$SiF$_3$S [M−H$_2$O+H]$^+$: 612.2579, found 612.2581. [α]$^{22}_D$=−9.5° (c=0.50, CHCl$_3$).

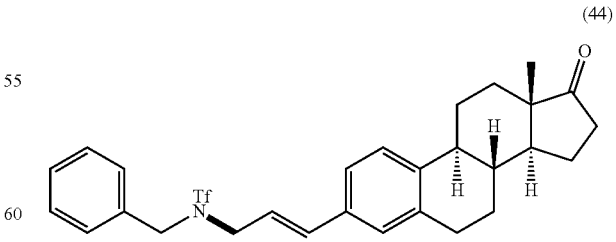

(44)

Estrone Derivative (+)-44

The reaction was performed according to the general procedure using Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), allylated estrone (S40) (58.9 mg, 0.2 mmol, 1.0 equiv) and 1,1,1-trifluoro-N-phenylmethanesulfonamide (S12) (47.8 mg, 0.2 mmol, 1.0 equiv) for 24 hours. The reaction mixture was purified by flash column chromatography (50 mL silica gel, 0%=>10% acetone in hexanes) to provide pure desired product (+)-44 as a colorless oil. Run 1: (79.9 mg, 75.2% yield); Run 2: (80.5 mg, 75.7% yield); Run 3: (79.1 mg, 74.3% yield). Average: 75% yield±0.7%. $^1$H NMR (500 MHz, Chloroform-d) δ 7.44-7.36 (m, 3H), 7.34 (d, J=6.7 Hz, 2H), 7.29 (d, J=8.1 Hz, 1H), 7.15 (d, J=8.1 Hz, 1H), 7.08 (s, 1H), 6.38 (d, J=15.7 Hz, 1H), 6.00 (dt, J=15.9, 7.0 Hz, 1H), 4.54 (br s, 2H), 4.01 (br s, 2H), 2.94 (dd, J=9.3, 4.2 Hz, 2H), 2.52 (dd, J=18.9, 8.7 Hz, 1H), 2.47-2.41 (m, 1H), 2.37-2.28 (m, 1H), 2.16 (dt, J=18.2, 8.8 Hz, 1H), 2.11-2.03 (m, 2H), 2.01-1.97 (m, 1H), 1.71-1.41 (m, 6H), 0.93 (s, 3H). $^{13}$C NMR (125 MHz, CDCl$_3$) δ 220.81, 140.51, 137.01, 136.30, 134.17, 133.31, 129.07, 128.69, 128.63, 127.35, 125.88, 124.16, 120.97, 120.19 (q, 322.8 Hz), 50.81, 50.58, 49.68, 48.06, 44.57, 38.20, 35.95, 31.68, 29.46, 26.52, 25.81, 21.70, 13.94. (470 MHz, CDCl$_3$) δ −73.31. HRMS (ESI) m/z calculated for C$_{29}$H$_{33}$NO$_3$F$_3$S [M+H]$^+$: 532.2133, found 532.2129. [α]$^{22}_D$=+46.7° (c=0.50, CHCl$_3$).

(45)

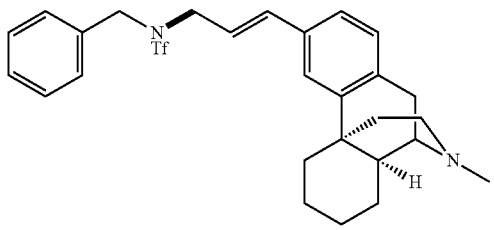

Dextramethorphan Derivative (−)-45

To a ½ dram vial equipped with a stir bar, (+)-Allylated dextromethorphan derivative (S42) (56.3 mg, 0.2 mmol, 1.0 equiv) and toluene (0.2 mL, 1.0 M) were added, followed by dichloroacetic acid (16.5 uL, 0.2 mmol, 1.0 equiv). The mixture was stirred at 45° C. for 20 min. Pd(OAc)$_2$ (4.4 mg, 0.02 mmol, 0.1 equiv), (±)-MeO—SOX ligand (L-5) (6.9 mg, 0.02 mmol, 0.1 equiv), 2,5-dimethylbenzoquinone (2,5 DMBQ) (30 mg, 0.22 mmol, 1.1 equiv) and 1,1,1-trifluoro-N-phenylmethanesulfonamide (S12) (47.8 mg, 0.2 mmol, 1.0 equiv) was added and the vial was capped and heated to 45° C. for 24 hours (monitored by TLC). The vial was allowed to cool to room temperature and diluted with ethyl acetate (1 mL). The reaction mixture was washed with sat. aq. K$_2$CO$_3$, layers are separated and the aqueous layer was extracted ethyl acetate (20 mL×3). The mixture was concentrated under reduced pressure, diluted with 2 mL CDCl$_3$ and an internal standard (trifluorotoluene 14.6 mg, 0.1 mmol, 0.5 equiv) was added for crude $^1$H NMR analysis. The mixture was then concentrated under reduced pressure and subjected to flash column chromatography (50 ml silica gel, 0%=>10% MeOH in CH$_2$Cl$_2$) to provide desired product (−)-45 as a colorless oil. Run 1: (95.7 mg, 92.3% yield); Run 2: (94.9 mg, 91.5% yield); Run 3: (94.8 mg, 91.4% yield). Average: 92% yield±0.5%. Without dichloroacetic acid following general procedure, 31.4 mg, 30% yield. $^1$H NMR (500 MHz, Chloroform-d) δ 7.42-7.32 (m, 5H), 7.17-7.13 (m, 2H), 7.10 (d, J=7.8 Hz, 1H), 6.38 (d, J=15.7 Hz, 1H), 5.94 (dt, J=15.7, 7.1 Hz, 1H), 4.55 (br s, 2H), 4.02 (br s, 2H), 3.05 (d, J=18.9 Hz, 1H), 3.00 (s, 1H), 2.79 (dd, J=18.9, 5.8 Hz, 1H), 2.68-2.60 (m, 1H), 2.51 (s, 3H), 2.41 (d, J=13.9 Hz, 1H), 2.18 (t, J=12.7 Hz, 1H), 2.02 (d, J=10.5 Hz, 1H), 1.91 (td, J=13.0, 4.7 Hz, 1H), 1.66 (d, J=12.5 Hz, 1H), 1.57 (d, J=13.4 Hz, 1H), 1.48-1.35 (m, 4H), 1.29-1.20 (m, 1H), 1.15-1.03 (m, 1H). $^{13}$C NMR (125 MHz, CDCl$_3$) δ 140.22, 137.19, 136.46, 134.28, 134.25, 129.03, 128.68, 128.62, 128.36, 124.26, 123.73, 120.89, 120.17 (q, 322.8 Hz), 58.46, 51.10, 49.90, 47.34, 44.24, 42.37, 41.15, 36.84, 36.11, 26.57, 26.34, 24.50, 22.07. $^{19}$F NMR (470 MHz, CDCl$_3$) δ −76.25. HRMS (ESI) m/z calculated for C$_{28}$H$_{34}$N$_2$O$_2$F$_3$S [M+H]$^+$: 519.2293, found 519.2301. [α]$^{23}_D$=+19.6° (c=0.50, CHCl$_3$).

(46)

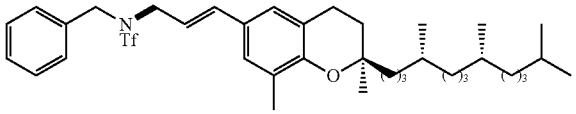

δ-Tocopherol Derivative (+)-46

The reaction was performed according to the general procedure using Pd(OAc)$_2$ (2.2 mg, 0.01 mmol, 0.05 equiv), (±)-MeO—SOX ligand (L-5) (3.4 mg, 0.01 mmol, 0.05 equiv), 2,5 DMBQ (2,5-dimethylbenzoquinone) (30 mg, 0.22 mmol, 1.1 equiv), (+)-Allylated-δ-Tocopherol derivative (S39) (85.3 mg, 0.2 mmol, 1.0 equiv) and 1,1,1-trifluoro-N-phenylmethanesulfonamide (S12) (47.8 mg, 0.2 mmol, 1.0 equiv) for 24 hours. The reaction mixture was purified by flash column chromatography (50 mL silica gel, 0%=>20% acetone in hexanes) to provide pure desired product (+)-46 as a colorless oil. Run 1: (116.8 mg, 88.0% yield); Run 2: (118.4 mg, 89.2% yield); Run 3: (117.0 mg, 88.1% yield). Average: 88% yield±0.7%. (MW=663.9). $^1$H NMR (500 MHz, Chloroform-d) δ 7.46-7.33 (m, 5H), 7.00 (d, J=2.2 Hz, 1H), 6.92 (d, J=2.2 Hz, 1H), 6.32 (d, J=15.6 Hz, 1H), 5.87 (dt, J=15.7, 7.2 Hz, 1H), 4.56 (br s, 2H), 4.01 (br s, 2H), 2.81-2.74 (m, 2H), 2.20 (s, 3H), 1.86 (dt, J=13.8, 6.7 Hz, 1H), 1.79 (dt, J=13.3, 6.5 Hz, 1H), 1.65-1.04 (m, 24H). 0.93-0.82 (m, 12H). $^{13}$C NMR (125 MHz, CDCl$_3$) δ 152.95, 136.86, 134.37, 129.06, 128.73, 128.56, 126.81, 126.75, 126.53, 125.70, 120.73, 120.25 (q, 322.7 Hz), 118.04, 76.67, 50.52, 49.86, 40.29, 39.52, 37.59, 37.57, 37.43, 32.95, 32.83, 31.28, 28.13, 24.96, 24.60, 24.41, 22.87, 22.78, 22.42, 21.12, 19.91, 19.81, 16.23. $^{19}$F NMR (470 MHz, CDCl$_3$) δ −76.37. HRMS (ESI) m/z calculated for C$_{38}$H$_{57}$NO$_3$F$_3$S [M+H]$^+$: 664.4011, found 664.3995. [α]$^{23}_D$=+17.2° (c=0.52, CHCl$_3$).

(47)

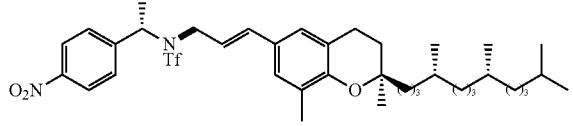

α-Methyl Benzylamine-Tocopherol Conjugate (+)-47

The reaction was performed according to the general procedure using Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (+)-Allylated-δ-Tocopherol derivative (S39) (85.3 mg, 0.2 mmol, 1.0 equiv) and (−)-(S)-1,1,1-trifluoro-N-(1-(4-nitrophenyl)ethyl)methanesulfonamide (S27) (59.6 mg, 0.2 mmol, 1.0 equiv) for 72 hours. The reaction mixture purified by flash column chromatography (column 1: 50 mL silica gel, 0%=>5% acetone in hexanes; column 2: 50 mL silica gel, 10%=>50% CH$_2$Cl$_2$ in hexanes) to provide pure desired product (+)-47 as a yellow oil. Run 1: (112.4 mg, 77.7% yield); Run 2: (112.9 mg, 78.1% yield); Run 3: (110.7 mg, 76.5% yield). Average: 77% yield±0.8%. With 5% Pd(OAc)$_2$ and (+)-MeO—SOX ligand (L-5): Run 1: (92.0 mg, 64.4% yield); Run 2: (93.1 mg, 64.4% yield); Average: 64% yield. $^1$H NMR (500 MHz, Chloroform-d) δ 8.20 (d, J=8.2 Hz, 2H), 7.61 (d, J=8.3 Hz, 2H), 6.73 (s, 1H), 6.61 (s, 1H), 6.08 (d, J=15.7 Hz, 1H), 5.54 (s, 1H), 5.41-5.32 (m, 1H), 4.09-3.85 (m, 2H), 2.75-2.58 (m, 2H), 2.11 (s, 3H), 1.81 (d, J=7.1, 3H), 1.79-1.70 (m, 2H), 1.62-1.02 (m, 24H), 0.92-0.81 (m, 12H). $^{13}$C NMR (125 MHz, CDCl$_3$) δ 152.84, 147.74, 146.07, 134.72, 128.97, 126.73, 126.43, 126.31, 125.41, 123.88, 120.65, 120.52, 120.07 (q, 321.3 Hz), 76.65, 56.68, 48.68, 40.35, 39.51, 37.58 37.55, 37.41, 32.93, 32.82, 31.20, 28.12, 24.94, 24.59, 24.32, 22.86, 22.77, 22.30, 21.10, 19.89, 19.79, 16.15. (one peak missing probably due to overlapping). $^{19}$F NMR (470 MHz, CDCl$_3$) δ −76.17. HRMS (ESI) m/z calculated for C$_{39}$H$_{57}$N$_2$O$_5$F$_3$S [M+H]$^+$: 722.3940, found 722.3926. [α]$^{23}_D$=+37.8° (c=0.5, CHCl$_3$). Complete stereoretention for this cross-coupling was determined by chiral HPLC analysis. (Product from reaction using (−)-(S)-1,1,1-trifluoro-N-(1-(4-nitrophenyl)ethyl)methanesulfonamide (S27) versus product from reaction using known mixture of 62% (−)-(S)-1,1,1-trifluoro-N-(1-(4-nitrophenyl)ethyl)methanesulfonamide (S27) and 38% (+)-(R)-1,1,1-trifluoro-N-(1-(4-nitrophenyl)ethyl)methanesulfonamide). Chiralpak AD-RH column, 0.5 mL/min, 10% EtOH in H$_2$O, λ=254 nm (4 nm). tR(major)=22.401 min.

(48)

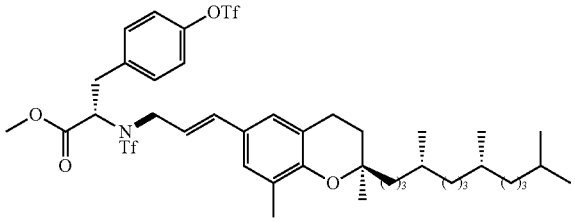

Tyrosine-Tocopherol Conjugate (−)-48

The reaction was performed according to the general procedure using Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (+)-Allylated-δ-Tocopherol derivative (S39) (85.3 mg, 0.2 mmol, 1.0 equiv) and methyl-(S)-2-((trifluoromethyl)sulfonamido)-3-(4-(((trifluoromethyl)sulfonyl) oxy) phenyl) propanoate (S29) (91.9 mg, 0.2 mmol, 1.0 equiv) for 72 hours. The reaction mixture was purified by flash column chromatography (column 1: 50 mL silica gel, 0%=>5% acetone in hexanes; column 2: 50 mL silica gel, 10%=>50% CH$_2$Cl$_2$ in hexanes) to provide pure desired product (−)-48 as a colorless oil. Run 1: (136.7 mg, 77.3% yield); Run 2: (135.4 mg, 76.6% yield); Run 3: (139.8 mg, 79.1% yield). Average: 78% yield±1.3%. $^1$H NMR (500 MHz, Chloroform-d) δ 7.30 (d, J=8.7 Hz, 2H), 7.18 (d, J=8.4 Hz, 2H), 6.98 (br s, 1H), 6.89 (br s, 1H), 6.43 (d, J=15.8 Hz, 1H), 5.88 (dt, J=15.8, 7.1 Hz, 1H), 4.71 (br s, 1H), 4.20 (br s, 2H), 3.69 (s, 3H), 3.50 (dd, J=14.3, 8.0 Hz, 1H), 3.09 (dd, J=14.2, 7.0 Hz, 1H), 2.79-2.68 (m, 2H), 2.16 (s, 3H), 1.83 (m, 1H), 1.76 (m, 1H), 1.62-0.99 (m, 24H), 0.88-0.82 (m, 12H). $^{13}$C NMR (125 MHz, CDCl$_3$) δ 169.42, 153.10, 148.80, 136.88, 135.83, 131.41, 126.86, 126.82, 126.54, 125.77, 121.60, 120.85, 119.92, 119.91 (q, J=323.1 Hz), 118.95 (q, 320.8 Hz), 76.75, 61.98, 52.96, 50.74, 40.51, 39.57, 37.65, 37.63, 37.60, 37.48, 36.61, 32.97, 32.87, 31.37, 28.14, 24.95, 24.61, 24.37, 22.83, 22.75, 22.46, 21.15, 19.89, 19.79, 16.14. $^{19}$F NMR (470 MHz, CDCl$_3$) δ −73.30, −75.91. HRMS (ESI) m/z calculated for C$_{42}$H$_{60}$NO$_8$F$_6$S$_2$ [M+H]$^+$: 884.3665, found 884.3657. [α]$^{22}_D$=−15.6° (c=0.50, CHCl$_3$).

(49)

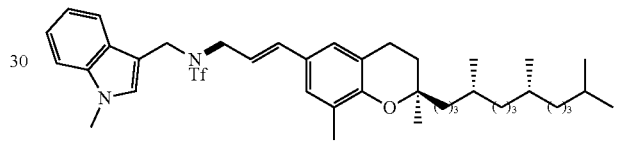

Gramine-Tocopherol Conjugate (+)-49

The reaction was performed according to the general procedure using Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (+)-Allylated-δ-Tocopherol derivative (S39) (85.3 mg, 0.2 mmol, 1.0 equiv) and 1,1,1-trifluoro-N-((1-methyl-1H-indol-3-yl) methyl) methanesulfonamide (S30) (58.2 mg, 0.2 mmol, 1.0 equiv) for 24 hours. The reaction mixture was purified by flash column chromatography (50 mL silica gel, 10%=>30% CH$_2$Cl$_2$ in hexanes) to provide pure desired product (+)-49 as a colorless oil. Run 1: (100.8 mg, 70.3% yield); Run 2: (101.6 mg, 70.9% yield); Run 3: (102.2 mg, 71.3% yield). Average: 71% yield±0.5%. $^1$H NMR (500 MHz, Chloroform-d) δ 7.76 (dd, J=8.0, 1.0 Hz, 1H), 7.35 (d, J=8.2 Hz, 1H), 7.30 (ddd, J=8.2, 6.8, 1.1 Hz, 1H), 7.20 (ddd, J=8.0, 6.8, 1.2 Hz, 1H), 7.11 (s, 1H), 6.97 (br s, 1H), 6.89 (br s, 1H), 6.33 (d, J=15.7 Hz, 1H), 5.89 (dt, J=15.7, 7.0 Hz, 1H), 4.76 (br s, 2H), 4.02 (br s, 2H), 3.80 (s, 3H), 2.84-2.71 (m, 2H), 2.20 (s, 3H), 1.86 (dt, J=13.8 Hz, 6.9 Hz, 1H), 1.79 (dt, J=13.3 Hz, 6.5 Hz, 1H), 1.64-1.01 (m, 24H), 0.98-0.81 (m, 12H). 13C NMR (125 MHz, CDCl$_3$) δ 152.80, 137.15, 135.95, 129.72, 127.44, 126.76, 126.73, 126.68, 125.56, 122.33, 120.71, 120.29 (q, 322.8 Hz), 120.00, 119.23, 118.92, 109.62, 107.53, 76.63, 49.36, 42.45, 40.29, 39.52, 37.58, 37.58, 37.42, 33.05, 32.94, 32.84, 31.29, 28.13, 24.96, 24.60, 24.41, 22.88, 22.78, 22.44, 21.13, 19.91, 19.81, 16.26. $^{19}$F NMR (470 MHz, CDCl$_3$) δ −76.40. HRMS (ESI) m/z calculated for C$_{41}$H$_{60}$N$_2$O$_3$F$_3$S [M+H]$^+$: 717.4277, found 717.4265. [α]$^{22}_D$=+7.3° (c=0.51, CHCl$_3$).

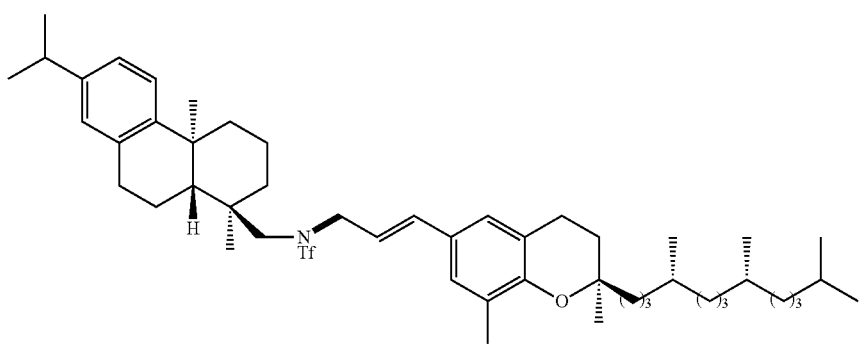

(50)

Leelamine-Tocopherol Conjugate (+)-50

The reaction was performed according to the general procedure using Pd(OAc)$_2$ (4.4 mg, 0.02 mmol, 0.1 equiv), (±)-MeO—SOX ligand (L-5) (6.9 mg, 0.02 mmol, 0.1 equiv), 2,5 DMBQ (2,5-dimethylbenzoquinone) (30 mg, 0.22 mmol, 1.1 equiv), (+)-Allylated-δ-Tocopherol derivative (S39) (85.3 mg, 0.2 mmol, 1.0 equiv) and (+)-N-triflyl protected dihydroabietylamine (S28) (83.5 mg, 0.2 mmol, 1.0 equiv) for 72 hours. The reaction mixture purified by flash column chromatography (50 mL silica gel, 0%=>10% acetone in hexanes) to provide pure desired product (+)-50 as a colorless oil. Run 1: (100.2 mg, 59.5% yield); Run 2: (98.9 mg, 58.7% yield); Run 3: (100.8 mg, 59.8% yield). Average: 59% yield±0.6%. (MW=842.2). $^1$H NMR (500 MHz, Chloroform-d) δ 7.17 (d, J=8.2 Hz, 1H), 7.01 (s, 2H), 6.92 (dd, J=9.2, 2.1 Hz, 2H), 6.46 (d, J=15.7 Hz, 1H), 5.93 (dt, J=15.1, 7.1 Hz, 1H), 4.33 (br s, 1H), 4.17 (br s, 1H), 3.46 (d, J=14.9 Hz, 1H), 3.24-3.16 (m, 1H), 2.97-2.88 (m, 2H), 2.84 (p, J=6.9 Hz, 1H), 2.80-2.73 (m, 2H), 2.35-2.29 (m, 1H), 2.19 (s, 3H), 1.91-1.66 (m, 6H), 1.64-1.03 (m, 40H), 0.93-0.83 (m, 12H). $^{13}$C NMR (125 MHz, CDCl$_3$) δ 152.95, 147.23, 145.86, 136.85, 134.44, 126.99, 126.82, 126.72, 126.49, 125.71, 124.03, 123.98, 120.73, 120.54 (q, J=325.3 Hz) 118.51, 76.66, 57.69, 53.61, 46.31, 40.28, 39.52, 39.34, 38.14, 37.79, 37.58, 37.55, 37.42, 33.60, 32.94, 32.83, 31.24, 29.88, 28.13, 25.78, 24.96, 24.59, 24.41, 24.15, 24.11, 22.88, 22.79, 22.40, 21.12, 19.91, 19.80, 19.42, 18.65, 16.25. (48 peaks in total, one peak missing probably due to overlapping). $^{19}$F NMR (470 MHz, CDCl$_3$) δ -74.31 HRMS (ESI) m/z calculated for C$_{51}$H$_{79}$NO$_3$F$_3$S [M+H]$^+$: 842.5733, found 842.5709. [α]$^{23}_D$=+42.7° (c=0.50, CHCl$_3$).

Synthetic Examples

Abamines

Scheme 2-7: 2-step synthesis of abamine core.

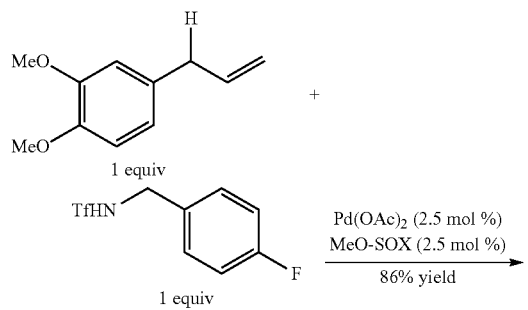

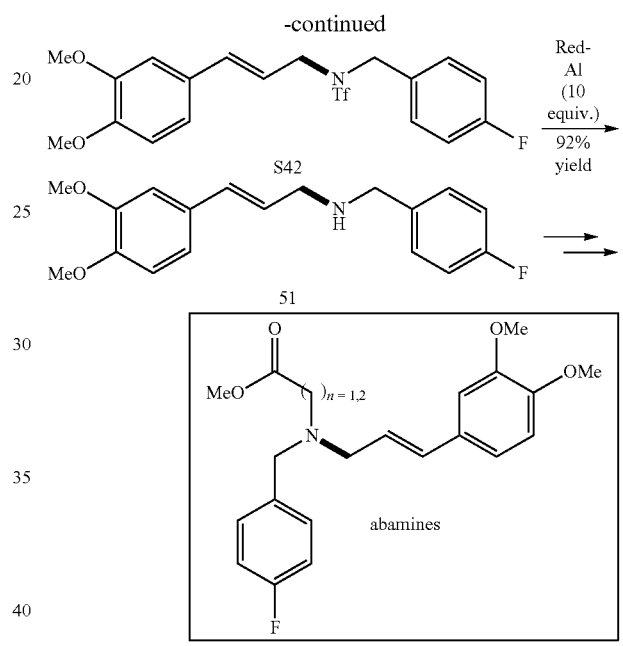

abamines (E)-N-(3-(3,4-dimethoxyphenyl)allyl)-1,1,1-trifluoro-N-(4-fluorobenzyl) methane Sulfonamide (S42)

To a 1 dram vial equipped with a stir bar was added Pd(OAc)$_2$ (5.6 mg, 0.025 mmol, 0.025 equiv), (±)-MeO—SOX ligand (L-5) (8.6 mg, 0.025 mmol, 0.025 equiv), 2,5 DMBQ (2,5-dimethylbenzoquinone) (150 mg, 1.1 mmol, 1.1 equiv), methyl eugenol (178.2 mg, 1.0 mmol, 1.0 equiv) and 1,1,1-trifluoro-N-(4-fluorobenzyl)methanesulfonamide (S24) (257.2 mg, 1.0 mmol, 1.0 equiv). Toluene (1.0 mL, 1.0 M) was added and the vial was capped and heated at 45° C. for 48 hours (monitored by TLC). The vial was allowed to cool to room temperature and diluted with acetone (1 mL). The reaction mixture was plug filtered a ½ inch pipette silica plug and concentrated under reduced pressure. The crude mixture was diluted with 10 mL CDCl$_3$ and an internal standard (trifluorotoluene 73 mg, 0.5 mmol, 0.5 equiv) was added for crude $^1$H NMR. The mixture was concentrated under reduced pressure and subjected to flash column chromatography (column 1: 100 mL silica gel 10%=>30% acetone in hexanes; column 2: 100 ml silica gel, 10%=>100% CH$_2$Cl$_2$ in hexanes) to provide pure desired product S42 as white solid. Run 1: (371.6 mg, 85.7% yield); Run 2: (374.1 mg, 86.3% yield Average: 86% yield. $^1$H NMR (500 MHz, Chloroform-d) δ 7.32 (dd, J=8.4, 5.2 Hz, 2H), 7.07 (t, J=8.4 Hz, 2H), 6.87 (dd, J=8.3, 1.8 Hz, 1H), 6.85-6.81 (m, 2H), 6.34 (d, J=15.7 Hz, 1H), 5.84 (dt, J=15.0, 7.1 Hz, 1H), 4.52 (br s, 2H), 4.01 (br s, 2H), 3.90 (s, 3H), 3.89 (s, 3H). $^{13}$C NMR (125 MHz, CDCl$_3$) δ 162.8 (d, J=247.6 Hz), 149.7, 149.2, 136.1, 130.5 (d, J=8.3 Hz), 130.2 (d, J=3.1 Hz), 128.6, 120.2 (q, J=322.8 Hz (124.0, 121.4, 118.9, 116.3)), 120.1, 119.5, 116.0 (d, J=21.6 Hz), 111.2, 108.9, 56.0, 55.9, 50.3, 50.0. $^{19}$F NMR (470 MHz, CDCl$_3$) δ −76.26, −113.55. HRMS (ESI) m/z calculated for C$_{19}$H$_{20}$NO$_4$F$_4$S [M+H]$^+$: 434.1049, found 434.1042.

(51)

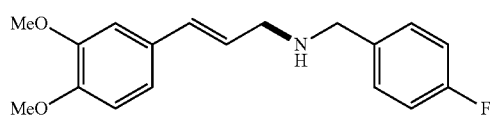

(E)-3-(3,4-dimethoxyphenyl)-N-(4-fluorobenzyl) prop-2-en-1-amine (51)

An oven-dried 25 ml flask was charged with a stir bar, S42 (216.7 mg, 0.5 mmol, 1.0 equiv) and toluene (10 ml, 0.05 M). The reaction was cooled to 0° C. and Red-Al (3.5 M in toluene) (sodium bis(2-methoxyethoxy)aluminumhydride) (5.0 mmol, 1.42 mL) was added dropwise and the reaction was allowed to warm up to room temperature and stirred at room temperature for 16 hours. Upon completion, the reaction was cooled to 0° C. and 5% NH$_4$Cl was added. Layers were separated and the aqueous layer was further extracted with CH$_2$Cl$_2$ (30 ml×3). The organic layers were combined and dried over Na$_2$SO$_4$, filtered, concentrated under vacuum and subjected to a flash column chromatography (100 mL silica gel, 0%=>10% MeOH in CH$_2$Cl$_2$) to provide pure product (51). Run 1: (138.9 mg, 92.2% yield); Run 2: (139.5 mg, 92.6% yield Average: 92% yield. $^1$H NMR (500 MHz, Chloroform-d) δ 7.31 (dd, J=8.4, 5.6 Hz, 2H), 7.01 (t, J=8.7 Hz, 2H), 6.93 (d, J=1.9 Hz, 1H), 6.89 (dd, J=8.2, 2.0 Hz, 1H), 6.80 (d, J=8.2 Hz, 1H), 6.47 (d, J=15.8 Hz, 1H), 6.17 (dt, J=15.6, 6.4 Hz, 1H), 3.88 (s, 3H), 3.86 (s, 3H), 3.80 (s, 2H), 3.41 (d, J=6.4 Hz, 2H), 2.18 (br s, 1H). Spectral data for S42 was consistent with previously literature report. (S, S)-Reboxetine:

Scheme 2-8: 5-step synthesis of (S,S)-Reboxetine

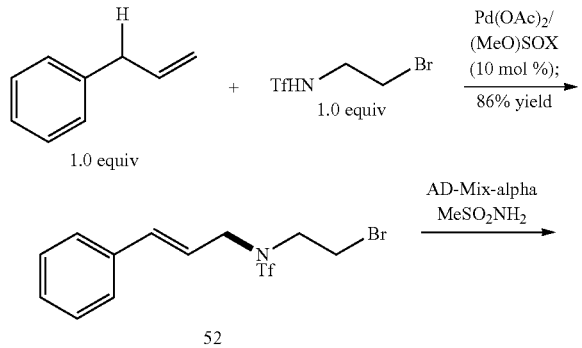

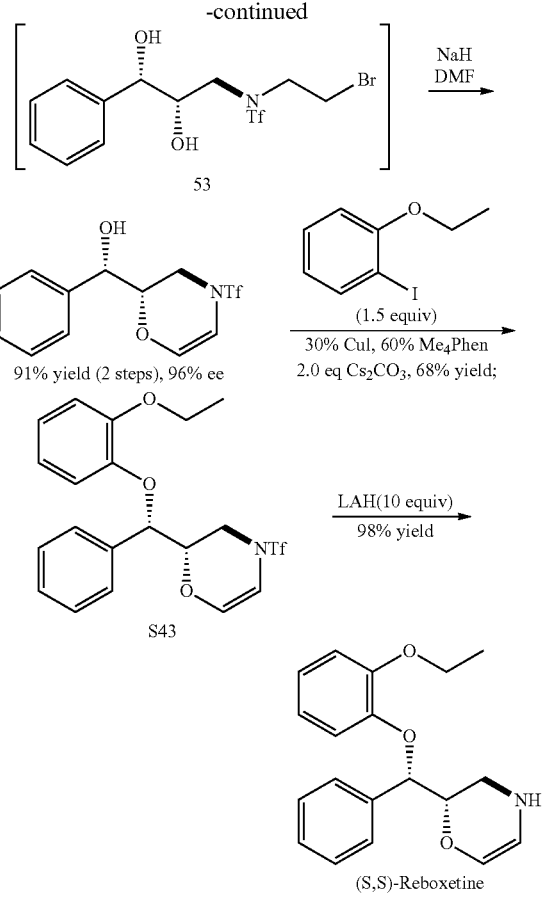

N-(2-bromoethyl)-N-cinnamyl-1,1,1-trifluoromethanesulfonamide (52)

To a 25 mL round bottom flask equipped with a stir bar was added Pd(OAc)$_2$ (67 mg, 0.3 mmol, 0.1 equiv), (±)-MeO—SOX ligand (L-5) (102.9 mg, 0.3 mmol, 0.1 equiv), 2,5 DMBQ (2,5-dimethylbenzoquinone) (450 mg, 33 mmol, 1.1 equiv), allylbenzene (354.5 mg, 3.0 mmol, 1.0 equiv) and N-(2-bromoethyl)-1,1,1-trifluoromethanesulfonamide (S18) (768.1 mg, 3.0 mmol, 1.0 equiv). Toluene (3.0 mL, 1.0 M) was added and the flask was capped and heated at 45° C. for 72 hours (monitored by TLC). The vial was allowed to cool to room temperature and diluted with acetone (10 mL). The reaction mixture was filtered through a ½ pipette silica plug into a 100 mL vial using acetone (30 mL), concentrated under reduced pressure and subjected to flash column chromatography (200 mL silica gel, 10%=>30% CH$_2$Cl$_2$ in hexanes) to provide pure desired product 52 as a colorless oil. Run 1: (962.1 mg, 86.2% yield); Run 2: (970.5 mg, 86.9% yield; Run 3: (951.1 mg, 85.2% yield) Average: 86% yield±0.9%. The reaction has also been run under smaller scale (0.3 mmol) using Pd(OAc)$_2$ (6.7 mg, 0.03 mmol, 0.1 equiv), ligand 5 (10.3 mg, 0.03 mmol, 0.1 equiv), 2,5-dimethylbenzoquinone (2,5 DMBQ) (45.0 mg, 3.3 mmol, 1.1 equiv), allylbenzene (35.5 mg, 0.3 mmol, 1.0 equiv) and N-(2-bromoethyl)-1,1,1-trifluoromethanesulfonamide (S18) (76.8 mg, 0.3 mmol, 1.0 equiv). Toluene (0.3 mL, 1.0 M), the reaction gave comparable result: 100.6 mg, 90% yield. $^1$H NMR (500 MHz, Chloroform-d) δ 7.42-7.39 (m, 2H), 7.39-7.35 (m, 2H), 7.34-7.30 (m, 1H), 6.66 (d, J=15.8 Hz, 1H), 6.13 (dt, J=15.6, 7.0 Hz, 1H), 4.23 (m, 2H), 3.75 (br s, 2H), 3.50 (t, J=7.3 Hz, 2H). $^{13}$C NMR (125 MHz, CDCl$_3$) δ 136.5, 135.4, 128.9, 128.8, 126.8, 121.9, 120.0 (q, J=323.0 Hz), 52.1, 49.0, 28.0. $^{19}$F NMR (470 MHz, CDCl$_3$) δ −76.16. HRMS (ESI) m/z calculated for C$_{12}$H$_{13}$NO$_2$F$_3$SBrNa [M+Na]$^+$: 393.9700, found 393.9708.

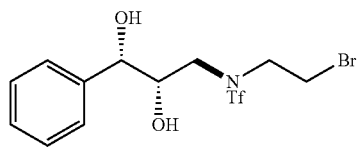

(53)

N-(2-bromoethyl)-N-((2S,3S)-2,3-dihydroxy-3-phenylpropyl)-1,1,1-trifluoromethane Sulfonamide (53)

To a 50 mL round bottom flask equipped with a stir bar was added 52 (744.4 mg, 2 mmol, 1 equiv), t-BuOH (10 mL) and H$_2$O (10 mL). The reaction was cooled to 0° C. AD-mix-α (2.8 g), additional (DHQ)$_2$PHAL (75 mg, 0.096 mmol, 0.048 equiv) and K$_2$OsO$_4$·H$_2$O (10.2 mg, 0.028 mmol, 0.014 equiv) were added. The reaction was stirred at 0° C. until all solid was fully dissolved and two clear phases were produced. MeSO$_2$NH$_2$ (190 mg, 2.0 mmol, 1.0 equiv) was added and the reaction was slowly warmed up to room temperature and stirred under room temperature for 24 hours (monitored by TLC). Upon completion, the reaction was cooled to 0° C. and Na$_2$SO$_3$ (3 g) was added. The reaction mixture was allowed to warm up to room temperature over 30 mins. The reaction was diluted with ethyl acetate (30 mL) and the layers were separated. The aqueous layer was extracted with ethyl acetate (20 mL×3). Combined organic layers were dried over anhydrous Na$_2$SO$_4$, filtered and concentrated under reduced pressure. The mixture was filtered through a short silica plug (ethyl acetate/hexane), concentrated under reduced pressure to provide the product 53 without further purification.

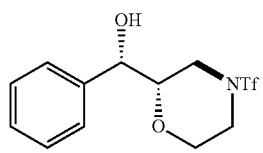

(54)

(S)-phenyl((S)-4-((trifluoromethyl)sulfonyl)morpholin-2-yl)methanol (54)

To an oven-dried 25 mL round bottom flask under N$_2$, 53 (carried through from last step) was added as a solution in DMF (14 mL 0.13M). The reaction was cooled to 0° C., then NaH (120 mg, 5 mmol, 2.5 equiv) was added in one portion. The reaction was stirred for 1 hour at 0° C. and slowly quenched with H$_2$O (20 ml) at 0° C. Ethyl acetate (20 mL) was added, and the layers were separated. The aqueous layer was extracted with ethyl acetate (20 mL×3). And the combined organic layers were dried over anhydrous MgSO$_4$, filtered and concentrated under reduced pressure. The crude mixture was purified via flash column chromatography (100 mL silica gel, 30% ethyl acetate in hexanes) to afford the desired product 54 as a white solid. Run 1: (588.8 mg, 90.5% yield); Run 2: (595.9 mg, 91.6% yield) Average: 91% yield over two steps. $^1$H NMR (500 MHz, Chloroform-d) δ 7.45-7.26 (m, 5H), 4.55 (d, J=6.7 Hz, 1H), 4.07 (dd, J=11.7, 3.3 Hz, 1H), 3.70 (br d, J=15.2 Hz, 1H), 3.68-3.62 (m, 2H), 3.45 (br d, J=12.8 Hz, 1H), 3.22 (br t, J=11.9 Hz, 1H), 3.01 (br t, J=11.7 Hz, 1H), 2.85 (br s, 1H). $^{13}$C NMR (125 MHz, CDCl$_3$) δ 138.5, 129.0, 126.8, 120.1 (q, J=323.6 Hz) 79.2, 74.7, 66.4, 47.4, 45.9. (one peak missing probably due to overlapping). HRMS (ESI) m/z calculated for C$_{12}$H$_{14}$NO$_4$F$_3$SNa [M+Na]$^+$: 348.0493, found 348.0494.

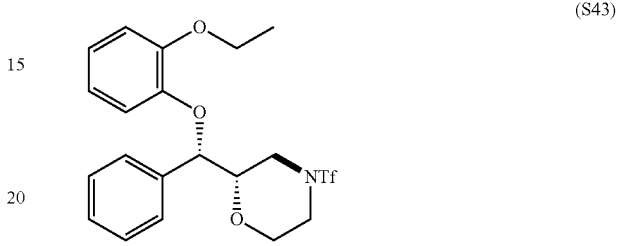

(S43)

(S)-2-((S)-(2-ethoxyphenoxy)(phenyl)methyl)morpholine (S43)

To an oven-dried sealed tube under N$_2$ equipped with a stir bar was added alcohol 54 (325.3 mg, 1.0 mmol, 1.0 equiv), CuI (57.1 mg, 0.30 mmol, 0.3 equiv), 4-methyl-1,10-phenanthroline (141.8 mg, 0.60 mmol, 0.6 equiv), Cs$_2$CO$_3$ (651.6 mg, 2.0 mmol, 2.0 equiv), 1-ethoxy-2-iodobenzene (372.1 mg, 1.5 mmol, 1.5 equiv) and toluene (0.5 mL, 2.0 M), the tube was sealed and heated to 100° C. for 96 hours. The reaction was cooled to room temperature, diluted with ethyl ether (5 mL), and filtered through a silica plug. The mixture was concentrated under reduced pressure and purified via flash column chromatography (100 mL silica gel, 0%=>15% ethyl acetate in hexanes) to afford desired product S43 as a colorless oil. Run 1: (278.3 mg, 62.5% yield; 101.2 mg recover alcohol 53, 31.1%); Run 2: (284.2 mg, 63.8% yield; 100.6 mg recover alcohol 53, 30.9%); Average: 63% yield. $^1$H NMR (500 MHz, Chloroform-d) δ 7.45-7.40 (m, 2H), 7.39-7.30 (m, 3H), 6.94-6.84 (m, 2H), 6.79-6.69 (m, 2H), 5.19 (d, J=4.4 Hz, 1H), 4.11-4.03 (m, 3H), 3.95 (ddd, J=10.6, 4.4, 2.6 Hz, 1H), 3.86 (d, J=12.9 Hz, 1H), 3.70 (dd, J=12.9, 1.5 Hz, 1H), 3.64 (td, J=11.8, 2.8 Hz, 1H), 3.32-3.18 (m, 2H), 1.47 (t, J=7.0 Hz, 3H). $^{13}$C NMR (125 MHz, CDCl$_3$) δ 150.3, 147.2, 136.9, 128.5, 128.4, 127.5, 123.2, 120.8, 120.1 (q, J=323.4), 119.3, 113.8, 81.9, 78.1, 66.7, 64.5, 47.6, 46.1, 15.0. $^{19}$F NMR (470 MHz, CDCl$_3$) δ −75.43. HRMS (ESI) m/z calculated for C$_{20}$H$_{22}$NO$_5$F$_3$SNa [M+Na]$^+$: 468.1068, found 468.1060.

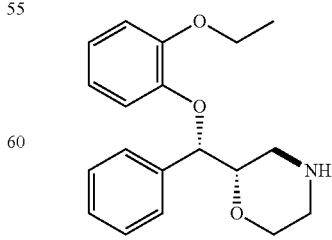

(Reboxetin)

(S, S)-Reboxetine

To an oven-dried 50 mL round bottom flask equipped with a stir bar and condenser under $N_2$ was added S43 (222.8 mg, 0.50 mmol, 0.5 equiv), dioxane (20 ml, 0.025 M) and LAH (190 mg, 5.0 mmol, 10 equiv). The reaction was heated up to 100° C. for 1 hour, then cooled to 0° C. Sequentially, 0.5 mL of $H_2O$, 0.5 mL of 15% NaOH solution and 1.5 mL of $H_2O$ were added dropwise, followed by anhydrous $MgSO_4$. The mixture was filtered through a celite plug, concentrated under reduced pressure and purified via flash column chromatography (100 mL silica gel, 0%=>7% MeOH in $CH_2Cl_2$) to afford the (S, S)-Reboxetine as a colorless oil. Run 1: (152.9 mg, 97.6% yield); Run 2: (154.5 mg, 98.5% yield). Average: 98% yield. $^1$H NMR (500 MHz, Methanol-d4) δ 7.40-7.36 (m, 2H), 7.28 (t, J=7.4 Hz, 2H), 7.25-7.21 (m, 1H), 6.86 (dd, J=7.9, 1.6 Hz, 1H), 6.82-6.76 (m, 2H), 6.67 (ddd, J=8.5, 7.3, 1.6 Hz, 1H), 5.16 (d, J=6.0 Hz, 1H), 4.09-3.96 (m, 2H), 3.94-3.86 (m, 2H), 3.60 (ddd, J=11.9, 7.9, 6.1 Hz, 1H), 2.74 (dd, J=6.3, 2.0 Hz, 2H), 2.67-2.54 (m, 2H), 1.39 (t, J=6.9 Hz, 3H). $^{13}$C NMR (125 MHz, $CD_3OD$) δ 150.9, 149.0, 139.0, 129.2, 129.1, 128.5, 123.2, 122.0, 118.6, 115.5, 83.7, 79.8, 68.2, 65.7, 47.6, 45.9, 15.4. $[\alpha]^{25}_D$=+15.73° (c=1.03, $CHCl_3$); HRMS (ESI) m/z calculated for $C_{19}H_{24}NO_3$ $[M+H]^+$: 314.1756, found 314.1755. These data are in agreement with that previously reported in the literature[29]. The enantiomeric excess was determined to be 96% by chiral HPLC analysis (Chiralpak IB3 column, 1.0 mL/min, 10% Isopropanol in hexanes (0.2% $Et_2NH$), λ=215 nm (4 nm). tR(minor)=9.868 min, tR(major)=11.308 min.

Preparation of (±)-MeO—SOX SOX Ligand (L5)/Pd(OAc)$_2$

To a 1-dram vial was added Pd(OAc)$_2$ (22.5 mg, 0.1 mmol, 1.0 equiv) and (±)-MeO—SOX ligand (L5) (34.3 mg, 0.1 mmol, 1.0 equiv) and 1.0 mL toluene (0.1 M), the mixture was stirred at 45° C. for 30 min. Upon completion, the complex was separated from the reaction mixture by filtration as a light green powder (51.8 mg, 93% yield). $^1$H NMR (500 MHz, Chloroform-d) δ 8.08-8.04 (m, 3H), 7.37 (d, J=2.6 Hz, 1H), 7.34 (dd, J=8.8, 2.6 Hz, 1H), 7.31-7.30 (m, 1H), 7.30-7.29 (m, 1H), 4.22 (d, J=8.5 Hz, 1H), 3.96 (s, 3H), 3.85 (d, J=8.5 Hz, 1H), 2.41 (s, 3H), 1.99 (s, 3H), 1.96 (s, 3H), 1.47 (s, 3H), 1.38 (s, 3H). $^{13}$C NMR (126 MHz, $CDCl_3$) δ 178.3, 177.7, 163.4, 161.1, 145.2, 139.3, 130.1, 128.8, 128.4, 127.2, 124.6, 118.6, 117.6, 81.9, 71.4, 56.4, 27.0, 26.8, 23.6, 22.3, 21.8. HRMS (FAB) m/z calculated for $C_{21}H_{24}NO_5SPd$ $[M-OAc]^+$: 508.04101, found 508.04103. The complex was not bench-stable and has to be stored in the glove box (stable for at least a month). Reactions using the complex gave comparable yields to reactions using (±)-MeO—SOX ligand ligand and Pd(OAc)$_2$.

X-Ray Crystal Structure Analysis of (±)-MeO—SOX Ligand (L5)/Pd(OAc)$_2$

Figure 3:
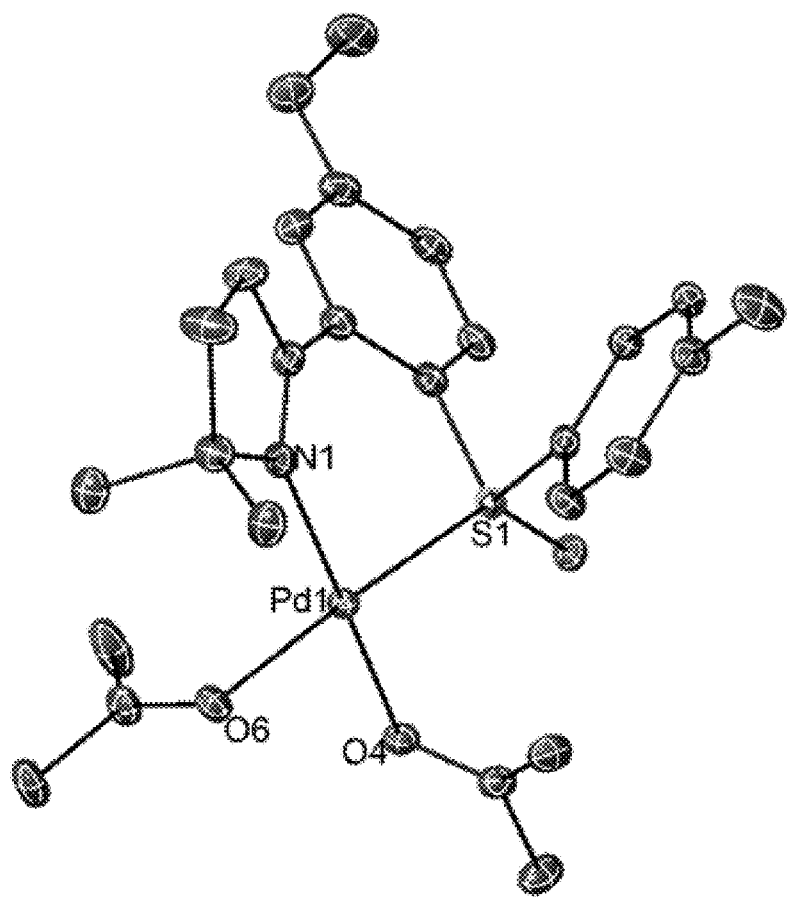
FIG. 3. X-ray crystal structure for (±)-MeO—SOX ligand (L5)/Pd(OAc)$_2$.

A suitable crystal was mounted with Paratone-N oil (Exxon) on a 0.3 mm cryo-loop (Hampton Research) and transferred to the goniometer of a Bruker D8 Venture/Photon 100 diffractometer. Data was collected at 100 K utilizing a cold stream of $N_2$(g). Microfocus sealed tube Mo $K_\alpha$ radiation (λ=0.71073 Å) was used. The structure was phased by intrinsic methods with SHELXT (v2014/4) (Sheldrick, G. M. Acta Cryst., 2015, A71, 3-8) and refined by full-matrix least-squares refinement on $F^2$ using SHELXL (v2014/7) (Sheldrick, G. M. Acta Cryst., 2015, C71, 3-8). The intensities were corrected for Lorentz and polarization effects by integration using SADABS (v2014/5). All non-hydrogen atoms were refined anisotropically. Methyl H atom positions, R—$CH_3$, were optimized by rotation about R—C bonds with idealized C—H, R—H and H—H distances. Remaining H atoms were included as riding idealized contributors. Methyl H atom U's were assigned as 1.5 times $U_{eq}$ of the carrier atom; remaining H atom U's were assigned as 1.2 times carrier $U_{eq}$. Details of the crystal data and a summary of the intensity data for (±)-MeO—SOX (L5)/Pd(OAc)$_2$ are listed in Table 2-2 (See FIG. 3).

TABLE 2-2

Crystal data and structure refinement for dd16dsa (±)-MeO-SOX ligand (L5)/Pd(OAc)$_2$.

| | |
|---|---|
| Identification code | dd16dsa ((±)-MeO-SOX ligand (L5)/Pd(OAc)$_2$) |
| Empirical formula | C23 H27 N 07 Pd S |
| Formula weight | 567.91 |
| Temperature | 100(2)K |
| Wavelength | 0.71073 Å |
| Crystal system | Tetragonal |
| Space group | I4$_1$/a |
| Unit cell dimensions | a = 27.5166(8) Å  a = 90°. |
| | b = 27.5166(8) Å  b = 90°. |
| | c = 12.2492(4) Å  g = 90°. |
| Volume | 9274.6(6) Å3 |
| Z | 16 |
| Density (calculated) | 1.627 Mg/m3 |
| Absorption coefficient | 0.935 mm−1 |
| F(000) | 4640 |
| Crystal size | 0.359 × 0.173 × 0.129 mm |
| Theta range for data collection | 2.346 to 28.287° |
| Index ranges | −36 <= h <= 36, |
| | −36 <= k <= 36, |
| | −16 <= l <= 15 |
| Reflections collected | 63453 |
| Independent reflections | 5757 [R(int) = 0.0375] |
| Completeness to theta = 25.242° | 99.9% |
| Absorption correction | Integration |
| Max. and min. transmission | 0.9481 and 0.8474 |
| Refinement method | Full-matrix least-squares on F2 |
| Data/restraints/parameters | 5757/6/307 |
| Goodness-of-fit on F2 | 1.115 |
| Final R indices [l > 2sigma(l)] | R1 = 0.0249, wR2 = 0.0597 |
| R indices (all data) | R1 = 0.0301, wR2 = 0.0620 |
| Extinction coefficient | n/a |
| Largest diff. peak and hole | 0.668 and −0.813 e.Å−3 |

CONCLUSIONS

Disclosed herein is a catalytic system for enantioselective Pd(II)-catalyzed allylic C—H oxidations, with an ArSOX ligand that enables both C—H cleavage and a stable chiral environment for asymmetric induction during functionalization. We have demonstrated the utility of this operationally simple method (open to air and moisture) to furnish isochromans with broad scope, in good yields and high enantioselectivities. It is also possible that the disclosed Pd(II)/ (ArSOX) composition will be useful in other types of allylic C—H functionalizations.

The ability of C—H functionalizations to serve as cross-coupling methods that simultaneously introduce new functionality while joining two complex fragments has been underexplored. We have developed a (±)-MeO—SOX ligand/Pd(OAc)$_2$-catalyzed intermolecular allylic C—H amination that cross couples complex α-olefins (1 equiv.) with complex alkyl and aryl amines (1 equiv.) to furnish stereochemically defined linear E-allylic amines with excellent regio- and stereoselectivity. The emergence of such reactive and selective methods that operate using only one equivalent of both the hydrocarbon and functionalization reagent enable C—H functionalization methods to emerge as powerful methods for fragment coupling.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

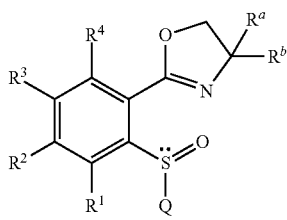

(I)

wherein
- $R^a$ is H, alkyl, heteroalkyl, cycloalkyl, heterocycle, aryl, or heteroaryl;
- $R^b$ is alkyl, heteroalkyl, cycloalkyl, heterocycle, aryl, or heteroaryl;
- Q is alkyl, heteroalkyl, cycloalkyl, heterocycle, heteroaryl, phenanthryl, 2-naphthyl, 1-naphthyl provided that $R^1$, $R^2$, $R^3$, or $R^4$ is not H, or Q is the moiety Q1:

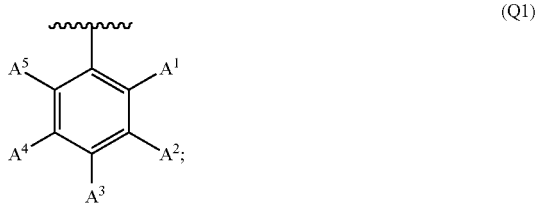

(Q1)

- $R^1$, $R^2$, $R^3$, $R^4$, $A^1$, $A^2$, $A^4$, and $A^5$ are each independently H, halo, alkyl, heteroalkyl, trifluoromethyl, trifluoromethoxy, $OR^x$, $N(R^x)_2$, nitro, cycloalkyl, aryl, or heteroaryl;
- $A^3$ is H, halo, $(C_3\text{-}C_8)$alkyl, a heteroalkyl, a trifluoromethyl, trifluoromethoxy, $OR^x$, $N(R^x)_2$, nitro, cycloalkyl, aryl, or heteroaryl; and
- each $R^x$ is independently H, $(C_1\text{-}C_8)$alkyl, or benzyl; wherein at least one of $R^a$ and $R^b$ is cycloalkyl, heterocycle, aryl, or heteroaryl.

2. The compound of claim 1 wherein the sulfoxide moiety is in the (S)-configuration and the $R^a$—C—$R^b$ moiety is in the (S)-configuration or in the (R)-configuration.

3. The compound of claim 1 wherein the sulfoxide moiety is in the (R)-configuration and the $R^a$—C—$R^b$ moiety is in the (S)-configuration, or in the (R)-configuration.

4. The compound of claim 1 wherein:
- $R^a$ is H, $(C_1\text{-}C_8)$alkyl, heteroalkyl, $(C_3\text{-}C_8)$cycloalkyl, or phenyl, wherein phenyl is optionally substituted with 1-5 substituents J;
- $R^b$ is $(C_1\text{-}C_8)$alkyl, heteroalkyl, $(C_3\text{-}C_8)$cycloalkyl, or phenyl, wherein phenyl is optionally substituted with 1-5 substituents J;
- Q is $(C_1\text{-}C_8)$alkyl, heteroalkyl, $(C_3\text{-}C_8)$cycloalkyl, or Q1;
- $R^1$, $R^2$, $R^3$, $R^4$, $A^1$, $A^2$, $A^4$ and $A^5$ are each independently H, halo, $(C_1\text{-}C_8)$alkyl, trifluoromethyl, trifluoromethoxy, $OR^x$, $N(R^x)_2$, nitro, $(C_3\text{-}C_8)$cycloalkyl, or phenyl, wherein phenyl is optionally substituted with 1-5 substituents J;
- $A^3$ is H, halo, $(C_3\text{-}C_8)$alkyl, trifluoromethyl, trifluoromethoxy, $OR^x$, $N(R^x)_2$, nitro, $(C_3\text{-}C_8)$cycloalkyl, or phenyl, wherein phenyl is optionally substituted with 1-5 substituents J; and
- each J is independently H, halo, $(C_1\text{-}C_8)$alkyl, trifluoromethyl, trifluoromethoxy, $OR^x$, $N(R^x)_2$, nitro, or $(C_3\text{-}C_8)$cycloalkyl.

5. The compound of claim 4 wherein:
- $R^a$ is H, methyl, ethyl, n-propyl, 2-propyl, cyclopropyl, n-butyl, tert-butyl, iso-butyl, cyclopentyl, cyclohexyl, phenyl, p-tolyl, 4-methoxyphenyl, 4-trifluoromethylphenyl, or 4-trifluoromethoxyphenyl; and
- $R^b$ is methyl, ethyl, n-propyl, 2-propyl, cyclopropyl, n-butyl, tert-butyl, iso-butyl, cyclopentyl, cyclohexyl, phenyl, p-tolyl, 4-methoxyphenyl, 4-trifluoromethylphenyl, 4-trifluoromethoxyphenyl, 4-tert-butylphenyl, 4-tert-butoxylphenyl, 3,4,5-trimethoxylphenyl, or 3,5-di-tert-butyl-4-methoxyphenyl.

6. The compound of claim 4 wherein Q is isopropyl, cyclohexyl, 4-methylcyclohexyl, phenyl, 4-bromophenyl, 4-methoxyphenyl, 4-trifluoromethylphenyl, 4-trifluoromethoxyphenyl, 4-tert-butylphenyl, 4-tert-butoxylphenyl, 3,5-dimethylphenyl, 3,5-di-tert-butyl-4-methoxyphenyl, or 9-phenanthryl.

7. The compound of claim 4 wherein $R^1$, $R^2$, $R^3$, $R^4$, $A^1$, $A^2$, $A^4$ and $A^5$ are each independently fluoro, chloro, bromo, methyl, ethyl, 2-propyl, tert-butyl, cyclopropyl, cyclopentyl, cyclohexyl, trifluoromethoxy, nitro, trifluoromethyl, pentafluoroethyl, $OR^x$, or $N(R^x)_2$;
- $A^3$ is fluoro, chloro, bromo, ethyl, 2-propyl, tert-butyl, cyclopropyl, cyclopentyl, cyclohexyl, trifluoromethoxy, nitro, trifluoromethyl, pentafluoroethyl, $OR^x$, or $N(R^x)_2$; and
- each $R^x$ is independently H, methyl, ethyl, n-propyl, iso-propyl, cyclopropyl, n-butyl, sec-butyl, tert-butyl, or benzyl.

8. The compound of claim 1 wherein the compound of Formula I is a compound of Formula II:

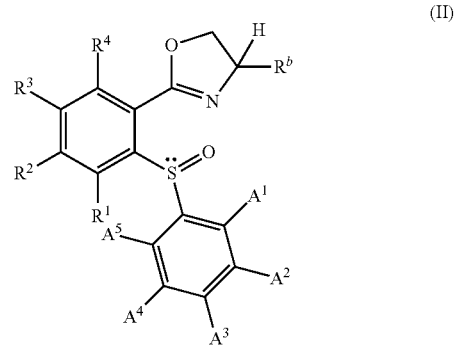

(II)

wherein

R$^b$ is (C$_3$-C$_8$)cycloalkyl, or phenyl, wherein phenyl is optionally substituted with 1-5 substituents J;

R$^1$, R$^2$, R$^3$, R$^4$, A$^1$, A$^2$, A$^4$ and A$^5$ are each independently H, halo, (C$_1$-C$_8$)alkyl, trifluoromethyl, trifluoromethoxy, OR$^x$, N(R$^x$)$_2$, nitro, (C$_3$-C$_8$)cycloalkyl, or phenyl, wherein phenyl is optionally substituted with 1-5 substituents J;

A$^3$ is H, halo, (C$_3$-C$_8$)alkyl, trifluoromethyl, trifluoromethoxy, OR$^x$, N(R$^x$)$_2$, nitro, (C$_3$-C$_8$)cycloalkyl, or phenyl, wherein phenyl is optionally substituted with 1-5 substituents J;

each J is independently H, halo, (C$_1$-C$_8$)alkyl, trifluoromethyl, trifluoromethoxy, OR$^x$, N(R$^x$)$_2$, nitro, or (C$_3$-C$_8$)cycloalkyl; and the H—C—R$^b$ moiety is in the (S)-configuration and the sulfoxide moiety is in the (R)-configuration, or the H—C—R$^b$ moiety is in the (R)-configuration and the sulfoxide moiety is in the (S)-configuration.

9. The compound of claim 8 wherein the compound of Formula II is a compound of Formula III:

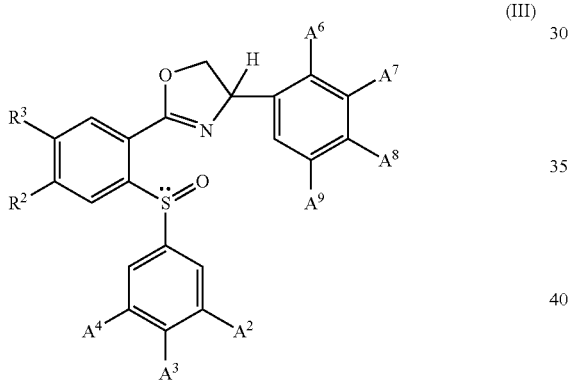

(III)

wherein

R$^2$, R$^3$, A$^2$, A$^4$, A$^6$, A$^7$, A$^8$, and A$^9$ are each independently H, halo, (C$_1$-C$_8$)alkyl, trifluoromethyl, trifluoromethoxy, OR$^x$, N(R$^x$)$_2$, nitro, (C$_3$-C$_8$)cycloalkyl, or phenyl, wherein phenyl is optionally substituted with 1-5 substituents J;

A$^3$ is H, halo, (C$_3$-C$_8$)alkyl, trifluoromethyl, OR$^x$, trifluoromethoxy, N(R$^x$)$_2$, nitro, (C$_3$-C$_8$)cycloalkyl, or phenyl, wherein phenyl is optionally substituted with 1-5 substituents J;

each J is independently H, halo, (C$_1$-C$_8$)alkyl, trifluoromethyl, OR$^x$, trifluoromethoxy, N(R$^x$)$_2$, nitro, or (C$_3$-C$_8$)cycloalkyl; and the dihydrooxazole moiety is in the (S)-configuration at position-4 and the sulfoxide moiety is in the (R)-configuration, or the dihydrooxazole moiety is in the (R)-configuration at position-4 and the sulfoxide moiety is in the (S)-configuration.

10. The compound of claim 1 wherein the compound is a compound of Formula IIA:

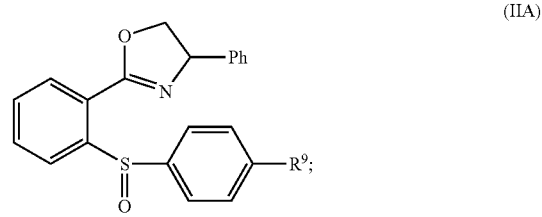

(IIA)

wherein R$^9$ is methoxy, t-butyl, or trifluoromethoxy.

11. The compound:

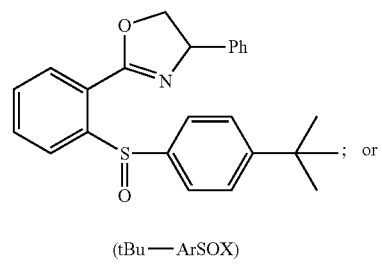

(tBu—ArSOX)

; or

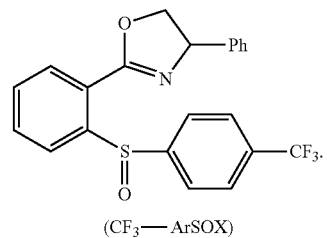

(CF$_3$—ArSOX)

12. A compound of Formula IB:

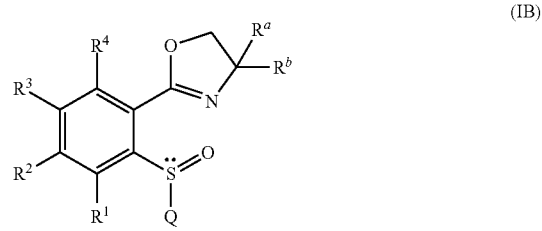

(IB)

wherein

R$^a$ is alkyl, heteroalkyl, cycloalkyl, heterocycle, aryl, or heteroaryl;

R$^b$ is alkyl, heteroalkyl, cycloalkyl, heterocycle, aryl, or heteroaryl;

Q is alkyl, heteroalkyl, cycloalkyl, heterocycle, heteroaryl, phenanthryl, 2-naphthyl, 1-naphthyl provided that R$^1$, R$^2$, R$^3$, or R$^4$ is not H, or Q is the moiety Q1:

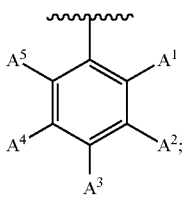
(Q1)

$R^1$, $R^2$, $R^3$, $R^4$, $A^1$, $A^2$, $A^4$, and $A^5$ are each independently H, halo, alkyl, heteroalkyl, trifluoromethyl, trifluoromethoxy, $OR^x$, $N(R^x)_2$, nitro, cycloalkyl, aryl, or heteroaryl;

$A^3$ is H, halo, $(C_2$-$C_8)$alkyl, a heteroalkyl, a trifluoromethyl, trifluoromethoxy, $OR^x$, $N(R^x)_2$, nitro, cycloalkyl, aryl, heteroaryl, or methyl; and each $R^x$ is independently H, $(C_1$-$C_8)$alkyl, or benzyl.

13. The compound of claim 12 wherein the compound of Formula I is a compound of Formula IV:

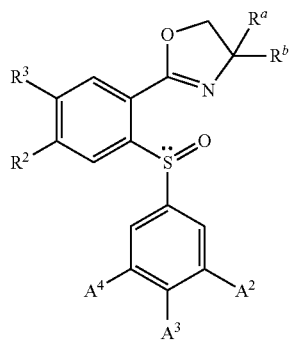
(IV)

wherein $R^a$ and $R^b$ are each independently methyl, ethyl, n-propyl, 2-propyl, cyclopropyl, tert-butyl, iso-butyl, cyclopentyl, cyclohexyl, phenyl, 4-tolyl, 4-methoxyphenyl, 4-trifluoromethylphenyl, or 4-trifluoromethoxyphenyl;

$R^2$, $R^3$, $A^2$, $A^3$, and $A^4$ are each independently, H, fluoro, chloro, bromo, methyl, ethyl, 2-propyl, tert-butyl, cyclopropyl, cyclopentyl, cyclohexyl, trifluoromethoxy, nitro, trifluoromethyl, pentafluoroethyl, $OR^x$, or $N(R^x)_2$; and each $R^x$ is independently H, methyl, ethyl, n-propyl, iso-propyl, cyclopropyl, n-butyl, sec-butyl, tert-butyl, or benzyl.

14. The compound of claim 13 wherein the compound is a compound of Formula IVA:

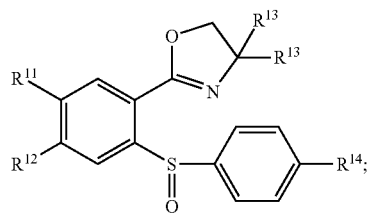
(IVA)

wherein $R^{11}$ and $R^{12}$ are each independently H, methoxy, trifluoromethyl, or trifluoromethoxy;

$R^{13}$ is methyl or phenyl; and $R^{14}$ is methyl, methoxy, or phenyl.

* * * * *